US012636344B2

(12) United States Patent (10) Patent No.: US 12,636,344 B2
Bowerman et al. (45) Date of Patent: May 26, 2026

(54) PREFERENTIALLY EXPRESSED ANTIGEN IN MELANOMA (PRAME) T CELL RECEPTORS AND METHODS OF USE THEREOF

(71) Applicant: Regeneron Pharmaceuticals, Inc., Tarrytown, NY (US)

(72) Inventors: Natalie Bowerman, Stamford, CT (US); Johanna Hansen, Greenwich, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 887 days.

(21) Appl. No.: 17/793,952

(22) PCT Filed: Jan. 22, 2021

(86) PCT No.: PCT/US2021/014490
§ 371 (c)(1),
(2) Date: Jul. 20, 2022

(87) PCT Pub. No.: WO2021/150804
PCT Pub. Date: Jul. 29, 2021

(65) Prior Publication Data
US 2023/0060095 A1 Feb. 23, 2023

Related U.S. Application Data

(60) Provisional application No. 62/965,231, filed on Jan. 24, 2020.

(51) Int. Cl.
| | |
|---|---|
| *A61K 38/17* | (2006.01) |
| *A61K 35/17* | (2025.01) |
| *A61K 39/00* | (2006.01) |
| *C07K 14/705* | (2006.01) |
| *C07K 14/725* | (2006.01) |
| *C07K 16/32* | (2006.01) |
| *C12N 5/0783* | (2010.01) |
| *C12N 15/62* | (2006.01) |
| *C12N 15/86* | (2006.01) |

(52) U.S. Cl.
CPC .......... *A61K 38/1774* (2013.01); *A61K 35/17* (2013.01); *A61K 39/001189* (2018.08); *C07K 14/7051* (2013.01); *C07K 16/32* (2013.01); *C12N 5/0636* (2013.01); *C12N 15/625* (2013.01); *C12N 15/86* (2013.01); *A61K 2039/5156* (2013.01); *C12N 2740/10043* (2013.01)

(58) Field of Classification Search
None
See application file for complete search history.

(56) References Cited

U.S. PATENT DOCUMENTS

2018/0273602 A1* 9/2018 Alten .................. A61K 40/427

FOREIGN PATENT DOCUMENTS

| WO | WO-01/52614 A2 | 7/2001 | |
|---|---|---|---|
| WO | WO-2016142783 A2 * | 9/2016 | ............. A61P 37/04 |
| WO | WO-2017175006 A1 | 10/2017 | |
| WO | WO-2018/172533 A2 | 9/2018 | |
| WO | WO-2018/234319 A1 | 12/2018 | |
| WO | WO-2021/150804 A1 | 7/2021 | |

OTHER PUBLICATIONS

Amir et al, "PRAME-specific Allo-HLA-restricted T cells with potent antitumor reactivity useful for therapeutic T-cell receptor gene transfer", Clinical Cancer Research, American Association for Cancer Research, US, vol. 17, No. 17, doi:10.1158/1078-0432.CCR-11-1066, ISSN 1078-0432, (Sep. 1, 2011), pp. 5615-5625.
Orlando et al., "Adoptive immunotherapy using PRAME-specific T cells in medulloblastoma", Cancer Research, US, (Jan. 1, 2010), doi:10.1158/0008-5472.CAN-17-3140.
Griffioen et al., "Detection and functional analysis of CD8+ T cells specific for PRAME: a target for T-cell therapy", Clinical Cancer Research, American Association for Cancer Research, US, (May 15, 2006), vol. 12, No. 10, doi:10.1158/1078-0432.CCR-05-2578, pp. 3130-3136.
Kessler et al, "Efficient identification of novel HLA-A(*)0201-presented cytotoxic T lymphocyte epitopes in the widely expressed tumor antigen PRAME by proteasome-mediated digestion analysis", Journal of Experimental Medicine, Rockefeller University Press, US, (Jan. 1, 2001), vol. 193, No. 1, pp. 73-88.
Kessler et al., "Identification of T-cell epitopes for cancer immunotherapy", Leukemia, Stockton Press, London, vol. 21, No. 9, pp. 1859-1874.
International Preliminary Report on Patentability from PCT/US2021014490, mailed Aug. 4, 2022.
Gloger et al., "Mass spectrometric analysis of the HLA class I peptidome of melanoma cell lines as a promising tool for the identification of putative tumor-associated HLA epitopes", Cancer Immunol Immunother (2016) 65:1377-1393.

* cited by examiner

*Primary Examiner* — Peter Johansen
(74) *Attorney, Agent, or Firm* — McCarter & English, LLP; Marcie B. Clarke; Deborah L. Nagle

(57) ABSTRACT

The present invention provides isolated T cell receptors (TCRs) that specifically bind to an HLA-displayed cancer testis antigen preferentially expressed antigen in melanoma (FRAME) peptide, as well as therapeutic and diagnostic methods of using those isolated TCRs.

30 Claims, No Drawings

Specification includes a Sequence Listing.

SEQUENCE LISTING

```
<160> NUMBER OF SEQ ID NOS: 954

<210> SEQ ID NO 1
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Thr Arg Asp Thr Thr Tyr Tyr
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Arg Asn Ser Phe Asp Glu Gln Asn
1               5

<210> SEQ ID NO 3
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Leu Ser Glu Phe Asp Arg Gly Ser Thr Leu Gly Arg Leu Tyr
1               5                   10                  15

<210> SEQ ID NO 4
```

-continued

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Gly His Lys Ser
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Tyr Glu Lys Glu Glu
1               5

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ala Ser Ser Arg Asp Ile Asn Glu Lys Leu Phe
1               5                   10

<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Val Ser Gly Leu Arg Gly
1               5

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Leu Tyr Ser Ala Gly Glu Glu
1               5

<210> SEQ ID NO 9
<211> LENGTH: 13
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 9

Ala Val Gln Ala Asp Gly Gly Ser Gln Gly Asn Leu Ile
1               5                   10

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ser Gly His Lys Ser
1               5

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Tyr Tyr Glu Lys Glu Glu
1               5

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Ser Ser Leu Asp Ile Asn Ser Pro Leu His
1               5                   10

<210> SEQ ID NO 13
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Val Ser Gly Leu Arg Gly
1               5

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 14

Leu Tyr Ser Ala Gly Glu Glu
1               5

<210> SEQ ID NO 15
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ala Val Gln Glu Asp Gly Gly Ser Gln Gly Asn Leu Ile
1               5                  10

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ser Gly His Lys Ser
1               5

<210> SEQ ID NO 17
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Tyr Tyr Glu Lys Glu Glu
1               5

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Ser Ser Arg Asp Ile Asn Glu Lys Leu Phe
1               5                  10

<210> SEQ ID NO 19
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Asp Ser Ala Ser Asn Tyr
1               5
```

```
<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ile Arg Ser Asn Val Gly Glu
1               5

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ala Ala Trp Asn Tyr Gly Gln Asn Phe Val
1               5                   10

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Pro Arg His Asp Thr
1               5

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Phe Tyr Glu Lys Met Gln
1               5

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ala Ser Ser Leu Glu Gly Ser Glu Ala Phe
1               5                   10

<210> SEQ ID NO 25
<211> LENGTH: 6
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asn Ser Ala Ser Asp Tyr
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ile Arg Ser Asn Met Asp Lys
1               5

<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ala Glu Asn Asn Tyr Gly Gln Asn Phe Val
1               5                   10

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Met Asn His Asn Ser
1               5

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Ala Ser Glu Gly Thr
1               5

<210> SEQ ID NO 30
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 30

Ala Ser Ser Asp Trp Gly Gln Gly Val Glu Ala Phe
1               5                  10

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Thr Ile Ser Gly Thr Asp Tyr
1               5

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Leu Thr Ser Asn
1               5

<210> SEQ ID NO 33
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ile Leu Arg Glu Tyr Met Tyr Ser Gly Gly Gly Ala Asp Gly Leu Thr
1               5                  10                  15

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ser Gly His Lys Ser
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35
```

```
Tyr Tyr Glu Lys Glu Glu
1               5

<210> SEQ ID NO 36
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Ser Ser Phe Gln Ala Gly Val Asn Tyr Gly Tyr Thr
1               5                   10

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Thr Ser Glu Asn Asn Tyr Tyr
1               5

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gln Glu Ala Tyr Lys Gln Gln Asn
1               5

<210> SEQ ID NO 39
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ala Phe Gly Met Tyr Ser Gly Gly Gly Ala Asp Gly Leu Thr
1               5                   10

<210> SEQ ID NO 40
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Trp Ser His Ser Tyr
1               5
```

-continued

```
<210> SEQ ID NO 41
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ser Ala Ala Ala Asp Ile
1               5

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Ser Ser Asp Gly Thr Gly Tyr Tyr Gly Tyr Thr
1               5                   10

<210> SEQ ID NO 43
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Thr Ser Glu Asn Asn Tyr Tyr
1               5

<210> SEQ ID NO 44
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gln Glu Ala Tyr Lys Gln Gln Asn
1               5

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ala Leu Met Glu Tyr Gly Asn Lys Leu Val
1               5                   10

<210> SEQ ID NO 46
<211> LENGTH: 5
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Trp Ser His Ser Tyr
1               5

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ser Ala Ala Ala Asp Ile
1               5

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Ala Ser Ser Asp Gly Thr Gly Tyr Tyr Gly Tyr Thr
1               5                   10

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Ser Glu Asn Asn Tyr Tyr
1               5

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gln Glu Ala Tyr Lys Gln Gln Asn
1               5

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 51

Ala Leu Met Glu Tyr Glu Asn Lys Leu Val
1               5                   10

<210> SEQ ID NO 52
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Trp Ser His Ser Tyr
1               5

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ser Ala Ala Ala Asp Ile
1               5

<210> SEQ ID NO 54
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ala Ser Ser Asp Gly Thr Gly Tyr Tyr Gly Tyr Thr
1               5                   10

<210> SEQ ID NO 55
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ser Ser Asn Phe Tyr Ala
1               5

<210> SEQ ID NO 56
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

```
Met Thr Leu Asn Gly Asp Glu
1               5

<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ala Cys Gly Gly Ser Gly Asn Thr Gly Lys Leu Ile
1               5                   10

<210> SEQ ID NO 58
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Pro Arg His Asp Thr
1               5

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Phe Tyr Glu Lys Met Gln
1               5

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ala Ser Ser Ser Gln Gly Gln Pro Gln His
1               5                   10

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Thr Arg Asp Thr Thr Tyr Tyr
1               5
```

-continued

```
<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Arg Asn Ser Phe Asp Glu Gln Asn
1               5

<210> SEQ ID NO 63
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ala Leu Ser Glu Gly Tyr Gly Asn Lys Leu Val
1               5                   10

<210> SEQ ID NO 64
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Lys Gly His Ser His
1               5

<210> SEQ ID NO 65
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Leu Gln Lys Glu Asn Ile
1               5

<210> SEQ ID NO 66
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Ala Ser Ser His Arg Asp Asp Thr Glu Ala Phe
1               5                   10

<210> SEQ ID NO 67
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 67

Asp Ser Ala Ile Tyr Asn
1               5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ile Gln Ser Ser Gln Arg Glu
1               5

<210> SEQ ID NO 69
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Ala Val Glu Gly Thr Thr Asp Ser Trp Gly Lys Phe Gln
1               5                   10

<210> SEQ ID NO 70
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Pro Arg His Asp Thr
1               5

<210> SEQ ID NO 71
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Phe Tyr Glu Lys Met Gln
1               5

<210> SEQ ID NO 72
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 72

Ala Ser Ser Ser Gln Gly Gln Pro Gln His
1               5                   10

<210> SEQ ID NO 73
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Tyr Ser Gly Ser Pro Glu
1               5

<210> SEQ ID NO 74
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

His Ile Ser Arg
1

<210> SEQ ID NO 75
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ala Leu Ser Gly Ala Ser Gly Gly Ser Tyr Ile Pro Thr
1               5                   10

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Lys Gly His Ser His
1               5

<210> SEQ ID NO 77
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Leu Gln Lys Glu Asn Ile

-continued

```
1               5

<210> SEQ ID NO 78
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Ala Ser Ser His Arg Asp Asp Thr Glu Ala Phe
1               5                   10

<210> SEQ ID NO 79
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Thr Arg Asp Thr Thr Tyr Tyr
1               5

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Arg Asn Ser Phe Asp Glu Gln Asn
1               5

<210> SEQ ID NO 81
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Ala Leu Ser Val Ser Ser Tyr Asn Thr Asp Lys Leu Ile
1               5                   10

<210> SEQ ID NO 82
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Lys Gly His Ser His
1               5

<210> SEQ ID NO 83
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Leu Gln Lys Glu Asn Ile
1               5

<210> SEQ ID NO 84
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ala Ser Ser His Arg Asp Asp Thr Glu Ala Phe
1               5                   10

<210> SEQ ID NO 85
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Thr Arg Asp Thr Thr Tyr Tyr
1               5

<210> SEQ ID NO 86
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Arg Asn Ser Phe Asp Glu Gln Asn
1               5

<210> SEQ ID NO 87
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Ala Leu Ser Glu Gly Tyr Asn Thr Asp Lys Leu Ile
1               5                   10

<210> SEQ ID NO 88
<211> LENGTH: 5
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 88

Met Asp His Glu Asn
1               5

<210> SEQ ID NO 89
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ser Tyr Asp Val Lys Met
1               5

<210> SEQ ID NO 90
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ala Ser Ser Leu Gly Gly Ala Asn Thr Ile Tyr
1               5                   10

<210> SEQ ID NO 91
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Asp Arg Gly Ser Gln Ser
1               5

<210> SEQ ID NO 92
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ile Tyr Ser Asn Gly Asp
1               5

<210> SEQ ID NO 93
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 93

Ala Val Asn Ile Pro Asn Ser Gly Tyr Ser Thr Leu Thr
1               5                   10

<210> SEQ ID NO 94
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Met Asn His Glu Tyr
1               5

<210> SEQ ID NO 95
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ser Val Gly Glu Gly Thr
1               5

<210> SEQ ID NO 96
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ala Ser Ser Tyr Trp Glu Gly Thr Glu Ala Phe
1               5                   10

<210> SEQ ID NO 97
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Thr Ser Glu Asn Asn Tyr Tyr
1               5

<210> SEQ ID NO 98
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gln Glu Ala Tyr Lys Gln Gln Asn
1               5
```

-continued

```
<210> SEQ ID NO 99
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Ala Phe Asp Tyr Gly Gln Asn Phe Val
1               5

<210> SEQ ID NO 100
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Met Asn His Asn Tyr
1               5

<210> SEQ ID NO 101
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ser Val Gly Ala Gly Ile
1               5

<210> SEQ ID NO 102
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ala Ser Ser Tyr Gly Gly Gly Gln Thr Glu Ala Phe
1               5                   10

<210> SEQ ID NO 103
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Thr Arg Asp Thr Thr Tyr Tyr
1               5

<210> SEQ ID NO 104
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Arg Asn Ser Phe Asp Glu Gln Asn
1               5

<210> SEQ ID NO 105
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ala Leu Ser Glu Gly Tyr Asn Gln Gly Gly Lys Leu Ile
1               5                   10

<210> SEQ ID NO 106
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Met Asp His Glu Asn
1               5

<210> SEQ ID NO 107
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Ser Tyr Asp Val Lys Met
1               5

<210> SEQ ID NO 108
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ala Ser Gly Ala Asp Ser Asn Gln Pro Gln His
1               5                   10

<210> SEQ ID NO 109
<211> LENGTH: 21
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"

<400> SEQUENCE: 109
acccgtgata ctacttatta c                                           21

<210> SEQ ID NO 110
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
cggaactctt ttgatgagca aaat                                        24

<210> SEQ ID NO 111
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
gctctgagtg agtttgacag aggctcaacc ctggggaggc tatac                 45

<210> SEQ ID NO 112
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
tctgggcaca agagt                                                  15

<210> SEQ ID NO 113
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
tattatgaga aagaagag                                               18

<210> SEQ ID NO 114
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gccagcagcc gggacattaa tgaaaaactg ttt                              33

<210> SEQ ID NO 115
```

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
gtcagcggtt taagaggg                                              18

<210> SEQ ID NO 116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
ctgtattcag ctggggaaga a                                          21

<210> SEQ ID NO 117
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
gctgtgcagg ccgatggagg aagccaagga aatctcatc                       39

<210> SEQ ID NO 118
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
tctgggcaca agagt                                                 15

<210> SEQ ID NO 119
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
tattatgaga aagaagag                                              18

<210> SEQ ID NO 120
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
gccagcagct tggacattaa ttcacccctc cac                                          33

<210> SEQ ID NO 121
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
gtcagcggtt taagaggg                                                          18

<210> SEQ ID NO 122
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
ctgtattcag ctggggaaga a                                                      21

<210> SEQ ID NO 123
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
gctgtgcagg aggatggagg aagccaagga aatctcatc                                   39

<210> SEQ ID NO 124
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
tctgggcaca agagt                                                             15

<210> SEQ ID NO 125
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
tattatgaga aagaagag                                                          18

<210> SEQ ID NO 126
<211> LENGTH: 33
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 126
gccagcagcc gggacattaa tgaaaaactg ttt                                    33

<210> SEQ ID NO 127
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
gacagtgcct caaactac                                                     18

<210> SEQ ID NO 128
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
attcgttcaa atgtgggcga a                                                 21

<210> SEQ ID NO 129
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
gcagcatgga actatggtca gaattttgtc                                        30

<210> SEQ ID NO 130
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
cctagacacg acact                                                        15

<210> SEQ ID NO 131
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
ttttatgaaa agatgcag                                                     18

-continued

```
<210> SEQ ID NO 132
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gccagcagct tagaggggtc tgaagctttc                                    30

<210> SEQ ID NO 133
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
aacagcgcct cagactac                                                 18

<210> SEQ ID NO 134
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
attcgttcaa atatggacaa a                                             21

<210> SEQ ID NO 135
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
gcagagaata actatggtca gaattttgtc                                    30

<210> SEQ ID NO 136
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
atgaaccata actcc                                                    15

<210> SEQ ID NO 137
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 137
tcagcttctg agggtacc                                              18

<210> SEQ ID NO 138
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gccagcagtg actggggaca gggggttgaa gctttc                          36

<210> SEQ ID NO 139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
acaatcagtg gaactgatta c                                          21

<210> SEQ ID NO 140
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
ggtcttacaa gcaat                                                 15

<210> SEQ ID NO 141
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
atcctgagag aatacatgta ttcaggagga ggtgctgacg gactcacc            48

<210> SEQ ID NO 142
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
tctgggcaca agagt                                                 15

<210> SEQ ID NO 143
<211> LENGTH: 18
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 143
tattatgaga aagaagag                                                    18

<210> SEQ ID NO 144
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
gccagcagct tccaagcagg ggttaactat ggctacacc                            39

<210> SEQ ID NO 145
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
accagtgaga ataattatta t                                               21

<210> SEQ ID NO 146
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
caagaagctt ataagcaaca gaat                                            24

<210> SEQ ID NO 147
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
gctttcggta tgtattcagg aggaggtgct gacggactca cc                        42

<210> SEQ ID NO 148
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
tggagccaca gctat                                                      15
```

```
<210> SEQ ID NO 149
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
tcagcagctg ctgatatt                                                          18

<210> SEQ ID NO 150
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
gccagcagtg atgggacagg gtactatggc tacacc                                      36

<210> SEQ ID NO 151
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
accagtgaga ataattatta t                                                      21

<210> SEQ ID NO 152
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
caagaagctt ataagcaaca gaat                                                   24

<210> SEQ ID NO 153
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
gcccttatgg aatatggaaa caaactggtc                                             30

<210> SEQ ID NO 154
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 154
tggagccaca gctat                                                             15

<210> SEQ ID NO 155
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
tcagcagctg ctgatatt                                                          18

<210> SEQ ID NO 156
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
gccagcagtg atgggacagg gtactatggc tacacc                                      36

<210> SEQ ID NO 157
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
accagtgaga ataattatta t                                                      21

<210> SEQ ID NO 158
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
caagaagctt ataagcaaca gaat                                                   24

<210> SEQ ID NO 159
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
gcccttatgg aatatgaaaa caaactggtc                                             30

<210> SEQ ID NO 160
<211> LENGTH: 15
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
tggagccaca gctat                                                      15

<210> SEQ ID NO 161
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
tcagcagctg ctgatatt                                                   18

<210> SEQ ID NO 162
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
gccagcagtg atgggacagg gtactatggc tacacc                               36

<210> SEQ ID NO 163
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
tccagcaatt tttatgcc                                                   18

<210> SEQ ID NO 164
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
atgactttaa atggggat                                                   18

<210> SEQ ID NO 165
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
gcctgtgggg gttctggcaa cacaggcaaa ctaatc                               36

```
<210> SEQ ID NO 166
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
cctagacacg acact                                                         15

<210> SEQ ID NO 167
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
ttttatgaaa agatgcag                                                      18

<210> SEQ ID NO 168
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
gccagcagct cccagggtca gccccagcat                                         30

<210> SEQ ID NO 169
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
acccgtgata ctacttatta c                                                  21

<210> SEQ ID NO 170
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
cggaactctt ttgatgagca aaat                                               24

<210> SEQ ID NO 171
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

```
<400> SEQUENCE: 171
gctctgagtg agggatatgg aaacaaactg gtc                                    33

<210> SEQ ID NO 172
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
aaaggacaca gtcat                                                        15

<210> SEQ ID NO 173
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
ctccagaaag aaaatatc                                                     18

<210> SEQ ID NO 174
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gccagctcac acagggacga cactgaagct ttc                                    33

<210> SEQ ID NO 175
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gatagcgcta tttacaac                                                     18

<210> SEQ ID NO 176
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
attcagtcaa gtcagagaga g                                                 21

<210> SEQ ID NO 177
<211> LENGTH: 39
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
gctgtggagg ggacaactga cagctggggg aaattccag                              39

<210> SEQ ID NO 178
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
cctagacacg acact                                                       15

<210> SEQ ID NO 179
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
ttttatgaaa agatgcag                                                    18

<210> SEQ ID NO 180
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gccagcagct cccagggtca gccccagcat                                       30

<210> SEQ ID NO 181
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
tattctggga gtcctgaa                                                    18

<210> SEQ ID NO 182
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
```

-continued

```
cacatctcta ga                                                    12

<210> SEQ ID NO 183
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
gctctaagtg gggcatcagg aggaagctac atacctaca                       39

<210> SEQ ID NO 184
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
aaaggacaca gtcat                                                 15

<210> SEQ ID NO 185
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
ctccagaaag aaaatatc                                              18

<210> SEQ ID NO 186
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gccagctcac acagggacga cactgaagct ttc                             33

<210> SEQ ID NO 187
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
acccgtgata ctacttatta c                                          21

<210> SEQ ID NO 188
<211> LENGTH: 24
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"

<400> SEQUENCE: 188
cggaactctt ttgatgagca aaat                                                   24

<210> SEQ ID NO 189
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
gctctgagtg tatcatctta taacaccgac aagctcatc                                   39

<210> SEQ ID NO 190
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
aaaggacaca gtcat                                                             15

<210> SEQ ID NO 191
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
ctccagaaag aaaatatc                                                         18

<210> SEQ ID NO 192
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
gccagctcac acaggatga cactgaagct ttc                                          33

<210> SEQ ID NO 193
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
acccgtgata ctacttatta c                                                      21

<210> SEQ ID NO 194

```
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
cggaactctt ttgatgagca aaat                                                    24

<210> SEQ ID NO 195
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
gctctgagtg aggggtataa caccgacaag ctcatc                                       36

<210> SEQ ID NO 196
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
atggaccatg aaaat                                                              15

<210> SEQ ID NO 197
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
tcatatgatg ttaaaatg                                                           18

<210> SEQ ID NO 198
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
gccagcagtt tagggggggc gaacaccata tat                                          33

<210> SEQ ID NO 199
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
```

-continued gaccgaggtt cccagtcc                                                       18

<210> SEQ ID NO 200
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
atatactcca atggtgac                                                      18

<210> SEQ ID NO 201
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
gccgtgaaca ttccgaattc aggatacagc accctcacc                               39

<210> SEQ ID NO 202
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
atgaaccatg aatac                                                         15

<210> SEQ ID NO 203
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
tcagttggtg agggtaca                                                      18

<210> SEQ ID NO 204
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
gccagcagtt actgggaggg cactgaagct ttc                                     33

<210> SEQ ID NO 205
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 205
accagtgaga ataattatta t                                             21

<210> SEQ ID NO 206
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
caagaagctt ataagcaaca gaat                                          24

<210> SEQ ID NO 207
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
gctttcgact atggtcagaa ttttgtc                                       27

<210> SEQ ID NO 208
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
atgaaccata actac                                                    15

<210> SEQ ID NO 209
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
tcagttggtg ctggtatc                                                 18

<210> SEQ ID NO 210
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gccagcagtt acggggggggg gcagactgaa gctttc                            36
```

```
<210> SEQ ID NO 211
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
acccgtgata ctacttatta c                                             21

<210> SEQ ID NO 212
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
cggaactctt ttgatgagca aaat                                          24

<210> SEQ ID NO 213
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
gctctgagtg agggttataa ccagggagga aagcttatc                          39

<210> SEQ ID NO 214
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
atggaccatg aaaat                                                    15

<210> SEQ ID NO 215
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
tcatatgatg ttaaaatg                                                 18

<210> SEQ ID NO 216
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 216
gccagcgggg cagatagcaa tcagccccag cat                                      33

<210> SEQ ID NO 217
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Ala Gln Lys Val Thr Gln Ala Gln Pro Glu Ile Ser Val Val Glu Lys
1               5                   10                  15

Glu Asp Val Thr Leu Asp Cys Val Tyr Glu Thr Arg Asp Thr Thr Tyr
            20                  25                  30

Tyr Leu Phe Trp Tyr Lys Gln Pro Pro Ser Gly Glu Leu Val Phe Leu
        35                  40                  45

Ile Arg Arg Asn Ser Phe Asp Glu Gln Asn Glu Ile Ser Gly Arg Tyr
    50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Glu
                85                  90                  95

Phe Asp Arg Gly Ser Thr Leu Gly Arg Leu Tyr Phe Gly Arg Gly Thr
            100                 105                 110

Gln Leu Thr Val Trp Pro
        115

<210> SEQ ID NO 218
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218
gctcagaagg taactcaagc gcagcctgaa atttctgtgg tggagaagga ggatgtgacc    60
ttggactgtg tgtatgaaac ccgtgatact acttattact tattctggta caagcaacca   120
ccaagtggag aattggtttt ccttattcgt cggaactctt ttgatgagca aaatgaaata   180
agtggtcggt attcttggaa cttccagaaa tccaccagtt ccttcaactt caccatcaca   240
gcctcacaag tcgtggactc agcagtatac ttctgtgctc tgagtgagtt tgacagaggc   300
tcaaccctgg ggaggctata ctttggaaga ggaactcagt tgactgtctg gcct         354

<210> SEQ ID NO 219
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Asp Ala Gly Val Thr Gln Ser Pro Thr His Leu Ile Lys Thr Arg Gly
1               5                   10                  15

```
Gln Gln Val Thr Leu Arg Cys Ser Pro Ile Ser Gly His Lys Ser Val
        20                  25                  30

Ser Trp Tyr Gln Gln Val Leu Gly Gln Gly Pro Gln Phe Ile Phe Gln
        35                  40                  45

Tyr Tyr Glu Lys Glu Glu Arg Gly Arg Gly Asn Phe Pro Asp Arg Phe
        50                  55                  60

Ser Ala Arg Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Arg Asp
                85                  90                  95

Ile Asn Glu Lys Leu Phe Phe Gly Ser Gly Thr Gln Leu Ser Val Leu
        100                 105                 110
```

<210> SEQ ID NO 220
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 220

```
gacgctggag tcacccaaag tcccacacac ctgatcaaaa cgagaggaca gcaagtgact      60
ctgagatgct ctcctatctc tgggcacaag agtgtgtcct ggtaccaaca ggtcctgggt     120
caggggcccc agtttatctt tcagtattat gagaaagaag agagaggaag aggaaacttc     180
cctgatcgat tctcagctcg ccagttccct aactatagct ctgagctgaa tgtgaacgcc     240
ttgttgctgg gggactcggc cctgtatctc tgtgccagca gccgggacat taatgaaaaa     300
ctgttttttg gcagtggaac ccagctctct gtcttg                              336
```

<210> SEQ ID NO 221
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

```
Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
        20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
        50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Gln Ala Asp Gly Gly Ser
                85                  90                  95

Gln Gly Asn Leu Ile Phe Gly Lys Gly Thr Lys Leu Ser Val Lys Pro
        100                 105                 110
```

<210> SEQ ID NO 222
<211> LENGTH: 336
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222
gaagaccagg tgacgcagag tcccgaggcc ctgagactcc aggagggaga gagtagcagt      60
ctcaactgca gttacacagt cagcggttta agagggctgt tctggtatag gcaagatcct     120
gggaaaggcc ctgaattcct cttcaccctg tattcagctg gggaagaaaa ggagaaagaa     180
aggctaaaag ccacattaac aaagaaggaa agctttctgc acatcacagc ccctaaacct     240
gaagactcag ccacttatct ctgtgctgtg caggccgatg gaggaagcca aggaaatctc     300
atctttggaa aaggcactaa actctctgtt aaacca                               336

<210> SEQ ID NO 223
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 223

Asp Ala Gly Val Thr Gln Ser Pro Thr His Leu Ile Lys Thr Arg Gly
1               5                   10                  15

Gln Gln Val Thr Leu Arg Cys Ser Pro Ile Ser Gly His Lys Ser Val
            20                  25                  30

Ser Trp Tyr Gln Gln Val Leu Gly Gln Gly Pro Gln Phe Ile Phe Gln
        35                  40                  45

Tyr Tyr Glu Lys Glu Glu Arg Gly Arg Gly Asn Phe Pro Asp Arg Phe
    50                  55                  60

Ser Ala Arg Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Asp
                85                  90                  95

Ile Asn Ser Pro Leu His Phe Gly Asn Gly Thr Arg Leu Thr Val Thr
            100                 105                 110

<210> SEQ ID NO 224
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
gacgctggag tcacccaaag tcccacacac ctgatcaaaa cgagaggaca gcaagtgact      60
ctgagatgct ctcctatctc tgggcacaag agtgtgtcct ggtaccaaca ggtcctgggt     120
caggggcccc agtttatctt tcagtattat gagaaagaag agagaggaag aggaaacttc     180
cctgatcgat tctcagctcg ccagttccct aactatagct ctgagctgaa tgtgaacgcc     240
ttgttgctgg gggactcggc cctgtatctc tgtgccagca gcttggacat taattcaccc     300
ctccactttg ggaacgggac caggctcact gtgaca                               336

<210> SEQ ID NO 225
```

-continued

```
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 225

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
                20                  25                  30

Leu Phe Trp Tyr Arg Gln Asp Pro Gly Lys Gly Pro Glu Phe Leu Phe
            35                  40                  45

Thr Leu Tyr Ser Ala Gly Glu Glu Lys Glu Lys Glu Arg Leu Lys Ala
        50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Gln Glu Asp Gly Gly Ser
                85                  90                  95

Gln Gly Asn Leu Ile Phe Gly Lys Gly Thr Lys Leu Ser Val Lys Pro
            100                 105                 110

<210> SEQ ID NO 226
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 226
gaagaccagg tgacgcagag tcccgaggcc ctgagactcc aggagggaga gagtagcagt        60
ctcaactgca gttacacagt cagcggttta agagggctgt tctggtatag gcaagatcct       120
gggaaaggcc ctgaattcct cttcaccctg tattcagctg gggaagaaaa ggagaaagaa       180
aggctaaaag ccacattaac aaagaaggaa agctttctgc acatcacagc ccctaaacct       240
gaagactcag ccacttatct ctgtgctgtg caggaggatg gaggaagcca aggaaatctc       300
atctttggaa aaggcactaa actctctgtt aaacca                                 336

<210> SEQ ID NO 227
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 227

Asp Ala Gly Val Thr Gln Ser Pro Thr His Leu Ile Lys Thr Arg Gly
1               5                   10                  15

Gln Gln Val Thr Leu Arg Cys Ser Pro Ile Ser Gly His Lys Ser Val
                20                  25                  30

Ser Trp Tyr Gln Gln Val Leu Gly Gln Gly Pro Gln Phe Ile Phe Gln
            35                  40                  45

Tyr Tyr Glu Lys Glu Glu Arg Gly Arg Gly Asn Phe Pro Asp Arg Phe
        50                  55                  60
```

```
Ser Ala Arg Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Arg Asp
                85                  90                  95

Ile Asn Glu Lys Leu Phe Phe Gly Ser Gly Thr Gln Leu Ser Val Leu
            100                 105                 110
```

```
<210> SEQ ID NO 228
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 228
gacgctggag tcacccaaag tcccacacac ctgatcaaaa cgagaggaca gcaagtgact      60
ctgagatgct ctcctatctc tgggcacaag agtgtgtcct ggtaccaaca ggtcctgggt     120
caggggcccc agtttatctt tcagtattat gagaaagaag agagaggaag aggaaacttc     180
cctgatcgat tctcagctcg ccagttccct aactatagct ctgagctgaa tgtgaacgcc     240
ttgttgctgg gggactcggc cctgtatctc tgtgccagca gccgggacat taatgaaaaa     300 ctgtttttg gcagtggaac ccagctctct gtcttg                                336
```

```
<210> SEQ ID NO 229
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

Gly Glu Asn Val Glu Gln His Pro Ser Thr Leu Ser Val Gln Glu Gly
1                   5                   10                  15

Asp Ser Ala Val Ile Lys Cys Thr Tyr Ser Asp Ser Ala Ser Asn Tyr
                20                  25                  30

Phe Pro Trp Tyr Lys Gln Glu Leu Gly Lys Arg Pro Gln Leu Ile Ile
            35                  40                  45

Asp Ile Arg Ser Asn Val Gly Glu Lys Lys Asp Gln Arg Ile Ala Val
        50                  55                  60

Thr Leu Asn Lys Thr Ala Lys His Phe Ser Leu His Ile Thr Glu Thr
65                  70                  75                  80

Gln Pro Glu Asp Ser Ala Val Tyr Phe Cys Ala Ala Trp Asn Tyr Gly
                85                  90                  95

Gln Asn Phe Val Phe Gly Pro Gly Thr Arg Leu Ser Val Leu Pro
            100                 105                 110
```

```
<210> SEQ ID NO 230
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230
ggagagaatg tggagcagca tccttcaacc ctgagtgtcc aggagggaga cagcgctgtt      60
```

-continued

```
atcaagtgta cttattcaga cagtgcctca aactacttcc cttggtataa gcaagaactt     120
ggaaaaagac ctcagcttat tatagacatt cgttcaaatg tgggcgaaaa gaaagaccaa     180
cgaattgctg ttacattgaa caagacagcc aaacatttct ccctgcacat cacagagacc     240
caacctgaag actcggctgt ctacttctgt gcagcatgga actatggtca gaattttgtc     300
tttggtcccg gaaccagatt gtccgtgctg ccc                                  333
```

<210> SEQ ID NO 231
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 231

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Leu Glu
                85                  90                  95

Gly Ser Glu Ala Phe Phe Gly Gln Gly Thr Arg Leu Thr Val Val
            100                 105                 110
```

<210> SEQ ID NO 232
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 232

```
gctgctggag tcatccagtc cccaagacat ctgatcaaag aaaagaggga aacagccact      60
ctgaaatgct atcctatccc tagacacgac actgtctact ggtaccagca gggtccaggt     120
caggaccccc agttcctcat ttcgtttat gaaaagatgc agagcgataa aggaagcatc     180
cctgatcgat tctcagctca acagttcagt gactatcatt ctgaactgaa catgagctcc     240
ttggagctgg gggactcagc cctgtacttc tgtgccagca gcttagaggg gtctgaagct     300
ttctttggac aaggcaccag actcacagtt gta                                  333
```

<210> SEQ ID NO 233
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 233

```
Gly Glu Ser Val Gly Leu His Leu Pro Thr Leu Ser Val Gln Glu Gly
1               5                   10                  15

Asp Asn Ser Ile Ile Asn Cys Ala Tyr Ser Asn Ser Ala Ser Asp Tyr
            20                  25                  30

Phe Ile Trp Tyr Lys Gln Glu Ser Gly Lys Gly Pro Gln Phe Ile Ile
            35                  40                  45

Asp Ile Arg Ser Asn Met Asp Lys Arg Gln Gly Gln Arg Val Thr Val
        50                  55                  60

Leu Leu Asn Lys Thr Val Lys His Leu Ser Leu Gln Ile Ala Ala Thr
65                  70                  75                  80

Gln Pro Gly Asp Ser Ala Val Tyr Phe Cys Ala Glu Asn Asn Tyr Gly
                85                  90                  95

Gln Asn Phe Val Phe Gly Pro Gly Thr Arg Leu Ser Val Leu Pro
            100                 105                 110
```

<210> SEQ ID NO 234
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 234

```
ggagagagtg tggggctgca tcttcctacc ctgagtgtcc aggagggtga caactctatt      60
atcaactgtg cttattcaaa cagcgcctca gactacttca tttggtacaa gcaagaatct     120
ggaaaaggtc ctcaattcat tatagacatt cgttcaaata tggacaaaag gcaaggccaa     180
agagtcaccg tttttattga ataagacagtg aaacatctct ctctgcaaat tgcagctact     240
caacctggag actcagctgt ctacttttgt gcagagaata actatggtca gaattttgtc     300
tttggtcccg gaaccagatt gtccgtgctg ccc                                  333
```

<210> SEQ ID NO 235
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Asn Ser Met
            20                  25                  30

Tyr Trp Tyr Arg Gln Asp Pro Gly Met Gly Leu Arg Leu Ile Tyr Tyr
            35                  40                  45

Ser Ala Ser Glu Gly Thr Thr Asp Lys Gly Glu Val Pro Asn Gly Tyr
        50                  55                  60

Asn Val Ser Arg Leu Asn Lys Arg Glu Phe Ser Leu Arg Leu Glu Ser
65                  70                  75                  80

Ala Ala Pro Ser Gln Thr Ser Val Tyr Phe Cys Ala Ser Ser Asp Trp
                85                  90                  95

Gly Gln Gly Val Glu Ala Phe Phe Gly Gln Gly Thr Arg Leu Thr Val
            100                 105                 110
```

Val

<210> SEQ ID NO 236
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 236
aatgctggtg tcactcagac cccaaaattc caggtcctga agacaggaca gagcatgaca        60
ctgcagtgtg cccaggatat gaaccataac tccatgtact ggtatcgaca agacccaggc       120
atgggactga ggctgattta ttactcagct tctgagggta ccactgacaa aggagaagtc       180
cccaatggct acaatgtctc cagattaaac aaacgggagt ctcgctcag gctggagtcg        240 gctgctccct cccagacatc tgtgtacttc tgtgccagca gtgactgggg acaggggggtt      300 gaagctttct ttggacaagg caccagactc acagttgta                               339

<210> SEQ ID NO 237
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Glu Tyr Met Tyr Ser
                85                  90                  95

Gly Gly Gly Ala Asp Gly Leu Thr Phe Gly Lys Gly Thr His Leu Ile
            100                 105                 110

Ile Gln Pro
        115

<210> SEQ ID NO 238
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 238
gatgctaaga ccacacagcc aaattcaatg gagagtaacg aagaagagcc tgttcacttg        60
ccttgtaacc actccacaat cagtggaact gattacatac attggtatcg acagcttccc       120
tcccagggtc cagagtacgt gattcatggt cttacaagca atgtgaacaa cagaatggcc       180

```
tctctggcaa tcgctgaaga cagaaagtcc agtaccttga tcctgcaccg tgctaccttg        240
agagatgctg ctgtgtacta ctgcatcctg agagaataca tgtattcagg aggaggtgct        300
gacggactca cctttggcaa agggactcat ctaatcatcc agccc                        345
```

```
<210> SEQ ID NO 239
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Asp Ala Gly Val Thr Gln Ser Pro Thr His Leu Ile Lys Thr Arg Gly
1               5                   10                  15

Gln Gln Val Thr Leu Arg Cys Ser Pro Ile Ser Gly His Lys Ser Val
            20                  25                  30

Ser Trp Tyr Gln Gln Val Leu Gly Gln Gly Pro Gln Phe Ile Phe Gln
        35                  40                  45

Tyr Tyr Glu Lys Glu Glu Arg Gly Arg Gly Asn Phe Pro Asp Arg Phe
    50                  55                  60

Ser Ala Arg Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Phe Gln
                85                  90                  95

Ala Gly Val Asn Tyr Gly Tyr Thr Phe Gly Ser Gly Thr Arg Leu Thr
            100                 105                 110

Val Val
```

```
<210> SEQ ID NO 240
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 240
gacgctggag tcacccaaag tcccacacac ctgatcaaaa cgagaggaca gcaagtgact         60
ctgagatgct ctcctatctc tgggcacaag agtgtgtcct ggtaccaaca ggtcctgggt        120
caggggcccc agtttatctt tcagtattat gagaaagaag agagaggaag aggaaacttc        180
cctgatcgat tctcagctcg ccagttccct aactatagct ctgagctgaa tgtgaacgcc        240
ttgttgctgg gggactcggc cctgtatctc tgtgccagca gcttccaagc aggggttaac        300
tatggctaca ccttcggttc ggggaccagg ttaaccgttg ta                          342
```

```
<210> SEQ ID NO 241
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

Ala Gln Thr Val Thr Gln Ser Gln Pro Glu Met Ser Val Gln Glu Ala
```

-continued

```
1               5                   10                  15
Glu Thr Val Thr Leu Ser Cys Thr Tyr Asp Thr Ser Glu Asn Asn Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Phe Gly Met
            85                  90                  95

Tyr Ser Gly Gly Gly Ala Asp Gly Leu Thr Phe Gly Lys Gly Thr His
            100                 105                 110

Leu Ile Ile Gln Pro
        115
```

```
<210> SEQ ID NO 242
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242
gcccagacag tcactcagtc tcaaccagag atgtctgtgc aggaggcaga gactgtgacc      60
ctgagttgca catatgacac cagtgagaat aattattatt tgttctggta caagcagcct     120
cccagcaggc agatgattct cgttattcgc caagaagctt ataagcaaca gaatgcaacg     180
gagaatcgtt tctctgtgaa cttccagaaa gcagccaaat ccttcagtct caagatctca     240
gactcacagc tgggggacac tgcgatgtat ttctgtgctt tcggtatgta ttcaggagga     300
ggtgctgacg gactcacctt tggcaaaggg actcatctaa tcatccagcc c              351
```

```
<210> SEQ ID NO 243
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243

Asp Ala Gly Ile Thr Gln Ser Pro Arg Tyr Lys Ile Thr Glu Thr Gly
1               5                   10                  15

Arg Gln Val Thr Leu Met Cys His Gln Thr Trp Ser His Ser Tyr Met
            20                  25                  30

Phe Trp Tyr Arg Gln Asp Leu Gly His Gly Leu Arg Leu Ile Tyr Tyr
        35                  40                  45

Ser Ala Ala Ala Asp Ile Thr Asp Lys Gly Glu Val Pro Asp Gly Tyr
    50                  55                  60

Val Val Ser Arg Ser Lys Thr Glu Asn Phe Pro Leu Thr Leu Glu Ser
65                  70                  75                  80

Ala Thr Arg Ser Gln Thr Ser Val Tyr Phe Cys Ala Ser Ser Asp Gly
            85                  90                  95

Thr Gly Tyr Tyr Gly Tyr Thr Phe Gly Ser Gly Thr Arg Leu Thr Val
            100                 105                 110
```

Val

<210> SEQ ID NO 244
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 244
gatgctggaa tcacccagag cccaagatac aagatcacag agacaggaag gcaggtgacc      60
ttgatgtgtc accagacttg gagccacagc tatatgttct ggtatcgaca agacctggga     120
catgggctga ggctgatcta ttactcagca gctgctgata ttacagataa aggagaagtc     180
cccgatggct atgttgtctc cagatccaag acagagaatt tcccctcac tctggagtca      240 gctacccgct cccagacatc tgtgtatttc tgcgccagca gtgatgggac agggtactat     300
ggctacacct tcggttcggg gaccaggtta accgttgta                            339

<210> SEQ ID NO 245
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Asn Asn Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Leu Met Glu
                85                  90                  95

Tyr Gly Asn Lys Leu Val Phe Gly Ala Gly Thr Ile Leu Arg Val Lys
            100                 105                 110

Ser

<210> SEQ ID NO 246
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246
gcccagacag tcactcagtc tcaaccagag atgtctgtgc aggaggcaga gactgtgacc      60
ctgagttgca catatgacac cagtgagaat aattattatt tgttctggta caagcagcct     120
cccagcaggc agatgattct cgttattcgc caagaagctt ataagcaaca gaatgcaacg     180

```
gagaatcgtt tctctgtgaa cttccagaaa gcagccaaat ccttcagtct caagatctca        240
gactcacagc tgggggacac tgcgatgtat ttctgtgccc ttatggaata tggaaacaaa        300
ctggtctttg gcgcaggaac cattctgaga gtcaagtcc                                339
```

<210> SEQ ID NO 247
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 247

```
Asp Ala Gly Ile Thr Gln Ser Pro Arg Tyr Lys Ile Thr Glu Thr Gly
1               5                   10                  15

Arg Gln Val Thr Leu Met Cys His Gln Thr Trp Ser His Ser Tyr Met
            20                  25                  30

Phe Trp Tyr Arg Gln Asp Leu Gly His Gly Leu Arg Leu Ile Tyr Tyr
        35                  40                  45

Ser Ala Ala Ala Asp Ile Thr Asp Lys Gly Glu Val Pro Asp Gly Tyr
    50                  55                  60

Val Val Ser Arg Ser Lys Thr Glu Asn Phe Pro Leu Thr Leu Glu Ser
65                  70                  75                  80

Ala Thr Arg Ser Gln Thr Ser Val Tyr Phe Cys Ala Ser Ser Asp Gly
                85                  90                  95

Thr Gly Tyr Tyr Gly Tyr Thr Phe Gly Ser Gly Thr Arg Leu Thr Val
            100                 105                 110

Val
```

<210> SEQ ID NO 248
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248

```
gatgctggaa tcacccagag cccaagatac aagatcacag agacaggaag gcaggtgacc         60
ttgatgtgtc accagacttg gagccacagc tatatgttct ggtatcgaca agacctggga        120
catgggctga ggctgatcta ttactcagca gctgctgata ttacagataa aggagaagtc        180
cccgatggct atgttgtctc cagatccaag acagagaatt tccccctcac tctggagtca        240
gctacccgct cccagacatc tgtgtatttc tgcgccagca gtgatgggac agggtactat        300
ggctacacct tcggttcggg gaccaggtta accgttgta                                339
```

<210> SEQ ID NO 249
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

```
Ala Gln Thr Val Thr Gln Ser Gln Pro Glu Met Ser Val Gln Glu Ala
```

```
1              5                   10                  15
Glu Thr Val Thr Leu Ser Cys Thr Tyr Asp Thr Ser Glu Asn Asn Tyr
            20                  25                  30

Tyr Leu Phe Trp Tyr Lys Gln Pro Pro Ser Arg Gln Met Ile Leu Val
            35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Leu Met Glu
                85                  90                  95

Tyr Glu Asn Lys Leu Val Phe Gly Ala Gly Thr Ile Leu Arg Val Lys
                100                 105                 110

Ser
```

```
<210> SEQ ID NO 250
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250
gcccagacag tcactcagtc tcaaccagag atgtctgtgc aggaggcaga gactgtgacc       60
ctgagttgca catatgacac cagtgagaat aattattatt tgttctggta caagcagcct      120
cccagcaggc agatgattct cgttattcgc caagaagctt ataagcaaca gaatgcaacg      180
gagaatcgtt tctctgtgaa cttccagaaa gcagccaaat ccttcagtct caagatctca      240
gactcacagc tggggacac tgcgatgtat ttctgtgccc ttatggaata tgaaaacaaa      300
ctggtctttg gcgcaggaac cattctgaga gtcaagtcc                             339
```

```
<210> SEQ ID NO 251
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

Asp Ala Gly Ile Thr Gln Ser Pro Arg Tyr Lys Ile Thr Glu Thr Gly
1              5                   10                  15

Arg Gln Val Thr Leu Met Cys His Gln Thr Trp Ser His Ser Tyr Met
            20                  25                  30

Phe Trp Tyr Arg Gln Asp Leu Gly His Gly Leu Arg Leu Ile Tyr Tyr
            35                  40                  45

Ser Ala Ala Ala Asp Ile Thr Asp Lys Gly Glu Val Pro Asp Gly Tyr
    50                  55                  60

Val Val Ser Arg Ser Lys Thr Glu Asn Phe Pro Leu Thr Leu Glu Ser
65                  70                  75                  80

Ala Thr Arg Ser Gln Thr Ser Val Tyr Phe Cys Ala Ser Ser Asp Gly
                85                  90                  95

Thr Gly Tyr Tyr Gly Tyr Thr Phe Gly Ser Gly Thr Arg Leu Thr Val
                100                 105                 110
```

Val

<210> SEQ ID NO 252
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252
gatgctggaa tcacccagag cccaagatac aagatcacag agacaggaag gcaggtgacc      60
ttgatgtgtc accagacttg gagccacagc tatatgttct ggtatcgaca agacctggga     120
catgggctga ggctgatcta ttactcagca gctgctgata ttacagataa aggagaagtc     180
cccgatggct atgttgtctc cagatccaag acagagaatt ccccctcac tctggagtca      240 gctacccgct cccagacatc tgtgtatttc tgcgccagca gtgatgggac agggtactat     300
ggctacacct tcggttcggg gaccaggtta accgttgta                            339

<210> SEQ ID NO 253
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Ile Leu Asn Val Glu Gln Ser Pro Gln Ser Leu His Val Gln Glu Gly
1               5                   10                  15

Asp Ser Thr Asn Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Cys Gly Gly Ser Gly
                85                  90                  95

Asn Thr Gly Lys Leu Ile Phe Gly Gln Gly Thr Thr Leu Gln Val Lys
            100                 105                 110

Pro

<210> SEQ ID NO 254
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 254
atactgaacg tggaacaaag tcctcagtca ctgcatgttc aggagggaga cagcaccaat      60
ttcacctgca gcttcccttc cagcaatttt tatgccttac actggtacag atgggaaact     120
gcaaaaagcc ccgaggcctt gtttgtaatg actttaaatg gggatgaaaa gaagaaagga     180

```
cgaataagtg ccactcttaa taccaaggag ggttacagct atttgtacat caaaggatcc       240
cagcctgaag actcagccac atacctctgt gcctgtgggg gttctggcaa cacaggcaaa       300
ctaatctttg ggcaagggac aactttacaa gtaaaacca                              339
```

<210> SEQ ID NO 255
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 255

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Gln
                85                  90                  95

Gly Gln Pro Gln His Phe Gly Asp Gly Thr Arg Leu Ser Ile Leu
            100                 105                 110
```

<210> SEQ ID NO 256
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 256

```
gctgctggag tcatccagtc cccaagacat ctgatcaaag aaaagaggga aacagccact        60
ctgaaatgct atcctatccc tagacacgac actgtctact ggtaccagca gggtccaggt       120 caggacccc agttcctcat ttcgttttat gaaaagatgc agagcgataa aggaagcatc        180
cctgatcgat tctcagctca acagttcagt gactatcatt ctgaactgaa catgagctcc       240
ttggagctgg gggactcagc cctgtacttc tgtgccagca gctcccaggg tcagccccag       300
cattttggtg atgggactcg actctccatc cta                                    333
```

<210> SEQ ID NO 257
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 257

```
Ala Gln Lys Val Thr Gln Ala Thr Arg Glu Ile Ser Val Val Glu Lys
1               5                   10                  15

Glu Asp Val Thr Leu Asp Cys Val Tyr Glu Thr Arg Asp Thr Thr Tyr
```

-continued

```
                   20                25                30

Tyr Leu Phe Trp Tyr Lys Gln Pro Pro Ser Gly Glu Leu Val Phe Leu
         35            40                45

Ile Arg Arg Asn Ser Phe Asp Glu Gln Asn Glu Ile Ser Gly Arg Tyr
    50            55                60

Ser Trp Asn Phe Gln Lys Ser Thr Ser Ser Phe Asn Phe Thr Ile Thr
65            70                75                80

Ala Ser Gln Val Val Asp Ser Ala Val Tyr Phe Cys Ala Leu Ser Glu
              85                90                95

Gly Tyr Gly Asn Lys Leu Val Phe Gly Ala Gly Thr Ile Leu Arg Val
         100               105               110

Lys Ser
```

<210> SEQ ID NO 258
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 258

```
gctcagaagg taactcaagc gactagagaa atttctgtgg tggagaagga ggatgtgacc      60
ttggactgtg tgtatgaaac ccgtgatact acttattact tattctggta caagcaacca     120
ccaagtggag aattggtttt ccttattcgt cggaactctt ttgatgagca aaatgaaata     180
agtggtcggt attcttggaa cttccagaaa tccaccagtt ccttcaactt caccatcaca     240
gcctcacaag tcgtggactc agcagtatac ttctgtgctc tgagtgaggg atatggaaac     300
aaactggtct ttggcgcagg aaccattctg agagtcaagt cc                        342
```

<210> SEQ ID NO 259
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 259

```
Asn Ala Gly Val Met Gln Asn Pro Arg His Leu Val Arg Arg Arg Gly
1             5                10                15

Gln Glu Ala Arg Leu Arg Cys Ser Pro Met Lys Gly His Ser His Val
              20                25                30

Tyr Trp Tyr Arg Gln Leu Pro Glu Glu Gly Leu Lys Phe Met Val Tyr
         35                40                45

Leu Gln Lys Glu Asn Ile Ile Asp Glu Ser Gly Met Pro Lys Glu Arg
    50                55                60

Phe Ser Ala Glu Phe Pro Lys Glu Gly Pro Ser Ile Leu Arg Ile Gln
65                70                75                80

Gln Val Val Arg Gly Asp Ser Ala Ala Tyr Phe Cys Ala Ser Ser His
              85                90                95

Arg Asp Asp Thr Glu Ala Phe Phe Gly Gln Gly Thr Arg Leu Thr Val
         100               105               110

Val
```

-continued

<210> SEQ ID NO 260
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 260

```
aatgccggcg tcatgcagaa cccaagacac ctggtcagga ggaggggaca ggaggcaaga      60
ctgagatgca gcccaatgaa aggacacagt catgtttact ggtatcggca gctcccagag     120
gaaggtctga aattcatggt ttatctccag aaagaaaata tcatagatga gtcaggaatg     180
ccaaaggaac gattttctgc tgaatttccc aaagagggcc ccagcatcct gaggatccag     240
caggtagtgc gaggagattc ggcagcttat ttctgtgcca gctcacacag ggacgacact     300
gaagctttct ttggacaagg caccagactc acagttgta                            339
```

<210> SEQ ID NO 261
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 261

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Glu Gly Thr Thr
                85                  90                  95

Asp Ser Trp Gly Lys Phe Gln Phe Gly Ala Gly Thr Gln Val Val Val
            100                 105                 110

Thr Pro
```

<210> SEQ ID NO 262
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262

```
aaacaggagg tgacgcagat tcctgcagct ctgagtgtcc cagaaggaga aaacttggtt      60
ctcaactgca gtttcactga tagcgctatt tacaacctcc agtggtttag gcaggaccct     120
gggaaaggtc tcacatctct gttgcttatt cagtcaagtc agagagagca aacaagtgga     180
agacttaatg cctcgctgga taaatcatca ggacgtagta cttttatacat tgcagcttct     240 cagcctggtg actcagccac ctacctctgt gctgtggagg ggacaactga cagctggggg     300
```
aaattccagt ttggagcagg gacccaggtt gtggtcaccc ca          342

<210> SEQ ID NO 263
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 263

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
                20                  25                  30

Tyr Trp Tyr Gln Gln Gly Pro Gly Gln Asp Pro Gln Phe Leu Ile Ser
            35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Gln
                85                  90                  95

Gly Gln Pro Gln His Phe Gly Asp Gly Thr Arg Leu Ser Ile Leu
            100                 105                 110

<210> SEQ ID NO 264
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 264
gctgctggag tcatccagtc cccaagacat ctgatcaaag aaaagaggga aacagccact      60
ctgaaatgct atcctatccc tagacacgac actgtctact ggtaccagca gggtccaggt     120
caggaccccc agttcctcat ttcgttttat gaaaagatgc agagcgataa aggaagcatc     180
cctgatcgat tctcagctca acagttcagt gactatcatt ctgaactgaa catgagctcc     240
ttggagctgg gggactcagc cctgtacttc tgtgccagca gctcccaggg tcagccccag     300
cattttggtg atgggactcg actctccatc cta                                  333

<210> SEQ ID NO 265
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 265

Ala Gln Arg Val Thr Gln Pro Glu Lys Leu Leu Ser Val Phe Lys Gly
1               5                   10                  15

Ala Pro Val Glu Leu Lys Cys Asn Tyr Ser Tyr Ser Gly Ser Pro Glu
                20                  25                  30

Leu Phe Trp Tyr Val Gln Tyr Ser Arg Gln Arg Leu Gln Leu Leu Leu

-continued

```
           35                  40                  45
Arg His Ile Ser Arg Glu Ser Ile Lys Gly Phe Thr Ala Asp Leu Asn
    50                  55                  60

Lys Gly Glu Thr Ser Phe His Leu Lys Lys Pro Phe Ala Gln Glu Glu
65                  70                  75                  80

Asp Ser Ala Met Tyr Tyr Cys Ala Leu Ser Gly Ala Ser Gly Gly Ser
                85                  90                  95

Tyr Ile Pro Thr Phe Gly Arg Gly Thr Ser Leu Ile Val His Pro
            100                 105                 110
```

```
<210> SEQ ID NO 266
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 266
gcccagagag tgactcagcc cgagaagctc ctctctgtct ttaaaggggc cccagtggag      60
ctgaagtgca actattccta ttctgggagt cctgaactct tctggtatgt ccagtactcc     120
agacaacgcc tccagttact cttgagacac atctctagag agagcatcaa aggcttcact     180
gctgacctta caaaggcga  gacatctttc cacctgaaga aaccatttgc tcaagaggaa     240
gactcagcca tgtattactg tgctctaagt ggggcatcag gaggaagcta catacctaca     300
tttggaagag gaaccagcct tattgttcat ccg                                 333
```

```
<210> SEQ ID NO 267
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 267

Asn Ala Gly Val Met Gln Asn Pro Arg His Leu Val Arg Arg Arg Gly
1               5                   10                  15

Gln Glu Ala Arg Leu Arg Cys Ser Pro Met Lys Gly His Ser His Val
                20                  25                  30

Tyr Trp Tyr Arg Gln Leu Pro Glu Glu Gly Leu Lys Phe Met Val Tyr
            35                  40                  45

Leu Gln Lys Glu Asn Ile Ile Asp Glu Ser Gly Met Pro Lys Glu Arg
    50                  55                  60

Phe Ser Ala Glu Phe Pro Lys Glu Gly Pro Ser Ile Leu Arg Ile Gln
65                  70                  75                  80

Gln Val Val Arg Gly Asp Ser Ala Ala Tyr Phe Cys Ala Ser Ser His
                85                  90                  95

Arg Asp Asp Thr Glu Ala Phe Phe Gly Gln Gly Thr Arg Leu Thr Val
            100                 105                 110

Val
```

```
<210> SEQ ID NO 268
<211> LENGTH: 339
<212> TYPE: DNA
<213> ORGANISM: Artificial Sequence
<220> FEATURE:
```

-continued

<221> NAME/KEY: source
<223> OTHER INFORMATION: /note="Description of Artificial Sequence:
     Synthetic polynucleotide"

<400> SEQUENCE: 268

```
aatgccggcg tcatgcagaa cccaagacac ctggtcagga ggaggggaca ggaggcaaga      60
ctgagatgca gcccaatgaa aggacacagt catgtttact ggtatcggca gctcccagag     120
gaaggtctga aattcatggt ttatctccag aaagaaaata tcatagatga gtcaggaatg     180
ccaaaggaac gattttctgc tgaatttccc aaagagggcc ccagcatcct gaggatccag     240
caggtagtgc gaggagattc ggcagcttat ttctgtgcca gctcacacag ggacgacact     300
gaagctttct ttggacaagg caccagactc acagttgta                            339
```

<210> SEQ ID NO 269
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 269

```
Ala Gln Lys Val Thr Gln Ala Gln Thr Glu Ile Ser Val Val Glu Lys
1               5                   10                  15

Glu Asp Val Thr Leu Asp Cys Val Tyr Glu Thr Arg Asp Thr Thr Tyr
                20                  25                  30

Tyr Leu Phe Trp Tyr Lys Gln Pro Pro Ser Gly Glu Leu Val Phe Leu
            35                  40                  45

Ile Arg Arg Asn Ser Phe Asp Glu Gln Asn Glu Ile Ser Gly Arg Tyr
        50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Val
                85                  90                  95

Ser Ser Tyr Asn Thr Asp Lys Leu Ile Phe Gly Thr Gly Thr Arg Leu
                100                 105                 110

Gln Val Phe Pro
        115
```

<210> SEQ ID NO 270
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 270

```
gctcagaagg taactcaagc gcagactgaa atttctgtgg tggagaagga ggatgtgacc      60
ttggactgtg tgtatgaaac ccgtgatact acttattact tattctggta caagcaacca     120
ccaagtggag aattggtttt ccttattcgt cggaactctt ttgatgagca aaatgaaata     180
agtggtcggt attcttggaa cttccagaaa tccaccagtt ccttcaactt caccatcaca     240
gcctcacaag tcgtggactc agcagtatac ttctgtgctc tgagtgtatc atcttataac     300
accgacaagc tcatctttgg gactgggacc agattacaag tctttcca                 348
```

<210> SEQ ID NO 271
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 271

Asn Ala Gly Val Met Gln Asn Pro Arg His Leu Val Arg Arg Arg Gly
1               5                   10                  15

Gln Glu Ala Arg Leu Arg Cys Ser Pro Met Lys Gly His Ser His Val
            20                  25                  30

Tyr Trp Tyr Arg Gln Leu Pro Glu Glu Gly Leu Lys Phe Met Val Tyr
        35                  40                  45

Leu Gln Lys Glu Asn Ile Ile Asp Glu Ser Gly Met Pro Lys Glu Arg
    50                  55                  60

Phe Ser Ala Glu Phe Pro Lys Glu Gly Pro Ser Ile Leu Arg Ile Gln
65                  70                  75                  80

Gln Val Val Arg Gly Asp Ser Ala Ala Tyr Phe Cys Ala Ser Ser His
            85                  90                  95

Arg Asp Asp Thr Glu Ala Phe Phe Gly Gln Gly Thr Arg Leu Thr Val
            100                 105                 110

Val

<210> SEQ ID NO 272
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 272
aatgccggcg tcatgcagaa cccaagacac ctggtcagga ggaggggaca ggaggcaaga      60
ctgagatgca gcccaatgaa aggacacagt catgtttact ggtatcggca gctcccagag     120
gaaggtctga aattcatggt ttatctccag aaagaaaata tcatagatga gtcaggaatg     180
ccaaaggaac gattttctgc tgaatttccc aaagagggcc ccagcatcct gaggatccag     240
caggtagtgc gaggagattc ggcagcttat ttctgtgcca gctcacacag ggatgacact     300
gaagctttct ttggacaagg caccagactc acagttgta                            339

<210> SEQ ID NO 273
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 273

Ala Gln Lys Val Thr Gln Ala Gln Pro Glu Ile Ser Val Val Glu Lys
1               5                   10                  15

Glu Asp Val Thr Leu Asp Cys Val Tyr Glu Thr Arg Asp Thr Thr Tyr
            20                  25                  30

Tyr Leu Phe Trp Tyr Lys Gln Pro Pro Ser Gly Glu Leu Val Phe Leu
        35                  40                  45

-continued

```
Ile Arg Arg Asn Ser Phe Asp Glu Gln Asn Glu Ile Ser Gly Arg Tyr
    50              55              60

Ser Trp Asn Phe Gln Lys Ser Thr Ser Ser Phe Asn Phe Thr Ile Thr
65              70              75              80

Ala Ser Gln Val Val Asp Ser Ala Val Tyr Phe Cys Ala Leu Ser Glu
                85              90              95

Gly Tyr Asn Thr Asp Lys Leu Ile Phe Gly Thr Gly Thr Arg Leu Gln
            100             105             110

Val Phe Pro
        115
```

```
<210> SEQ ID NO 274
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 274
gctcagaagg taactcaagc gcagcctgaa atttctgtgg tggagaagga ggatgtgacc     60
ttggactgtg tgtatgaaac ccgtgatact acttattact tattctggta caagcaacca    120
ccaagtggag aattggtttt ccttattcgt cggaactctt ttgatgagca aaatgaaata    180
agtggtcggt attcttggaa cttccagaaa tccaccagtt ccttcaactt caccatcaca    240
gcctcacaag tcgtggactc agcagtatac ttctgtgctc tgagtgaggg gtataacacc    300
gacaagctca tctttgggac tgggaccaga ttacaagtct ttcca                    345
```

```
<210> SEQ ID NO 275
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 275

Asp Val Lys Val Thr Gln Ser Ser Arg Tyr Leu Val Lys Arg Thr Gly
1               5               10              15

Glu Lys Val Phe Leu Glu Cys Val Gln Asp Met Asp His Glu Asn Met
                20              25              30

Phe Trp Tyr Arg Gln Asp Pro Gly Leu Gly Leu Arg Leu Ile Tyr Phe
            35              40              45

Ser Tyr Asp Val Lys Met Lys Glu Lys Gly Asp Ile Pro Glu Gly Tyr
    50              55              60

Ser Val Ser Arg Glu Lys Lys Glu Arg Phe Ser Leu Ile Leu Glu Ser
65              70              75              80

Ala Ser Thr Asn Gln Thr Ser Met Tyr Leu Cys Ala Ser Ser Leu Gly
                85              90              95

Gly Ala Asn Thr Ile Tyr Phe Gly Glu Gly Ser Trp Leu Thr Val Val
            100             105             110
```

```
<210> SEQ ID NO 276
<211> LENGTH: 336
<212> TYPE: DNA
<213> ORGANISM: Artificial Sequence
<220> FEATURE:
<221> NAME/KEY: source
```

-continued

<223> OTHER INFORMATION: /note="Description of Artificial Sequence:
      Synthetic polynucleotide"

<400> SEQUENCE: 276

```
gatgtgaaag taacccagag ctcgagatat ctagtcaaaa ggacgggaga gaaagttttt      60
ctggaatgtg tccaggatat ggaccatgaa aatatgttct ggtatcgaca agacccaggt     120
ctggggctac ggctgatcta tttctcatat gatgttaaaa tgaaagaaaa aggagatatt     180
cctgaggggt acagtgtctc tagagagaag aaggagcgct tctccctgat tctggagtcc     240
gccagcacca accagacatc tatgtacctc tgtgccagca gtttaggggg ggcgaacacc     300
atatattttg gagagggaag ttggctcact gttgta                                336
```

<210> SEQ ID NO 277
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ile Pro Asn Ser
                85                  90                  95

Gly Tyr Ser Thr Leu Thr Phe Gly Lys Gly Thr Met Leu Leu Val Ser
            100                 105                 110

Pro
```

<210> SEQ ID NO 278
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 278

```
cagaaggagg tggagcagaa ttctggaccc ctcagtgttc cagagggagc cattgcctct      60
ctcaactgca cttacagtga ccgaggttcc cagtccttct tctggtacag acaatattct     120
gggaaaagcc ctgagttgat aatgtccata tactccaatg gtgacaaaga agatggaagg     180
tttacagcac agctcaataa agccagccag tatgtttctc tgctcatcag agactcccag     240
cccagtgatt cagccaccta cctctgtgcc gtgaacattc cgaattcagg atacagcacc     300
ctcacctttg ggaaggggac tatgcttcta gtctctcca                             339
```

<210> SEQ ID NO 279
<211> LENGTH: 112

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 279

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Gly Glu Gly Thr Thr Ala Lys Gly Glu Val Pro Asp Gly Tyr
    50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys Ala Ser Ser Tyr Trp
                85                  90                  95

Glu Gly Thr Glu Ala Phe Phe Gly Gln Gly Thr Arg Leu Thr Val Val
            100                 105                 110

<210> SEQ ID NO 280
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 280
aatgctggtg tcactcagac cccaaaattc cgggtcctga agacaggaca gagcatgaca       60
ctgctgtgtg cccaggatat gaaccatgaa tacatgtact ggtatcgaca gacccaggc      120 atggggctga ggctgattca ttactcagtt ggtgagggta caactgccaa aggagaggtc      180
cctgatggct acaatgtctc cagattaaaa aaacagaatt tcctgctggg gttggagtcg      240
gctgctccct cccaaacatc tgtgtacttc tgtgccagca gttactggga gggcactgaa      300
gctttctttg gacaaggcac cagactcaca gttgta                               336

<210> SEQ ID NO 281
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 281

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Asn Asn Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
```

| 65 | 70 | 75 | 80 |
|---|---|---|---|

Asp Ser Gln Leu Gly Asp Thr Ala Met Tyr Phe Cys Ala Phe Asp Tyr
            85                  90                  95

Gly Gln Asn Phe Val Phe Gly Pro Gly Thr Arg Leu Ser Val Leu Pro
            100                 105                 110

<210> SEQ ID NO 282
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 282
gcccagacag tcactcagtc tcaaccagag atgtctgtgc aggaggcaga gactgtgacc        60
ctgagttgca catatgacac cagtgagaat aattattatt tgttctggta caagcagcct       120
cccagcaggc agatgattct cgttattcgc caagaagctt ataagcaaca gaatgcaacg       180
gagaatcgtt tctctgtgaa cttccagaaa gcagccaaat ccttcagtct caagatctca       240
gactcacagc tggggggacac tgcgatgtat ttctgtgctt tcgactatgg tcagaatttt      300
gtctttggtc ccggaaccag attgtccgtg ctgccc                                 336

<210> SEQ ID NO 283
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 283

Asn Ala Gly Val Thr Gln Thr Pro Lys Phe Arg Ile Leu Lys Ile Gly
1               5                   10                  15

Gln Ser Met Thr Leu Gln Cys Ala Gln Asp Met Asn His Asn Tyr Met
            20                  25                  30

Tyr Trp Tyr Arg Gln Asp Pro Gly Met Gly Leu Lys Leu Ile Tyr Tyr
            35                  40                  45

Ser Val Gly Ala Gly Ile Thr Asp Lys Gly Glu Val Pro Asn Gly Tyr
        50                  55                  60

Asn Val Ser Arg Ser Thr Thr Glu Tyr Phe Pro Leu Arg Leu Glu Leu
65                  70                  75                  80

Ala Ala Pro Ser Gln Thr Ser Val Tyr Phe Cys Ala Ser Ser Tyr Gly
            85                  90                  95

Gly Gly Gln Thr Glu Ala Phe Phe Gly Gln Gly Thr Arg Leu Thr Val
            100                 105                 110

Val

<210> SEQ ID NO 284
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 284

-continued

```
aatgctggtg tcactcagac cccaaaattc cgcatcctga agataggaca gagcatgaca          60
ctgcagtgtg cccaggatat gaaccataac tacatgtact ggtatcgaca agacccaggc         120
atggggctga agctgattta ttattcagtt ggtgctggta tcactgataa aggagaagtc         180
ccgaatggct acaacgtctc cagatcaacc acagagtatt tcccgctcag gctggagttg         240
gctgctccct cccagacatc tgtgtacttc tgtgccagca gttacggggg ggggcagact         300
gaagctttct ttggacaagg caccagactc acagttgta                                339
```

<210> SEQ ID NO 285
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 285

```
Ala Gln Lys Val Thr Gln Ala Gln Pro Glu Ile Ser Val Val Glu Lys
1               5                   10                  15

Glu Asp Val Thr Leu Asp Cys Val Tyr Glu Thr Arg Asp Thr Thr Tyr
            20                  25                  30

Tyr Leu Phe Trp Tyr Lys Gln Pro Pro Ser Gly Glu Leu Val Phe Leu
        35                  40                  45

Ile Arg Arg Asn Ser Phe Asp Glu Gln Asn Glu Ile Ser Gly Arg Tyr
        50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Glu
                85                  90                  95

Gly Tyr Asn Gln Gly Gly Lys Leu Ile Phe Gly Gln Gly Thr Glu Leu
            100                 105                 110

Ser Val Lys Pro
        115
```

<210> SEQ ID NO 286
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 286

```
gctcagaagg taactcaagc gcagcctgaa atttctgtgg tggagaagga ggatgtgacc          60
ttggactgtg tgtatgaaac ccgtgatact acttattact tattctggta caagcaacca         120
ccaagtggag aattggtttt ccttattcgt cggaactctt ttgatgagca aaatgaaata         180
agtggtcggt attcttggaa cttccagaaa tccaccagtt ccttcaactt caccatcaca         240
gcctcacaag tcgtggactc agcagtatac ttctgtgctc tgagtgaggg ttataaccag         300
ggaggaaagc ttatcttcgg acagggaacg gagttatctg tgaaaccc                      348
```

<210> SEQ ID NO 287
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 287

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Gly Ala Asp
                85                  90                  95

Ser Asn Gln Pro Gln His Phe Gly Asp Gly Thr Arg Leu Ser Ile Leu
            100                 105                 110
```

<210> SEQ ID NO 288
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 288

```
gatgtgaaag taacccagag ctcgagatat ctagtcaaaa ggacgggaga gaaagttttt        60
ctggaatgtg tccaggatat ggaccatgaa aatatgttct ggtatcgaca agacccaggt       120
ctggggctac ggctgatcta tttctcatat gatgttaaaa tgaaagaaaa aggagatatt       180
cctgaggggt acagtgtctc tagagagaag aaggagcgct tctccctgat tctggagtcc       240
gccagcacca accagacatc tatgtacctc tgtgccagcg gggcagatag caatcagccc       300
cagcattttg gtgatgggac tcgactctcc atccta                                 336
```

<210> SEQ ID NO 289
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

```
Ser Val Phe Ser Ser
1               5
```

<210> SEQ ID NO 290
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

```
Val Val Thr Gly Gly Glu Val
1               5
```

```
<210> SEQ ID NO 291
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Ala Ala Asn Gly Gly Ser Gln Gly Asn Leu Ile
1               5                   10

<210> SEQ ID NO 292
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Ser Gly His Asp Thr
1               5

<210> SEQ ID NO 293
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Tyr Tyr Glu Glu Glu Glu
1               5

<210> SEQ ID NO 294
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Ala Ser Ser Leu Gln Asp Tyr Gly Tyr Thr
1               5                   10

<210> SEQ ID NO 295
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Thr Ile Ser Gly Thr Asp Tyr
1               5

<210> SEQ ID NO 296
<211> LENGTH: 5
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Gly Leu Thr Ser Asn
1               5

<210> SEQ ID NO 297
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Ile Leu Arg Pro Asp Ser Trp Gly Lys Phe Gln
1               5                   10

<210> SEQ ID NO 298
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Ser Gly His Asp Thr
1               5

<210> SEQ ID NO 299
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Tyr Tyr Glu Glu Glu Glu
1               5

<210> SEQ ID NO 300
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Ala Ser Ser Leu Gln Asp Tyr Gly Tyr Thr
1               5                   10

<210> SEQ ID NO 301
<211> LENGTH: 5
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic peptide"

<400> SEQUENCE: 301

Ser Val Phe Ser Ser
1               5

<210> SEQ ID NO 302
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Val Val Thr Gly Gly Glu Val
1               5

<210> SEQ ID NO 303
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Ala Thr Asn Gly Gly Ser Gln Gly Asn Leu Ile
1               5                   10

<210> SEQ ID NO 304
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Ser Gly His Asp Thr
1               5

<210> SEQ ID NO 305
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Tyr Tyr Glu Glu Glu Glu
1               5

<210> SEQ ID NO 306
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306
```

```
Ala Ser Ser Leu Gln Asp Tyr Gly Tyr Thr
1               5                   10

<210> SEQ ID NO 307
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Thr Ile Ser Gly Thr Asp Tyr
1               5

<210> SEQ ID NO 308
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Gly Leu Thr Ser Asn
1               5

<210> SEQ ID NO 309
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Ile Arg Arg Pro Gly Asn Gln Phe Tyr
1               5

<210> SEQ ID NO 310
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Met Asn His Glu Tyr
1               5

<210> SEQ ID NO 311
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ser Met Asn Val Glu Val
1               5
```

<210> SEQ ID NO 312
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Ala Ser Ser Leu Trp Thr Gly Ser Glu Ala Phe
1               5                   10

<210> SEQ ID NO 313
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Ser Val Phe Ser Ser
1               5

<210> SEQ ID NO 314
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Val Val Thr Gly Gly Glu Val
1               5

<210> SEQ ID NO 315
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Ala Gly Gly Thr Ser Gly Thr Tyr Lys Tyr Ile
1               5                   10

<210> SEQ ID NO 316
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Met Asn His Glu Tyr
1               5

<210> SEQ ID NO 317
<211> LENGTH: 6
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Ser Met Asn Val Glu Val
1               5

<210> SEQ ID NO 318
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Ala Ser Ser Pro Gly Thr Ala Asn Tyr Gly Tyr Thr
1               5                   10

<210> SEQ ID NO 319
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Tyr Ser Gly Ser Pro Glu
1               5

<210> SEQ ID NO 320
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

His Ile Ser Arg
1

<210> SEQ ID NO 321
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Ala Leu Gly Asn Thr Asp Lys Leu Ile
1               5

<210> SEQ ID NO 322
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 322

Met Asp His Glu Asn
1               5

<210> SEQ ID NO 323
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Ser Tyr Asp Val Lys Met
1               5

<210> SEQ ID NO 324
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Ala Ser Ser Ser Pro Arg Thr Gly Trp Tyr Gly Tyr Thr
1               5                   10

<210> SEQ ID NO 325
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Thr Ile Ser Gly Thr Asp Tyr
1               5

<210> SEQ ID NO 326
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Gly Leu Thr Ser Asn
1               5

<210> SEQ ID NO 327
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

-continued

```
Ile Leu Arg Pro Asp Ser Trp Gly Lys Phe Gln
1               5                   10

<210> SEQ ID NO 328
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Ser Gly His Asp Thr
1               5

<210> SEQ ID NO 329
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Tyr Tyr Glu Glu Glu Glu
1               5

<210> SEQ ID NO 330
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Ala Ser Ser Leu Val Asp Tyr Gly Tyr Thr
1               5                   10

<210> SEQ ID NO 331
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Thr Ile Ser Gly Thr Asp Tyr
1               5

<210> SEQ ID NO 332
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Gly Leu Thr Ser Asn
1               5
```

```
<210> SEQ ID NO 333
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Ile Leu Arg Pro Asp Ser Trp Gly Lys Phe Gln
1               5                   10

<210> SEQ ID NO 334
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Met Asp His Glu Tyr
1               5

<210> SEQ ID NO 335
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Ser Met Asn Val Glu Val
1               5

<210> SEQ ID NO 336
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Ala Ser Ser Leu Gly Gly Val Asp Glu Arg Leu Ser
1               5                   10

<210> SEQ ID NO 337
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Ser Val Phe Ser Ser
1               5

<210> SEQ ID NO 338
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 338

Val Val Thr Gly Gly Glu Val
1               5

<210> SEQ ID NO 339
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Ala Gly Asp Gly Gly Ser Gln Gly Asn Leu Ile
1               5                   10

<210> SEQ ID NO 340
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Met Asn His Glu Tyr
1               5

<210> SEQ ID NO 341
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Ser Met Asn Val Glu Val
1               5

<210> SEQ ID NO 342
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Ala Ser Ser Leu Gly Gly Ala Asp Glu Lys Leu Phe
1               5                   10

<210> SEQ ID NO 343
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 343

Thr Ile Ser Gly Thr Asp Tyr
1               5

<210> SEQ ID NO 344
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Gly Leu Thr Ser Asn
1               5

<210> SEQ ID NO 345
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Ile Leu Gly Gln Gly Ala Gln Lys Leu Val
1               5                   10

<210> SEQ ID NO 346
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Met Asn His Glu Tyr
1               5

<210> SEQ ID NO 347
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Ser Met Asn Val Glu Val
1               5

<210> SEQ ID NO 348
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Ala Ser Ser Leu Trp Thr Gly Gly Gly Tyr Thr

-continued

```
1               5                    10

<210> SEQ ID NO 349
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Ser Val Phe Ser Ser
1               5

<210> SEQ ID NO 350
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Val Val Thr Gly Gly Glu Val
1               5

<210> SEQ ID NO 351
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Ala Gly Asp Gly Gly Ser Gln Gly Asn Leu Ile
1               5                    10

<210> SEQ ID NO 352
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Ser Gly His Asp Thr
1               5

<210> SEQ ID NO 353
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Tyr Tyr Glu Glu Glu Glu
1               5

<210> SEQ ID NO 354
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Ala Ser Ser Leu Val Asp Tyr Gly Tyr Thr
1               5                   10

<210> SEQ ID NO 355
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Asp Ser Val Asn Asn
1               5

<210> SEQ ID NO 356
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Ile Pro Ser Gly Thr
1               5

<210> SEQ ID NO 357
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

Val Leu Gly Gly Gly Ser Gln Gly Asn Leu Ile
1               5                   10

<210> SEQ ID NO 358
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Ser Gly His Asp Thr
1               5

<210> SEQ ID NO 359
<211> LENGTH: 6
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 359

Tyr Tyr Glu Glu Glu Glu
1               5

<210> SEQ ID NO 360
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Ala Ser Ser Phe Thr Asp Tyr Gly Tyr Thr
1               5                   10

<210> SEQ ID NO 361
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Thr Ile Ser Gly Thr Asp Tyr
1               5

<210> SEQ ID NO 362
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Gly Leu Thr Ser Asn
1               5

<210> SEQ ID NO 363
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Ile Leu Arg Asp Gly Thr Gly Asn Gln Phe Tyr
1               5                   10

<210> SEQ ID NO 364
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 364

Met Asn His Glu Tyr
1               5

<210> SEQ ID NO 365
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Ser Met Asn Val Glu Val
1               5

<210> SEQ ID NO 366
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Ala Ser Ser Leu Trp Thr Gly Gly Gly Tyr Thr
1               5                   10

<210> SEQ ID NO 367
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Ser Val Phe Ser Ser
1               5

<210> SEQ ID NO 368
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Val Val Thr Gly Gly Glu Val
1               5

<210> SEQ ID NO 369
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Ala Gly Gly Pro Ser Gly Thr Tyr Lys Tyr Ile
1               5                   10
```

-continued

```
<210> SEQ ID NO 370
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Met Asn His Glu Tyr
1               5

<210> SEQ ID NO 371
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Ser Met Asn Val Glu Val
1               5

<210> SEQ ID NO 372
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Ala Ser Ser Pro Gly Thr Pro Asn Tyr Gly Tyr Thr
1               5                   10

<210> SEQ ID NO 373
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Asp Arg Gly Ser Gln Ser
1               5

<210> SEQ ID NO 374
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Ile Tyr Ser Asn Gly Asp
1               5

<210> SEQ ID NO 375
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Ala Gly Asn Tyr Gly Gln Asn Phe Val
1               5

<210> SEQ ID NO 376
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Pro Arg His Asp Thr
1               5

<210> SEQ ID NO 377
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Phe Tyr Glu Lys Met Gln
1               5

<210> SEQ ID NO 378
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Ala Ser Ser Ile Gly Leu Asn Gln Pro Gln His
1               5                   10

<210> SEQ ID NO 379
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Thr Ile Ser Gly Thr Asp Tyr
1               5

<210> SEQ ID NO 380
<211> LENGTH: 5
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 380

Gly Leu Thr Ser Asn
1               5

<210> SEQ ID NO 381
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Ile Leu Arg Asp Gly Ile Gly Asn Gln Phe Tyr
1               5                   10

<210> SEQ ID NO 382
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

Met Asn His Glu Tyr
1               5

<210> SEQ ID NO 383
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Ser Met Asn Val Glu Val
1               5

<210> SEQ ID NO 384
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Ala Ser Ser Leu Trp Thr Gly Gly Gly Tyr Thr
1               5                   10

<210> SEQ ID NO 385
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385

```
Thr Ile Ser Gly Thr Asp Tyr
1               5

<210> SEQ ID NO 386
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386

Gly Leu Thr Ser Asn
1               5

<210> SEQ ID NO 387
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 387

Ile Leu Arg Pro Asp Ser Trp Gly Lys Phe Gln
1               5                   10

<210> SEQ ID NO 388
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Met Asn His Glu Tyr
1               5

<210> SEQ ID NO 389
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 389

Ser Met Asn Val Glu Val
1               5

<210> SEQ ID NO 390
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Ala Ser Ser Leu Trp Thr Gly Gly Gly Tyr Thr
1               5                   10
```

<210> SEQ ID NO 391
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Thr Ile Ser Gly Thr Asp Tyr
1               5

<210> SEQ ID NO 392
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

Gly Leu Thr Ser Asn
1               5

<210> SEQ ID NO 393
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

Ile Leu Arg Asp Gly Thr Gly Asn Gln Phe Tyr
1               5                   10

<210> SEQ ID NO 394
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

Met Asn His Glu Tyr
1               5

<210> SEQ ID NO 395
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

Ser Met Asn Val Glu Val
1               5

<210> SEQ ID NO 396
<211> LENGTH: 11
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

Ala Ser Ser Ser Thr Gly Tyr Tyr Gly Tyr Thr
1               5                   10

<210> SEQ ID NO 397
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

Thr Ile Ser Gly Thr Asp Tyr
1               5

<210> SEQ ID NO 398
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Gly Leu Thr Ser Asn
1               5

<210> SEQ ID NO 399
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

Ile Leu Arg Asp Arg Glu Tyr Gly Asn Lys Leu Val
1               5                   10

<210> SEQ ID NO 400
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Met Asn His Glu Tyr
1               5

<210> SEQ ID NO 401
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 401

Ser Met Asn Val Glu Val
1               5

<210> SEQ ID NO 402
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Ala Ser Ser Leu Trp Thr Gly Gly Gly Tyr Thr
1               5                   10

<210> SEQ ID NO 403
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 403

Ser Val Phe Ser Ser
1               5

<210> SEQ ID NO 404
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 404

Val Val Thr Gly Gly Glu Val
1               5

<210> SEQ ID NO 405
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 405

Ala Glu Asp Gly Gly Ser Gln Gly Asn Leu Ile
1               5                   10

<210> SEQ ID NO 406
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

-continued

```
Ser Gly His Asp Thr
1               5

<210> SEQ ID NO 407
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

Tyr Tyr Glu Glu Glu Glu
1               5

<210> SEQ ID NO 408
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

Ala Ser Ser Leu Ser Asp Tyr Gly Tyr Thr
1               5                   10

<210> SEQ ID NO 409
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

Asp Ser Val Asn Asn
1               5

<210> SEQ ID NO 410
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

Ile Pro Ser Gly Thr
1               5

<210> SEQ ID NO 411
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Ala Val Glu Ala Ser Gly Thr Tyr Lys Tyr Ile
1               5                   10
```

-continued

```
<210> SEQ ID NO 412
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Met Asn His Glu Tyr
1               5

<210> SEQ ID NO 413
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

Ser Met Asn Val Glu Val
1               5

<210> SEQ ID NO 414
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

Ala Ser Ser Trp Gly Thr Gly Gly Tyr Gly Tyr Thr
1               5                   10

<210> SEQ ID NO 415
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 415

Asn Ser Ala Ser Asp Tyr
1               5

<210> SEQ ID NO 416
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 416

Ile Arg Ser Asn Met Asp Lys
1               5

<210> SEQ ID NO 417
<211> LENGTH: 13
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 417

Ala Glu Asn Lys Arg Asp Asn Tyr Gly Gln Asn Phe Val
1               5                   10

<210> SEQ ID NO 418
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 418

Met Asn His Glu Tyr
1               5

<210> SEQ ID NO 419
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 419

Ser Met Asn Val Glu Val
1               5

<210> SEQ ID NO 420
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 420

Ala Ser Ser Phe Trp Val Asn Thr Glu Ala Phe
1               5                   10

<210> SEQ ID NO 421
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 421

Asp Ser Val Asn Asn
1               5

<210> SEQ ID NO 422
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 422

Ile Pro Ser Gly Thr
1               5

<210> SEQ ID NO 423
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Ala Val Gly Ser Ser Asn Gly Tyr Lys Leu Ser
1               5                   10

<210> SEQ ID NO 424
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 424

Met Asn His Glu Tyr
1               5

<210> SEQ ID NO 425
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 425

Ser Met Asn Val Glu Val
1               5

<210> SEQ ID NO 426
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 426

Ala Ser Ser Pro Gly Thr Gly Gly Phe Ser Pro Leu His
1               5                   10

<210> SEQ ID NO 427
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 427

Asp Ser Val Asn Asn

-continued

```
1               5

<210> SEQ ID NO 428
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 428

Ile Pro Ser Gly Thr
1               5

<210> SEQ ID NO 429
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 429

Ala Val Gly Ser Ser Asn Asp Tyr Lys Leu Ser
1               5                   10

<210> SEQ ID NO 430
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 430

Met Asn His Glu Tyr
1               5

<210> SEQ ID NO 431
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 431

Ser Met Asn Val Glu Val
1               5

<210> SEQ ID NO 432
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 432

Ala Ser Ser Pro Gly Thr Gly Gly Phe Ser Pro Leu His
1               5                   10

<210> SEQ ID NO 433
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 433

Asn Ser Ala Ser Asp Tyr
1               5

<210> SEQ ID NO 434
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 434

Ile Arg Ser Asn Met Asp Lys
1               5

<210> SEQ ID NO 435
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 435

Ala Glu Asn Arg Gln Asp Asn Tyr Gly Gln Asn Phe Val
1               5                   10

<210> SEQ ID NO 436
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 436

Met Asn His Glu Tyr
1               5

<210> SEQ ID NO 437
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 437

Ser Met Asn Val Glu Val
1               5

<210> SEQ ID NO 438
<211> LENGTH: 11
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 438

Ala Ser Ser Leu Trp Val Asn Thr Glu Ala Phe
1               5                   10

<210> SEQ ID NO 439
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 439

Thr Ile Ser Gly Thr Asp Tyr
1               5

<210> SEQ ID NO 440
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 440

Gly Leu Thr Ser Asn
1               5

<210> SEQ ID NO 441
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 441

Ile Leu Arg Pro Asp Ser Trp Gly Lys Phe Gln
1               5                   10

<210> SEQ ID NO 442
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 442

Met Asp His Glu Asn
1               5

<210> SEQ ID NO 443
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 443

Ser Tyr Asp Val Lys Met
1               5

<210> SEQ ID NO 444
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 444

Ala Ser Ser Thr Val Arg Gln Gly Asn Tyr Gly Tyr Thr
1               5                   10

<210> SEQ ID NO 445
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 445

Thr Ile Ser Gly Thr Asp Tyr
1               5

<210> SEQ ID NO 446
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 446

Gly Leu Thr Ser Asn
1               5

<210> SEQ ID NO 447
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 447

Ile Leu Asn Thr Gly Thr Ala Ser Lys Leu Thr
1               5                   10

<210> SEQ ID NO 448
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 448

Met Asn His Glu Tyr
1               5
```

```
<210> SEQ ID NO 449
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 449

Ser Met Asn Val Glu Val
1               5

<210> SEQ ID NO 450
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 450

Ala Ser Ser Leu Ser Ser Asn Thr Glu Ala Phe
1               5                   10

<210> SEQ ID NO 451
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 451

Asp Arg Gly Ser Gln Ser
1               5

<210> SEQ ID NO 452
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 452

Ile Tyr Ser Asn Gly Asp
1               5

<210> SEQ ID NO 453
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 453

Ala Val Asn Arg Gly Thr Asp Lys Leu Ile
1               5                   10

<210> SEQ ID NO 454
<211> LENGTH: 5
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 454

Ser Gly His Asp Thr
1               5

<210> SEQ ID NO 455
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 455

Tyr Tyr Glu Glu Glu Glu
1               5

<210> SEQ ID NO 456
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 456

Ala Ser Ser Trp Thr Asp Tyr Gly Tyr Thr
1               5                   10

<210> SEQ ID NO 457
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 457

Thr Ile Ser Gly Thr Asp Tyr
1               5

<210> SEQ ID NO 458
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 458

Gly Leu Thr Ser Asn
1               5

<210> SEQ ID NO 459
<211> LENGTH: 11
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 459

Ile Leu Arg Pro Asp Ser Trp Gly Lys Phe Gln
1               5                   10

<210> SEQ ID NO 460
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 460

Ser Gly His Asp Thr
1               5

<210> SEQ ID NO 461
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 461

Tyr Tyr Glu Glu Glu Glu
1               5

<210> SEQ ID NO 462
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 462

Ala Ser Ser Trp Thr Asp Tyr Gly Tyr Thr
1               5                   10

<210> SEQ ID NO 463
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 463

Ser Val Phe Ser Ser
1               5

<210> SEQ ID NO 464
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 464
```

```
Val Val Thr Gly Gly Glu Val
1               5

<210> SEQ ID NO 465
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 465

Ala Gly Gly Thr Ser Gly Thr Tyr Lys Tyr Ile
1               5                   10

<210> SEQ ID NO 466
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 466

Met Asn His Glu Tyr
1               5

<210> SEQ ID NO 467
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 467

Ser Met Asn Val Glu Val
1               5

<210> SEQ ID NO 468
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 468

Ala Ser Ser Pro Gly Thr Pro Asn Tyr Gly Tyr Thr
1               5                   10

<210> SEQ ID NO 469
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 469

Asn Ser Ala Ser Gln Ser
1               5
```

-continued

<210> SEQ ID NO 470
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 470

Val Tyr Ser Ser Gly Asn
1               5

<210> SEQ ID NO 471
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 471

Val Val Asn Gly Gly Ser Gln Gly Asn Leu Ile
1               5                   10

<210> SEQ ID NO 472
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472

Ser Gly His Asp Thr
1               5

<210> SEQ ID NO 473
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 473

Tyr Tyr Glu Glu Glu Glu
1               5

<210> SEQ ID NO 474
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 474

Ala Ser Ser Val Gly Asp Tyr Gly Tyr Thr
1               5                   10

<210> SEQ ID NO 475
<211> LENGTH: 6
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 475

Asn Ser Ala Ser Asp Tyr
1               5

<210> SEQ ID NO 476
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 476

Ile Arg Ser Asn Met Asp Lys
1               5

<210> SEQ ID NO 477
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 477

Ala Glu Asn Asn Tyr Gly Gln Asn Phe Val
1               5                   10

<210> SEQ ID NO 478
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 478

Met Asn His Glu Tyr
1               5

<210> SEQ ID NO 479
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 479

Ser Met Asn Val Glu Val
1               5

<210> SEQ ID NO 480
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic peptide"

<400> SEQUENCE: 480

Ala Ser Ser Leu Trp Asp Ser Ser Pro Leu His
1               5                   10

<210> SEQ ID NO 481
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 481

Asn Ser Met Phe Asp Tyr
1               5

<210> SEQ ID NO 482
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 482

Ile Ser Ser Ile Lys Asp Lys
1               5

<210> SEQ ID NO 483
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 483

Ala Ala Ser Ala Gly Ser Ala Arg Gln Leu Thr
1               5                   10

<210> SEQ ID NO 484
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 484

Met Asn His Glu Tyr
1               5

<210> SEQ ID NO 485
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 485
```

-continued

```
Ser Met Asn Val Glu Val
1               5

<210> SEQ ID NO 486
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 486

Ala Ser Ser Leu Tyr Thr His Thr Glu Ala Phe
1               5                   10

<210> SEQ ID NO 487
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 487

Thr Ile Ser Gly Asn Glu Tyr
1               5

<210> SEQ ID NO 488
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 488

Gly Leu Lys Asn Asn
1               5

<210> SEQ ID NO 489
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 489

Ile Val Arg Asp Thr Thr Ser Gly Thr Tyr Lys Tyr Ile
1               5                   10

<210> SEQ ID NO 490
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 490

Met Asn His Glu Tyr
1               5
```

-continued

```
<210> SEQ ID NO 491
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 491

Ser Met Asn Val Glu Val
1               5

<210> SEQ ID NO 492
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 492

Ala Ser Ser Leu Ser Ser Thr Gly Phe Ser Pro Leu His
1               5                   10

<210> SEQ ID NO 493
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 493

Ser Val Phe Ser Ser
1               5

<210> SEQ ID NO 494
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 494

Val Val Thr Gly Gly Glu Val
1               5

<210> SEQ ID NO 495
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 495

Ala Glu Gly Gly Gly Ser Gln Gly Asn Leu Ile
1               5                   10

<210> SEQ ID NO 496
<211> LENGTH: 5
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 496

Ser Gly His Asp Thr
1               5

<210> SEQ ID NO 497
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 497

Tyr Tyr Glu Glu Glu Glu
1               5

<210> SEQ ID NO 498
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 498

Ala Ser Ser Trp Thr Asp Tyr Gly Tyr Thr
1               5                   10

<210> SEQ ID NO 499
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 499

Ser Val Phe Ser Ser
1               5

<210> SEQ ID NO 500
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 500

Val Val Thr Gly Gly Glu Val
1               5

<210> SEQ ID NO 501
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 501

Ala Gly Ile Arg Ser Asn Asp Tyr Lys Leu Ser
1               5                   10

<210> SEQ ID NO 502
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 502

Met Asn His Glu Tyr
1               5

<210> SEQ ID NO 503
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 503

Ser Met Asn Val Glu Val
1               5

<210> SEQ ID NO 504
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 504

Ala Ser Ser Ser Trp Thr Ala His Thr Glu Ala Phe
1               5                   10

<210> SEQ ID NO 505
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 505

Ser Val Phe Ser Ser
1               5

<210> SEQ ID NO 506
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 506

Val Val Thr Gly Gly Glu Val
```

-continued

```
1               5

<210> SEQ ID NO 507
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 507

Ala Glu Asn Ser Gly Gly Gly Ala Asp Gly Leu Thr
1               5                   10

<210> SEQ ID NO 508
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 508

Ser Gly His Asp Thr
1               5

<210> SEQ ID NO 509
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 509

Tyr Tyr Glu Glu Glu Glu
1               5

<210> SEQ ID NO 510
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 510

Ala Ser Ser Phe Thr Asp Tyr Gly Tyr Thr
1               5                   10

<210> SEQ ID NO 511
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 511

Ser Val Phe Ser Ser
1               5

<210> SEQ ID NO 512
```

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 512

Val Val Thr Gly Gly Glu Val
1               5

<210> SEQ ID NO 513
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 513

Ala Gly Glu Asp Phe Gly Asn Glu Lys Leu Thr
1               5                   10

<210> SEQ ID NO 514
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 514

Ser Gly His Asp Thr
1               5

<210> SEQ ID NO 515
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 515

Tyr Tyr Glu Glu Glu Glu
1               5

<210> SEQ ID NO 516
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 516

Ala Ser Ser Trp Ala Asp Tyr Gly Tyr Thr
1               5                   10

<210> SEQ ID NO 517
<211> LENGTH: 6
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 517

Ser Ser Asn Phe Tyr Ala
1               5

<210> SEQ ID NO 518
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 518

Met Thr Leu Asn Gly Asp Glu
1               5

<210> SEQ ID NO 519
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 519

Ala Phe Leu Thr Gly Asn Gln Phe Tyr
1               5

<210> SEQ ID NO 520
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 520

Met Asp His Glu Asn
1               5

<210> SEQ ID NO 521
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 521

Ser Tyr Asp Val Lys Met
1               5

<210> SEQ ID NO 522
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 522

Ala Ser Ser Thr Val Arg Gln Gly Asn Tyr Gly Tyr Thr
1               5                   10

<210> SEQ ID NO 523
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 523

Asn Ser Met Phe Asp Tyr
1               5

<210> SEQ ID NO 524
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 524

Ile Ser Ser Ile Lys Asp Lys
1               5

<210> SEQ ID NO 525
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 525

Ala Ala Ser Ala Gly Ser Ala Arg Gln Leu Thr
1               5                   10

<210> SEQ ID NO 526
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 526

Met Asn His Glu Tyr
1               5

<210> SEQ ID NO 527
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 527

Ser Met Asn Val Glu Val
1               5

<210> SEQ ID NO 528
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 528

Ala Ser Ser Leu Trp Ser Asn Thr Glu Ala Phe
1               5                   10

<210> SEQ ID NO 529
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
agtgtttttt ccagc                                                    15

<210> SEQ ID NO 530
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
gtagttacgg gtggagaagt g                                             21

<210> SEQ ID NO 531
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
gccgctaatg gaggaagcca aggaaatctc atc                                33

<210> SEQ ID NO 532
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
tctgggcatg acact                                                    15

<210> SEQ ID NO 533
<211> LENGTH: 18
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 533
tattatgagg aggaagag                                                     18

<210> SEQ ID NO 534
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
gccagcagct tacaggacta tggctacacc                                        30

<210> SEQ ID NO 535
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
acaatcagtg gaactgatta c                                                 21

<210> SEQ ID NO 536
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
ggtcttacaa gcaat                                                        15

<210> SEQ ID NO 537
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
atcctgcggc ctgacagctg ggggaaattc cag                                    33

<210> SEQ ID NO 538
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
tctgggcatg acact                                                        15

<210> SEQ ID NO 539
```

-continued

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
tattatgagg aggaagag                                                    18

<210> SEQ ID NO 540
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
gccagcagct tacaggacta tggctacacc                                       30

<210> SEQ ID NO 541
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
agtgtttttt ccagc                                                       15

<210> SEQ ID NO 542
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
gtagttacgg gtggagaagt g                                                21

<210> SEQ ID NO 543
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
gccactaatg gaggaagcca aggaaatctc atc                                   33

<210> SEQ ID NO 544
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
```
tctgggcatg acact                                                    15

<210> SEQ ID NO 545
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
tattatgagg aggaagag                                                 18

<210> SEQ ID NO 546
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
gccagcagct tacaggacta tggctacacc                                    30

<210> SEQ ID NO 547
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
acaatcagtg gaactgatta c                                             21

<210> SEQ ID NO 548
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
ggtcttacaa gcaat                                                    15

<210> SEQ ID NO 549
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
atcaggcggc ccggtaacca gttctat                                       27

<210> SEQ ID NO 550
<211> LENGTH: 15
<212> TYPE: DNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 550
atgaaccatg agtat                                                        15

<210> SEQ ID NO 551
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
tcaatgaatg ttgaggtg                                                     18

<210> SEQ ID NO 552
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
gccagcagtt tatggacagg gtctgaagct ttc                                    33

<210> SEQ ID NO 553
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
agtgtttttt ccagc                                                        15

<210> SEQ ID NO 554
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
gtagttactg gtggagaagt g                                                 21

<210> SEQ ID NO 555
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
gcaggaggga cctcaggaac ctacaaatac atc                                    33
```

-continued

```
<210> SEQ ID NO 556
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
atgaaccatg agtat                                                        15

<210> SEQ ID NO 557
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
tcaatgaatg ttgaggtg                                                     18

<210> SEQ ID NO 558
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
gccagcagtc cagggacagc taactatggc tacacc                                 36

<210> SEQ ID NO 559
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
tattctggga gtcctgaa                                                     18

<210> SEQ ID NO 560
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
cacatctcta ga                                                           12

<210> SEQ ID NO 561
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 561
gctctaggga acaccgacaa gctcatc                                       27

<210> SEQ ID NO 562
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
atggaccatg aaaat                                                    15

<210> SEQ ID NO 563
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
tcatatgatg ttaaaatg                                                 18

<210> SEQ ID NO 564
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
gccagcagtt cgcccaggac agggtggtat ggctacacc                          39

<210> SEQ ID NO 565
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
acaatcagtg gaactgatta c                                             21

<210> SEQ ID NO 566
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
ggtcttacaa gcaat                                                    15

<210> SEQ ID NO 567
<211> LENGTH: 33
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 567
atcctgcggc ctgacagctg ggggaaattc cag                                33

<210> SEQ ID NO 568
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
tctgggcatg acact                                                    15

<210> SEQ ID NO 569
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
tattatgagg aggaagag                                                 18

<210> SEQ ID NO 570
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
gccagcagct tggtggatta tggctacacc                                    30

<210> SEQ ID NO 571
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
acaatcagtg gaactgatta c                                             21

<210> SEQ ID NO 572
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
ggtcttacaa gcaat                                                    15
```

-continued

```
<210> SEQ ID NO 573
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
atcctgcggc ctgacagctg ggggaaattc cag                              33

<210> SEQ ID NO 574
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
atggaccatg agtat                                                  15

<210> SEQ ID NO 575
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
tcaatgaatg ttgaggtg                                               18

<210> SEQ ID NO 576
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
gccagcagtt taggggcgt ggatgaaaga ctgtct                           36

<210> SEQ ID NO 577
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
agtgtttttt ccagc                                                  15

<210> SEQ ID NO 578
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 578
gtagttacgg gtggagaagt g                                               21

<210> SEQ ID NO 579
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
gcaggggatg gaggaagcca aggaaatctc atc                                  33

<210> SEQ ID NO 580
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
atgaaccatg agtat                                                      15

<210> SEQ ID NO 581
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
tcaatgaatg ttgaggtg                                                   18

<210> SEQ ID NO 582
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
gccagcagtt taggggcgc ggatgaaaaa ctgttt                                36

<210> SEQ ID NO 583
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
acaatcagtg gaactgatta c                                               21

<210> SEQ ID NO 584
<211> LENGTH: 15
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
ggtcttacaa gcaat                                                           15

<210> SEQ ID NO 585
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
atcctgggtc agggagccca gaagctggta                                           30

<210> SEQ ID NO 586
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
atgaaccatg agtat                                                           15

<210> SEQ ID NO 587
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
tcaatgaatg ttgaggtg                                                        18

<210> SEQ ID NO 588
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
gccagcagtt tatggacagg gggcggctac acc                                       33

<210> SEQ ID NO 589
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
agtgtttttt ccagc                                                           15
```

<210> SEQ ID NO 590
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
gtagttacgg gtggagaagt g                                               21

<210> SEQ ID NO 591
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
gcaggggatg gaggaagcca aggaaatctc atc                                  33

<210> SEQ ID NO 592
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
tctgggcatg acact                                                      15

<210> SEQ ID NO 593
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
tattatgagg aggaagag                                                   18

<210> SEQ ID NO 594
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
gccagcagct tggtggatta tggctacacc                                      30

<210> SEQ ID NO 595
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 595
gactctgtga acaat                                                        15

<210> SEQ ID NO 596
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
attccctcag ggaca                                                        15

<210> SEQ ID NO 597
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
gtcctagggg gaggaagcca aggaaatctc atc                                    33

<210> SEQ ID NO 598
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
tctgggcatg acact                                                        15

<210> SEQ ID NO 599
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
tattatgagg aggaagag                                                     18

<210> SEQ ID NO 600
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
gccagcagct ttacagacta tggctacacc                                        30

<210> SEQ ID NO 601
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
acaatcagtg gaactgatta c                                                  21

<210> SEQ ID NO 602
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
ggtcttacaa gcaat                                                         15

<210> SEQ ID NO 603
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
atcctgagag acgggaccgg taaccagttc tat                                     33

<210> SEQ ID NO 604
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
atgaaccatg agtat                                                         15

<210> SEQ ID NO 605
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
tcaatgaatg ttgaggtg                                                      18

<210> SEQ ID NO 606
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
```
gccagcagtt tatggacagg gggtggctac acc                                 33

<210> SEQ ID NO 607
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607 agtgttttt ccagc                                                     15

<210> SEQ ID NO 608
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
gtagttacgg gtggagaagt g                                             21

<210> SEQ ID NO 609
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
gcaggaggac cctcaggaac ctacaaatac atc                                33

<210> SEQ ID NO 610
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
atgaaccatg agtat                                                    15

<210> SEQ ID NO 611
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
tcaatgaatg ttgaggtg                                                 18

<210> SEQ ID NO 612
<211> LENGTH: 36
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 612
gccagcagtc ccgggacacc taactatggc tacacc                              36

<210> SEQ ID NO 613
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
gaccgaggtt cccagtcc                                                  18

<210> SEQ ID NO 614
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
atatactcca atggtgac                                                  18

<210> SEQ ID NO 615
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
gccgggaact atggtcagaa ttttgtc                                        27

<210> SEQ ID NO 616
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
cctagacacg acact                                                    15

<210> SEQ ID NO 617
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
ttttatgaaa agatgcag                                                  18

<210> SEQ ID NO 618
```

<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
gccagcagca tcggacttaa tcagccccag cat                                    33

<210> SEQ ID NO 619
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
acaatcagtg gaactgatta                                                   20

<210> SEQ ID NO 620
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
ggtcttacaa gcaat                                                        15

<210> SEQ ID NO 621
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
atcctgagag acggcatcgg taaccagttc tat                                    33

<210> SEQ ID NO 622
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
atgaaccatg agtat                                                        15

<210> SEQ ID NO 623
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623

-continued

```
tcaatgaatg ttgaggtg                                                   18

<210> SEQ ID NO 624
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
gccagcagtt tatggacagg gggaggctac acc                                  33

<210> SEQ ID NO 625
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
acaatcagtg gaactgatta c                                               21

<210> SEQ ID NO 626
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
ggtcttacaa gcaat                                                      15

<210> SEQ ID NO 627
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
atcctgcggc ctgacagctg ggggaaattc cag                                  33

<210> SEQ ID NO 628
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
atgaaccatg agtat                                                      15

<210> SEQ ID NO 629
<211> LENGTH: 18
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 629
tcaatgaatg ttgaggtg                                              18

<210> SEQ ID NO 630
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
gccagcagtt tatggacagg gggaggctac acc                            33

<210> SEQ ID NO 631
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
acaatcagtg gaactgatta c                                         21

<210> SEQ ID NO 632
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
ggtcttacaa gcaat                                                15

<210> SEQ ID NO 633
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
atcctgagag acggcaccgg taaccagttc tat                            33

<210> SEQ ID NO 634
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
atgaaccatg agtat                                                15

-continued

<210> SEQ ID NO 635
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
tcaatgaatg ttgaggtg                                                  18

<210> SEQ ID NO 636
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
gccagcagtt cgacagggta ctatggctac acc                                 33

<210> SEQ ID NO 637
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
acaatcagtg gaactgatta c                                              21

<210> SEQ ID NO 638
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
ggtcttacaa gcaat                                                     15

<210> SEQ ID NO 639
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
atcctgagag accgggaata tggaaacaaa ctggtc                              36

<210> SEQ ID NO 640
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

```
<400> SEQUENCE: 640
atgaaccatg agtat                                                    15

<210> SEQ ID NO 641
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
tcaatgaatg ttgaggtg                                                 18

<210> SEQ ID NO 642
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
gccagcagtt tatggacagg gggcggctac acc                                33

<210> SEQ ID NO 643
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
agtgtttttt ccagc                                                    15

<210> SEQ ID NO 644
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
gtagttacgg gtggagaagt g                                             21

<210> SEQ ID NO 645
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
gcagaagatg gaggaagcca aggaaatctc atc                                33

<210> SEQ ID NO 646
<211> LENGTH: 15
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 646
tctgggcatg acact                                                          15

<210> SEQ ID NO 647
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
tattatgagg aggaagag                                                       18

<210> SEQ ID NO 648
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
gccagcagct tatcagacta tggctacacc                                          30

<210> SEQ ID NO 649
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
gactctgtga acaat                                                          15

<210> SEQ ID NO 650
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
attccctcag ggaca                                                          15

<210> SEQ ID NO 651
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
gctgtggagg cctcaggaac ctacaaatac atc                                      33

```
<210> SEQ ID NO 652
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
atgaaccatg agtat                                                   15

<210> SEQ ID NO 653
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
tcaatgaatg ttgaggtg                                                18

<210> SEQ ID NO 654
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
gccagcagtt gggggacagg gggctatggc tacacc                            36

<210> SEQ ID NO 655
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
aacagcgcct cagactac                                                18

<210> SEQ ID NO 656
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
attcgttcaa atatggacaa a                                            21

<210> SEQ ID NO 657
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 657
gcagagaata agcgggataa ctatggtcag aattttgtc                                39

<210> SEQ ID NO 658
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
atgaaccatg agtat                                                          15

<210> SEQ ID NO 659
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
tcaatgaatg ttgaggtg                                                       18

<210> SEQ ID NO 660
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
gccagcagtt tctgggtgaa cactgaagct ttc                                      33

<210> SEQ ID NO 661
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
gactctgtga acaat                                                          15

<210> SEQ ID NO 662
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
attccctcag ggaca                                                          15

<210> SEQ ID NO 663
<211> LENGTH: 33
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
gctgtgggga gttctaacgg ctacaagctc agc                                33

<210> SEQ ID NO 664
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
atgaaccatg agtat                                                    15

<210> SEQ ID NO 665
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
tcaatgaatg ttgaggtg                                                 18

<210> SEQ ID NO 666
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
gccagcagtc ccgggacagg gggatttttca cccctccac                         39

<210> SEQ ID NO 667
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
gactctgtga acaat                                                    15

<210> SEQ ID NO 668
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
attccctcag ggaca                                                    15

-continued

```
<210> SEQ ID NO 669
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
gctgtgggga gttctaacga ctacaagctc agc                                    33

<210> SEQ ID NO 670
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
atgaaccatg agtat                                                        15

<210> SEQ ID NO 671
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
tcaatgaatg ttgaggtg                                                     18

<210> SEQ ID NO 672
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
gccagcagtc ccgggacagg gggattttca cccctccac                              39

<210> SEQ ID NO 673
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
aacagcgcct cagactac                                                     18

<210> SEQ ID NO 674
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 674
attcgttcaa atatggacaa a                                                    21

<210> SEQ ID NO 675
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
gcagagaata ggcaggataa ctatggtcag aattttgtc                                 39

<210> SEQ ID NO 676
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
atgaaccatg agtat                                                           15

<210> SEQ ID NO 677
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
tcaatgaatg ttgaggtg                                                        18

<210> SEQ ID NO 678
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
gccagcagtt tatgggttaa cactgaagct ttc                                       33

<210> SEQ ID NO 679
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
acaatcagtg gaactgatta c                                                    21

<210> SEQ ID NO 680
<211> LENGTH: 15

-continued

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
ggtcttacaa gcaat                                                          15

<210> SEQ ID NO 681
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
atcctgcggc ctgacagctg ggggaagttc cag                                      33

<210> SEQ ID NO 682
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
atggaccatg aaaat                                                          15

<210> SEQ ID NO 683
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
tcatatgatg ttaaaatg                                                       18

<210> SEQ ID NO 684
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
gccagcagta ccgtgaggca ggggaactat ggctacacc                                39

<210> SEQ ID NO 685
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685

-continued

```
acaatcagtg gaactgatta c                                          21

<210> SEQ ID NO 686
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
ggtcttacaa gcaat                                                 15

<210> SEQ ID NO 687
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
atcctgaata ccggcactgc cagtaaactc acc                             33

<210> SEQ ID NO 688
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
atgaaccatg agtat                                                 15

<210> SEQ ID NO 689
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
tcaatgaatg ttgaggtg                                              18

<210> SEQ ID NO 690
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
gccagcagtt tatcgtcgaa cactgaagct ttc                             33

<210> SEQ ID NO 691
<211> LENGTH: 18
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 691
gaccgaggtt cccagtcc                                                  18

<210> SEQ ID NO 692
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
atatactcca atggtgac                                                  18

<210> SEQ ID NO 693
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
gccgtgaaca gaggcaccga caagctcatc                                     30

<210> SEQ ID NO 694
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
tctgggcatg acact                                                     15

<210> SEQ ID NO 695
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
tattatgagg aggaagag                                                  18

<210> SEQ ID NO 696
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
gccagcagct ggacagacta tggctacacc                                     30

<210> SEQ ID NO 697
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
acaatcagtg gaactgatta c                                                  21

<210> SEQ ID NO 698
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
ggtcttacaa gcaat                                                         15

<210> SEQ ID NO 699
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
atcctgcggc ctgacagctg ggggaaattc cag                                     33

<210> SEQ ID NO 700
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
tctgggcatg acact                                                         15

<210> SEQ ID NO 701
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
tattatgagg aggaagag                                                      18

<210> SEQ ID NO 702
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
```

-continued

```
gccagcagct ggacagacta tggctacacc                                     30

<210> SEQ ID NO 703
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
agtgtttttt ccagc                                                     15

<210> SEQ ID NO 704
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
gtagttacgg gtggagaagt g                                              21

<210> SEQ ID NO 705
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
gcaggaggaa cctcaggaac ctacaaatac atc                                 33

<210> SEQ ID NO 706
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
atgaaccatg agtat                                                     15

<210> SEQ ID NO 707
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
tcaatgaatg ttgaggtg                                                  18

<210> SEQ ID NO 708
<211> LENGTH: 36
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic oligonucleotide"

<400> SEQUENCE: 708
gccagcagtc ccgggacacc caactatggc tacacc                               36

<210> SEQ ID NO 709
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
aacagtgctt ctcagtct                                                   18

<210> SEQ ID NO 710
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
gtatactcca gtggtaat                                                   18

<210> SEQ ID NO 711
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
gtggtgaatg gaggaagcca aggaaatctc atc                                  33

<210> SEQ ID NO 712
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
tctgggcatg acact                                                      15

<210> SEQ ID NO 713
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
tattatgagg aggaagag                                                   18
```

```
<210> SEQ ID NO 714
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
gccagcagcg taggg'gacta tggctacacc                                30

<210> SEQ ID NO 715
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715
aacagcgcct cagactac                                              18

<210> SEQ ID NO 716
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
attcgttcaa atatggacaa a                                          21

<210> SEQ ID NO 717
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
gcagagaaca actatggtca gaattttgtc                                 30

<210> SEQ ID NO 718
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
atgaaccatg agtat                                                 15

<210> SEQ ID NO 719
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 719
tcaatgaatg ttgaggtg                                              18

<210> SEQ ID NO 720
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
gccagcagtt tatgggacag ttcacccctc cac                            33

<210> SEQ ID NO 721
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
aacagcatgt ttgattat                                             18

<210> SEQ ID NO 722
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
ataagttcca ttaaggataa a                                         21

<210> SEQ ID NO 723
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
gcagcaagcg ccggttctgc aaggcaactg acc                            33

<210> SEQ ID NO 724
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
atgaaccatg agtat                                                15

<210> SEQ ID NO 725
<211> LENGTH: 18
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 725
tcaatgaatg ttgaggtg                                                  18

<210> SEQ ID NO 726
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
gccagcagtt tatacaccca cactgaagct ttc                                 33

<210> SEQ ID NO 727
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
accatcagtg gaaatgagta t                                              21

<210> SEQ ID NO 728
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
ggtctaaaaa acaat                                                     15

<210> SEQ ID NO 729
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
atcgtcagag acactacctc aggaacctac aaatacatc                           39

<210> SEQ ID NO 730
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
atgaaccatg agtat                                                     15
```

-continued

```
<210> SEQ ID NO 731
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
tcaatgaatg ttgaggtg                                                18

<210> SEQ ID NO 732
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
gccagcagtt tatcctcgac aggttttca cccctccac                          39

<210> SEQ ID NO 733
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733 agtgttttt ccagc                                                    15

<210> SEQ ID NO 734
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
gtagttacgg gtggagaagt g                                            21

<210> SEQ ID NO 735
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735 gcagagggg gaggaagcca aggaaatctc atc                                33

<210> SEQ ID NO 736
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 736
tctgggcatg acact                                                              15

<210> SEQ ID NO 737
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
tattatgagg aggaagag                                                           18

<210> SEQ ID NO 738
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
gccagcagct ggacagacta tggctacacc                                              30

<210> SEQ ID NO 739
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
agtgtttttt ccagc                                                              15

<210> SEQ ID NO 740
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
gtagttacgg gtggagaagt g                                                       21

<210> SEQ ID NO 741
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
gcagggatac gttctaacga ctacaagctc agc                                          33

<210> SEQ ID NO 742
<211> LENGTH: 15
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
atgaaccatg agtat                                                    15

<210> SEQ ID NO 743
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
tcaatgaatg ttgaggtg                                                 18

<210> SEQ ID NO 744
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
gccagcagtt cctggacagc ccacactgaa gctttc                             36

<210> SEQ ID NO 745
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
agtgtttttt ccagc                                                    15

<210> SEQ ID NO 746
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
gtagttacgg gtggagaagt g                                             21

<210> SEQ ID NO 747
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
gcagaaaatt caggaggagg tgctgacgga ctcacc                             36

-continued

```
<210> SEQ ID NO 748
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
tctgggcatg acact                                                      15

<210> SEQ ID NO 749
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
tattatgagg aggaagag                                                   18

<210> SEQ ID NO 750
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
gccagcagct tcacagacta tggctacacc                                      30

<210> SEQ ID NO 751
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
agtgtttttt ccagc                                                      15

<210> SEQ ID NO 752
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752
gtagttacgg gtggagaagt g                                               21

<210> SEQ ID NO 753
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 753
gcaggagagg actttggaaa tgagaaatta acc                                    33

<210> SEQ ID NO 754
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 754
tctgggcatg acact                                                        15

<210> SEQ ID NO 755
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 755
tattatgagg aggaagag                                                     18

<210> SEQ ID NO 756
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 756
gccagcagct gggcggatta tggctacacc                                        30

<210> SEQ ID NO 757
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 757
tccagcaatt tttatgcc                                                     18

<210> SEQ ID NO 758
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 758
atgactttaa atggggatga a                                                 21

<210> SEQ ID NO 759
<211> LENGTH: 27

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
gcctttctca ccggtaacca gttctat                                          27

<210> SEQ ID NO 760
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
atggaccatg aaaat                                                       15

<210> SEQ ID NO 761
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
tcatatgatg ttaaaatg                                                    18

<210> SEQ ID NO 762
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
gccagcagta ccgtgaggca ggggaactat ggctacacc                            39

<210> SEQ ID NO 763
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
aacagcatgt ttgattat                                                    18

<210> SEQ ID NO 764
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
```

```
ataagttcca ttaaggataa a                                            21

<210> SEQ ID NO 765
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
gcagcaagcg ccggttctgc aaggcaactg acc                               33

<210> SEQ ID NO 766
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
atgaaccatg agtat                                                   15

<210> SEQ ID NO 767
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
tcaatgaatg ttgaggtg                                                18

<210> SEQ ID NO 768
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
gccagcagtt tatggtcgaa cactgaagct ttc                               33

<210> SEQ ID NO 769
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 769

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
                20                  25                  30

Gln Trp Tyr Arg Gln Glu Pro Gly Glu Gly Pro Val Leu Leu Val Thr
        35                  40                  45
```

-continued

```
Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Ala Asn Gly Gly Ser Gln
                85                  90                  95

Gly Asn Leu Ile Phe Gly Lys Gly Thr Lys Leu Ser Val Lys Pro
            100                 105                 110
```

<210> SEQ ID NO 770
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 770

```
acccagctgc tggagcagag ccctcagttt ctaagcatcc aagagggaga aaatctcact     60
gtgtactgca actcctcaag tgttttttcc agcttacaat ggtacagaca ggagcctggg    120
gaaggtcctg tcctcctggt gacagtagtt acgggtggag aagtgaagaa gctgaagaga    180
ctaacctttc agtttggtga tgcaagaaag gacagttctc tccacatcac tgcggcccag    240
cctggtgata caggcctcta cctctgtgcc gctaatggag gaagccaagg aaatctcatc    300
tttggaaaag gcactaaact ctctgttaaa cca                                 333
```

<210> SEQ ID NO 771
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 771

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Gln
                85                  90                  95

Asp Tyr Gly Tyr Thr Phe Gly Ser Gly Thr Arg Leu Thr Val Val
            100                 105                 110
```

<210> SEQ ID NO 772
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 772

```
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120
caggggcccc agtttatctt tcagtattat gaggaggaag agagacagag aggcaacttc     180
cctgatcgat tctcaggtca ccagttccct aactatagct ctgagctgaa tgtgaacgcc     240
ttgttgctgg gggactcggc cctctatctc tgtgccagca gcttacagga ctatggctac     300
accttcggtt cggggaccag gttaaccgtt gta                                  333
```

<210> SEQ ID NO 773
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 773

```
Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ser Thr Leu
65                  70                  75                  80

Arg Asp Ala Ala Val Tyr Tyr Cys Ile Leu Arg Pro Asp Ser Trp Gly
                85                  90                  95

Lys Phe Gln Phe Gly Ala Gly Thr Gln Val Val Val Thr Pro
            100                 105                 110
```

<210> SEQ ID NO 774
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 774

```
gatgctaaga ccacacagcc aaattcaatg gagagtaacg aagaagagcc tgttcacttg      60
ccttgtaacc actccacaat cagtggaact gattacatac attggtatcg acagcttccc     120
tcccagggtc cagagtacgt gattcatggt cttacaagca atgtgaacaa cagaatggcc     180
tctctggcaa tcgctgaaga cagaaagtcc agtaccttga tcctgcaccg ttctaccttg     240
agagatgctg ctgtgtacta ctgcatcctg cggcctgaca gctgggggaa attccagttt     300
ggagcaggga cccaggttgt ggtcacccca                                      330
```

<210> SEQ ID NO 775
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 775

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Gln
                85                  90                  95

Asp Tyr Gly Tyr Thr Phe Gly Ser Gly Thr Arg Leu Thr Val Val
            100                 105                 110
```

<210> SEQ ID NO 776
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 776

```
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120
cagggggccc agtttatctt tcagtattat gaggaggaag agagacagag aggcaacttc     180
cctgatcgat tctcaggtca ccagttccct aactatagct ctgagctgaa tgtgaacgcc     240
ttgttgctgg gggactcggc cctctatctc tgtgccagca gcttacagga ctatggctac     300
accttcggtt cggggaccag gttaaccgtt gta                                  333
```

<210> SEQ ID NO 777
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 777

```
Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Thr Asn Gly Gly Ser Gln
                85                  90                  95
```

```
Gly Asn Leu Ile Phe Gly Lys Gly Thr Lys Leu Ser Val Lys Pro
            100                 105                 110
```

<210> SEQ ID NO 778
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 778

```
acccagctgc tggagcagag ccctcagttt ctaagcatcc aagagggaga aaatctcact      60
gtgtactgca actcctcaag tgtttttttcc agcttacaat ggtacagaca ggagcctggg     120
gaaggtcctg tcctcctggt gacagtagtt acgggtggag aagtgaagaa gctgaagaga     180
ctaacctttc agtttggtga tgcaagaaag gacagttctc tccacatcac tgcggcccag     240
cctggtgata caggcctcta cctctgtgcc actaatggag gaagccaagg aaatctcatc     300
tttggaaaag gcactaaact ctctgttaaa cca                                  333
```

<210> SEQ ID NO 779
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 779

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Gln
                85                  90                  95

Asp Tyr Gly Tyr Thr Phe Gly Ser Gly Thr Arg Leu Thr Val Val
            100                 105                 110
```

<210> SEQ ID NO 780
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 780

```
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120 cagggggcccc agtttatctt tcagtattat gaggaggaag agagacagag aggcaacttc     180
cctgatcgat tctcaggtca ccagttccct aactatagct ctgagctgaa tgtgaacgcc     240
```

-continued ttgttgctgg gggactcggc cctctatctc tgtgccagca gcttacagga ctatggctac        300
accttcggtt cggggaccag gttaaccgtt gta                                      333

<210> SEQ ID NO 781
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 781

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Arg Arg Pro Gly Asn Gln Phe
                85                  90                  95

Tyr Phe Gly Thr Gly Thr Ser Leu Thr Val Ile Pro
            100                 105

<210> SEQ ID NO 782
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 782
gatgctaaga ccacacagcc aaattcaatg gagagtaacg aagaagagcc tgttcacttg         60
ccttgtaacc actccacaat cagtggaact gattacatac attggtatcg acagcttccc        120
tcccagggtc cagagtacgt gattcatggt cttacaagca atgtgaacaa cagaatggcc        180
tctctggcaa tcgctgaaga cagaaagtcc agtaccttga tcctgcaccg tgctaccttg        240
agagatgctg ctgtgtacta ctgcatcagg cggcccggta accagttcta ttttgggaca        300
gggacaagtt tgacggtcat tcca                                               324

<210> SEQ ID NO 783
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 783

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
                20                  25                  30

-continued

```
Ser Trp Tyr Arg Gln Asp Pro Gly Leu Gly Leu Arg Gln Ile Tyr Tyr
        35              40              45

Ser Met Asn Val Glu Val Thr Asp Lys Gly Asp Val Pro Glu Gly Tyr
        50              55              60

Lys Val Ser Arg Lys Glu Lys Arg Asn Phe Pro Leu Ile Leu Glu Ser
65              70              75              80

Pro Ser Pro Asn Gln Thr Ser Leu Tyr Phe Cys Ala Ser Ser Leu Trp
                85              90              95

Thr Gly Ser Glu Ala Phe Phe Gly Gln Gly Thr Arg Leu Thr Val Val
                100             105             110
```

<210> SEQ ID NO 784
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 784

```
gaagcccaag tgacccagaa cccaagatac ctcatcacag tgactggaaa gaagttaaca        60
gtgacttgtt ctcagaatat gaaccatgag tatatgtcct ggtatcgaca agacccaggg       120
ctgggcttaa ggcagatcta ctattcaatg aatgttgagg tgactgataa gggagatgtt       180
cctgaagggt acaaagtctc tcgaaaagag aagaggaatt tccccctgat cctggagtcg       240
cccagcccca accagacctc tctgtacttc tgtgccagca gtttatggac agggtctgaa       300
gctttctttg gacaaggcac cagactcaca gttgta                                  336
```

<210> SEQ ID NO 785
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 785

```
Thr Gln Leu Leu Glu Gln Ser Pro Gln Phe Leu Ser Ile Gln Glu Gly
1               5               10              15

Glu Asn Leu Thr Val Tyr Cys Asn Ser Ser Ser Val Phe Ser Ser Leu
                20              25              30

Gln Trp Tyr Arg Gln Glu Pro Gly Glu Gly Pro Val Leu Leu Val Thr
        35              40              45

Val Val Thr Gly Gly Glu Val Lys Lys Leu Lys Arg Leu Thr Phe Gln
        50              55              60

Phe Gly Asp Ala Arg Lys Asp Ser Ser Leu His Ile Thr Ala Ala Gln
65              70              75              80

Pro Gly Asp Thr Gly Leu Tyr Leu Cys Ala Gly Gly Thr Ser Gly Thr
                85              90              95

Tyr Lys Tyr Ile Phe Gly Thr Gly Thr Arg Leu Lys Val Leu Ala
                100             105             110
```

<210> SEQ ID NO 786
<211> LENGTH: 333
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 786

```
acccagctgc tggagcagag ccctcagttt ctaagcatcc aagagggaga aaatctcact      60
gtgtactgca actcctcaag tgttttttcc agcttacaat ggtacagaca ggagcctggg     120
gaaggtcctg tcctcctggt gacagtagtt actggtggag aagtgaagaa gctgaagaga     180
ctaacctttc agtttggtga tgcaagaaag gacagttctc tccacatcac tgcggcccag     240
cctggtgata caggcctcta cctctgtgca ggagggacct caggaaccta caaatacatc     300
tttggaacag gcaccaggct gaaggtttta gca                                  333
```

<210> SEQ ID NO 787
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 787

```
Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Pro Gly
                85                  90                  95

Thr Ala Asn Tyr Gly Tyr Thr Phe Gly Ser Gly Thr Arg Leu Thr Val
                100                 105                 110

Val
```

<210> SEQ ID NO 788
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 788

```
gaagcccaag tgacccagaa cccaagatac ctcatcacag tgactggaaa gaagttaaca      60
gtgacttgtt ctcagaatat gaaccatgag tatatgtcct ggtatcgaca gacccaggg     120 ctgggcttaa ggcagatcta ctattcaatg aatgttgagg tgactgataa gggagatgtt     180
cctgaagggt acaaagtctc tcgaaaagag aagaggaatt ccccctgat cctggagtcg      240 cccagcccca accagacctc tctgtacttc tgtgccagca gtccagggac agctaactat     300
ggctacacct tcggttcggg gaccaggtta accgttgta                            339
```

<210> SEQ ID NO 789

<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 789

Ala Gln Arg Val Thr Gln Pro Glu Lys Leu Leu Ser Val Phe Lys Gly
1               5                   10                  15

Ala Pro Val Glu Leu Lys Cys Asn Tyr Ser Tyr Ser Gly Ser Pro Glu
                20                  25                  30

Leu Phe Trp Tyr Val Gln Tyr Ser Arg Gln Arg Leu Gln Leu Leu Leu
            35                  40                  45

Arg His Ile Ser Arg Glu Ser Ile Lys Gly Phe Thr Ala Asp Leu Asn
        50                  55                  60

Lys Gly Glu Thr Ser Phe His Leu Lys Lys Pro Phe Ala Gln Glu Glu
65                  70                  75                  80

Asp Ser Ala Met Tyr Tyr Cys Ala Leu Gly Asn Thr Asp Lys Leu Ile
                85                  90                  95

Phe Gly Thr Gly Thr Arg Leu Gln Val Phe Pro
            100                 105

<210> SEQ ID NO 790
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 790
gcccagagag tgactcagcc cgagaagctc ctctctgtct ttaaaggggc cccagtggag      60
ctgaagtgca actattccta ttctgggagt cctgaactct tctggtatgt ccagtactcc     120
agacaacgcc tccagttact cttgagacac atctctagag agagcatcaa aggcttcact     180
gctgacctta caaaggcgga gacatctttc cacctgaaga aaccatttgc tcaagaggaa     240
gactcagcca tgtattactg tgctctaggg aacaccgaca agctcatctt tgggactggg     300
accagattac aagtctttcc a                                               321

<210> SEQ ID NO 791
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 791

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

```
Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Pro
                85                  90                  95

Arg Thr Gly Trp Tyr Gly Tyr Thr Phe Gly Ser Gly Thr Arg Leu Thr
            100                 105                 110

Val Val
```

<210> SEQ ID NO 792
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 792

```
gatgtgaaag taacccagag ctcgagatat ctagtcaaaa ggacgggaga gaaagttttt    60
ctggaatgtg tccaggatat ggaccatgaa aatatgttct ggtatcgaca agacccaggt   120
ctggggctac ggctgatcta tttctcatat gatgttaaaa tgaaagaaaa aggagatatt   180 cctgagggggt acagtgtctc tagagagaag aaggagcgct ctccctgat tctggagtcc   240 gccagcacca accagacatc tatgtacctc tgtgccagca gttcgcccag gacagggtgg   300
tatggctaca ccttcggttc ggggaccagg ttaaccgttg ta                       342
```

<210> SEQ ID NO 793
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 793

```
Asp Ala Lys Thr Thr Gln Pro Asn Ser Met Glu Ser Asn Glu Glu Glu
1                   5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
            35                  40                  45

His Gly Leu Thr Ser Asn Val Asn Asn Arg Met Ala Ser Leu Ala Ile
        50                  55                  60

Ala Glu Asp Arg Lys Ser Ser Thr Leu Ile Leu His Arg Ser Thr Leu
65                  70                  75                  80

Arg Asp Ala Ala Val Tyr Tyr Cys Ile Leu Arg Pro Asp Ser Trp Gly
                85                  90                  95

Lys Phe Gln Phe Gly Ala Gly Thr Gln Val Val Val Thr Pro
            100                 105                 110
```

<210> SEQ ID NO 794
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 794

```
gatgctaaga ccacacagcc aaattcaatg gagagtaacg aagaagagcc tgttcacttg     60
ccttgtaacc actccacaat cagtggaact gattacatac attggtatcg acagcttccc    120
tcccagggtc cagagtacgt gattcatggt cttacaagca atgtgaacaa cagaatggcc    180
tctctggcaa tcgctgaaga cagaaagtcc agtaccttga tcctgcaccg ttctaccttg    240
agagatgctg ctgtgtacta ctgcatcctg cggcctgaca gctgggggaa attccagttt    300
ggagcaggga cccaggttgt ggtcacccca                                      330
```

<210> SEQ ID NO 795
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 795

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Val
                85                  90                  95

Asp Tyr Gly Tyr Thr Phe Gly Ser Gly Thr Arg Leu Thr Val Val
            100                 105                 110
```

<210> SEQ ID NO 796
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 796

```
gacgctggag tcacccaaag ccccacacac ctgatcaaaa cgagaggaca gcaagtgact     60
ctgagatgct ctcctaagtc tgggcatgac actgtgtcct ggtaccaaca ggccctgggt    120
cagggggccc agtttatctt tcagtattat gaggaggaag agagacagag aggcaacttc    180
cctgatcgat tctcaggtca ccagttccct aactatagct ctgagctgaa tgtgaacgcc    240
ttgttgctgg gggactcggc cctctatctc tgtgccagca gcttggtgga ttatggctac    300
accttcggtt cggggaccag gttaaccgtt gta                                  333
```

<210> SEQ ID NO 797
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 797

```
Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ser Thr Leu
65                  70                  75                  80

Arg Asp Ala Ala Val Tyr Tyr Cys Ile Leu Arg Pro Asp Ser Trp Gly
                85                  90                  95

Lys Phe Gln Phe Gly Ala Gly Thr Gln Val Val Val Thr Pro
                100                 105                 110
```

<210> SEQ ID NO 798
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 798

```
gatgctaaga ccacacagcc aaattcaatg gagagtaacg aagaagagcc tgttcacttg      60
ccttgtaacc actccacaat cagtggaact gattacatac attggtatcg acagcttccc     120
tcccagggtc cagagtacgt gattcatggt cttacaagca atgtgaacaa cagaatggcc     180
tctctggcaa tcgctgaaga cagaaagtcc agtaccttga tcctgcaccg ttctaccttg     240
agagatgctg ctgtgtacta ctgcatcctg cggcctgaca gctgggggaa attccagttt     300
ggagcaggga cccaggttgt ggtcacccca                                      330
```

<210> SEQ ID NO 799
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 799

```
Glu Ala Gln Val Thr Gln Ser Pro Arg Tyr Leu Ile Thr Val Thr Gly
1               5                   10                  15

Lys Lys Leu Thr Val Thr Cys Ser Gln Asn Met Asp His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Pro Arg Lys Glu Lys Arg Ser Phe Pro Leu Ile Leu Glu Ser
65                  70                  75                  80

Pro Cys Cys Ser Gln Thr Pro Leu Tyr Leu Cys Ala Ser Ser Leu Gly
                85                  90                  95

Gly Val Asp Glu Arg Leu Ser Phe Gly Ser Gly Thr Gln Leu Ser Val
```

```
            100             105             110

Leu

<210> SEQ ID NO 800
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 800
gaagcccaag tgacccagag cccaagatac ctcatcacag tgactggaaa gaagttaaca      60
gtgacttgtt ctcagaatat ggaccatgag tatatgtcct ggtatcgaca ggacccgggg     120
ctgggcctaa ggcagatcta ctattcaatg aatgttgagg tgacagataa gggagatgtt     180
cctgaagggt acaaagtccc tcgaaaagag aagaggagtt tccccctgat cctggagtcg     240
ccctgctgca gccagacccc tctgtacctc tgtgccagca gtttaggggg cgtggatgaa     300
agactgtctt ttggcagtgg aacccagctc tccgtcttg                           339

<210> SEQ ID NO 801
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 801

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Asp Gly Gly Ser Gln
                85                  90                  95

Gly Asn Leu Ile Phe Gly Lys Gly Thr Lys Leu Ser Val Lys Pro
            100                 105                 110

<210> SEQ ID NO 802
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 802
acccagctgc tggagcagag ccctcagttt ctaagcatcc aagagggaga aaatctcact      60
gtgtactgca actcctcaag tgtttttttcc agcttacaat ggtacagaca ggagcctggg     120
gaaggtcctg tcctcctggt gacagtagtt acgggtggaa aagtgaagaa gctgaagaga     180
```

-continued

```
ctaacctttc agtttggtga tgcaagaaag gacagttctc tccacatcac tgcggcccag      240
cctggtgata caggcctcta cctctgtgca ggggatggag gaagccaagg aaatctcatc      300
tttggaaaag gcactaaact ctctgttaaa cca                                   333
```

```
<210> SEQ ID NO 803
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 803

Glu Ala Gln Val Thr Gln Ser Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Gly
                85                  90                  95

Gly Ala Asp Glu Lys Leu Phe Phe Gly Ser Gly Thr Gln Leu Ser Val
                100                 105                 110

Leu
```

```
<210> SEQ ID NO 804
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 804
gaagcccaag tgacccagag cccaagatac ctcatcacag tgactggaaa gaagttaaca       60
gtgacttgtt ctcagaatat gaaccatgag tatatgtcct ggtatcgaca agacccaggg      120
ctgggcttaa ggcagatcta ctattcaatg aatgttgagg tgactgataa gggagatgtt      180
cctgaagggt acaaagtctc tcgaaaagag aagaggaatt tccccctgat cctggagtcg      240
cccagcccca accagacctc tctgtacttc tgtgccagca gtttagggggg cgcggatgaa      300 aaactgtttt ttggcagtgg aacccagctc tctgtcttg                             339
```

```
<210> SEQ ID NO 805
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 805

Asp Ala Lys Thr Thr Gln Pro Asn Ser Met Glu Ser Asn Glu Glu Glu
1               5                   10                  15
```

Pro Val His Leu Pro Cys Asn His Ser Thr Ile Ser Gly Thr Asp Tyr
          20                  25                  30

Ile His Trp Tyr Arg Gln Leu Pro Ser Gln Gly Pro Glu Tyr Val Ile
          35                  40                  45

His Gly Leu Thr Ser Asn Val Asn Asn Arg Met Ala Ser Leu Ala Ile
          50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Gly Gln Gly Ala Gln Lys
                    85                  90                  95

Leu Val Phe Gly Gln Gly Thr Arg Leu Thr Ile Asn Pro
          100                 105

<210> SEQ ID NO 806
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 806
gatgctaaga ccacacagcc aaattcaatg gagagtaacg aagaagagcc tgttcacttg      60
ccttgtaacc actccacaat cagtggaact gattacatac attggtatcg acagcttccc     120
tcccagggtc cagagtacgt gattcatggt cttacaagca atgtgaacaa cagaatggcc     180
tctctggcaa tcgctgaaga cagaaagtcc agtaccttga tcctgcaccg tgctaccttg     240
agagatgctg ctgtgtacta ctgcatcctg ggtcagggag cccagaagct ggtatttggc     300
caaggaacca ggctgactat caaccca                                          327

<210> SEQ ID NO 807
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 807

Glu Ala Gln Val Thr Gln Asn Pro Arg Tyr Leu Ile Thr Val Thr Gly
1                   5                   10                  15

Lys Lys Leu Thr Val Thr Cys Ser Gln Asn Met Asn His Glu Tyr Met
          20                  25                  30

Ser Trp Tyr Arg Gln Asp Pro Gly Leu Gly Leu Arg Gln Ile Tyr Tyr
          35                  40                  45

Ser Met Asn Val Glu Val Thr Asp Lys Gly Asp Val Pro Glu Gly Tyr
          50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Trp
                    85                  90                  95

Thr Gly Gly Gly Tyr Thr Phe Gly Ser Gly Thr Arg Leu Thr Val Val
          100                 105                 110

<210> SEQ ID NO 808
<211> LENGTH: 336

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 808
gaagcccaag tgacccagaa cccaagatac ctcatcacag tgactggaaa gaagttaaca      60
gtgacttgtt ctcagaatat gaaccatgag tatatgtcct ggtatcgaca agacccaggg     120
ctgggcttaa ggcagatcta ctattcaatg aatgttgagg tgactgataa gggagatgtt     180
cctgaagggt acaaagtctc tcgaaaagag aagaggaatt cccccctgat cctggagtcg     240 cccagccca accagacctc tctgtacttc tgtgccagca gtttatggac aggggggcggc     300 tacaccttcg gttcggggac caggttaacc gttgta                               336

<210> SEQ ID NO 809
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 809

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Asp Gly Gly Ser Gln
                85                  90                  95

Gly Asn Leu Ile Phe Gly Lys Gly Thr Lys Leu Ser Val Lys Pro
            100                 105                 110

<210> SEQ ID NO 810
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 810
acccagctgc tggagcagag ccctcagttt ctaagcatcc aagagggaga aaatctcact      60
gtgtactgca actcctcaag tgtttttttcc agcttacaat ggtacagaca ggagcctggg     120
gaaggtcctg tcctcctggt gacagtagtt acgggtggag aagtgaagaa gctgaagaga     180
ctaacctttc agtttggtga tgcaagaaag gacagttctc tccacatcac tgcggcccag     240
cctggtgata caggcctcta cctctgtgca ggggatggag gaagccaagg aaatctcatc     300
tttggaaaag gcactaaaact ctctgttaaa cca                                 333

-continued

```
<210> SEQ ID NO 811
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 811

Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Val
                85                  90                  95

Asp Tyr Gly Tyr Thr Phe Gly Ser Gly Thr Arg Leu Thr Val Val
            100                 105                 110

<210> SEQ ID NO 812
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 812
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120
caggggcccc agtttatctt tcagtattat gaggaggaag agagacagag aggcaacttc     180
cctgatcgat tctcaggtca ccagttccct aactatagct ctgagctgaa tgtgaacgcc     240
ttgttgctgg gggactcggc cctctatctc tgtgccagca gcttggtgga ttatggctac     300
accttcggtt cggggaccag gttaaccgtt gta                                   333

<210> SEQ ID NO 813
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 813

Gly Ile Gln Val Glu Gln Ser Pro Pro Asp Leu Ile Leu Gln Glu Gly
1               5                   10                  15

Ala Asn Ser Thr Leu Arg Cys Asn Phe Ser Asp Ser Val Asn Asn Leu
            20                  25                  30

Gln Trp Phe His Gln Asn Pro Trp Gly Gln Leu Ile Asn Leu Phe Tyr
        35                  40                  45

Ile Pro Ser Gly Thr Lys Gln Asn Gly Arg Leu Ser Ala Thr Thr Val
    50                  55                  60
```

```
Ala Thr Glu Arg Tyr Ser Leu Leu Tyr Ile Ser Ser Ser Gln Thr Thr
65                  70                  75                  80

Asp Ser Gly Val Tyr Phe Cys Val Leu Gly Gly Gly Ser Gln Gly Asn
                85                  90                  95

Leu Ile Phe Gly Lys Gly Thr Lys Leu Ser Val Lys Pro
            100                 105
```

<210> SEQ ID NO 814
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 814

```
ggaatacaag tggagcagag tcctccagac ctgattctcc aggagggagc caattccacg      60
ctgcggtgca atttttctga ctctgtgaac aatttgcagt ggtttcatca aaacccttgg     120
ggacagctca tcaacctgtt ttacattccc tcagggacaa aacagaatgg aagattaagc     180
gccacgactg tcgctacgga acgctacagc ttattgtaca tttcctcttc ccagaccaca     240
gactcaggcg tttatttctg tgtcctaggg ggaggaagcc aaggaaatct catctttgga     300
aaaggcacta aactctctgt taaacca                                         327
```

<210> SEQ ID NO 815
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 815

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
                20                  25                  30

Ser Trp Tyr Gln Gln Ala Leu Gly Gln Gly Pro Gln Phe Ile Phe Gln
            35                  40                  45

Tyr Tyr Glu Glu Glu Glu Arg Gln Arg Gly Asn Phe Pro Asp Arg Phe
        50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Phe Thr
                85                  90                  95

Asp Tyr Gly Tyr Thr Phe Gly Ser Gly Thr Arg Leu Thr Val Val
            100                 105                 110
```

<210> SEQ ID NO 816
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 816
gacgctggag tcacccaaag tcccacacac ctgatcaaaa cgagaggaca gcaagtgact          60
ctgagatgct ctcctaagtc tgggcatgac actgtgtcct ggtaccaaca ggccctgggt         120 cagggggcccc agtttatctt tcagtattat gaggaggaag agagacagag aggcaacttc        180
cctgatcgat tctcaggtca ccagttccct aactatagct ctgagctgaa tgtgaacgcc        240
ttgttgctgg gggactcggc cctctatctc tgtgccagca gctttacaga ctatggctac        300
accttcggtt cggggaccag gttaaccgtt gta                                      333

<210> SEQ ID NO 817
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 817

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Asp Gly Thr Gly Asn
                85                  90                  95

Gln Phe Tyr Phe Gly Thr Gly Thr Ser Leu Thr Val Ile Pro
            100                 105                 110

<210> SEQ ID NO 818
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 818
gatgctaaga ccacacagcc aaattcaatg gagagtaacg aagaagagcc tgttcacttg          60
ccttgtaacc actccacaat cagtggaact gattacatac attggtatcg acagcttccc         120
tcccagggtc cagagtacgt gattcatggt cttacaagca atgtgaacaa cagaatggcc        180
tctctggcaa tcgctgaaga cagaaagtcc agtaccttga tcctgcaccg tgctaccttg        240
agagatgctg ctgtgtacta ctgcatcctg agagacggga ccggtaacca gttctatttt        300
gggacaggga caagtttgac ggtcattcca                                          330

<210> SEQ ID NO 819
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 819

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Trp
                85                  90                  95

Thr Gly Gly Gly Tyr Thr Phe Gly Ser Gly Thr Arg Leu Thr Val Val
            100                 105                 110

<210> SEQ ID NO 820
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 820
gaagcccaag tgacccagaa cccaagatac ctcatcacag tgactggaaa gaagttaaca       60
gtgacttgtt ctcagaatat gaaccatgag tatatgtcct ggtatcgaca agacccaggg      120
ctgggcttaa ggcagatcta ctattcaatg aatgttgagg tgactgataa gggagatgtt      180
cctgaagggt acaaagtctc tcgaaaagag aagaggaatt tcccccctgat cctggagtcg      240 cccagcccca accagacctc tctgtacttc tgtgccagca gtttatggac aggggggtggc     300 tacaccttcg gttcggggac caggttaacc gttgta                                336

<210> SEQ ID NO 821
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 821

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Gly Pro Ser Gly Thr
                85                  90                  95

Tyr Lys Tyr Ile Phe Gly Thr Gly Thr Arg Leu Lys Val Leu Ala
            100                 105                 110

```
<210> SEQ ID NO 822
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 822
acccagctgc tggagcagag ccctcagttt ctaagcatcc aagagggaga aaatctcact     60
gtgtactgca actcctcaag tgttttttcc agcttacaat ggtacagaca ggagcctggg    120
gaaggtcctg tcctcctggt gacagtagtt acgggtggag aagtgaagaa gctgaagaga    180
ctaacctttc agtttggtga tgcaagaaag gacagttctc tccacatcac tgcggcccag    240
cctggtgata caggcctcta cctctgtgca ggaggaccct caggaaccta caaatacatc    300
tttggaacag gcaccaggct gaaggtttta gca                                 333

<210> SEQ ID NO 823
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 823

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Pro Gly
                85                  90                  95

Thr Pro Asn Tyr Gly Tyr Thr Phe Gly Ser Gly Thr Arg Leu Thr Val
            100                 105                 110

Val

<210> SEQ ID NO 824
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 824
gaagcccaag tgacccagaa cccaagatac ctcatcacag tgactggaaa gaagttaaca     60
gtgacttgtt ctcagaatat gaaccatgag tatatgtcct ggtatcgaca agacccaggg    120
ctgggcttaa ggcagatcta ctattcaatg aatgttgagg tgactgataa gggagatgtt    180
cctgaagggt acaaagtctc tcgaaaagag aagaggaatt tccccctgat cctggagtcg    240
```

-continued

```
cccagcccca accagacctc tctgtacttc tgtgccagca gtcccgggac acctaactat      300
ggctacacct tcggttcggg gaccaggtta accgttgta                            339

<210> SEQ ID NO 825
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 825

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Gly Asn Tyr Gly Gln Asn
                85                  90                  95

Phe Val Phe Gly Pro Gly Thr Arg Leu Ser Val Leu Pro
            100                 105

<210> SEQ ID NO 826
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 826
cagaaggagg tggagcagaa ttctggaccc ctcagtgttc cagagggagc cattgcctct       60
ctcaactgca cttacagtga ccgaggttcc cagtccttct tctggtacag acaatattct      120
gggaaaagcc ctgagttgat aatgtccata tactccaatg gtgacaaaga agatggaagg      180
tttacagcac agctcaataa agccagccag tatgtttctc tgctcatcag agactcccag      240
cccagtgatt cagccaccta cctctgtgcc gggaactatg gtcagaattt tgtctttggt      300
cccggaacca gattgtccgt gctgccc                                         327

<210> SEQ ID NO 827
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 827

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30
```

```
Tyr Trp Tyr Gln Gln Gly Pro Gly Gln Asp Pro Gln Phe Leu Ile Ser
        35              40              45

Phe Tyr Glu Lys Met Gln Ser Asp Lys Gly Ser Ile Pro Asp Arg Phe
    50              55              60

Ser Ala Gln Gln Phe Ser Asp Tyr His Ser Glu Leu Asn Met Ser Ser
65              70              75              80

Leu Glu Leu Gly Asp Ser Ala Leu Tyr Phe Cys Ala Ser Ser Ile Gly
                85              90              95

Leu Asn Gln Pro Gln His Phe Gly Asp Gly Thr Arg Leu Ser Ile Leu
            100             105             110
```

<210> SEQ ID NO 828
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 828

```
gctgctggag tcatccagtc cccaagacat ctgatcaaag aaaagaggga aacagccact      60
ctgaaatgct atcctatccc tagacacgac actgtctact ggtaccagca gggtccaggt     120 caggacccccc agttcctcat ttcgttttat gaaaagatgc agagcgataa aggaagcatc    180
cctgatcgat tctcagctca acagttcagt gactatcatt ctgaactgaa catgagctcc    240
ttggagctgg gggactcagc cctgtacttc tgtgccagca gcatcggact taatcagccc    300
cagcattttg gtgatgggac tcgactctcc atccta                            336
```

<210> SEQ ID NO 829
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 829

```
Asp Ala Lys Thr Thr Gln Pro Asn Ser Met Glu Ser Asn Glu Glu Glu
1               5               10              15

Pro Val His Leu Pro Cys Asn His Ser Thr Ile Ser Gly Thr Asp Tyr
            20              25              30

Ile His Trp Tyr Arg Gln Leu Pro Ser Gln Gly Pro Glu Tyr Val Ile
        35              40              45

His Gly Leu Thr Ser Asn Val Asn Asn Arg Met Ala Ser Leu Ala Ile
    50              55              60

Ala Glu Asp Arg Lys Ser Ser Thr Leu Ile Leu His Arg Ala Thr Leu
65              70              75              80

Arg Asp Ala Ala Val Tyr Tyr Cys Ile Leu Arg Asp Gly Ile Gly Asn
                85              90              95

Gln Phe Tyr Phe Gly Thr Gly Thr Ser Leu Thr Val Ile Pro
            100             105             110
```

<210> SEQ ID NO 830
<211> LENGTH: 330
<212> TYPE: DNA
<213> ORGANISM: Artificial Sequence
<220> FEATURE:

<221> NAME/KEY: source
<223> OTHER INFORMATION: /note="Description of Artificial Sequence:
     Synthetic polynucleotide"

<400> SEQUENCE: 830
gatgctaaga ccacacagcc aaattcaatg gagagtaacg aagaagagcc tgttcacttg          60
ccttgtaacc actccacaat cagtggaact gattacatac attggtatcg acagcttccc         120
tcccagggtc cagagtacgt gattcatggt cttacaagca atgtgaacaa cagaatggcc         180
tctctggcaa tcgctgaaga cagaaagtcc agtaccttga tcctgcaccg tgctaccttg         240
agagatgctg ctgtgtacta ctgcatcctg agagacggca tcggtaacca gttctatttt         300
gggacaggga caagtttgac ggtcattcca                                         330

<210> SEQ ID NO 831
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 831

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Trp
                85                  90                  95

Thr Gly Gly Gly Tyr Thr Phe Gly Ser Gly Thr Arg Leu Thr Val Val
            100                 105                 110

<210> SEQ ID NO 832
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 832
gaagcccaag tgacccagaa cccaagatac ctcatcacag tgactggaaa gaagttaaca          60
gtgacttgtt ctcagaatat gaaccatgag tatatgtcct ggtatcgaca gacccaggg         120 ctgggcttaa ggcagatcta ctattcaatg aatgttgagg tgactgataa gggagatgtt         180
cctgaagggt acaaagtctc tcgaaaagag aagaggaatt tcccccctgat cctggagtcg         240 cccagcccca accagacctc tctgtacttc tgtgccagca gtttatggac aggggggaggc        300 tacaccttcg gttcggggac caggttaacc gttgta                                   336

<210> SEQ ID NO 833
<211> LENGTH: 110
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 833

Asp Ala Lys Thr Thr Gln Pro Asn Ser Met Glu Ser Asn Glu Glu Glu
1               5                  10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ser Thr Leu
65                  70                  75                  80

Arg Asp Ala Ala Val Tyr Tyr Cys Ile Leu Arg Pro Asp Ser Trp Gly
                85                  90                  95

Lys Phe Gln Phe Gly Ala Gly Thr Gln Val Val Val Thr Pro
            100                 105                 110

<210> SEQ ID NO 834
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 834
gatgctaaga ccacacagcc aaattcaatg gagagtaacg aagaagagcc tgttcacttg        60
ccttgtaacc actccacaat cagtggaact gattacatac attggtatcg acagcttccc       120
tcccagggtc cagagtacgt gattcatggt cttacaagca atgtgaacaa cagaatggcc       180
tctctggcaa tcgctgaaga cagaaagtcc agtaccttga tcctgcaccg ttctaccttg       240
agagatgctg ctgtgtacta ctgcatcctg cggcctgaca gctggggggaa attccagttt      300 ggagcaggga cccaggttgt ggtcaccccca                                        330

<210> SEQ ID NO 835
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 835

Glu Ala Gln Val Thr Gln Asn Pro Arg Tyr Leu Ile Thr Val Thr Gly
1               5                  10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80
```

-continued

```
Pro Ser Pro Asn Gln Thr Ser Leu Tyr Phe Cys Ala Ser Ser Leu Trp
            85                  90                  95

Thr Gly Gly Gly Tyr Thr Phe Gly Ser Gly Thr Arg Leu Thr Val Val
            100                 105                 110

<210> SEQ ID NO 836
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 836
gaagcccaag tgacccagaa cccaagatac ctcatcacag tgactggaaa gaagttaaca      60
gtgacttgtt ctcagaatat gaaccatgag tatatgtcct ggtatcgaca agacccaggg     120
ctgggcttaa ggcagatcta ctattcaatg aatgttgagg tgactgataa gggagatgtt     180
cctgaagggt acaaagtctc tcgaaaagag aagaggaatt ccccctgat cctggagtcg       240 cccagcccca accagacctc tctgtacttc tgtgccagca gtttatggac aggggggaggc     300 tacaccttcg gttcggggac caggttaacc gttgta                               336

<210> SEQ ID NO 837
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 837

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Asp Gly Thr Gly Asn
                85                  90                  95

Gln Phe Tyr Phe Gly Thr Gly Thr Ser Leu Thr Val Ile Pro
            100                 105                 110

<210> SEQ ID NO 838
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 838
gatgctaaga ccacacagcc aaattcaatg gagagtaacg aagaagagcc tgttcacttg      60
ccttgtaacc actccacaat cagtggaact gattacatac attggtatcg acagcttccc     120
```

```
tcccagggtc cagagtacgt gattcatggt cttacaagca atgtgaacaa cagaatggcc      180
tctctggcaa tcgctgaaga cagaaagtcc agtaccttga tcctgcaccg tgctaccttg      240
agagatgctg ctgtgtacta ctgcatcctg agagacggca ccggtaacca gttctatttt      300
gggacaggga caagtttgac ggtcattcca                                       330
```

```
<210> SEQ ID NO 839
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 839

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Ser Thr
                85                  90                  95

Gly Tyr Tyr Gly Tyr Thr Phe Gly Ser Gly Thr Arg Leu Thr Val Val
            100                 105                 110
```

```
<210> SEQ ID NO 840
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 840
gaagcccaag tgacccagaa cccaagatac ctcatcacag tgactggaaa gaagttaaca       60
gtgacttgtt ctcagaatat gaaccatgag tatatgtcct ggtatcgaca agacccaggg      120
ctgggcttaa ggcagatcta ctattcaatg aatgttgagg tgactgataa gggagatgtt      180
cctgaagggt acaaagtctc tcgaaaagag aagaggaatt tccccctgat cctggagtcg      240
cccagcccca accagacctc tctgtacttc tgtgccagca gttcgacagg gtactatggc      300
tacaccttcg gttcggggac caggttaacc gttgta                               336
```

```
<210> SEQ ID NO 841
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 841

Asp Ala Lys Thr Thr Gln Pro Asn Ser Met Glu Ser Asn Glu Glu Glu
```

```
1                 5                    10                   15

Pro Val His Leu Pro Cys Asn His Ser Thr Ile Ser Gly Thr Asp Tyr
          20                  25                  30

Ile His Trp Tyr Arg Gln Leu Pro Ser Gln Gly Pro Glu Tyr Val Ile
          35                  40                  45

His Gly Leu Thr Ser Asn Val Asn Asn Arg Met Ala Ser Leu Ala Ile
     50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Asp Arg Glu Tyr Gly
                    85                  90                  95

Asn Lys Leu Val Phe Gly Ala Gly Thr Ile Leu Arg Val Lys Ser
          100                 105                 110
```

<210> SEQ ID NO 842
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 842

```
gatgctaaga ccacacagcc aaattcaatg gagagtaacg aagaagagcc tgttcacttg        60
ccttgtaacc actccacaat cagtggaact gattacatac attggtatcg acagcttccc       120
tcccagggtc cagagtacgt gattcatggt cttacaagca atgtgaacaa cagaatggcc       180
tctctggcaa tcgctgaaga cagaaagtcc agtaccttga tcctgcaccg tgctaccttg       240
agagatgctg ctgtgtacta ctgcatcctg agagaccggg aatatggaaa caaactggtc       300
tttggcgcag gaaccattct gagagtcaag tcc                                    333
```

<210> SEQ ID NO 843
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 843

```
Glu Ala Gln Val Thr Gln Asn Pro Arg Tyr Leu Ile Thr Val Thr Gly
1                 5                    10                   15

Lys Lys Leu Thr Val Thr Cys Ser Gln Asn Met Asn His Glu Tyr Met
          20                  25                  30

Ser Trp Tyr Arg Gln Asp Pro Gly Leu Gly Leu Arg Gln Ile Tyr Tyr
          35                  40                  45

Ser Met Asn Val Glu Val Thr Asp Lys Gly Asp Val Pro Glu Gly Tyr
     50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Trp
                    85                  90                  95

Thr Gly Gly Gly Tyr Thr Phe Gly Ser Gly Thr Arg Leu Thr Val Val
          100                 105                 110
```

<210> SEQ ID NO 844

-continued

```
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 844
gaagcccaag tgacccagaa cccaagatac ctcatcacag tgactggaaa gaagttaaca      60
gtgacttgtt ctcagaatat gaaccatgag tatatgtcct ggtatcgaca agacccaggg     120
ctgggcttaa ggcagatcta ctattcaatg aatgttgagg tgactgataa gggagatgtt     180
cctgaagggt acaaagtctc tcgaaaagag aagaggaatt tcccctgat cctggagtcg       240 cccagcccca accagacctc tctgtacttc tgtgccagca gtttatggac aggggcggc      300 tacaccttcg gttcggggac caggttaacc gttgta                                336

<210> SEQ ID NO 845
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 845

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Glu Asp Gly Gly Ser Gln
                85                  90                  95

Gly Asn Leu Ile Phe Gly Lys Gly Thr Lys Leu Ser Val Lys Pro
            100                 105                 110

<210> SEQ ID NO 846
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 846
acccagctgc tggagcagag ccctcagttt ctaagcatcc aagagggaga aaatctcact      60
gtgtactgca actcctcaag tgttttttcc agcttacaat ggtacagaca ggagcctggg     120
gaaggtcctg tcctcctggt gacagtagtt acgggtggaa agtgaagaa gctgaagaga       180 ctaacctttc agtttggtga tgcaagaaag gacagttctc tccacatcac tgcggcccag     240
cctggtgata caggcctcta cctctgtgca gaagatggag gaagccaagg aaatctcatc     300
tttggaaaag gcactaaact ctctgttaaa cca                                   333
```

<210> SEQ ID NO 847
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 847

Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
                20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Ser
                85                  90                  95

Asp Tyr Gly Tyr Thr Phe Gly Ser Gly Thr Arg Leu Thr Val Val
            100                 105                 110

<210> SEQ ID NO 848
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 848
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120 cagggggcccc agtttatctt tcagtattat gaggaggaag agagacagag aggcaacttc     180
cctgatcgat tctcaggtca ccagttccct aactatagct ctgagctgaa tgtgaacgcc     240
ttgttgctgg gggactcggc cctctatctc tgtgccagca gcttatcaga ctatggctac     300
accttcggtt cggggaccag gttaaccgtt gta                                   333

<210> SEQ ID NO 849
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 849

Gly Ile Gln Val Glu Gln Ser Pro Pro Asp Leu Ile Leu Gln Glu Gly
1               5                   10                  15

Ala Asn Ser Thr Leu Arg Cys Asn Phe Ser Asp Ser Val Asn Asn Leu
                20                  25                  30

Gln Trp Phe His Gln Asn Pro Trp Gly Gln Leu Ile Asn Leu Phe Tyr
        35                  40                  45

Ile Pro Ser Gly Thr Lys Gln Asn Gly Arg Leu Ser Ala Thr Thr Val

```
        50              55              60

Ala Thr Glu Arg Tyr Ser Leu Leu Tyr Ile Ser Ser Ser Gln Thr Thr
65              70              75              80

Asp Ser Gly Val Tyr Phe Cys Ala Val Glu Ala Ser Gly Thr Tyr Lys
                85              90              95

Tyr Ile Phe Gly Thr Gly Thr Arg Leu Lys Val Leu Ala
            100             105
```

<210> SEQ ID NO 850
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 850

```
ggaatacaag tggagcagag tcctccagac ctgattctcc aggagggagc caattccacg     60
ctgcggtgca attttctga ctctgtgaac aatttgcagt ggtttcatca aaacccttgg     120
ggacagctca tcaacctgtt ttacattccc tcagggacaa aacagaatgg aagattaagc     180
gccacgactg tcgctacgga acgctacagc ttattgtaca tttcctcttc ccagaccaca     240
gactcaggcg tttatttctg tgctgtggag gcctcaggaa cctacaaata catctttgga     300
acaggcacca ggctgaaggt tttagca                                         327
```

<210> SEQ ID NO 851
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 851

```
Glu Ala Gln Val Thr Gln Asn Pro Arg Tyr Leu Ile Thr Val Thr Gly
1               5               10              15

Lys Lys Leu Thr Val Thr Cys Ser Gln Asn Met Asn His Glu Tyr Met
            20              25              30

Ser Trp Tyr Arg Gln Asp Pro Gly Leu Gly Leu Arg Gln Ile Tyr Tyr
        35              40              45

Ser Met Asn Val Glu Val Thr Asp Lys Gly Asp Val Pro Glu Gly Tyr
    50              55              60

Lys Val Ser Arg Lys Glu Lys Arg Asn Phe Pro Leu Ile Leu Glu Ser
65              70              75              80

Pro Ser Pro Asn Gln Thr Ser Leu Tyr Phe Cys Ala Ser Ser Trp Gly
            85              90              95

Thr Gly Gly Tyr Gly Tyr Thr Phe Gly Ser Gly Thr Arg Leu Thr Val
            100             105             110

Val
```

<210> SEQ ID NO 852
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

<400> SEQUENCE: 852
gaagcccaag tgacccagaa cccaagatac ctcatcacag tgactggaaa gaagttaaca        60
gtgacttgtt ctcagaatat gaaccatgag tatatgtcct ggtatcgaca agacccaggg       120
ctgggcttaa ggcagatcta ctattcaatg aatgttgagg tgactgataa gggagatgtt       180
cctgaagggt acaaagtctc tcgaaaagag aagaggaatt cccccctgat cctggagtcg       240
cccagcccca accagacctc tctgtacttc tgtgccagca gttgggggac agggggctat       300
ggctacacct tcggttcggg gaccaggtta accgttgta                              339

<210> SEQ ID NO 853
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 853

Gly Glu Ser Val Gly Leu His Leu Pro Thr Leu Ser Val Gln Glu Gly
1               5                   10                  15

Asp Asn Ser Ile Ile Asn Cys Ala Tyr Ser Asn Ser Ala Ser Asp Tyr
            20                  25                  30

Phe Ile Trp Tyr Lys Gln Glu Ser Gly Lys Gly Pro Gln Phe Ile Ile
        35                  40                  45

Asp Ile Arg Ser Asn Met Asp Lys Arg Gln Gly Gln Arg Val Thr Val
    50                  55                  60

Leu Leu Asn Lys Thr Val Lys His Leu Ser Leu Gln Ile Ala Ala Thr
65                  70                  75                  80

Gln Pro Gly Asp Ser Ala Val Tyr Phe Cys Ala Glu Asn Lys Arg Asp
                85                  90                  95

Asn Tyr Gly Gln Asn Phe Val Phe Gly Pro Gly Thr Arg Leu Ser Val
            100                 105                 110

Leu Pro

<210> SEQ ID NO 854
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 854
ggagagagtg tggggctgca tcttcctacc ctgagtgtcc aggagggtga caactctatt        60
atcaactgtg cttattcaaa cagcgcctca gactacttca tttggtacaa gcaagaatct       120
ggaaaaggtc ctcaattcat tatagacatt cgttcaaata tggacaaaag gcaaggccaa       180
agagtcaccg tttttattga ataagacagtg aaacatctct ctctgcaaat tgcagctact       240
caacctggag actcagctgt ctacttttgt gcagagaata gcgggataa ctatggtcag       300 aattttgtct ttggtcccgg aaccagattg tccgtgctgc cc                          342

<210> SEQ ID NO 855
<211> LENGTH: 112
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"

<400> SEQUENCE: 855

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Phe Trp
            85                  90                  95

Val Asn Thr Glu Ala Phe Phe Gly Gln Gly Thr Arg Leu Thr Val Val
            100                 105                 110

<210> SEQ ID NO 856
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 856
gaagcccaag tgacccagaa cccaagatac ctcatcacag tgactggaaa gaagttaaca        60
gtgacttgtt ctcagaatat gaaccatgag tatatgtcct ggtatcgaca gacccagggg       120
ctgggcttaa ggcagatcta ctattcaatg aatgttgagg tgactgataa gggagatgtt       180
cctgaagggt acaaagtctc tcgaaaagag aagaggaatt tcccctgat cctggagtcg        240 cccagcccca accagacctc tctgtacttc tgtgccagca gtttctgggt gaacactgaa       300
gctttctttg gacaaggcac cagactcaca gttgta                                 336

<210> SEQ ID NO 857
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 857

Gly Ile Gln Val Glu Gln Ser Pro Pro Asp Leu Ile Leu Gln Glu Gly
1               5                   10                  15

Val Asn Ser Thr Leu Arg Cys Asn Phe Ser Asp Ser Val Asn Asn Leu
            20                  25                  30

Gln Trp Phe His Gln Asn Pro Trp Gly Gln Leu Ile Asn Leu Phe Tyr
        35                  40                  45

Ile Pro Ser Gly Thr Lys Gln Asn Gly Arg Leu Ser Ala Thr Thr Val
    50                  55                  60

Ala Thr Glu Arg Tyr Ser Leu Leu Tyr Ile Ser Ser Ser Arg Thr Thr
65                  70                  75                  80
```

```
Asp Ser Gly Val Tyr Phe Cys Ala Val Gly Ser Ser Asn Gly Tyr Lys
                85                  90                  95

Leu Ser Phe Gly Ala Gly Thr Thr Val Thr Val Arg Ala
            100                 105

<210> SEQ ID NO 858
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 858
ggaatacaag tggagcagag tcctccagac ctgattctcc aggagggagt caattccacg      60
ctgcggtgca attttctga ctctgtgaac aatttgcagt ggtttcatca aaacccttgg     120
ggacagctca tcaacctgtt ttacattccc tcagggacaa aacagaatgg aagattaagc     180
gccacgactg tggctacgga acgctacagc ttattgtaca tttcctcttc ccggaccaca     240
gactcaggcg tttatttctg tgctgtgggg agttctaacg ctacaagct cagctttgga     300 gctggaacca cagtaactgt aagagca                                         327

<210> SEQ ID NO 859
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 859

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Pro Gly
                85                  90                  95

Thr Gly Gly Phe Ser Pro Leu His Phe Gly Asn Gly Thr Arg Leu Thr
            100                 105                 110

Val Thr

<210> SEQ ID NO 860
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 860
gaagcccaag tgacccagaa cccaagatac ctcatcacag tgactggaaa gaagttaaca      60
```

```
gtgacttgtt ctcagaatat gaaccatgag tatatgtcct ggtatcgaca agacccaggg        120
ctgggcttaa ggcagatcta ctattcaatg aatgttgagg tgactgataa gggagatgtt        180
cctgaagggt acaaagtctc tcgaaaagag aagaggaatt tccccctgat cctggagtcg        240
cccagcccca accagacctc tctgtacttc tgtgccagca gtcccgggac aggggggattt        300 tcacccctcc actttgggaa cgggaccagg ctcactgtga ca                          342
```

```
<210> SEQ ID NO 861
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 861

Gly Ile Gln Val Glu Gln Ser Pro Pro Asp Leu Ile Leu Gln Glu Gly
1               5                   10                  15

Ala Asn Ser Thr Leu Arg Cys Asn Phe Ser Asp Ser Val Asn Asn Leu
            20                  25                  30

Gln Trp Phe His Gln Asn Pro Trp Gly Gln Leu Ile Asn Leu Phe Tyr
        35                  40                  45

Ile Pro Ser Gly Thr Lys Gln Asn Gly Arg Leu Ser Ala Thr Thr Val
    50                  55                  60

Ala Thr Glu Arg Tyr Ser Leu Leu Tyr Ile Ser Ser Ser Gln Thr Thr
65                  70                  75                  80

Asp Ser Gly Val Tyr Phe Cys Ala Val Gly Ser Ser Asn Asp Tyr Lys
                85                  90                  95

Leu Ser Phe Gly Ala Gly Thr Thr Val Thr Val Arg Ala
            100                 105
```

```
<210> SEQ ID NO 862
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 862
ggaatacaag tggagcagag tcctccagac ctgattctcc aggagggagc caattccacg         60
ctgcggtgca atttttctga ctctgtgaac aatttgcagt ggtttcatca aaacccttgg        120
ggacagctca tcaacctgtt ttacattccc tcagggacaa aacagaatgg aagattaagc        180
gccacgactg tcgctacgga acgctacagc ttattgtaca tttcctcttc ccagaccaca        240
gactcaggcg tttatttctg tgctgtgggg agttctaacg actacaagct cagctttgga        300
gccggaacca cagtaactgt aagagca                                            327
```

```
<210> SEQ ID NO 863
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 863
```

Glu Ala Gln Val Thr Gln Asn Pro Arg Tyr Leu Ile Thr Val Thr Gly
1                5                  10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Pro Gly
                85                  90                  95

Thr Gly Gly Phe Ser Pro Leu His Phe Gly Asn Gly Thr Arg Leu Thr
            100                 105                 110

Val Thr

<210> SEQ ID NO 864
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 864
gaagcccaag tgacccagaa cccaagatac ctcatcacag tgactggaaa gaagttaaca        60
gtgacttgtt ctcagaatat gaaccatgag tatatgtcct ggtatcgaca agacccaggg       120
ctgggcttaa ggcagatcta ctattcaatg aatgttgagg tgactgataa gggagatgtt       180
cctgaagggt acaaagtctc tcgaaaagag aagaggaatt tcccccctgat cctggagtcg      240 cccagcccca accagacctc tctgtacttc tgtgccagca gtcccgggac agggggattt       300
tcacccctcc actttgggaa cgggaccagg ctcactgtga ca                         342

<210> SEQ ID NO 865
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 865

Gly Glu Ser Val Gly Leu His Leu Pro Thr Leu Ser Val Gln Glu Gly
1                5                  10                  15

Asp Asn Ser Ile Ile Asn Cys Ala Tyr Ser Asn Ser Ala Ser Asp Tyr
            20                  25                  30

Phe Ile Trp Tyr Lys Gln Glu Ser Gly Lys Gly Pro Gln Phe Ile Ile
        35                  40                  45

Asp Ile Arg Ser Asn Met Asp Lys Arg Gln Gly Gln Arg Val Thr Val
    50                  55                  60

Leu Leu Asn Lys Thr Val Lys His Leu Ser Leu Gln Ile Ala Ala Thr
65                  70                  75                  80

Gln Pro Gly Asp Ser Ala Val Tyr Phe Cys Ala Glu Asn Arg Gln Asp
                85                  90                  95

Asn Tyr Gly Gln Asn Phe Val Phe Gly Pro Gly Thr Arg Leu Ser Val
            100                 105                 110

Leu Pro

<210> SEQ ID NO 866
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 866
ggagagagtg tggggctgca tcttcctacc ctgagtgtcc aggagggtga caactctatt      60
atcaactgtg cttattcaaa cagcgcctca gactacttca tttggtacaa gcaagaatct     120
ggaaaaggtc ctcaattcat tatagacatt cgttcaaata tggacaaaag gcaaggccaa     180
agagtcaccg tttattgaa taagacagtg aaacatctct ctctgcaaat tgcagctact      240
caacctggag actcagctgt ctactttgt gcagagaata ggcaggataa ctatggtcag      300
aattttgtct ttggtcccgg aaccagattg tccgtgctgc cc                        342

<210> SEQ ID NO 867
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 867

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Trp
                85                  90                  95

Val Asn Thr Glu Ala Phe Phe Gly Gln Gly Thr Arg Leu Thr Val Val
            100                 105                 110

<210> SEQ ID NO 868
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 868
gaagcccaag tgacccagaa cccaagatac ctcatcacag tgactggaaa gaagttaaca      60
gtgacttgtt ctcagaatat gaaccatgag tatatgtcct ggtatcgaca agacccaggg     120
ctgggcttaa ggcagatcta ctattcaatg aatgttgagg tgactgataa gggagatgtt     180
cctgaagggt acaaagtctc tcgaaaagag aagaggaatt tccccctgat cctggagtcg     240

-continued

```
cccagcccca accagacctc tctgtacttc tgtgccagca gtttatgggt taacactgaa    300
gctttctttg gacaaggcac cagactcaca gttgta                               336
```

<210> SEQ ID NO 869
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 869

```
Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ser Thr Leu
65                  70                  75                  80

Arg Asp Ala Ala Val Tyr Tyr Cys Ile Leu Arg Pro Asp Ser Trp Gly
                85                  90                  95

Lys Phe Gln Phe Gly Ala Gly Thr Gln Val Val Val Thr Pro
            100                 105                 110
```

<210> SEQ ID NO 870
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 870

```
gatgctaaga ccacacagcc aaattcaatg gagagtaacg aagaagagcc tgttcacttg     60
ccttgtaacc actccacaat cagtggaact gattacatac attggtatcg acagcttccc    120
tcccagggtc cagagtacgt gattcatggt cttacaagca atgtgaacaa cagaatggcc    180
tctctggcaa tcgctgaaga cagaaagtcc agtaccttga tcctgcaccg ttctaccttg    240
agagatgctg ctgtgtacta ctgcatcctg cggcctgaca gctgggggaa gttccagttt    300
ggagcaggga cccaggttgt ggtcacccca                                      330
```

<210> SEQ ID NO 871
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 871

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30
```

-continued

```
Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Thr Val
                85                  90                  95

Arg Gln Gly Asn Tyr Gly Tyr Thr Phe Gly Ser Gly Thr Arg Leu Thr
                100                 105                 110

Val Val
```

```
<210> SEQ ID NO 872
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 872
gatgtgaaag taacccagag ctcgagatat ctagtcaaaa ggacgggaga gaaagttttt       60
ctggaatgtg tccaggatat ggaccatgaa aatatgttct ggtatcgaca agacccaggt      120
ctggggctac ggctgatcta tttctcatat gatgttaaaa tgaaagaaaa aggagatatt      180
cctgaggggt acagtgtctc tagagagaag aaggagcgct tctccctgat tctggagtcc      240
gccagcacca accagacatc tatgtacctc tgtgccagca gtaccgtgag gcaggggaac      300
tatggctaca ccttcggttc ggggaccagg ttaaccgttg ta                        342
```

```
<210> SEQ ID NO 873
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 873
```

```
Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Asn Thr Gly Thr Ala Ser
                85                  90                  95

Lys Leu Thr Phe Gly Thr Gly Thr Arg Leu Gln Val Thr Leu
                100                 105                 110
```

```
<210> SEQ ID NO 874
<211> LENGTH: 330
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 874
gatgctaaga ccacacagcc aaattcaatg gagagtaacg aagaagagcc tgttcacttg       60
ccttgtaacc actccacaat cagtggaact gattacatac attggtatcg acagcttccc      120
tcccagggtc cagagtacgt gattcatggt cttacaagca atgtgaacaa cagaatggcc      180
tctctggcaa tcgctgaaga cagaaagtcc agtaccttga tcctgcaccg tgctaccttg      240
agagatgctg ctgtgtacta ctgcatcctg aataccggca ctgccagtaa actcaccttt      300
gggactggaa caagacttca ggtcacgctc                                        330

<210> SEQ ID NO 875
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 875

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Ser
                85                  90                  95

Ser Asn Thr Glu Ala Phe Phe Gly Gln Gly Thr Arg Leu Thr Val Val
            100                 105                 110

<210> SEQ ID NO 876
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 876
gaagcccaag tgacccagaa cccaagatac ctcatcacag tgactggaaa gaagttaaca       60
gtgacttgtt ctcagaatat gaaccatgag tatatgtcct ggtatcgaca gacccaggg      120 ctgggcttaa ggcagatcta ctattcaatg aatgttgagg tgactgataa gggagatgtt      180
cctgaagggt acaaagtctc tcgaaaagag aagaggaatt tcccctgat cctggagtcg       240 cccagcccca accagacctc tctgtacttc tgtgccagca gtttatcgtc gaacactgaa       300
gctttctttg acaaggcac cagactcaca gttgta                                 336

<210> SEQ ID NO 877
```

```
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 877

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
                20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
        50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Arg Gly Thr Asp
                85                  90                  95

Lys Leu Ile Phe Gly Thr Gly Thr Arg Leu Gln Val Phe Pro
            100                 105                 110

<210> SEQ ID NO 878
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 878
cagaaggagg tggagcagaa ttctggaccc ctcagtgttc cagagggagc cattgcctct      60
ctcaactgca cttacagtga ccgaggttcc cagtccttct tctggtacag acaatattct     120
gggaaaagcc ctgagttgat aatgtccata tactccaatg gtgacaaaga agatggaagg     180
tttacagcac agctcaataa agccagccag tatgtttctc tgctcatcag agactcccag     240
cccagtgatt cagccaccta cctctgtgcc gtgaacagag gcaccgacaa gctcatcttt     300
gggactggga ccagattaca agtctttcca                                      330

<210> SEQ ID NO 879
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 879

Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
                20                  25                  30

Ser Trp Tyr Gln Gln Ala Leu Gly Gln Gly Pro Gln Phe Ile Phe Gln
            35                  40                  45

Tyr Tyr Glu Glu Glu Glu Arg Gln Arg Gly Asn Phe Pro Asp Arg Phe
        50                  55                  60
```

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Trp Thr
                85                  90                  95

Asp Tyr Gly Tyr Thr Phe Gly Ser Gly Thr Arg Leu Thr Val Val
            100                 105                 110

<210> SEQ ID NO 880
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 880
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120
caggggcccc agtttatctt tcagtattat gaggaggaag agagacagag aggcaacttc     180
cctgatcgat tctcaggtca ccagttccct aactatagct ctgagctgaa tgtgaacgcc     240
ttgttgctgg gggactcggc cctctatctc tgtgccagca gctggacaga ctatggctac     300
accttcggtt cggggaccag gttaaccgtt gta                                  333

<210> SEQ ID NO 881
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 881

Asp Ala Lys Thr Thr Gln Pro Asn Ser Met Glu Ser Asn Glu Glu Glu
1                   5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ser Thr Leu
65                  70                  75                  80

Arg Asp Ala Ala Val Tyr Tyr Cys Ile Leu Arg Pro Asp Ser Trp Gly
                85                  90                  95

Lys Phe Gln Phe Gly Ala Gly Thr Gln Val Val Val Thr Pro
            100                 105                 110

<210> SEQ ID NO 882
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 882
gatgctaaga ccacacagcc aaattcaatg gagagtaacg aagaagagcc tgttcacttg      60

-continued

```
ccttgtaacc actccacaat cagtggaact gattacatac attggtatcg acagcttccc      120
tcccagggtc cagagtacgt gattcatggt cttacaagca atgtgaacaa cagaatggcc      180
tctctggcaa tcgctgaaga cagaaagtcc agtaccttga tcctgcaccg ttctaccttg      240
agagatgctg ctgtgtacta ctgcatcctg cggcctgaca gctgggggaa attccagttt      300
ggagcaggga cccaggttgt ggtcacccca                                      330
```

<210> SEQ ID NO 883
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 883

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Trp Thr
                85                  90                  95

Asp Tyr Gly Tyr Thr Phe Gly Ser Gly Thr Arg Leu Thr Val Val
            100                 105                 110
```

<210> SEQ ID NO 884
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 884

```
gacgctggag tcacccaaag tcccacacac ctgatcaaaa cgagaggaca gcaagtgact       60
ctgagatgct ctcctaagtc tgggcatgac actgtgtcct ggtaccaaca ggccctgggt      120
caggggcccc agtttatctt tcagtattat gaggaggaag agagacagag aggcaacttc      180
cctgatcgat tctcaggtca ccagttccct aactatagct ctgagctgaa tgtgaacgcc      240
ttgttgctgg gggactcggc cctctatctc tgtgccagca gctggacaga ctatggctac      300
accttcggtt cggggaccag gttaaccgtt gta                                   333
```

<210> SEQ ID NO 885
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 885

```
Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
                20                  25                  30

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
        50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Gly Thr Ser Gly Thr
                85                  90                  95

Tyr Lys Tyr Ile Phe Gly Thr Gly Thr Arg Leu Lys Val Leu Ala
            100                 105                 110
```

<210> SEQ ID NO 886
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 886

```
acccagctgc tggagcagag ccctcagttt ctaagcatcc aagagggaga aaatctcact        60
gtgtactgca actcctcaag tgttttttcc agcttacaat ggtacagaca ggagcctggg       120
gaaggtcctg tcctcctggt gacagtagtt acgggtggag aagtgaagaa gctgaagaga       180
ctaacctttc agtttggtga tgcaagaaag gacagttctc tccacatcac tgcggcccag       240
cctggtgata caggcctcta cctctgtgca ggaggaacct caggaaccta caaatacatc       300
tttggaacag gcaccaggct gaaggtttta gca                                    333
```

<210> SEQ ID NO 887
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 887

```
Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
            35                  40                  45

Ser Met Asn Val Glu Val Thr Asp Lys Gly Asp Val Pro Glu Gly Tyr
        50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Pro Gly
                85                  90                  95

Thr Pro Asn Tyr Gly Tyr Thr Phe Gly Ser Gly Thr Arg Leu Thr Val
            100                 105                 110
```

Val

<210> SEQ ID NO 888
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 888
gaagcccaag tgacccagaa cccaagatac ctcatcacag tgactggaaa gaagttaaca      60
gtgacttgtt ctcagaatat gaaccatgag tatatgtcct ggtatcgaca agacccaggg     120
ctgggcttaa ggcagatcta ctattcaatg aatgttgagg tgactgataa gggagatgtt     180
cctgaagggt acaaagtctc tcgaaaagag aagaggaatt tccccctgat cctggagtcg     240
cccagcccca accagacctc tctgtacttc tgtgccagca gtcccgggac acccaactat     300
ggctacacct tcggttcggg gaccaggtta accgttgta                            339

<210> SEQ ID NO 889
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 889

Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
            20                  25                  30

Phe Phe Trp Tyr Arg Gln Asp Cys Arg Lys Glu Pro Lys Leu Leu Met
        35                  40                  45

Ser Val Tyr Ser Ser Gly Asn Glu Asp Gly Arg Phe Thr Ala Gln Leu
    50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys Val Val Asn Gly Gly Ser Gln Gly
                85                  90                  95

Asn Leu Ile Phe Gly Lys Gly Thr Lys Leu Ser Val Lys Pro
            100                 105                 110

<210> SEQ ID NO 890
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 890
cggaaggagg tggagcagga tcctggaccc ttcaatgttc cagagggagc cactgtcgct      60
ttcaactgta cttacagcaa cagtgcttct cagtctttct tctggtacag acaggattgc     120
aggaaagaac ctaagttgct gatgtccgta tactccagtg gtaatgaaga tggaaggttt     180
acagcacagc tcaatagagc cagccagtat atttccctgc tcatcagaga ctccaagctc     240

```
agtgattcag ccacctacct ctgtgtggtg aatggaggaa gccaaggaaa tctcatcttt      300
ggaaaaggca ctaaactctc tgttaaacca                                      330
```

<210> SEQ ID NO 891
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 891

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Val Gly
                85                  90                  95

Asp Tyr Gly Tyr Thr Phe Gly Ser Gly Thr Arg Leu Thr Val Val
            100                 105                 110
```

<210> SEQ ID NO 892
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 892

```
gacgctggag tcacccaaag tcccacacac ctgatcaaaa cgagaggaca gcaagtgact       60
ctgagatgct ctcctaagtc tgggcatgac actgtgtcct ggtaccaaca ggccctgggt      120
caggggcccc agtttatctt tcagtattat gaggaggaag agagacagag aggcaacttc      180
cctgatcgat tctcaggtca ccagttccct aactatagct ctgagctgaa tgtgaacgcc      240
ttgttgctgg gggactcggc cctctatctc tgtgccagca gcgtagggga ctatggctac      300
accttcggtt cggggaccag gttaaccgtt gta                                  333
```

<210> SEQ ID NO 893
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 893

```
Gly Glu Ser Val Gly Leu His Leu Pro Thr Leu Ser Val Gln Glu Gly
1               5                   10                  15

Asp Asn Ser Ile Ile Asn Cys Ala Tyr Ser Asn Ser Ala Ser Asp Tyr
            20                  25                  30
```

-continued

```
Phe Ile Trp Tyr Lys Gln Glu Ser Gly Lys Gly Pro Gln Phe Ile Ile
        35                  40                  45

Asp Ile Arg Ser Asn Met Asp Lys Arg Gln Gly Gln Arg Val Thr Val
    50                  55                  60

Leu Leu Asn Lys Thr Val Lys His Leu Ser Leu Gln Ile Ala Ala Thr
65                  70                  75                  80

Gln Pro Gly Asp Ser Ala Val Tyr Phe Cys Ala Glu Asn Asn Tyr Gly
                85                  90                  95

Gln Asn Phe Val Phe Gly Pro Gly Thr Arg Leu Ser Val Leu Pro
                100                 105                 110
```

<210> SEQ ID NO 894
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 894

```
ggagagagtg tggggctgca tcttcctacc ctgagtgtcc aggagggtga caactctatt       60
atcaactgtg cttattcaaa cagcgcctca gactacttca tttggtacaa gcaagaatct      120
ggaaaaggtc ctcaattcat tatagacatt cgttcaaata tggacaaaag gcaaggccaa      180
agagtcaccg tttattgaa  taagacagtg aaacatctct ctctgcaaat tgcagctact      240
caacctggag actcagctgt ctacttttgt gcagagaaca actatggtca gaattttgtc      300
tttggtcccg gaaccagatt gtccgtgctg ccc                                   333
```

<210> SEQ ID NO 895
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 895

```
Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Trp
                85                  90                  95

Asp Ser Ser Pro Leu His Phe Gly Asn Gly Thr Arg Leu Thr Val Thr
                100                 105                 110
```

<210> SEQ ID NO 896
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 896
gaagcccaag tgacccagaa cccaagatac ctcatcacag tgactggaaa gaagttaaca        60
gtgacttgtt ctcagaatat gaaccatgag tatatgtcct ggtatcgaca agacccaggg       120
ctgggcttaa ggcagatcta ctattcaatg aatgttgagg tgactgataa gggagatgtt       180
cctgaagggt acaaagtctc tcgaaaagag aagaggaatt ccccctgat cctggagtcg        240 cccagcccca accagacctc tctgtacttc tgtgccagca gtttatggga cagttcaccc       300
ctccactttg ggaacgggac caggctcact gtgaca                                 336

<210> SEQ ID NO 897
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 897

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Ala Gly Ser
                85                  90                  95

Ala Arg Gln Leu Thr Phe Gly Ser Gly Thr Gln Leu Thr Val Leu Pro
            100                 105                 110

<210> SEQ ID NO 898
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 898
gaccagcaag ttaagcaaaa ttcaccatcc ctgagcgtcc aggaaggaag aatttctatt       60
ctgaactgtg actatactaa cagcatgttt gattatttcc tatggtacaa aaaataccct      120
gctgaaggtc ctacattcct gatatctata agttccatta aggataaaaa tgaagatgga      180
agattcactg ttttcttaaa caaaagtgcc aagcacctct ctctgcacat tgtgccctcc      240
cagcctggag actctgcagt gtacttctgt gcagcaagcg ccggttctgc aaggcaactg      300
acctttggat ctgggacaca attgactgtt ttacct                                336

<210> SEQ ID NO 899
<211> LENGTH: 112
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 899

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Tyr
                85                  90                  95

Thr His Thr Glu Ala Phe Phe Gly Gln Gly Thr Arg Leu Thr Val Val
            100                 105                 110

<210> SEQ ID NO 900
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 900
gaagcccaag tgacccagaa cccaagatac ctcatcacag tgactggaaa gaagttaaca      60
gtgacttgtt ctcagaatat gaaccatgag tatatgtcct ggtatcgaca agacccaggg     120
ctgggcttaa ggcagatcta ctattcaatg aatgttgagg tgactgataa gggagatgtt     180
cctgaagggt acaaagtctc tcgaaaagag aagaggaatt tccccctgat cctggagtcg     240
cccagcccca accagacctc tctgtacttc tgtgccagca gtttatacac ccacactgaa     300
gctttctttg gacaaggcac cagactcaca gttgta                              336

<210> SEQ ID NO 901
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 901

Asp Ala Lys Thr Thr Gln Pro Pro Ser Met Asp Cys Ala Glu Gly Arg
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80
```

-continued

```
Arg Asp Thr Ala Val Tyr Tyr Cys Ile Val Arg Asp Thr Thr Ser Gly
                85                  90                  95

Thr Tyr Lys Tyr Ile Phe Gly Thr Gly Thr Arg Leu Lys Val Leu Ala
            100                 105                 110

<210> SEQ ID NO 902
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 902
gatgctaaga ccacccagcc cccctccatg gattgcgctg aaggaagagc tgcaaacctg      60
ccttgtaatc actctaccat cagtggaaat gagtatgtgt attggtatcg acagattcac     120
tcccaggggc cacagtatat cattcatggt ctaaaaaaca atgaaaccaa tgaaatggcc     180
tctctgatca tcacagaaga cagaaagtcc agcaccttga tcctgcccca cgctacgctg     240
agagacactg ctgtgtacta ttgcatcgtc agagacacta cctcaggaac ctacaaatac     300
atctttggaa caggcaccag gctgaaggtt ttagca                               336

<210> SEQ ID NO 903
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 903

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Ser
                85                  90                  95

Ser Thr Gly Phe Ser Pro Leu His Phe Gly Asn Gly Thr Arg Leu Thr
            100                 105                 110

Val Thr

<210> SEQ ID NO 904
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 904
gaagcccaag tgacccagaa cccaagatac ctcatcacag tgactggaaa gaagttaaca      60
```

```
gtgacttgtt ctcagaatat gaaccatgag tatatgtcct ggtatcgaca agacccaggg    120
ctgggcttaa ggcagatcta ctattcaatg aatgttgagg tgactgataa gggagatgtt    180
cctgaagggt acaaagtctc tcgaaaagag aagaggaatt tccccctgat cctggagtcg    240
cccagcccca accagacctc tctgtacttc tgtgccagca gtttatcctc gacaggtttt    300
tcacccctcc actttgggaa cgggaccagg ctcactgtga ca                        342
```

```
<210> SEQ ID NO 905
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 905

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
        50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Glu Gly Gly Gly Ser Gln
                85                  90                  95

Gly Asn Leu Ile Phe Gly Lys Gly Thr Lys Leu Ser Val Lys Pro
            100                 105                 110
```

```
<210> SEQ ID NO 906
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 906
acccagctgc tggagcagag ccctcagttt ctaagcatcc aagagggaga aaatctcact     60
gtgtactgca actcctcaag tgttttttcc agcttacaat ggtacagaca ggagcctggg    120
gaaggtcctg tcctcctggt gacagtagtt acgggtggag aagtgaagaa gctgaagaga    180
ctaacctttc agtttggtga tgcaagaaag gacagttctc tccacatcac tgcggcccag    240
cctggtgata caggcctcta cctctgtgca gagggggagg gaagccaagg aaatctcatc    300
tttggaaaag gcactaaact ctctgttaaa cca                                 333
```

```
<210> SEQ ID NO 907
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 907
```

---

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Trp Thr
                85                  90                  95

Asp Tyr Gly Tyr Thr Phe Gly Ser Gly Thr Arg Leu Thr Val Val
                100                 105                 110
```

<210> SEQ ID NO 908
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 908

```
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120
caggggcccc agtttatctt tcagtattat gaggaggaag agagacagag aggcaacttc     180
cctgatcgat tctcaggtca ccagttccct aactatagct ctgagctgaa tgtgaacgcc     240
ttgttgctgg gggactcggc cctctatctc tgtgccagca gctggacaga ctatggctac     300
accttcggtt cggggaccag gttaaccgtt gta                                  333
```

<210> SEQ ID NO 909
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 909

```
Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Ile Arg Ser Asn Asp
                85                  90                  95

Tyr Lys Leu Ser Phe Gly Ala Gly Thr Thr Val Thr Val Arg Ala
                100                 105                 110
```

```
<210> SEQ ID NO 910
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 910
acccagctgc tggagcagag ccctcagttt ctaagcatcc aagagggaga aaatctcact      60
gtgtactgca actcctcaag tgttttttcc agcttacaat ggtacagaca ggagcctggg     120
gaaggtcctg tcctcctggt gacagtagtt acgggtggag aagtgaagaa gctgaagaga     180
ctaacctttc agtttggtga tgcaagaaag gacagttctc tccacatcac tgcggcccag     240
cctggtgata caggcctcta cctctgtgca gggatacgtt ctaacgacta caagctcagc     300
tttggagccg gaaccacagt aactgtaaga gca                                  333

<210> SEQ ID NO 911
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 911

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Ser Trp
                85                  90                  95

Thr Ala His Thr Glu Ala Phe Phe Gly Gln Gly Thr Arg Leu Thr Val
            100                 105                 110

Val

<210> SEQ ID NO 912
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 912
gaagcccaag tgacccagaa cccaagatac ctcatcacag tgactggaaa gaagttaaca      60
gtgacttgtt ctcagaatat gaaccatgag tatatgtcct ggtatcgaca agacccaggg     120
ctgggcttaa ggcagatcta ctattcaatg aatgttgagg tgactgataa gggagatgtt     180
cctgaagggt acaaagtctc tcgaaaagag aagaggaatt tccccctgat cctggagtcg     240
cccagcccca accagacctc tctgtacttc tgtgccagca gttcctggac agcccacact     300
```

```
gaagctttct ttggacaagg caccagactc acagttgta                              339
```

<210> SEQ ID NO 913
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 913

```
Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Glu Asn Ser Gly Gly Gly
            85                  90                  95

Ala Asp Gly Leu Thr Phe Gly Lys Gly Thr His Leu Ile Ile Gln Pro
            100                 105                 110
```

<210> SEQ ID NO 914
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 914

```
acccagctgc tggagcagag ccctcagttt ctaagcatcc aagagggaga aaatctcact     60
gtgtactgca actcctcaag tgttttttcc agcttacaat ggtacagaca ggagcctggg    120
gaaggtcctg tcctcctggt gacagtagtt acgggtggag aagtgaagaa gctgaagaga    180
ctaacctttc agtttggtga tgcaagaaag gacagttctc tccacatcac tgcggcccag    240
cctggtgata caggcctcta cctctgtgca gaaaattcag gaggaggtgc tgacggactc    300
acctttggca aagggactca tctaatcatc cagccc                             336
```

<210> SEQ ID NO 915
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 915

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
```

```
              35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Phe Thr
                85                  90                  95

Asp Tyr Gly Tyr Thr Phe Gly Ser Gly Thr Arg Leu Thr Val Val
                100                 105                 110

<210> SEQ ID NO 916
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 916
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt     120
caggggcccc agtttatctt tcagtattat gaggaggaag agagacagag aggcaacttc     180
cctgatcgat tctcaggtca ccagttccct aactatagct ctgagctgaa tgtgaacgcc     240
ttgttgctgg gggactcggc cctctatctc tgtgccagca gcttcacaga ctatggctac     300
accttcggtt cggggaccag gttaaccgtt gta                                  333

<210> SEQ ID NO 917
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 917

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
                20                  25                  30

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Glu Asp Phe Gly Asn
                85                  90                  95

Glu Lys Leu Thr Phe Gly Thr Gly Thr Arg Leu Thr Ile Ile Pro
                100                 105                 110

<210> SEQ ID NO 918
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 918
acccagctgc tggagcagag tcctcagttt ctaagcatcc aagagggaga aaatctcact        60
gtgtactgca actcctcaag tgttttttcc agcttacaat ggtacagaca ggagcctggg        120
gaaggtcctg tcctcctggt gacagtagtt acgggtggag aagtgaagaa gctgaagaga        180
ctaacctttc agtttggtga tgcaagaaag gacagttctc tccacatcac tgcggcccag        240
cctggtgata caggcctcta cctctgtgca ggagaggact ttggaaatga gaaattaacc        300
tttgggactg gaacaagact caccatcata ccc                                     333

<210> SEQ ID NO 919
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 919

Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Trp Ala
                85                  90                  95

Asp Tyr Gly Tyr Thr Phe Gly Ser Gly Thr Arg Leu Thr Val Val
            100                 105                 110

<210> SEQ ID NO 920
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 920
gacgctggag tcacccaaag tcccacacac ctgatcaaaa cgagaggaca gcaagtgact        60
ctgagatgct ctcctaagtc tgggcatgac actgtgtcct ggtaccaaca ggccctgggt        120
caggggcccc agtttatctt tcagtattat gaggaggaag agagacagag aggcaacttc        180
cctgatcgat tctcaggtca ccagttccct aactatagct ctgagctgaa tgtgaacgcc        240
ttgttgctgg gggactcggc cctctatctc tgtgccagca gctgggcgga ttatggctac        300
accttcggtt cggggaccag gttaaccgtt gta                                     333

<210> SEQ ID NO 921
<211> LENGTH: 110
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 921

Ile Leu Asn Val Glu Gln Ser Pro Gln Ser Leu His Val Gln Glu Gly
1               5                   10                  15

Asp Ser Thr Asn Phe Thr Cys Ser Phe Pro Ser Ser Asn Phe Tyr Ala
                20                  25                  30

Leu His Trp Tyr Arg Trp Glu Thr Ala Lys Ser Pro Glu Ala Leu Phe
            35                  40                  45

Val Met Thr Leu Asn Gly Asp Glu Lys Lys Lys Gly Arg Ile Ser Ala
        50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Phe Leu Thr Gly Asn
                85                  90                  95

Gln Phe Tyr Phe Gly Thr Gly Thr Ser Leu Thr Val Ile Pro
            100                 105                 110

<210> SEQ ID NO 922
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 922
atactgaacg tggaacaaag tcctcagtca ctgcatgttc aggagggaga cagcaccaat      60
ttcacctgca gcttcccttc cagcaatttt tatgccttac actggtacag atgggaaact     120
gcaaaaagcc ccgaggcctt gtttgtaatg actttaaatg gggatgaaaa gaagaaagga     180
cgaataagtg ccactcttaa taccaaggag ggttacagct atttgtacat caaaggatcc     240
cagcctgaag actcagccac atacctctgt gcctttctca ccggtaacca gttctatttt     300
gggacaggga caagtttgac ggtcattcca                                       330

<210> SEQ ID NO 923
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 923

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Thr Val

-continued

```
                85                  90                  95

Arg Gln Gly Asn Tyr Gly Tyr Thr Phe Gly Ser Gly Thr Arg Leu Thr
            100                 105                 110

Val Val
```

```
<210> SEQ ID NO 924
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 924
gatgtgaaag taacccagag ctcgagatat ctagtcaaaa ggacgggaga gaaagttttt      60
ctggaatgtg tccaggatat ggaccatgaa aatatgttct ggtatcgaca agacccaggt     120
ctggggctac ggctgatcta tttctcatat gatgttaaaa tgaaagaaaa aggagatatt     180
cctgaggggt acagtgtctc tagagagaag aaggagcgct tctccctgat tctggagtcc     240
gccagcacca accagacatc tatgtacctc tgtgccagca gtaccgtgag gcaggggaac     300
tatggctaca ccttcggttc ggggaccagg ttaaccgttg ta                        342
```

```
<210> SEQ ID NO 925
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 925

Asp Gln Gln Val Lys Gln Ser Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Ala Gly Ser
                85                  90                  95

Ala Arg Gln Leu Thr Phe Gly Ser Gly Thr Gln Leu Thr Val Leu Pro
            100                 105                 110
```

```
<210> SEQ ID NO 926
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 926
gaccagcaag ttaagcaaag ttcaccatcc ctgagcgtcc aggaaggaag aatttctatt      60
ctgaactgtg actatactaa cagcatgttt gattatttcc tatggtacaa aaaataccct     120
```

```
gctgaaggtc ctacattcct gatatctata agttccatta aggataaaaa tgaagatgga       180
agattcactg ttttcttaaa caaaagtgcc aagcacctct ctctgcacat tgtgccctcc       240
cagcctggag actctgcagt gtacttctgt gcagcaagcg ccggttctgc aaggcaactg       300
acctttggat ctgggacaca attgactgtt ttacct                                336
```

```
<210> SEQ ID NO 927
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 927

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Trp
                85                  90                  95

Ser Asn Thr Glu Ala Phe Phe Gly Gln Gly Thr Arg Leu Thr Val Val
            100                 105                 110
```

```
<210> SEQ ID NO 928
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 928
gaagcccaag tgacccagaa cccaagatac ctcatcacag tgactggaaa gaagttaaca        60
gtgacttgtt ctcagaatat gaaccatgag tatatgtcct ggtatcgaca agacccaggg       120
ctgggcttaa ggcagatcta ctattcaatg aatgttgagg tgactgataa gggagatgtt       180
cctgaagggt acaaagtctc tcgaaaagag aagaggaatt tccccctgat cctggagtcg       240
cccagcccca accagacctc tctgtacttc tgtgccagca gtttatggtc gaacactgaa       300
gctttctttg gacaaggcac cagactcaca gttgta                                336
```

```
<210> SEQ ID NO 929
<211> LENGTH: 9
<212> TYPE: PRT
<213> ORGANISM: Homo sapiens

<400> SEQUENCE: 929

Arg Leu Asp Gln Leu Leu Arg His Val
1               5
```

```
<210> SEQ ID NO 930
```

```
<211> LENGTH: 9
<212> TYPE: PRT
<213> ORGANISM: Homo sapiens

<400> SEQUENCE: 930

Ser Leu Leu Gln His Leu Ile Gly Leu
1               5

<210> SEQ ID NO 931
<211> LENGTH: 2082
<212> TYPE: DNA
<213> ORGANISM: Homo sapiens

<400> SEQUENCE: 931
acgcagcggc tagggcgctt agctgagcca ttgtctcgtt ctttccttcc agcaacttcg      60
cggtgtggtg aactctctga ggaaaaacca tttttgattat tactctcaga cgtgcgtggc     120
aacaagtgac tgagacctag aaatccaagc gttggaggtc ctgaggccag cctaagtcgc     180
ttcaaaatgg aacgaaggcg tttgtggggt tccattcaga gccgatacat cagcatgagt     240
gtgtggacaa gcccacggag acttgtggag ctggcagggc agagcctgct gaaggatgag     300
gccctggcca ttgccgccct ggagttgctg cccagggagc tcttcccgcc actcttcatg     360
gcagcctttg acgggagaca cagccagacc ctgaaggcaa tggtgcaggc ctggcccttc     420
acctgcctcc ctctgggagt gctgatgaag ggacaacatc ttcacctgga gaccttcaaa     480
gctgtgcttg atggacttga tgtgctcctt gcccaggagg ttcgccccag gaggtggaaa     540
cttcaagtgc tggatttacg gaagaactct catcaggact tctggactgt atggtctgga     600
aacagggcca gtctgtactc atttccagag ccagaagcag ctcagcccat gacaaagaag     660
cgaaaagtag atggtttgag cacagaggca gagcagccct tcattccagt agaggtgctc     720
gtagacctgt tcctcaagga aggtgcctgt gatgaattgt tctcctacct cattgagaaa     780
gtgaagcgaa agaaaaatgt actacgcctg tgctgtaaga agctgaagat ttttgcaatg     840
cccatgcagg atatcaagat gatcctgaaa atggtgcagc tggactctat tgaagatttg     900
gaagtgactt gtacctggaa gctacccacc ttggcgaaat tttctcctta cctgggccag     960
atgattaatc tgcgtagact cctcctctcc cacatccatg catcttccta catttccccg    1020
gagaaggaag agcagtatat cgcccagttc acctctcagt tcctcagtct gcagtgcctg    1080
caggctctct atgtggactc tttatttttc cttagaggcc gcctggatca gttgctcagg    1140
cacgtgatga accccttgga aaccctctca ataactaact gccggctttc ggaaggggat    1200
gtgatgcatc tgtcccagag tcccagcgtc agtcagctaa gtgtcctgag tctaagtggg    1260
gtcatgctga ccgatgtaag tcccgagccc ctccaagctc tgctggagag agcctctgcc    1320
accctccagg acctggtctt tgatgagtgt gggatcacgg atgatcagct ccttgccctc    1380
ctgccttccc tgagccactg ctcccagctt acgaccttaa gcttctacgg gaattccatc    1440
tccatatctg ccctgcagag tctcctgcag cacctcatcg ggctgagcaa tctgacccac    1500
gtgctgtatc ctgtcccccct ggagagttat gaggacatcc atggtaccct ccacctggag    1560
aggcttgcct atctgcatgc caggctcagg gagttgctgt gtgagttggg gcggcccagc    1620
atggtctggc ttagtgccaa cccctgtcct cactgtgggg acagaacctt ctatgacccg    1680
gagcccatcc tgtgcccctg tttcatgcct aattagctgg gtgcacatat caaatgcttc    1740
attctgcata cttggacact aaagccagga tgtgcatgca tcttgaagca acaaagcagc    1800
cacagtttca gacaaatgtt cagtgtgagt gaggaaaaca tgttcagtga ggaaaaaaca    1860
```

-continued

```
ttcagacaaa tgttcagtga ggaaaaaaag gggaagttgg gggtaggcag atgttgactt   1920
gaggagttaa tgtgatcttt ggggagatac atcttataga gttagaaata gaatctgaat   1980
ttctaaaggg agattctggc ttgggaagta catgtaggag ttaatccctg tgtagactgt   2040
tgtaaagaaa ctgttgaaaa taaagagaag caatgtgaag ca                       2082

<210> SEQ ID NO 932
<211> LENGTH: 2061
<212> TYPE: DNA
<213> ORGANISM: Homo sapiens

<400> SEQUENCE: 932
acgcagcggc tagggcgctt agctgagcca ttgtctcgtt ctttccttcc agcaacttcg     60
cggtgtggtg aactctctga ggaaaaacac gtgcgtggca acaagtgact gagacctaga    120
aatccaagcg ttggaggtcc tgaggccagc ctaagtcgct tcaaaatgga acgaaggcgt    180 ttgtgggggtt ccattcagag ccgatacatc agcatgagtg tgtggacaag cccacggaga   240
cttgtggagc tggcagggca gagcctgctg aaggatgagg ccctggccat tgccgccctg    300
gagttgctgc ccagggagct cttcccgcca ctcttcatgg cagcctttga cgggagacac    360
agccagaccc tgaaggcaat ggtgcaggcc tggcccttca cctgcctccc tctgggagtg    420
ctgatgaagg dacaacatct tcacctggag accttcaaag ctgtgcttga tggacttgat    480
gtgctccttg cccaggaggt tcgccccagg aggtggaaac ttcaagtgct ggatttacgg    540
aagaactctc atcaggactt ctggactgta tggtctggaa acagggccag tctgtactca    600
tttccagagc cagaagcagc tcagcccatg acaaagaagc gaaaagtaga tggtttgagc    660
acagaggcag agcagccctt cattccagta gaggtgctcg tagacctgtt cctcaaggaa    720
ggtgcctgtg atgaattgtt ctcctacctc attgagaaag tgaagcgaaa gaaaaatgta    780
ctacgcctgt gctgtaagaa gctgaagatt tttgcaatgc ccatgcagga tatcaagatg    840
atcctgaaaa tggtgcagct ggactctatt gaagatttgg aagtgacttg tacctggaag    900
ctacccacct tggcgaaatt ttctccttac ctgggccaga tgattaatct gcgtagactc    960
ctcctctccc acatccatgc atcttcctac atttccccgg agaaggaaga gcagtatatc   1020
gcccagttca cctctcagtt cctcagtctg cagtgcctgc aggctctcta tgtggactct   1080 ttattttcc ttagaggccg cctggatcag ttgctcaggc acgtgatgaa ccccttggaa    1140
accctctcaa taactaactg ccggcttcg gaaggggatg tgatgcatct gtcccagagt    1200
cccagcgtca gtcagctaag tgtcctgagt ctaagtgggg tcatgctgac cgatgtaagt    1260
cccgagcccc tccaagctct gctggagaga gcctctgcca ccctccagga cctggtcttt    1320
gatgagtgtg ggatcacgga tgatcagctc cttgccctcc tgccttccct gagccactgc    1380
tcccagctta cgaccttaag cttctacggg aattccatct ccatatctgc cctgcagagt   1440
ctcctgcagc acctcatcgg gctgagcaat ctgacccacg tgctgtatcc tgtcccctg    1500 gagagttatg aggacatcca tggtaccctc cacctggaga ggcttgccta tctgcatgcc   1560
aggctcaggg agttgctgtg tgagttgggg cggcccagca tggtctggct tagtgccaac   1620
ccctgtcctc actgtgggga cagaaccttc tatgacccgg agccatcct gtgcccctgt    1680 ttcatgccta attagctggg tgcacatatc aaatgcttca ttctgcatac ttggacacta   1740
aagccaggat gtgcatgcat cttgaagcaa caaagcagcc acagtttcag acaaatgttc   1800
agtgtgagtg aggaaaacat gttcagtgag gaaaaaacat tcagacaaat gttcagtgag   1860
gaaaaaaagg ggaagttggg ggtaggcaga tgttgacttg aggagttaat gtgatctttg   1920
```

-continued

```
gggagataca tcttatagag ttagaaatag aatctgaatt tctaaaggga gattctggct    1980
tgggaagtac atgtaggagt taatccctgt gtagactgtt gtaaagaaac tgttgaaaat    2040
aaagagaagc aatgtgaagc a                                              2061

<210> SEQ ID NO 933
<211> LENGTH: 2206
<212> TYPE: DNA
<213> ORGANISM: Homo sapiens

<400> SEQUENCE: 933
acagctcccc cgcagccaga agccgggcct gcagcgcctc agcaccgctc cgggacaccc      60
cacccgcttc ccaggcgtga cctgtcaaca ggtctgtatt ggcgacaaaa ggagcagccc     120
tgaatgtagg gaaagcaggg cggagtcctc tgcaggctcg ggggagggga ggggcgtgaa     180
tgcgtggatt tctgtggaga gtggaaacac ggggagtcga ggggagcatg cgcgggcctc     240
agaaagttct gggaaaccga ctcccgggag cagggaggaa cgcgcgctcc agagacaact     300
tcgcggtgtg gtgaactctc tgaggaaaaa cggttccatt cagagccgat acatcagcat     360
gagtgtgtgg acaagcccac ggagacttgt ggagctggca gggcagagcc tgctgaagga     420
tgaggccctg gccattgccg ccctggagtt gctgcccagg gagctcttcc cgccactctt     480
catggcagcc tttgacggga gacacagcca gaccctgaag gcaatggtgc aggcctggcc     540
cttcacctgc ctccctctgg gagtgctgat gaagggacaa catcttcacc tggagacctt     600
caaagctgtg cttgatggac ttgatgtgct ccttgcccag gaggttcgcc ccaggaggtg     660
gaaacttcaa gtgctggatt tacggaagaa ctctcatcag gacttctgga ctgtatggtc     720
tggaaacagg gccagtctgt actcatttcc agagccagaa gcagctcagc ccatgacaaa     780
gaagcgaaaa gtagatggtt tgagcacaga ggcagagcag cccttcattc cagtagaggt     840
gctcgtagac ctgttcctca aggaaggtgc ctgtgatgaa ttgttctcct acctcattga     900
gaaagtgaag cgaaagaaaa atgtactacg cctgtgctgt aagaagctga agattttttgc     960 aatgcccatg caggatatca agatgatcct gaaaatggtg cagctggact ctattgaaga    1020
tttggaagtg acttgtacct ggaagctacc caccttggcg aaattttctc cttacctggg    1080
ccagatgatt aatctgcgta gactcctcct ctcccacatc catgcatctt cctacatttc    1140
cccggagaag gaagagcagt atatcgccca gttcacctct cagttcctca gtctgcagtg    1200
cctgcaggct ctctatgtgg actctttatt tttccttaga ggccgcctgg atcagttgct    1260
caggcacgtg atgaacccct ggaaaccct ctcaataact aactgccggc tttcggaagg    1320
ggatgtgatg catctgtccc agagtcccag cgtcagtcag ctaagtgtcc tgagtctaag    1380
tggggtcatg ctgaccgatg taagtcccga gcccctccaa gctctgctgg agagagcctc    1440
tgccaccctc caggacctgg tctttgatga gtgtgggatc acggatgatc agctccttgc    1500
cctcctgcct tccctgagcc actgctccca gcttacgacc ttaagcttct acgggaattc    1560
catctccata tctgccctgc agagtctcct gcagcacctc atcgggctga gcaatctgac    1620
ccacgtgctg tatcctgtcc ccctggagag ttatgaggac atccatggta ccctccacct    1680
ggagaggctt gcctatctgc atgccaggct caggagttg ctgtgtgagt tggggcggcc    1740
cagcatggtc tggcttagtg ccaacccctg tcctcactgt ggggacagaa ccttctatga    1800 cccgagccc atcctgtgcc cctgtttcat gcctaattag ctgggtgcac atatcaaatg    1860
cttcattctg catacttgga cactaaagcc aggatgtgca tgcatcttga agcaacaaag    1920
```

```
cagccacagt ttcagacaaa tgttcagtgt gagtgaggaa aacatgttca gtgaggaaaa        1980
aacattcaga caaatgttca gtgaggaaaa aaaggggaag ttgggggtag gcagatgttg        2040
acttgaggag ttaatgtgat ctttggggag atacatctta tagagttaga aatagaatct        2100
gaatttctaa agggagattc tggcttggga agtacatgta ggagttaatc cctgtgtaga        2160
ctgttgtaaa gaaactgttg aaaataaaga gaagcaatgt gaagca                      2206

<210> SEQ ID NO 934
<211> LENGTH: 1963
<212> TYPE: DNA
<213> ORGANISM: Homo sapiens

<400> SEQUENCE: 934
acgcagcggc tagggcgctt agctgagcca ttgtctcgtt ctttccttcc agcaacttcg          60
cggtgtggtg aactctctga ggaaaaacgg ttccattcag agccgataca tcagcatgag         120
tgtgtggaca gcccacggga gacttgtgga gctggcaggg cagagcctgc tgaaggatga         180
ggccctggcc attgccgccc tggagttgct gcccaggggg ctcttccccgc cactcttcat        240 ggcagccttt gacgggagac acagccagac cctgaaggca atggtgcagg cctggcccctt        300 cacctgcctc cctctgggag tgctgatgaa gggacaacat cttcacctgg agaccttcaa         360
agctgtgctt gatggacttg atgtgctcct tgcccaggag gttcgcccca ggaggtggaa         420
acttcaagtg ctggatttac ggaagaactc tcatcaggac ttctggactg tatggtctgg         480
aaacagggcc agtctgtact catttccaga gccagaagca gctcagccca tgacaaagaa         540
gcgaaaagta gatggtttga gcacagaggc agagcagccc ttcattccag tagaggtgct         600
cgtagacctg ttcctcaagg aaggtgcctg tgatgaattg ttctcctacc tcattgagaa         660
agtgaagcga aagaaaaatg tactacgcct gtgctgtaag aagctgaaga tttttgcaat         720
gcccatgcag gatatcaaga tgatcctgaa aatggtgcag ctggactcta ttgaagattt        780
ggaagtgact tgtacctgga agctacccac cttggcgaaa ttttctcctt acctgggcca        840
gatgattaat ctgcgtagac tcctcctctc ccacatccat gcatcttcct acatttcccc        900
ggagaaggaa gagcagtata tcgcccagtt cacctctcag ttcctcagtc tgcagtgcct         960
gcaggctctc tatgtggact ctttatttt cccttagaggc cgcctggatc agttgctcag       1020
gcacgtgatg aaccccttgg aaaccctctc aataactaac tgccggcttt cggaagggga        1080
tgtgatgcat ctgtcccaga gtcccagcgt cagtcagcta agtgtcctga gtctaagtgg        1140
ggtcatgctg accgatgtaa gtcccgagcc cctccaagct ctgctggaga gagcctctgc        1200
caccctccag gacctggtct ttgatgagtg tgggatcacg gatgatcagc tccttgccct        1260
cctgccttcc ctgagccact gctcccagct tacgacctta agcttctacg ggaattccat       1320
ctccatatct gccctgcaga gtctcctgca gcacctcatc gggctgagca atctgaccca       1380
cgtgctgtat cctgtccccc tggagagtta tgaggacatc catggtaccc tccacctgga       1440
gaggcttgcc tatctgcatg ccaggctcag ggagttgctg tgtgagttgg ggcggcccag        1500
catggtctgg cttagtgcca acccctgtcc tcactgtggg gacagaacct tctatgaccc       1560
ggagcccatc ctgtgcccct gtttcatgcc taattagctg ggtgcacata tcaaatgctt        1620
cattctgcat acttggacac taaagccagg atgtgcatgc atcttgaagc aacaaagcag        1680
ccacagtttc agacaaatgt tcagtgtgag tgaggaaaac atgttcagtg aggaaaaaac       1740
attcagacaa atgttcagtg aggaaaaaaa ggggaagttg ggggtaggca gatgttgact        1800
tgaggagtta atgtgatctt ggggagagata catcttatag agttagaaat agaatctgaa       1860
```

```
tttctaaagg gagattctgg cttgggaagt acatgtagga gttaatccct gtgtagactg      1920
ttgtaaagaa actgttgaaa ataaagagaa gcaatgtgaa gca                        1963

<210> SEQ ID NO 935
<211> LENGTH: 1980
<212> TYPE: DNA
<213> ORGANISM: Homo sapiens

<400> SEQUENCE: 935
agacgcaaaa gcccacactt ccagtggtgt cagagagtat gagctccagg aggctttgat        60
ctcactgccc catgggcttg ggccattagg gggttccatt cagagccgat acatcagcat       120
gagtgtgtgg acaagcccac ggagacttgt ggagctggca gggcagagcc tgctgaagga       180
tgaggccctg gccattgccg ccctggagtt gctgcccagg gagctcttcc cgccactctt       240
catggcagcc tttgacggga gacacagcca gaccctgaag gcaatggtgc aggcctggcc       300
cttcacctgc ctccctctgg gagtgctgat gaagggacaa catcttcacc tggagacctt       360
caaagctgtg cttgatggac ttgatgtgct ccttgcccag gaggttcgcc ccaggaggtg       420
gaaacttcaa gtgctggatt tacggaagaa ctctcatcag gacttctgga ctgtatggtc       480
tggaaacagg gccagtctgt actcatttcc agagccagaa gcagctcagc ccatgacaaa       540
gaagcgaaaa gtagatggtt tgagcacaga ggcagagcag cccttcattc cagtagaggt       600
gctcgtagac ctgttcctca aggaaggtgc ctgtgatgaa ttgttctcct acctcattga       660
gaaagtgaag cgaaagaaaa atgtactacg cctgtgctgt aagaagctga agatttttgc       720
aatgcccatg caggatatca agatgatcct gaaaatggtg cagctggact ctattgaaga       780
tttggaagtg acttgtacct ggaagctacc caccttggcg aaattttctc cttacctggg       840
ccagatgatt aatctgcgta gactcctcct ctcccacatc catgcatctt cctacatttc       900
cccggagaag gaagagcagt atatcgccca gttcacctct cagttcctca gtctgcagtg       960
cctgcaggct ctctatgtgg actctttatt tttccttaga ggccgcctgg atcagttgct      1020
caggcacgtg atgaaccect tggaaaccct ctcaataact aactgccggc tttcggaagg      1080
ggatgtgatg catctgtccc agagtcccag cgtcagtcag ctaagtgtcc tgagtctaag      1140
tggggtcatg ctgaccgatg taagtcccga gccctccaa gctctgctgg agagagcctc       1200
tgccaccctc caggacctgg tctttgatga gtgtgggatc acggatgatc agctccttgc      1260
cctcctgcct tccctgagcc actgctccca gcttacgacc ttaagcttct acgggaattc      1320
catctccata tctgccctgc agagtctcct gcagcacctc atcgggctga gcaatctgac      1380
ccacgtgctg tatcctgtcc ccctggagag ttatgaggac atccatggta ccctccacct      1440
ggagaggctt gcctatctgc atgccaggct cagggagttg ctgtgtgagt gggggcggcc      1500
cagcatggtc tggcttagtg ccaacccctg tcctcactgt ggggacagaa ccttctatga      1560
cccggagccc atcctgtgcc cctgtttcat gcctaattag ctgggtgcac atatcaaatg      1620
cttcattctg catacttgga cactaaagcc aggatgtgca tgcatcttga agcaacaaag      1680
cagccacagt ttcagacaaa tgttcagtgt gagtgaggaa aacatgttca gtgaggaaaa      1740
aacattcaga caaatgttca gtgaggaaaa aaagggggaag ttgggggtag gcagatgttg      1800
acttgaggag ttaatgtgat ctttggggag atacatctta tagagttaga aatagaatct      1860
gaatttctaa agggagattc tggcttggga agtacatgta ggagttaatc cctgtgtaga      1920
ctgttgtaaa gaaactgttg aaaataaaga gaagcaatgt gaagcacctg gaaaaaaaaa      1980
```

-continued

<210> SEQ ID NO 936
<211> LENGTH: 2242
<212> TYPE: DNA
<213> ORGANISM: Homo sapiens

<400> SEQUENCE: 936

```
aaaagcacca gtgggtgatc aggcccagga taggaatcat ccctaagcag atccttaaat       60
gccaaatata acttcaattt tttgtgacgg aaaatgtatt tgtgcactgt gcctagcatg      120
gaaatagaga aaaactgagt ctaattgata ggcctgattg catctcgctg accagaatct      180
ctgtacctga gcagcttagg ggcaagaaag aacagctgtt ttcttgaagt gtggaaacat      240
tagtaatact taggaagggg ctggccattg gagattatgt ttgtggtaaa ggcctgacct      300
gctgcttgtg aacagcccca gtgtggaaga ggacacctaa ccataaagag aagggttcca      360
ttcagagccg atacatcagc atgagtgtgt ggacaagccc acggagactt gtggagctgg      420
cagggcagag cctgctgaag gatgaggccc tggccattgc cgccctggag ttgctgccca      480
gggagctctt cccgccactc ttcatggcag cctttgacgg gagacacagc cagaccctga      540
aggcaatggt gcaggcctgg cccttcacct gcctccctct gggagtgctg atgaagggac      600
aacatcttca cctggagacc ttcaaagctg tgcttgatgg acttgatgtg ctccttgccc      660
aggaggttcg ccccaggagg tggaaacttc aagtgctgga tttacggaag aactctcatc      720
aggacttctg gactgtatgg tctggaaaca gggccagtct gtactcattt ccagagccag      780
aagcagctca gcccatgaca aagaagcgaa aagtagatgg tttgagcaca gaggcagagc      840
agcccttcat tccagtagag gtgctcgtag acctgttcct caaggaaggt gcctgtgatg      900
aattgttctc ctacctcatt gagaaagtga agcgaaagaa aaatgtacta cgcctgtgct      960
gtaagaagct gaagattttt gcaatgccca tgcaggatat caagatgatc ctgaaaatgg     1020
tgcagctgga ctctattgaa gatttggaag tgacttgtac ctggaagcta cccaccttgg     1080
cgaaattttc tccttacctg ggccagatga ttaatctgcg tagactcctc ctctcccaca     1140
tccatgcatc ttcctacatt tccccggaga aggaagagca gtatatcgcc cagttcacct     1200
ctcagttcct cagtctgcag tgcctgcagg ctctctatgt ggactcttta tttttcctta     1260
gaggccgcct ggatcagttg ctcaggcacg tgatgaaccc cttggaaacc ctctcaataa     1320
ctaactgccg gctttcggaa ggggatgtga tgcatctgtc ccagagtccc agcgtcagtc     1380
agctaagtgt cctgagtcta agtggggtca tgctgaccga tgtaagtccc gagcccctcc     1440
aagctctgct ggagagagcc tctgccaccc tccaggacct ggtctttgat gagtgtggga     1500
tcacggatga tcagctcctt gccctcctgc cttccctgag ccactgctcc cagcttacga     1560
ccttaagctt ctacgggaat tccatctcca tatctgccct gcagagtctc ctgcagcacc     1620
tcatcgggct gagcaatctg acccacgtgc tgtatcctgt ccccctggag agttatgagg     1680
acatccatgg taccctccac ctggagaggc ttgcctatct gcatgccagg ctcagggagt     1740
tgctgtgtga gttggggcgg cccagcatgg tctggcttag tgccaacccc tgtcctcact     1800
gtggggacag aaccttctat gacccggagc ccatcctgtg cccctgtttc atgcctaatt     1860
agctgggtgc acatatcaaa tgcttcattc tgcatacttg gacactaaag ccaggatgtg     1920
catgcatctt gaagcaacaa agcagccaca gtttcagaca aatgttcagt gtgagtgagg     1980
aaaacatgtt cagtgaggaa aaaacattca gacaaatgtt cagtgaggaa aaaaaggggga     2040 agttgggggt aggcagatgt tgacttgagg agttaatgtg atctttgggg agatacatct     2100
tatagagtta gaaatagaat ctgaatttct aaagggagat tctggcttgg gaagtacatg     2160
```

```
taggagttaa tccctgtgta gactgttgta aagaaactgt tgaaaataaa gagaagcaat    2220
gtgaagcacc tggaaaaaaa aa                                              2242

<210> SEQ ID NO 937
<211> LENGTH: 2121
<212> TYPE: DNA
<213> ORGANISM: Homo sapiens

<400> SEQUENCE: 937
acagctcccc cgcagccaga agccgggcct gcagcgcctc agcaccgctc cgggacaccc      60
cacccgcttc ccaggcgtga cctgtcaaca gcaacttcgc ggtgtggtga actctctgag     120
gaaaaaccat tttgattatt actctcagac gtgcgtggca acaagtgact gagacctaga     180
aatccaagcg ttggaggtcc tgaggccagc ctaagtcgct tcaaaatgga acgaaggcgt     240 ttgtgggggtt ccattcagag ccgatacatc agcatgagtg tgtggacaag cccacggaga    300 cttgtgagc tggcagggca gagcctgctg aaggatgagg ccctggccat tgccgccctg      360
gagttgctgc ccagggagct cttcccgcca ctcttcatgg cagcctttga cgggagacac     420
agccagaccc tgaaggcaat ggtgcaggcc tggcccttca cctgcctccc tctgggagtg     480
ctgatgaagg gacaacatct tcacctggag accttcaaag ctgtgcttga tggacttgat     540
gtgctccttg cccaggaggt tcgccccagg aggtggaaac ttcaagtgct ggatttacgg     600
aagaactctc atcaggactt ctggactgta tggtctggaa acagggccag tctgtactca     660
tttccagagc cagaagcagc tcagcccatg acaaagaagc gaaaagtaga tggtttgagc     720
acagaggcag agcagcccct cattccagta gaggtgctcg tagacctgtt cctcaaggaa     780
ggtgcctgtg atgaattgtt ctcctacctc attgagaaag tgaagcgaaa gaaaaatgta     840
ctacgcctgt gctgtaagaa gctgaagatt tttgcaatgc ccatgcagga tatcaagatg     900
atcctgaaaa tggtgcagct ggactctatt gaagatttgg aagtgacttg tacctggaag     960
ctacccacct tggcgaaatt ttctccttac ctgggccaga tgattaatct gcgtagactc    1020
ctcctctccc acatccatgc atcttcctac atttcccgg agaaggaaga gcagtatatc     1080
gcccagttca cctctcagtt cctcagtctg cagtgcctgc aggctctcta tgtggactct    1140 ttattttttcc ttagaggccg cctggatcag ttgctcaggc acgtgatgaa ccccttggaa    1200
accctctcaa taactaactg ccggctttcg gaaggggatg tgatgcatct gtcccagagt    1260
cccagcgtca gtcagctaag tgtcctgagt ctaagtgggg tcatgctgac cgatgtaagt    1320
cccgagcccc tccaagctct gctggagaga gcctctgcca ccctccagga cctggtcttt    1380
gatgagtgtg ggatcacgga tgatcagctc cttgccctcc tgccttccct gagccactgc    1440
tcccagctta cgaccttaag cttctacggg aattccatct ccatatctgc cctgcagagt    1500
ctcctgcagc acctcatcgg gctgagcaat ctgacccacg tgctgtatcc tgtccccctg    1560
gagagttatg aggacatcca tggtaccctc cacctggaga ggcttgccta tctgcatgcc    1620
aggctcaggg agttgctgtg tgagttgggg cggcccagca tggtctggct tagtgccaac    1680
ccctgtcctc actgtgggga cagaaccttc tatgacccgg agcccatcct gtgcccctgt    1740
ttcatgccta attagctggg tgcacatatc aaatgcttca ttctgcatac ttggacacta    1800
aagccaggat gtgcatgcat cttgaagcaa caaagcagcc acagtttcag acaaatgttc    1860
agtgtgagtg aggaaaacat gttcagtgag gaaaaaacat tcagacaaat gttcagtgag    1920
gaaaaaaagg ggaagttggg ggtaggcaga tgttgacttg aggagttaat gtgatctttg    1980
```

-continued

```
gggagataca tcttatagag ttagaaatag aatctgaatt tctaaaggga gattctggct    2040
tgggaagtac atgtaggagt taatccctgt gtagactgtt gtaaagaaac tgttgaaaat    2100
aaagagaagc aatgtgaagc a                                              2121

<210> SEQ ID NO 938
<211> LENGTH: 2304
<212> TYPE: DNA
<213> ORGANISM: Homo sapiens

<400> SEQUENCE: 938
acagctcccc cgcagccaga agccgggcct gcagcgcctc agcaccgctc cgggacaccc      60
cacccgcttc ccaggcgtga cctgtcaaca ggtctgtatt ggcgacaaaa ggagcagccc     120
tgaatgtagg gaaagcaggg cggagtcctc tgcaggctcg ggggaggggg ggggcgtgaa     180
tgcgtggatt tctgtggaga gtggaaacac ggggagtcga ggggagcatg cgcgggcctc     240
agaaagttct gggaaaccga ctcccgggag cagggaggaa cgcgcgctcc agagacaact     300
tcgcggtgtg gtgaactctc tgaggaaaaa cacgtgcgtg gcaacaagtg actgagacct     360
agaaatccaa gcgttggagg tcctgaggcc agcctaagtc gcttcaaaat ggaacgaagg     420
cgtttgtggg gttccattca gagccgatac atcagcatga gtgtgtggac aagcccacgg     480
agacttgtgg agctggcagg gcagagcctg ctgaaggatg aggccctggc cattgccgcc     540
ctggagttgc tgcccaggga gctcttcccg ccactcttca tggcagcctt tgacgggaga     600
cacagccaga ccctgaaggc aatggtgcag gcctggccct tcacctgcct ccctctggga     660
gtgctgatga agggacaaca tcttcacctg gagaccttca aagctgtgct tgatggactt     720
gatgtgctcc ttgcccagga ggttcgcccc aggaggtgga aacttcaagt gctggattta     780
cggaagaact ctcatcagga cttctggact gtatggtctg gaaacagggc cagtctgtac     840
tcatttccag agccagaagc agctcagccc atgacaaaga agcgaaaagt agatggtttg     900
agcacagagg cagagcagcc cttcattcca gtagaggtgc tcgtagacct gttcctcaag     960
gaaggtgcct gtgatgaatt gttctcctac ctcattgaga aagtgaagcg aaagaaaaat    1020
gtactacgcc tgtgctgtaa gaagctgaag atttttgcaa tgcccatgca ggatatcaag    1080
atgatcctga aaatggtgca gctggactct attgaagatt tggaagtgac ttgtacctgg    1140
aagctaccca ccttggcgaa attttctcct tacctgggcc agatgattaa tctgcgtaga    1200
ctcctcctct cccacatcca tgcatcttcc tacatttccc cggagaagga agagcagtat    1260
atcgcccagt tcacctctca gttcctcagt ctgcagtgcc tgcaggctct ctatgtggac    1320
tctttatttt tccttagagg ccgcctggat cagttgctca ggcacgtgat gaaccccttg    1380
gaaaccctct caataactaa ctgccggctt tcggaagggg atgtgatgca tctgtcccag    1440
agtcccagcg tcagtcagct aagtgtcctg agtctaagtg gggtcatgct gaccgatgta    1500
agtcccgagc ccctccaagc tctgctggag agagcctctg ccaccctcca ggacctggtc    1560
tttgatgagt gtgggatcac ggatgatcag ctccttgccc tcctgccttc cctgagccac    1620
tgctcccagc ttacgacctt aagcttctac gggaattcca tctccatatc tgccctgcag    1680
agtctcctgc agcacctcat cgggctgagc aatctgaccc acgtgctgta tcctgtcccc    1740
ctggagagtt atgaggacat ccatggtacc ctccacctgg agaggcttgc ctatctgcat    1800
gccaggctca gggagttgct gtgtgagttg ggcggcccca gcatggtctg gcttagtgcc    1860 aaccccctgtc ctcactgtgg ggacagaacc ttctatgacc cggagcccat cctgtgcccc    1920
tgtttcatgc ctaattagct gggtgcacat atcaaatgct tcattctgca tacttggaca    1980
```

-continued

```
ctaaagccag gatgtgcatg catcttgaag caacaaagca gccacagttt cagacaaatg    2040
ttcagtgtga gtgaggaaaa catgttcagt gaggaaaaaa cattcagaca aatgttcagt    2100
gaggaaaaaa aggggaagtt gggggtaggc agatgttgac ttgaggagtt aatgtgatct    2160
ttggggagat acatcttata gagttagaaa tagaatctga atttctaaag ggagattctg    2220
gcttgggaag tacatgtagg agttaatccc tgtgtagact gttgtaaaga aactgttgaa    2280
aataaagaga agcaatgtga agca                                          2304
```

<210> SEQ ID NO 939
<211> LENGTH: 2435
<212> TYPE: DNA
<213> ORGANISM: Homo sapiens

<400> SEQUENCE: 939

```
agagggcctg ggaggaagtg ggttttgcat acagtccctg ttgactctag tgcccctgc      60 tggccccaga cgcgagttcc ggcgaggctt cagggtacag ctcccccgca gccagaagcc     120
gggcctgcag cgcctcagca ccgctccggg acaccccacc cgcttcccag gcgtgacctg     180
tcaacaggtc tgtattggcg acaaaaggag cagccctgaa tgtagggaaa gcagggcgga     240
gtcctctgca ggctcggggg aggggagggg cgtgaatgcg tggatttctg tggagagtgg     300
aaacacgggg agtcgagggg agcatgcgcg ggcctcagaa agttctggga aaccgactcc     360
cgggagcagg gaggaacgcg cgctccagag acaacttcgc ggtgtggtga actctctgag     420
gaaaaaccat tttgattatt actctcagac gtgcgtggca acaagtgact gagacctaga     480
aatccaagcg ttggaggtcc tgaggccagc ctaagtcgct tcaaaatgga acgaaggcgt     540
ttgtggggtt ccattcagag ccgatacatc agcatgagtg tgtggacaag cccacgagaa     600
cttgtggagc tggcagggca gagcctgctg aaggatgagg ccctggccat tgccgccctg     660
gagttgctgc ccagggagct cttcccgcca ctcttcatgg cagcctttga cgggagacac     720
agccagaccc tgaaggcaat ggtgcaggcc tggcccttca cctgcctccc tctgggagtg     780
ctgatgaagg gacaacatct tcacctggag accttcaaag ctgtgcttga tggacttgat     840
gtgctccttg cccaggaggt tcgccccagg aggtggaaac ttcaagtgct ggatttacgg     900
aagaactctc atcaggactt ctggactgta tggtctggaa acagggccag tctgtactca     960
tttccagagc cagaagcagc tcagcccatg acaaagaagc gaaaagtaga tggtttgagc    1020
acagaggcag agcagccctt cattccagta gaggtgctcg tagacctgtt cctcaaggaa    1080
ggtgcctgtg atgaattgtt ctcctacctc attgagaaag tgaagcgaaa gaaaaatgta    1140
ctacgcctgt gctgtaagaa gctgaagatt tttgcaatgc ccatgcagga tatcaagatg    1200
atcctgaaaa tggtgcagct ggactctatt gaagatttgg aagtgacttg tacctggaag    1260
ctacccacct tggcgaaatt ttctccttac ctgggccaga tgattaatct gcgtagactc    1320
ctcctctccc acatccatgc atcttcctac atttccccgg agaaggaaga gcagtatatc    1380
gcccagttca cctctcagtt cctcagtctg cagtgcctgc aggctctcta tgtggactct    1440
ttatttttcc ttagaggccg cctggatcag ttgctcaggc acgtgatgaa ccccttggaa    1500
accctctcaa taactaactg ccggctttcg gaaggggatg tgatgcatct gtcccagagt    1560
cccagcgtca gtcagctaag tgtcctgagt ctaagtgggg tcatgctgac cgatgtaagt    1620
cccgagcccc tccaagctct gctggagaga gcctctgcca ccctccagga cctggtcttt    1680
gatgagtgtg ggatcacgga tgatcagctc cttgccctcc tgccttccct gagccactgc    1740
```

-continued

```
tcccagctta cgaccttaag cttctacggg aattccatct ccatatctgc cctgcagagt    1800
ctcctgcagc acctcatcgg gctgagcaat ctgacccacg tgctgtatcc tgtccccctg    1860
gagagttatg aggacatcca tggtaccctc cacctggaga ggcttgccta tctgcatgcc    1920
aggctcaggg agttgctgtg tgagttgggg cggcccagca tggtctggct tagtgccaac    1980
ccctgtcctc actgtgggga cagaaccttc tatgacccgg agcccatcct gtgcccctgt    2040
ttcatgccta attagctggg tgcacatatc aaatgcttca ttctgcatac ttggacacta    2100
aagccaggat gtgcatgcat cttgaagcaa caaagcagcc acagtttcag acaaatgttc    2160
agtgtgagtg aggaaaacat gttcagtgag gaaaaaacat tcagacaaat gttcagtgag    2220
gaaaaaaagg ggaagttggg ggtaggcaga tgttgacttg aggagttaat gtgatctttg    2280
gggagataca tcttatagag ttagaaatag aatctgaatt tctaaaggga gattctggct    2340
tgggaagtac atgtaggagt taatccctgt gtagactgtt gtaaagaaac tgttgaaaat    2400
aaagagaagc aatgtgaagc acctggaaaa aaaaa                                2435
```

```
<210> SEQ ID NO 940
<211> LENGTH: 2100
<212> TYPE: DNA
<213> ORGANISM: Homo sapiens

<400> SEQUENCE: 940
```

```
acagctcccc cgcagccaga agccgggcct gcagcgcctc agcaccgctc cgggacaccc      60
cacccgcttc ccaggcgtga cctgtcaaca gcaacttcgc ggtgtggtga actctctgag     120
gaaaaacacg tgcgtggcaa caagtgactg agacctagaa atccaagcgt tggaggtcct     180
gaggccagcc taagtcgctt caaaatggaa cgaaggcgtt tgtgggggttc cattcagagc     240 cgatacatca gcatgagtgt gtggacaagc ccacggagac ttgtggagct ggcagggcag     300
agcctgctga aggatgaggc cctggccatt gccgccctgg agttgctgcc cagggagctc     360
ttcccgccac tcttcatggc agcctttgac gggagacaca gccagaccct gaaggcaatg     420
gtgcaggcct ggcccttcac ctgcctccct ctgggagtgc tgatgaaggg acaacatctt     480
cacctggaga ccttcaaagc tgtgcttgat ggacttgatg tgctccttgc ccaggaggtt     540
cgccccagga ggtggaaact tcaagtgctg gatttacgga agaactctca tcaggacttc     600
tggactgtat ggtctggaaa cagggccagt ctgtactcat ttccagagcc agaagcagct     660
cagcccatga caaagaagcg aaaagtagat ggtttgagca cagaggcaga gcagcccttc     720
attccagtag aggtgctcgt agacctgttc ctcaaggaag gtgcctgtga tgaattgttc     780
tcctacctca ttgagaaagt gaagcgaaag aaaaatgtac tacgcctgtg ctgtaagaag     840
ctgaagattt ttgcaatgcc catgcaggat atcaagatga tcctgaaaat ggtgcagctg     900
gactctattg aagatttgga agtgacttgt acctggaagc tacccacctt ggcgaaattt     960
tctccttacc tgggccagat gattaatctg cgtagactcc tcctctccca catccatgca    1020
tcttcctaca tttccccgga gaaggaagag cagtatatcg cccagttcac ctctcagttc    1080
ctcagtctgc agtgcctgca ggctctctat gtggactctt tatttttcct tagaggccgc    1140
ctggatcagt tgctcaggca cgtgatgaac cccttggaaa ccctctcaat aactaactgc    1200
cggctttcgg aaggggatgt gatgcatctg tcccagagtc ccagcgtcag tcagctaagt    1260
gtcctgagtc taagtggggt catgctgacc gatgtaagtc ccgagcccct ccaagctctg    1320
ctggagagag cctctgccac cctccaggac ctggtctttg atgagtgtgg gatcacggat    1380
gatcagctcc ttgccctcct gccttccctg agccactgct cccagcttac gaccttaagc    1440
```

```
ttctacggga attccatctc catatctgcc ctgcagagtc tcctgcagca cctcatcggg      1500
ctgagcaatc tgacccacgt gctgtatcct gtccccctgg agagttatga ggacatccat      1560
ggtaccctcc acctggagag gcttgcctat ctgcatgcca ggctcaggga gttgctgtgt      1620
gagttggggc ggcccagcat ggtctggctt agtgccaacc cctgtcctca ctgtgggggac     1680 agaaccttct atgacccgga gcccatcctg tgccctgtt tcatgcctaa ttagctgggt       1740
gcacatatca aatgcttcat tctgcatact tggacactaa agccaggatg tgcatgcatc      1800
ttgaagcaac aaagcagcca cagtttcaga caaatgttca gtgtgagtga ggaaaacatg      1860
ttcagtgagg aaaaaacatt cagacaaatg ttcagtgagg aaaaaaaggg gaagttgggg      1920
gtaggcagat gttgacttga ggagttaatg tgatctttgg ggagatacat cttatagagt      1980
tagaaataga atctgaattt ctaaagggag attctggctt gggaagtaca tgtaggagtt      2040
aatccctgtg tagactgttg taaagaaact gttgaaaata aagagaagca atgtgaagca      2100
```

```
<210> SEQ ID NO 941
<211> LENGTH: 2845
<212> TYPE: DNA
<213> ORGANISM: Homo sapiens

<400> SEQUENCE: 941
agagggcctg ggaggaagtg ggtttttgcat acagtccctg ttgactctag tgccccctgc        60
tggccccaga cgcgagttcc ggcgaggctt cagggtacag ctcccccgca gccagaagcc       120
gggcctgcag cgcctcagca ccgctccggg acaccccacc cgcttcccag gcgtgacctg       180
tcaacagcaa cttcgcggtg tggtgaactc tctgaggaaa aacgtaagtt cgagccctga       240
ttcctccgct tccccgcagg gtgaccttgg gcttgtgccc ccagcaccac ccctgtcccg       300
ggtccctgtt ttctctctgg aaatgggttg aagaccaaag aaaataatgt gcgccacttg       360
ggtcaccccg ggccgcctgc cccggaaaat tggccccagt tgaggagttg tggctgtaag       420
gatgccttga accgaggcgg cggtgctcgt ggttggagct ctccagggtg ggtgcgcatt       480
tgtaatgcgg tggatgctct gggactcggc ccctctgaag gtgctggggg ttggggacgg       540
cccaggcagt ggcgtaggcg tcctaggaag gcgggagcag aggcagaaat gtcgctgcaa       600
gaccgtagtc agggtccttg accacagggg tcacttgtga ccaaccacat ggtctgttgt       660
tcctcctgcc ccctggttca gcccaggaaa cactggtgct caggtttgga gccagagatt       720
tgcactgaaa gggcgggatt gagtcgccag ttgtcagttt cctcagcagt atttgcggag       780
gttttcacag gaggccgttg cttcgtaaat attatacatg tattcttctt tttggagcat       840
tttgattatt actctcagac gtgcgtggca caagtgact gagacctaga aatccaagcg        900
ttggaggtcc tgaggccagc ctaagtcgct tcaaaatgga acgaaggcgt ttgtgggggtt      960 ccattcagag ccgatacatc agcatgagtg tgtggacaag cccacggaga cttgtggagc     1020
tggcagggca gagcctgctg aaggatgagg ccctggccat tgccgccctg gagttgctgc     1080
ccagggagct cttcccgcca ctcttcatgg cagcctttga cgggagacac agccagaccc     1140
tgaaggcaat ggtgcaggcc tggcccttca cctgcctccc tctgggagtg ctgatgaagg     1200
gacaacatct tcacctggag accttcaaag ctgtgcttga tggacttgat gtgctccttg     1260
cccaggaggt tcgccccagg aggtggaaac ttcaagtgct ggatttacgg aagaactctc     1320
atcaggactt ctggactgta tggtctggaa acagggccag tctgtactca tttccagagc     1380
cagaagcagc tcagcccatg acaaagaagc gaaaagtaga tggtttgagc acagaggcag     1440
```

-continued

```
agcagccctt cattccagta gaggtgctcg tagacctgtt cctcaaggaa ggtgcctgtg      1500
atgaattgtt ctcctacctc attgagaaag tgaagcgaaa gaaaaatgta ctacgcctgt      1560
gctgtaagaa gctgaagatt tttgcaatgc ccatgcagga tatcaagatg atcctgaaaa      1620
tggtgcagct ggactctatt gaagatttgg aagtgacttg tacctggaag ctacccacct      1680
tggcgaaatt ttctccttac ctgggccaga tgattaatct gcgtagactc ctcctctccc      1740
acatccatgc atcttcctac atttccccgg agaaggaaga gcagtatatc gcccagttca      1800
cctctcagtt cctcagtctg cagtgcctgc aggctctcta tgtggactct ttatttttcc      1860
ttagaggccg cctggatcag ttgctcaggc acgtgatgaa ccccttggaa accctctcaa      1920
taactaactg ccggctttcg aaggggatg tgatgcatct gtcccagagt cccagcgtca      1980
gtcagctaag tgtcctgagt ctaagtgggg tcatgctgac cgatgtaagt cccgagcccc      2040
tccaagctct gctggagaga gcctctgcca ccctccagga cctggtcttt gatgagtgtg      2100
ggatcacgga tgatcagctc cttgccctcc tgccttccct gagccactgc tcccagctta      2160
cgaccttaag cttctacggg aattccatct ccatatctgc cctgcagagt ctcctgcagc      2220
acctcatcgg gctgagcaat ctgacccacg tgctgtatcc tgtccccctg gagagttatg      2280
aggacatcca tggtaccctc cacctggaga ggcttgccta tctgcatgcc aggctcaggg      2340
agttgctgtg tgagttgggg cggcccagca tggtctggct tagtgccaac ccctgtcctc      2400
actgtgggga cagaaccttc tatgacccgg agcccatcct gtgcccctgt ttcatgccta      2460
attagctggg tgcacatatc aaatgcttca ttctgcatac ttggacacta aagccaggat      2520
gtgcatgcat cttgaagcaa caaagcagcc acagtttcag acaaatgttc agtgtgagtg      2580
aggaaaacat gttcagtgag gaaaaaacat tcagacaaat gttcagtgag gaaaaaaagg      2640
ggaagttggg ggtaggcaga tgttgacttg aggagttaat gtgatctttg gggagataca      2700
tcttatagag ttagaaatag aatctgaatt tctaaaggga gattctggct tgggaagtac      2760
atgtaggagt taatccctgt gtagactgtt gtaaagaaac tgttgaaaat aaagagaagc      2820
aatgtgaagc acctggaaaa aaaaa                                           2845
```

```
<210> SEQ ID NO 942
<211> LENGTH: 493
<212> TYPE: PRT
<213> ORGANISM: Homo sapiens

<400> SEQUENCE: 942

Met Ser Val Trp Thr Ser Pro Arg Arg Leu Val Glu Leu Ala Gly Gln
1               5                   10                  15

Ser Leu Leu Lys Asp Glu Ala Leu Ala Ile Ala Ala Leu Glu Leu Leu
            20                  25                  30

Pro Arg Glu Leu Phe Pro Pro Leu Phe Met Ala Ala Phe Asp Gly Arg
        35                  40                  45

His Ser Gln Thr Leu Lys Ala Met Val Gln Ala Trp Pro Phe Thr Cys
    50                  55                  60

Leu Pro Leu Gly Val Leu Met Lys Gly Gln His Leu His Leu Glu Thr
65                  70                  75                  80

Phe Lys Ala Val Leu Asp Gly Leu Asp Val Leu Leu Ala Gln Glu Val
                85                  90                  95

Arg Pro Arg Arg Trp Lys Leu Gln Val Leu Asp Leu Arg Lys Asn Ser
            100                 105                 110

His Gln Asp Phe Trp Thr Val Trp Ser Gly Asn Arg Ala Ser Leu Tyr
            115                 120                 125
```

-continued

```
Ser Phe Pro Glu Pro Glu Ala Ala Gln Pro Met Thr Lys Lys Arg Lys
    130                 135             140

Val Asp Gly Leu Ser Thr Glu Ala Glu Gln Pro Phe Ile Pro Val Glu
145             150                 155             160

Val Leu Val Asp Leu Phe Leu Lys Glu Gly Ala Cys Asp Glu Leu Phe
            165             170             175

Ser Tyr Leu Ile Glu Lys Val Lys Arg Lys Lys Asn Val Leu Arg Leu
            180             185             190

Cys Cys Lys Lys Leu Lys Ile Phe Ala Met Pro Met Gln Asp Ile Lys
        195             200             205

Met Ile Leu Lys Met Val Gln Leu Asp Ser Ile Glu Asp Leu Glu Val
    210             215             220

Thr Cys Thr Trp Lys Leu Pro Thr Leu Ala Lys Phe Ser Pro Tyr Leu
225             230             235             240

Gly Gln Met Ile Asn Leu Arg Arg Leu Leu Leu Ser His Ile His Ala
            245             250             255

Ser Ser Tyr Ile Ser Pro Glu Lys Glu Glu Gln Tyr Ile Ala Gln Phe
            260             265             270

Thr Ser Gln Phe Leu Ser Leu Gln Cys Leu Gln Ala Leu Tyr Val Asp
    275             280             285

Ser Leu Phe Phe Leu Arg Gly Arg Leu Asp Gln Leu Leu Arg His Val
    290             295             300

Met Asn Pro Leu Glu Thr Leu Ser Ile Thr Asn Cys Arg Leu Ser Glu
305             310             315             320

Gly Asp Val Met His Leu Ser Gln Ser Pro Ser Val Ser Gln Leu Ser
            325             330             335

Val Leu Ser Leu Ser Gly Val Met Leu Thr Asp Val Ser Pro Glu Pro
            340             345             350

Leu Gln Ala Leu Leu Glu Arg Ala Ser Ala Thr Leu Gln Asp Leu Val
            355             360             365

Phe Asp Glu Cys Gly Ile Thr Asp Asp Gln Leu Leu Ala Leu Leu Pro
    370             375             380

Ser Leu Ser His Cys Ser Gln Leu Thr Thr Leu Ser Phe Tyr Gly Asn
385             390             395             400

Ser Ile Ser Ile Ser Ala Leu Gln Ser Leu Leu Gln His Leu Ile Gly
            405             410             415

Leu Ser Asn Leu Thr His Val Leu Tyr Pro Val Pro Leu Glu Ser Tyr
            420             425             430

Glu Asp Ile His Gly Thr Leu His Leu Glu Arg Leu Ala Tyr Leu His
        435             440             445

Ala Arg Leu Arg Glu Leu Leu Cys Glu Leu Gly Arg Pro Ser Met Val
    450             455             460

Trp Leu Ser Ala Asn Pro Cys Pro His Cys Gly Asp Arg Thr Phe Tyr
465             470             475             480

Asp Pro Glu Pro Ile Leu Cys Pro Cys Phe Met Pro Asn
            485             490
```

<210> SEQ ID NO 943
<211> LENGTH: 509
<212> TYPE: PRT
<213> ORGANISM: Homo sapiens

<400> SEQUENCE: 943

Met Glu Arg Arg Arg Leu Trp Gly Ser Ile Gln Ser Arg Tyr Ile Ser

-continued

```
1                   5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430
```

-continued

```
Leu Ser Asn Leu Thr His Val Leu Tyr Pro Val Pro Leu Glu Ser Tyr
        435         440             445

Glu Asp Ile His Gly Thr Leu His Leu Glu Arg Leu Ala Tyr Leu His
    450             455             460

Ala Arg Leu Arg Glu Leu Leu Cys Glu Leu Gly Arg Pro Ser Met Val
465             470             475             480

Trp Leu Ser Ala Asn Pro Cys Pro His Cys Gly Asp Arg Thr Phe Tyr
            485             490             495

Asp Pro Glu Pro Ile Leu Cys Pro Cys Phe Met Pro Asn
            500             505

<210> SEQ ID NO 944
<211> LENGTH: 509
<212> TYPE: PRT
<213> ORGANISM: Homo sapiens

<400> SEQUENCE: 944

Met Glu Arg Arg Arg Leu Trp Gly Ser Ile Gln Ser Arg Tyr Ile Ser
1               5               10              15

Met Ser Val Trp Thr Ser Pro Arg Arg Leu Val Glu Leu Ala Gly Gln
            20              25              30

Ser Leu Leu Lys Asp Glu Ala Leu Ala Ile Ala Ala Leu Glu Leu Leu
        35              40              45

Pro Arg Glu Leu Phe Pro Pro Leu Phe Met Ala Ala Phe Asp Gly Arg
    50              55              60

His Ser Gln Thr Leu Lys Ala Met Val Gln Ala Trp Pro Phe Thr Cys
65              70              75              80

Leu Pro Leu Gly Val Leu Met Lys Gly Gln His Leu His Leu Glu Thr
            85              90              95

Phe Lys Ala Val Leu Asp Gly Leu Asp Val Leu Leu Ala Gln Glu Val
            100             105             110

Arg Pro Arg Arg Trp Lys Leu Gln Val Leu Asp Leu Arg Lys Asn Ser
        115             120             125

His Gln Asp Phe Trp Thr Val Trp Ser Gly Asn Arg Ala Ser Leu Tyr
    130             135             140

Ser Phe Pro Glu Pro Glu Ala Ala Gln Pro Met Thr Lys Lys Arg Lys
145             150             155             160

Val Asp Gly Leu Ser Thr Glu Ala Glu Gln Pro Phe Ile Pro Val Glu
            165             170             175

Val Leu Val Asp Leu Phe Leu Lys Glu Gly Ala Cys Asp Glu Leu Phe
            180             185             190

Ser Tyr Leu Ile Glu Lys Val Lys Arg Lys Lys Asn Val Leu Arg Leu
        195             200             205

Cys Cys Lys Lys Leu Lys Ile Phe Ala Met Pro Met Gln Asp Ile Lys
    210             215             220

Met Ile Leu Lys Met Val Gln Leu Asp Ser Ile Glu Asp Leu Glu Val
225             230             235             240

Thr Cys Thr Trp Lys Leu Pro Thr Leu Ala Lys Phe Ser Pro Tyr Leu
            245             250             255

Gly Gln Met Ile Asn Leu Arg Arg Leu Leu Leu Ser His Ile His Ala
            260             265             270

Ser Ser Tyr Ile Ser Pro Glu Lys Glu Glu Gln Tyr Ile Ala Gln Phe
        275             280             285

Thr Ser Gln Phe Leu Ser Leu Gln Cys Leu Gln Ala Leu Tyr Val Asp
```

-continued

```
          290                     295                     300

Ser Leu Phe Phe Leu Arg Gly Arg Leu Asp Gln Leu Leu Arg His Val
305                     310                     315                     320

Met Asn Pro Leu Glu Thr Leu Ser Ile Thr Asn Cys Arg Leu Ser Glu
                    325                     330                     335

Gly Asp Val Met His Leu Ser Gln Ser Pro Ser Val Ser Gln Leu Ser
                    340                     345                     350

Val Leu Ser Leu Ser Gly Val Met Leu Thr Asp Val Ser Pro Glu Pro
                    355                     360                     365

Leu Gln Ala Leu Leu Glu Arg Ala Ser Ala Thr Leu Gln Asp Leu Val
            370                     375                     380

Phe Asp Glu Cys Gly Ile Thr Asp Asp Gln Leu Leu Ala Leu Leu Pro
385                     390                     395                     400

Ser Leu Ser His Cys Ser Gln Leu Thr Thr Leu Ser Phe Tyr Gly Asn
                    405                     410                     415

Ser Ile Ser Ile Ser Ala Leu Gln Ser Leu Leu Gln His Leu Ile Gly
                    420                     425                     430

Leu Ser Asn Leu Thr His Val Leu Tyr Pro Val Pro Leu Glu Ser Tyr
            435                     440                     445

Glu Asp Ile His Gly Thr Leu His Leu Glu Arg Leu Ala Tyr Leu His
            450                     455                     460

Ala Arg Leu Arg Glu Leu Leu Cys Glu Leu Gly Arg Pro Ser Met Val
465                     470                     475                     480

Trp Leu Ser Ala Asn Pro Cys Pro His Cys Gly Asp Arg Thr Phe Tyr
                    485                     490                     495

Asp Pro Glu Pro Ile Leu Cys Pro Cys Phe Met Pro Asn
                    500                     505
```

```
<210> SEQ ID NO 945
<211> LENGTH: 509
<212> TYPE: PRT
<213> ORGANISM: Homo sapiens

<400> SEQUENCE: 945

Met Glu Arg Arg Arg Leu Trp Gly Ser Ile Gln Ser Arg Tyr Ile Ser
1                   5                   10                  15

Met Ser Val Trp Thr Ser Pro Arg Arg Leu Val Glu Leu Ala Gly Gln
                    20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
            50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                    85                  90                  95

Phe Lys Ala Val Leu Asp Gly Leu Asp Val Leu Leu Ala Gln Glu Val
                    100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
            130                 135                 140

Ser Phe Pro Glu Pro Glu Ala Ala Gln Pro Met Thr Lys Lys Arg Lys
145                 150                 155                 160
```

-continued

```
Val Asp Gly Leu Ser Thr Glu Ala Glu Gln Pro Phe Ile Pro Val Glu
            165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
            195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
            275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
            355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
            435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505
```

```
<210> SEQ ID NO 946
<211> LENGTH: 509
<212> TYPE: PRT
<213> ORGANISM: Homo sapiens

<400> SEQUENCE: 946

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30
```

-continued

```
Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
                115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
                180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
        210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
                260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
        290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
                355                 360                 365

Leu Gln Ala Leu Leu Glu Arg Ala Ser Ala Thr Leu Gln Asp Leu Val
        370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
        435                 440                 445
```

-continued

```
Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

<210> SEQ ID NO 947
<211> LENGTH: 509
<212> TYPE: PRT
<213> ORGANISM: Homo sapiens

<400> SEQUENCE: 947

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
                180                 185                 190

Ser Tyr Leu Ile Glu Lys Val Lys Arg Lys Lys Asn Val Leu Arg Leu
            195                 200                 205

Cys Cys Lys Lys Leu Lys Ile Phe Ala Met Pro Met Gln Asp Ile Lys
        210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
                260                 265                 270

Ser Ser Tyr Ile Ser Pro Glu Lys Glu Glu Gln Tyr Ile Ala Gln Phe
            275                 280                 285

Thr Ser Gln Phe Leu Ser Leu Gln Cys Leu Gln Ala Leu Tyr Val Asp
        290                 295                 300

Ser Leu Phe Phe Leu Arg Gly Arg Leu Asp Gln Leu Leu Arg His Val
305                 310                 315                 320
```

```
Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
                355                 360                 365

Leu Gln Ala Leu Leu Glu Arg Ala Ser Ala Thr Leu Gln Asp Leu Val
        370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
        450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
                500                 505
```

<210> SEQ ID NO 948
<211> LENGTH: 509
<212> TYPE: PRT
<213> ORGANISM: Homo sapiens
<400> SEQUENCE: 948

```
Met Glu Arg Arg Arg Leu Trp Gly Ser Ile Gln Ser Arg Tyr Ile Ser
1                 5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
```

-continued

```
               180              185              190

Ser Tyr Leu Ile Glu Lys Val Lys Arg Lys Lys Asn Val Leu Arg Leu
        195              200              205

Cys Cys Lys Lys Leu Lys Ile Phe Ala Met Pro Met Gln Asp Ile Lys
        210              215              220

Met Ile Leu Lys Met Val Gln Leu Asp Ser Ile Glu Asp Leu Glu Val
225              230              235              240

Thr Cys Thr Trp Lys Leu Pro Thr Leu Ala Lys Phe Ser Pro Tyr Leu
                245              250              255

Gly Gln Met Ile Asn Leu Arg Arg Leu Leu Leu Ser His Ile His Ala
            260              265              270

Ser Ser Tyr Ile Ser Pro Glu Lys Glu Glu Gln Tyr Ile Ala Gln Phe
            275              280              285

Thr Ser Gln Phe Leu Ser Leu Gln Cys Leu Gln Ala Leu Tyr Val Asp
        290              295              300

Ser Leu Phe Phe Leu Arg Gly Arg Leu Asp Gln Leu Leu Arg His Val
305              310              315              320

Met Asn Pro Leu Glu Thr Leu Ser Ile Thr Asn Cys Arg Leu Ser Glu
                325              330              335

Gly Asp Val Met His Leu Ser Gln Ser Pro Ser Val Ser Gln Leu Ser
            340              345              350

Val Leu Ser Leu Ser Gly Val Met Leu Thr Asp Val Ser Pro Glu Pro
            355              360              365

Leu Gln Ala Leu Leu Glu Arg Ala Ser Ala Thr Leu Gln Asp Leu Val
        370              375              380

Phe Asp Glu Cys Gly Ile Thr Asp Asp Gln Leu Leu Ala Leu Leu Pro
385              390              395              400

Ser Leu Ser His Cys Ser Gln Leu Thr Thr Leu Ser Phe Tyr Gly Asn
                405              410              415

Ser Ile Ser Ile Ser Ala Leu Gln Ser Leu Leu Gln His Leu Ile Gly
            420              425              430

Leu Ser Asn Leu Thr His Val Leu Tyr Pro Val Pro Leu Glu Ser Tyr
            435              440              445

Glu Asp Ile His Gly Thr Leu His Leu Glu Arg Leu Ala Tyr Leu His
        450              455              460

Ala Arg Leu Arg Glu Leu Leu Cys Glu Leu Gly Arg Pro Ser Met Val
465              470              475              480

Trp Leu Ser Ala Asn Pro Cys Pro His Cys Gly Asp Arg Thr Phe Tyr
                485              490              495

Asp Pro Glu Pro Ile Leu Cys Pro Cys Phe Met Pro Asn
            500              505
```

```
<210> SEQ ID NO 949
<211> LENGTH: 493
<212> TYPE: PRT
<213> ORGANISM: Homo sapiens

<400> SEQUENCE: 949
```

```
Met Ser Val Trp Thr Ser Pro Arg Arg Leu Val Glu Leu Ala Gly Gln
1               5               10              15

Ser Leu Leu Lys Asp Glu Ala Leu Ala Ile Ala Ala Leu Glu Leu Leu
            20              25              30

Pro Arg Glu Leu Phe Pro Pro Leu Phe Met Ala Ala Phe Asp Gly Arg
        35              40              45
```

```
His Ser Gln Thr Leu Lys Ala Met Val Gln Ala Trp Pro Phe Thr Cys
    50              55                  60

Leu Pro Leu Gly Val Leu Met Lys Gly Gln His Leu His Leu Glu Thr
65              70                  75                  80

Phe Lys Ala Val Leu Asp Gly Leu Asp Val Leu Leu Ala Gln Glu Val
                85                  90                  95

Arg Pro Arg Arg Trp Lys Leu Gln Val Leu Asp Leu Arg Lys Asn Ser
            100                 105                 110

His Gln Asp Phe Trp Thr Val Trp Ser Gly Asn Arg Ala Ser Leu Tyr
            115                 120                 125

Ser Phe Pro Glu Pro Glu Ala Ala Gln Pro Met Thr Lys Lys Arg Lys
    130                 135                 140

Val Asp Gly Leu Ser Thr Glu Ala Glu Gln Pro Phe Ile Pro Val Glu
145                 150                 155                 160

Val Leu Val Asp Leu Phe Leu Lys Glu Gly Ala Cys Asp Glu Leu Phe
                165                 170                 175

Ser Tyr Leu Ile Glu Lys Val Lys Arg Lys Lys Asn Val Leu Arg Leu
            180                 185                 190

Cys Cys Lys Lys Leu Lys Ile Phe Ala Met Pro Met Gln Asp Ile Lys
            195                 200                 205

Met Ile Leu Lys Met Val Gln Leu Asp Ser Ile Glu Asp Leu Glu Val
    210                 215                 220

Thr Cys Thr Trp Lys Leu Pro Thr Leu Ala Lys Phe Ser Pro Tyr Leu
225                 230                 235                 240

Gly Gln Met Ile Asn Leu Arg Arg Leu Leu Leu Ser His Ile His Ala
            245                 250                 255

Ser Ser Tyr Ile Ser Pro Glu Lys Glu Glu Gln Tyr Ile Ala Gln Phe
            260                 265                 270

Thr Ser Gln Phe Leu Ser Leu Gln Cys Leu Gln Ala Leu Tyr Val Asp
    275                 280                 285

Ser Leu Phe Phe Leu Arg Gly Arg Leu Asp Gln Leu Leu Arg His Val
    290                 295                 300

Met Asn Pro Leu Glu Thr Leu Ser Ile Thr Asn Cys Arg Leu Ser Glu
305                 310                 315                 320

Gly Asp Val Met His Leu Ser Gln Ser Pro Ser Val Ser Gln Leu Ser
            325                 330                 335

Val Leu Ser Leu Ser Gly Val Met Leu Thr Asp Val Ser Pro Glu Pro
            340                 345                 350

Leu Gln Ala Leu Leu Glu Arg Ala Ser Ala Thr Leu Gln Asp Leu Val
            355                 360                 365

Phe Asp Glu Cys Gly Ile Thr Asp Asp Gln Leu Leu Ala Leu Leu Pro
    370                 375                 380

Ser Leu Ser His Cys Ser Gln Leu Thr Thr Leu Ser Phe Tyr Gly Asn
385                 390                 395                 400

Ser Ile Ser Ile Ser Ala Leu Gln Ser Leu Leu Gln His Leu Ile Gly
            405                 410                 415

Leu Ser Asn Leu Thr His Val Leu Tyr Pro Val Pro Leu Glu Ser Tyr
            420                 425                 430

Glu Asp Ile His Gly Thr Leu His Leu Glu Arg Leu Ala Tyr Leu His
            435                 440                 445

Ala Arg Leu Arg Glu Leu Leu Cys Glu Leu Gly Arg Pro Ser Met Val
    450                 455                 460

Trp Leu Ser Ala Asn Pro Cys Pro His Cys Gly Asp Arg Thr Phe Tyr
```

```
465                 470                 475                 480

Asp Pro Glu Pro Ile Leu Cys Pro Cys Phe Met Pro Asn
                485                 490

<210> SEQ ID NO 950
<211> LENGTH: 493
<212> TYPE: PRT
<213> ORGANISM: Homo sapiens

<400> SEQUENCE: 950

Met Ser Val Trp Thr Ser Pro Arg Arg Leu Val Glu Leu Ala Gly Gln
1               5                   10                  15

Ser Leu Leu Lys Asp Glu Ala Leu Ala Ile Ala Ala Leu Glu Leu Leu
                20                  25                  30

Pro Arg Glu Leu Phe Pro Pro Leu Phe Met Ala Ala Phe Asp Gly Arg
            35                  40                  45

His Ser Gln Thr Leu Lys Ala Met Val Gln Ala Trp Pro Phe Thr Cys
        50                  55                  60

Leu Pro Leu Gly Val Leu Met Lys Gly Gln His Leu His Leu Glu Thr
65                  70                  75                  80

Phe Lys Ala Val Leu Asp Gly Leu Asp Val Leu Leu Ala Gln Glu Val
                85                  90                  95

Arg Pro Arg Arg Trp Lys Leu Gln Val Leu Asp Leu Arg Lys Asn Ser
            100                 105                 110

His Gln Asp Phe Trp Thr Val Trp Ser Gly Asn Arg Ala Ser Leu Tyr
        115                 120                 125

Ser Phe Pro Glu Pro Glu Ala Ala Gln Pro Met Thr Lys Lys Arg Lys
    130                 135                 140

Val Asp Gly Leu Ser Thr Glu Ala Glu Gln Pro Phe Ile Pro Val Glu
145                 150                 155                 160

Val Leu Val Asp Leu Phe Leu Lys Glu Gly Ala Cys Asp Glu Leu Phe
                165                 170                 175

Ser Tyr Leu Ile Glu Lys Val Lys Arg Lys Lys Asn Val Leu Arg Leu
            180                 185                 190

Cys Cys Lys Lys Leu Lys Ile Phe Ala Met Pro Met Gln Asp Ile Lys
        195                 200                 205

Met Ile Leu Lys Met Val Gln Leu Asp Ser Ile Glu Asp Leu Glu Val
    210                 215                 220

Thr Cys Thr Trp Lys Leu Pro Thr Leu Ala Lys Phe Ser Pro Tyr Leu
225                 230                 235                 240

Gly Gln Met Ile Asn Leu Arg Arg Leu Leu Leu Ser His Ile His Ala
                245                 250                 255

Ser Ser Tyr Ile Ser Pro Glu Lys Glu Glu Gln Tyr Ile Ala Gln Phe
            260                 265                 270

Thr Ser Gln Phe Leu Ser Leu Gln Cys Leu Gln Ala Leu Tyr Val Asp
        275                 280                 285

Ser Leu Phe Phe Leu Arg Gly Arg Leu Asp Gln Leu Leu Arg His Val
    290                 295                 300

Met Asn Pro Leu Glu Thr Leu Ser Ile Thr Asn Cys Arg Leu Ser Glu
305                 310                 315                 320

Gly Asp Val Met His Leu Ser Gln Ser Pro Ser Val Ser Gln Leu Ser
                325                 330                 335

Val Leu Ser Leu Ser Gly Val Met Leu Thr Asp Val Ser Pro Glu Pro
            340                 345                 350
```

```
Leu Gln Ala Leu Leu Glu Arg Ala Ser Ala Thr Leu Gln Asp Leu Val
        355                 360                 365

Phe Asp Glu Cys Gly Ile Thr Asp Asp Gln Leu Leu Ala Leu Leu Pro
        370                 375                 380

Ser Leu Ser His Cys Ser Gln Leu Thr Thr Leu Ser Phe Tyr Gly Asn
385                 390                 395                 400

Ser Ile Ser Ile Ser Ala Leu Gln Ser Leu Leu Gln His Leu Ile Gly
                405                 410                 415

Leu Ser Asn Leu Thr His Val Leu Tyr Pro Val Pro Leu Glu Ser Tyr
                420                 425                 430

Glu Asp Ile His Gly Thr Leu His Leu Glu Arg Leu Ala Tyr Leu His
                435                 440                 445

Ala Arg Leu Arg Glu Leu Leu Cys Glu Leu Gly Arg Pro Ser Met Val
        450                 455                 460

Trp Leu Ser Ala Asn Pro Cys Pro His Cys Gly Asp Arg Thr Phe Tyr
465                 470                 475                 480

Asp Pro Glu Pro Ile Leu Cys Pro Cys Phe Met Pro Asn
                485                 490
```

<210> SEQ ID NO 951
<211> LENGTH: 493
<212> TYPE: PRT
<213> ORGANISM: Homo sapiens

<400> SEQUENCE: 951

```
Met Ser Val Trp Thr Ser Pro Arg Arg Leu Val Glu Leu Ala Gly Gln
1               5                   10                  15

Ser Leu Leu Lys Asp Glu Ala Leu Ala Ile Ala Ala Leu Glu Leu Leu
                20                  25                  30

Pro Arg Glu Leu Phe Pro Pro Leu Phe Met Ala Ala Phe Asp Gly Arg
        35                  40                  45

His Ser Gln Thr Leu Lys Ala Met Val Gln Ala Trp Pro Phe Thr Cys
        50                  55                  60

Leu Pro Leu Gly Val Leu Met Lys Gly Gln His Leu His Leu Glu Thr
65                  70                  75                  80

Phe Lys Ala Val Leu Asp Gly Leu Asp Val Leu Leu Ala Gln Glu Val
                85                  90                  95

Arg Pro Arg Arg Trp Lys Leu Gln Val Leu Asp Leu Arg Lys Asn Ser
        100                 105                 110

His Gln Asp Phe Trp Thr Val Trp Ser Gly Asn Arg Ala Ser Leu Tyr
        115                 120                 125

Ser Phe Pro Glu Pro Glu Ala Ala Gln Pro Met Thr Lys Lys Arg Lys
        130                 135                 140

Val Asp Gly Leu Ser Thr Glu Ala Glu Gln Pro Phe Ile Pro Val Glu
145                 150                 155                 160

Val Leu Val Asp Leu Phe Leu Lys Glu Gly Ala Cys Asp Glu Leu Phe
                165                 170                 175

Ser Tyr Leu Ile Glu Lys Val Lys Arg Lys Lys Asn Val Leu Arg Leu
                180                 185                 190

Cys Cys Lys Lys Leu Lys Ile Phe Ala Met Pro Met Gln Asp Ile Lys
        195                 200                 205

Met Ile Leu Lys Met Val Gln Leu Asp Ser Ile Glu Asp Leu Glu Val
        210                 215                 220

Thr Cys Thr Trp Lys Leu Pro Thr Leu Ala Lys Phe Ser Pro Tyr Leu
225                 230                 235                 240
```

-continued

```
Gly Gln Met Ile Asn Leu Arg Arg Leu Leu Leu Ser His Ile His Ala
            245                 250                 255

Ser Ser Tyr Ile Ser Pro Glu Lys Glu Glu Gln Tyr Ile Ala Gln Phe
            260                 265                 270

Thr Ser Gln Phe Leu Ser Leu Gln Cys Leu Gln Ala Leu Tyr Val Asp
            275                 280                 285

Ser Leu Phe Phe Leu Arg Gly Arg Leu Asp Gln Leu Leu Arg His Val
            290                 295                 300

Met Asn Pro Leu Glu Thr Leu Ser Ile Thr Asn Cys Arg Leu Ser Glu
305                 310                 315                 320

Gly Asp Val Met His Leu Ser Gln Ser Pro Ser Val Ser Gln Leu Ser
            325                 330                 335

Val Leu Ser Leu Ser Gly Val Met Leu Thr Asp Val Ser Pro Glu Pro
            340                 345                 350

Leu Gln Ala Leu Leu Glu Arg Ala Ser Ala Thr Leu Gln Asp Leu Val
            355                 360                 365

Phe Asp Glu Cys Gly Ile Thr Asp Asp Gln Leu Leu Ala Leu Leu Pro
    370                 375                 380

Ser Leu Ser His Cys Ser Gln Leu Thr Thr Leu Ser Phe Tyr Gly Asn
385                 390                 395                 400

Ser Ile Ser Ile Ser Ala Leu Gln Ser Leu Leu Gln His Leu Ile Gly
            405                 410                 415

Leu Ser Asn Leu Thr His Val Leu Tyr Pro Val Pro Leu Glu Ser Tyr
            420                 425                 430

Glu Asp Ile His Gly Thr Leu His Leu Glu Arg Leu Ala Tyr Leu His
            435                 440                 445

Ala Arg Leu Arg Glu Leu Leu Cys Glu Leu Gly Arg Pro Ser Met Val
    450                 455                 460

Trp Leu Ser Ala Asn Pro Cys Pro His Cys Gly Asp Arg Thr Phe Tyr
465                 470                 475                 480

Asp Pro Glu Pro Ile Leu Cys Pro Cys Phe Met Pro Asn
            485                 490
```

```
<210> SEQ ID NO 952
<211> LENGTH: 509
<212> TYPE: PRT
<213> ORGANISM: Homo sapiens

<400> SEQUENCE: 952
```

```
Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
            85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
```

```
                  115                  120                  125

His Gln Asp Phe Trp Thr Val Trp Ser Gly Asn Arg Ala Ser Leu Tyr
    130                  135                  140

Ser Phe Pro Glu Pro Glu Ala Ala Gln Pro Met Thr Lys Lys Arg Lys
145                  150                  155                  160

Val Asp Gly Leu Ser Thr Glu Ala Glu Gln Pro Phe Ile Pro Val Glu
                  165                  170                  175

Val Leu Val Asp Leu Phe Leu Lys Glu Gly Ala Cys Asp Glu Leu Phe
                  180                  185                  190

Ser Tyr Leu Ile Glu Lys Val Lys Arg Lys Lys Asn Val Leu Arg Leu
                  195                  200                  205

Cys Cys Lys Lys Leu Lys Ile Phe Ala Met Pro Met Gln Asp Ile Lys
    210                  215                  220

Met Ile Leu Lys Met Val Gln Leu Asp Ser Ile Glu Asp Leu Glu Val
225                  230                  235                  240

Thr Cys Thr Trp Lys Leu Pro Thr Leu Ala Lys Phe Ser Pro Tyr Leu
                  245                  250                  255

Gly Gln Met Ile Asn Leu Arg Arg Leu Leu Leu Ser His Ile His Ala
                  260                  265                  270

Ser Ser Tyr Ile Ser Pro Glu Lys Glu Glu Gln Tyr Ile Ala Gln Phe
                  275                  280                  285

Thr Ser Gln Phe Leu Ser Leu Gln Cys Leu Gln Ala Leu Tyr Val Asp
    290                  295                  300

Ser Leu Phe Phe Leu Arg Gly Arg Leu Asp Gln Leu Leu Arg His Val
305                  310                  315                  320

Met Asn Pro Leu Glu Thr Leu Ser Ile Thr Asn Cys Arg Leu Ser Glu
                  325                  330                  335

Gly Asp Val Met His Leu Ser Gln Ser Pro Ser Val Ser Gln Leu Ser
                  340                  345                  350

Val Leu Ser Leu Ser Gly Val Met Leu Thr Asp Val Ser Pro Glu Pro
                  355                  360                  365

Leu Gln Ala Leu Leu Glu Arg Ala Ser Ala Thr Leu Gln Asp Leu Val
    370                  375                  380

Phe Asp Glu Cys Gly Ile Thr Asp Asp Gln Leu Leu Ala Leu Leu Pro
385                  390                  395                  400

Ser Leu Ser His Cys Ser Gln Leu Thr Thr Leu Ser Phe Tyr Gly Asn
                  405                  410                  415

Ser Ile Ser Ile Ser Ala Leu Gln Ser Leu Leu Gln His Leu Ile Gly
                  420                  425                  430

Leu Ser Asn Leu Thr His Val Leu Tyr Pro Val Pro Leu Glu Ser Tyr
    435                  440                  445

Glu Asp Ile His Gly Thr Leu His Leu Glu Arg Leu Ala Tyr Leu His
    450                  455                  460

Ala Arg Leu Arg Glu Leu Leu Cys Glu Leu Gly Arg Pro Ser Met Val
465                  470                  475                  480

Trp Leu Ser Ala Asn Pro Cys Pro His Cys Gly Asp Arg Thr Phe Tyr
                  485                  490                  495

Asp Pro Glu Pro Ile Leu Cys Pro Cys Phe Met Pro Asn
                  500                  505
```

```
<210> SEQ ID NO 953
<211> LENGTH: 9
<212> TYPE: PRT
<213> ORGANISM: Homo sapiens
```

```
<400> SEQUENCE: 953

Ser Leu Leu Met Trp Ile Thr Gln Cys
1                   5

<210> SEQ ID NO 954
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 954

His His His His His His
1                   5
```

PREFERENTIALLY EXPRESSED ANTIGEN IN MELANOMA (PRAME) T CELL RECEPTORS AND METHODS OF USE THEREOF

RELATED APPLICATIONS

This application is a 35 U.S.C. § 371 national stage filing of International Application No. PCT/US2021/014490, filed on Jan. 22, 2021, which in turn claims the benefit of priority to U.S. Provisional Application No. 62/965,231, filed on Jan. 24, 2020. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Jan. 20, 2021, is named 118003-00520_SL.txt and is 461,085 bytes in size.

BACKGROUND

T cell receptors (TCRs) are membrane bound heterodimers comprising an α and β chain resembling an immunoglobulin variable (V) and constant (C) region. The TCR α chain includes a covalently linked V-α chain and C-α chain, whereas the β chain includes a V-β chain covalently linked to a C-β chain. The V-α and V-β chains form a pocket or cleft that can bind an antigen in the context of a major histocompatibility complex (MHC) (known in humans as an HLA complex). (Davis *Ann. Rev. of Immunology* 3: 537 (1985); *Fundamental Immunology* 3rd Ed., W. Paul Ed. New York (1993)).

TCRs are primary effectors of the immune system that have unique advantages as a platform for developing therapeutics. While antibody therapeutics are limited to recognition of pathogens in the blood and extracellular spaces, or to protein targets on the cell surface, T cell receptors can recognize antigens displayed with MHC molecules on the surface of cells, including antigens derived from intracellular proteins. Depending on the subtype of T cells that recognize displayed antigen and become activated, TCRs can participate in controlling various immune responses. For instance, T cells are involved in regulation of the humoral immune response through induction of differentiation of B cells into antibody producing cells. In addition, activated T cells act to initiate cell-mediated immune responses. Thus, TCRs can recognize additional targets not available to antibodies. In addition, TCRs have been reported to mediate cell killing, increase B cell proliferation, and impact the development and severity of various disorders including cancer, allergies, viral infections and autoimmune disorders.

In view of the function of TCRs, antigen-specific TCRs have been evaluated for use in immunotherapy for their ability to redirect T cells to tumors expressing the antigen. TCRs will bind to a small peptide, only 8-12 amino acids in length, which are bound on the surface of a target cell by the Major Histocompatibility Complex (MHC). TCRs can therefore recognize intracellular antigens derived from cancer or viral proteins because these antigens are processed and displayed as peptides in the context of the surface MHC. Hence, TCRs can recognize additional internal cell targets not available to antibodies or therapies that cannot penetrate the cell.

However, the challenge of the industry is to engineer TCRs that lack immunogenicity when administered to a patient and have fine specificity to the particular peptide antigen of interest, without cross-reacting to other peptides on MHC or similar epitopes found in the natural protein repertoire.

Preferentially expressed antigen in melanoma, or PRAME, is a well-known cancer-testis antigen (CTA) encoded on the X chromosome. It was first identified as a tumor antigen that could be recognized by HLA-A*24 restricted cytotoxic T lymphocytes in metastatic cutaneous melanoma (Ikeda H., et al. (1997) *Immunity* 6:199-208). PRAME has been shown to act as a repressor of retinoic acid receptor and, thus, may confer a growth advantage to cancer cells via this mechanism (see, e.g., Epping M. T., et al. (2005) *Cell* 122:835-847).

PRAME is abundantly re-expressed by many tumors of different histological types, including melanoma, renal cell cancer, non-small cell lung cancer (NSCLC), neuroblastoma, breast cancer, multiple myeloma, acute leukemia, chronic myeloid leukemia, multiple sarcoma subtypes, and primary and metastatic uveal melanoma but, in normal healthy adult tissues, PRAME expression is restricted to the testes.

There is an unmet need in the art for new targeting agents based on T cell receptors that specifically bind to PRAME antigens, as well as methods for producing and using such agents in therapeutic and diagnostic settings.

SUMMARY

The present invention provides T cell receptors (TCRs) that were generated against a PRAME peptide antigen in the context of MHC (HLA-A2). The unique TCR sequences identified have shown specific binding to a small peptide PRAME presented in the groove of an HLA molecule.

Accordingly, in one aspect, the present invention provides a T cell receptor (TCR) (e.g., an isolated TCR or a TCR expressed on an isolated cell) that binds specifically to an HLA-A2 presented cancer testis antigen preferentially expressed antigen in melanoma (PRAME) peptide comprising the amino acid sequence of RLDQLLRHV (SEQ ID NO:929) (PRAME 312-320) wherein the TCR comprises an alpha chain variable domain comprising a complementary determining region (CDR)3, wherein the CDR3 comprises the amino acid sequence of any one of the alpha chain variable domain CDR3 amino acid sequences set forth in Table 3.

In another aspect, the present invention provides a T cell receptor (TCR) (e.g., an isolated TCR or a TCR expressed on an isolated cell) that binds specifically to an HLA-A2 presented cancer testis antigen preferentially expressed antigen in melanoma (PRAME) peptide comprising the amino acid sequence of RLDQLLRHV (SEQ ID NO:929) (PRAME 312-320), wherein the TCR comprises a beta chain variable domain comprising a complementary determining region (CDR)3, wherein the CDR3 comprises the amino acid sequence of any one of the beta chain variable domain CDR3 amino acid sequences set forth in Table 3.

In some embodiments, the alpha chain variable domain further comprises a CDR1 and a CDR2, wherein the CDR1 comprises any one of the alpha chain variable domain CDR1 amino acid sequences set forth in Table 3 and the CDR2 independently comprises any one of the alpha chain variable domain CDR2 amino acid sequences set forth in Table 3.

In some embodiments, the beta chain variable domain further comprises a CDR1 and a CDR2, wherein the CDR1 comprises any one of the beta chain variable CDR1 amino acid sequences set forth in Table 3 and the CDR2 independently comprises any one of the beta chain variable domain CDR2 amino acid sequences set forth in Table 3.

The TCR may include at least one TCR alpha chain variable domain and/or at least one beta chain variable domain; or the TCR may include a TCR alpha chain variable domain and a TCR beta chain variable domain.

In some embodiments, the TCR comprises alpha chain variable domain CDR1, CDR2 and CDR3 contained within any one of the alpha chain variable domain sequences listed in Table 5; and beta chain variable domain CDR1, CDR2 and CDR3 contained within any one of the beta chain variable domain sequences listed in Table 5.

In some embodiments, the TCR comprises an alpha chain variable domain having an amino acid sequence that has at least 85% amino acid identity to the entire amino acid sequence of any one of the amino acid sequences of the alpha chain variable domain amino acid sequences listed in Table 5.

In some embodiments, the TCR comprises a beta chain variable domain having an amino acid sequence that has at least 85% amino acid identity to the entire amino acid sequence of any one of the amino acid sequences of the beta chain variable domain amino acid sequences listed in Table 5.

In some embodiments, the TCR comprises (a) an alpha chain variable domain having an amino acid sequence that has at least 85% amino acid identity to the entire amino acid sequence of any one of the amino acid sequences of the alpha chain variable domain amino acid sequences listed in Table 5; and (b) a beta chain variable domain having an amino acid sequence that has at least 85% amino acid identity to the entire amino acid sequence of any one of the amino acid sequences of the beta chain variable domain amino acid sequences listed in Table 5.

In some embodiments, the TCR comprises (a) an alpha chain variable domain CDR1 domain having an amino acid sequence selected from the group consisting of SEQ ID NOs: 1, 7, 13, 19, 25, 31, 37, 43, 49, 55, 61, 67, 73, 79, 85, 91, 97, and 103; (b) an alpha chain variable domain CDR2 domain having an amino acid sequence selected from the group consisting of SEQ ID NOs: 2, 8, 14, 20, 26, 32, 38, 44, 50, 56, 62, 68, 74, 80, 86, 92, 98, and 104; (c) an alpha chain variable domain CDR3 domain having an amino acid sequence selected from the group consisting of SEQ ID NOs: 3, 9, 15, 21, 27, 33, 39, 45, 51, 57, 63, 69, 75, 81, 87, 93, 99, and 105; (d) a beta chain variable domain CDR1 having an amino acid sequence selected from the group consisting of SEQ ID NOs: 4, 10, 16, 22, 28, 34, 40, 46, 52, 58, 64, 70, 76, 82, 88, 94, 100, and 106; (e) a beta chain variable domain CDR2 having an amino acid sequence selected from the group consisting of SEQ ID NOs: 5, 11, 17, 23, 29, 35, 41, 47, 53, 59, 65, 71, 77, 83, 89, 95, 101, and 107; and (f) a beta chain variable domain CDR3 having an amino acid sequence selected from the group consisting of SEQ ID NOs: 6, 12, 18, 24, 30, 36, 42, 48, 54, 60, 66, 72, 78, 84, 90, 96, 102, and 108.

In some embodiments, the TCR comprises an alpha chain variable domain/beta chain variable domain amino acid sequence pair selected from the group consisting of SEQ ID NOs: 217/219, 229/231, 237/239, 241/243, and 285/287.

In some embodiments, the TCR comprises an alpha chain variable domain/beta chain variable domain amino acid sequence pair selected from the group consisting of SEQ ID NOs: 217/219, 221/223, 225/227, 229/231, 233/235, 237/

239, 241/243, 245/247, 249/251, 253/255, 257/259, 261/263, 265/267, 269/271, 273/275, 277/279, 281/283, and 285/287.

The present invention also provides a TCR (e.g., an isolated TCR or a TCR expressed on an isolated cell) that complete for binding to any one or more of the TCRs of the invention.

In one aspect, the present invention provides a T cell receptor (TCR) (e.g., an isolated TCR or a TCR expressed on an isolated cell) that binds specifically to an HLA-A2 presented cancer testis antigen preferentially expressed antigen in melanoma (PRAME) peptide comprising the amino acid sequence of SLLQHLIGL (SEQ ID NO:930) (PRAME 425-433), wherein the TCR comprises an alpha chain variable domain comprising a complementary determining region (CDR)3, wherein the CDR3 comprises the amino acid sequence of any one of the alpha chain variable domain CDR3 amino acid sequences set forth in Table 6.

In another aspect, the present invention provides a T cell receptor (TCR) (e.g., an isolated TCR or a TCR expressed on an isolated cell) that binds specifically to an HLA-A2 presented preferentially expressed antigen in melanoma (PRAME) peptide comprising the amino acid sequence of SLLQHLIGL (SEQ ID NO:930) (PRAME 425-433), wherein the TCR comprises a beta chain variable domain comprising a complementary determining region (CDR)3, wherein the CDR3 comprises the amino acid sequence of any one of the beta chain variable domain CDR3 amino acid sequences set forth in Table 6.

In some embodiments, the alpha chain variable domain further comprises a CDR1 and a CDR2, wherein the CDR1 comprises any one of the alpha chain variable domain CDR1 amino acid sequences set forth in Table 6 and the CDR2 independently comprises any one of the alpha chain variable domain CDR2 amino acid sequences set forth in Table 6.

In some embodiments, the beta chain variable domain further comprises a CDR1 and a CDR2, wherein the CDR1 comprises any one of the beta chain variable CDR1 amino acid sequences set forth in Table 6 and the CDR2 independently comprises any one of the beta chain variable domain CDR2 amino acid sequences set forth in Table 6.

The TCR may include at least one TCR alpha chain variable domain and/or at least one beta chain variable domain; or the TCR may include a TCR alpha chain variable domain and a TCR beta chain variable domain.

In some embodiments, the TCR comprises alpha chain variable domain CDR1, CDR2 and CDR3 contained within any one of the alpha chain variable domain sequences listed in Table 8; and beta chain variable domain CDR1, CDR2 and CDR3 contained within any one of the beta chain variable domain sequences listed in Table 8.

In some embodiments, the TCR comprises an alpha chain variable domain having an amino acid sequence that has at least 85% amino acid identity to the entire amino acid sequence of any one of the amino acid sequences of the alpha chain variable domain amino acid sequences listed in Table 8.

In some embodiments, the TCR comprises a beta chain variable domain having an amino acid sequence that has at least 85% amino acid identity to the entire amino acid sequence of any one of the amino acid sequences of the beta chain variable domain amino acid sequences listed in Table 8.

In some embodiments, the TCR comprises (a) an alpha chain variable domain having an amino acid sequence that has at least 85% amino acid identity to the entire amino acid sequence of any one of the amino acid sequences of the alpha chain variable domain amino acid sequences listed in Table 8; and (b) a beta chain variable domain having an amino acid sequence that has at least 85% amino acid identity to the entire amino acid sequence of any one of the amino acid sequences of the beta chain variable domain amino acid sequences listed in Table 8.

In some embodiments, the TCR comprises (a) an alpha chain variable domain CDR1 domain having an amino acid sequence selected from the group consisting of SEQ ID NOs: 289, 295, 301, 307, 313, 319, 325, 331, 337, 343, 349, 355, 361, 367, 373, 379, 385, 391, 397, 403, 409, 415, 421, 427, 433, 439, 445, 451, 457, 463, 469, 475, 481, 487, 493, 499, 505, 511, 517, and 523; (b) an alpha chain variable domain CDR2 domain having an amino acid sequence selected from the group consisting of SEQ ID NOs: 290, 296, 302, 308, 314, 320, 326, 332, 338, 344, 350, 356, 362, 368, 374, 380, 386, 392, 398, 404, 410, 416, 422, 428, 434, 440, 446, 452, 458, 464, 470, 476, 482, 488, 494, 500, 506, 512, 518, and 524; (c) an alpha chain variable domain CDR3 domain having an amino acid sequence selected from the group consisting of SEQ ID NOs: 291, 297, 303, 309, 315, 321, 327, 333, 339, 345, 351, 357, 363, 369, 375, 381, 387, 393, 399, 405, 411, 417, 423, 429, 435, 441, 447, 453, 459, 465, 471, 477, 483, 489, 495, 501, 507, 513, 519, and 525; (d) a beta chain variable domain CDR1 having an amino acid sequence selected from the group consisting of SEQ ID NOs: 292, 298, 304, 310, 316, 322, 328, 334, 340, 346, 352, 358, 364, 370, 376, 382, 388, 394, 400, 406, 412, 418, 424, 430, 436, 442, 448, 454, 460, 466, 472, 478, 484, 490, 496, 502, 508, 514, 520, and 526; (e) a beta chain variable domain CDR2 having an amino acid sequence selected from the group consisting of SEQ ID NOs: 293, 299, 305, 311, 317, 323, 329, 335, 341, 347, 353, 359, 365, 371, 377, 383, 389, 395, 401, 407, 413, 419, 425, 431, 437, 443, 449, 455, 461, 467, 473, 479, 485, 491, 497, 503, 509, 515, 521, and 527; and (f) a beta chain variable domain CDR3 having an amino acid sequence selected from the group consisting of SEQ ID NOs: 294, 300, 306, 312, 318, 324, 330, 336, 342, 348, 354, 360, 366, 372, 378, 384, 390, 396, 402, 408, 414, 420, 426, 432, 438, 444, 450, 456, 462, 468, 474, 480, 486, 492, 498, 504, 510, 516, 522, and 528.

In some embodiments, the TCR comprises an alpha chain variable domain/beta chain variable domain amino acid sequence pair selected from the group consisting of SEQ ID NOs: 825/827, 845/847, 853/855, 857/859, 865/867, 873/875, 885/887, 893/805, 897/899, 901/903, 913/915, and 925/927.

In some embodiments, the TCR comprises an alpha chain variable domain/beta chain variable domain amino acid sequence pair selected from the group consisting of SEQ ID NOs: 769/771, 773/775, 777/779, 781/783, 785/787, 789/791, 793/795, 797/799, 801/803, 805/807, 809/811, 813/815, 817/819, 821/823, 825/827, 829/831, 833/835, 837/839, 841/843, 845/847, 849/851, 853/855, 857/859, 861/863, 865/867, 869/871, 873/875, 877/879, 881/883, 885/887, 889/891, 893/805, 897/899, 901/903, 905/907, 909/911, 913/915, 917/919, 921/923, and 925/927.

The present invention also provides a TCR (e.g., an isolated TCR or a TCR expressed on an isolated cell) that complete for binding to any one or more of the TCRs of the invention.

In some embodiments, the TCRs of the invention further comprise a detectable moiety.

The present invention further provides pharmaceutical compositions comprising any of the TCRs of the invention, and a pharmaceutically acceptable carrier or diluent; as well as isolated cells presenting any of the TCRs of the invention.

In one aspect, the present invention provides isolated polynucleotide molecules comprising a polynucleotide sequence that encodes an alpha chain variable domain of any of the TCRs of the invention.

In another aspect, the present invention provides isolated polynucleotide molecules comprising a polynucleotide sequence that encodes a beta chain variable domain of any of the TCRs of the invention.

The present invention also provides vectors comprising the polynucleotide molecule of the invention; cells expressing the vectors of the invention.

In one aspect, the present invention provides a method of treating a subject having a PRAME-associated disease or disorder. The methods includes administering to the subject a therapeutically effective amount of a TCR (e.g., an isolated TCR or a TCR expressed on an isolated cell), pharmaceutical composition, or a plurality of the cells of the invention, thereby treating the subject.

In some embodiments, the PRAME-associated disease or disorder is PRAME-associated cancer.

In some embodiments, the PRAME-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, uterine corpus endometrial carcinoma, uterine carcinosarcoma, testicular germ cell tumor, uveal melanoma, kidney renal papillary cell carcinoma, kidney renal clear cell carcinoma, thymoma, colon adenocarcinoma, cervical squamous cell carcinoma, cervical tumor, pancreatic adenocarcinoma, liver cancer, hepatocellular carcinoma, mesothelioma, or a recurrent non-small cell lung cancer.

In some embodiments of the invention, a TCR (e.g., an isolated TCR or a TCR expressed on an isolated cell), pharmaceutical composition, or a plurality of the cells of the invention is administered to the subject in combination with a second therapeutic agent.

The TCR, the pharmaceutical composition, or the plurality of cells may be administered subcutaneously, intravenously, intradermally, intraperitoneally, orally, intramuscularly or intracranially to the subject.

In one aspect, the present invention provides an isolated nucleic acid molecule encoding a T cell receptor (TCR), wherein the TCR binds specifically to an HLA-A2 presented cancer testis antigen preferentially expressed antigen in melanoma (PRAME) peptide comprising the amino acid sequence of RLDQLLRHV (SEQ ID NO:929) (PRAME 312-320), wherein the TCR comprises an alpha chain variable domain comprising a complementary determining region (CDR)3, wherein the CDR3 comprises the amino acid sequence of any one of the alpha chain variable domain CDR3 amino acid sequences set forth in Table 5.

In another aspect, the present invention provides an isolated nucleic acid molecule encoding a T cell receptor (TCR), wherein the TCR binds specifically to an HLA-A2 presented cancer testis antigen preferentially expressed antigen in melanoma (PRAME) peptide comprising the amino acid sequence of RLDQLLRHV (SEQ ID NO:929) (PRAME 312-320), wherein the TCR comprises a beta chain variable domain comprising a complementary determining region (CDR)3, wherein the CDR3 comprises the amino acid sequence of any one of the beta chain variable domain CDR3 amino acid sequences set forth in Table 5.

In some embodiments, the isolated nucleic acid molecule encodes at least one TCR alpha chain variable domain and/or at least one beta chain variable domain.

In some embodiments, the TCR comprises alpha chain variable domain complementary determining regions (CDR) 1, CDR2, and CDR3 contained within any one of the alpha chain variable domain sequences listed in Table 5; and beta chain variable domain CDR1, CDR2 and CDR3 contained within any one of the beta chain variable domain sequences listed in Table 5.

In some embodiments, the TCR (e.g., isolated TCR or TCR expressed on an isolated cell) comprises alpha chain variable domain having an amino acid sequence that has at least 85% amino acid identity to the entire amino acid sequence of any one of the amino acid sequences of the alpha chain variable domain amino acid sequences listed in Table 5.

In some embodiments, the TCR comprises beta chain variable domain having an amino acid sequence that has at least 85% amino acid identity to the entire amino acid sequence of any one of the amino acid sequences of the beta chain variable domain amino acid sequences listed in Table 5.

In some embodiments, the TCR comprises (a) an alpha chain variable domain having an amino acid sequence that has at least 85% amino acid identity to the entire amino acid sequence of any one of the amino acid sequences of the alpha chain variable domain amino acid sequences listed in Table 5; and (b) a beta chain variable domain having an amino acid sequence that has at least 85% amino acid identity to the entire amino acid sequence of any one of the amino acid sequences of the beta chain variable domain amino acid sequences listed in Table 5.

In some embodiments, the isolated antigen-binding protein comprises (a) an alpha chain variable domain CDR1 domain having an amino acid sequence selected from the group consisting of SEQ ID NOs: 1, 7, 13, 19, 25, 31, 37, 43, 49, 55, 61, 67, 73, 79, 85, 91, 97, and 103; (b) an alpha chain variable domain CDR2 domain having an amino acid sequence selected from the group consisting of SEQ ID NOs: 2, 8, 14, 20, 26, 32, 38, 44, 50, 56, 62, 68, 74, 80, 86, 92, 98, and 104; (c) an alpha chain variable domain CDR3 domain having an amino acid sequence selected from the group consisting of SEQ ID NOs: 3, 9, 15, 21, 27, 33, 39, 45, 51, 57, 63, 69, 75, 81, 87, 93, 99, and 105; (d) a beta chain variable domain CDR1 having an amino acid sequence selected from the group consisting of SEQ ID NOs: 4, 10, 16, 22, 28, 34, 40, 46, 52, 58, 64, 70, 76, 82, 88, 94, 100, and 106; (e) a beta chain variable domain CDR2 having an amino acid sequence selected from the group consisting of SEQ ID NOs: 5, 11, 17, 23, 29, 35, 41, 47, 53, 59, 65, 71, 77, 83, 89, 95, 101, and 107; and (f) a beta chain variable domain CDR3 having an amino acid sequence selected from the group consisting of SEQ ID NOs: 6, 12, 18, 24, 30, 36, 42, 48, 54, 60, 66, 72, 78, 84, 90, 96, 102, and 108.

In some embodiments, the TCR comprises an alpha chain variable domain/beta chain variable domain amino acid sequence pair selected from the group consisting of SEQ ID NOs: 217/219, 229/231, 237/239, 241/243, and 285/287.

In some embodiments, the TCR comprises an alpha chain variable domain/beta chain variable domain amino acid sequence pair selected from the group consisting of SEQ ID NOs: 217/219, 221/223, 225/227, 229/231, 233/235, 237/239, 241/243, 245/247, 249/251, 253/255, 257/259, 261/263, 265/267, 269/271, 273/275, 277/279, 281/283, and 285/287.

In some embodiments, the isolated antigen-binding protein comprises (a) an alpha chain variable domain CDR1 encoded by a nucleic acid sequence selected from the group consisting of SEQ ID NOs: 109, 115, 121, 127, 133, 139, 145, 151, 157, 163, 169, 175, 181, 187, 193, 199, 205, and 211; (b) an alpha chain variable domain CDR2 encoded by a nucleic acid sequence selected from the group consisting of SEQ ID NOs: 110, 116, 122, 128, 134, 140, 146, 152, 158, 164, 170, 176, 182, 188, 194, 200, 206, and 212; (c) an alpha chain variable domain CDR3 encoded by a nucleic acid sequence selected from the group consisting of SEQ ID NOs: 111, 117, 123, 129, 135, 141, 147, 153, 159, 165, 171, 177, 183, 189, 195, 201, 207, and 213; (d) a beta chain variable domain CDR1 encoded by a nucleic acid sequence selected from the group consisting of SEQ ID NOs: 112, 118, 124, 130, 136, 142, 148, 154, 160, 166, 172, 178, 184, 190, 196, 202, 208, and 214; (e) a beta chain variable domain CDR2 encoded by a nucleic acid sequence selected from the group consisting of SEQ ID NOs: 113, 119, 125, 131, 137, 143, 149, 155, 161, 167, 173, 179, 185, 191, 197, 203, 209, and 215; and (f) a beta chain variable domain CDR3 encoded by a nucleic acid sequence selected from the group consisting of SEQ ID NOs: 114, 120, 126, 132, 138, 144, 150, 156, 162, 168, 174, 180, 186, 192, 198, 204, 210, and 216.

In some embodiments, the TCR comprises an alpha chain variable domain/beta chain variable domain nucleic acid sequence pair selected from the group consisting of SEQ ID NOs: 218/220, 222/224, 226/228, 230/232, 234/236, 238/240, 242/244, 246/248, 250/252, 254/256, 258/260, 262/264, 266/268, 270/272, 274/276, 278/280, 282/284, and 286/288.

The present invention also provides vectors comprising an isolated nucleic acid molecule of the invention and isolated cells comprising a vector of the invention.

In one aspect, the present invention provides isolated polynucleotide molecules comprising a polynucleotide sequence that encodes an alpha chain variable domain of any of the TCRs of the invention.

In another aspect, the present invention provides isolated polynucleotide molecules comprising a polynucleotide sequence that encodes a beta chain variable domain of any of the TCRs of the invention.

The present invention also provides vectors comprising the polynucleotide molecule of the invention; cells expressing the vectors of the invention.

In one aspect, the present invention provides a method of treating a subject having a PRAME-associated disease or disorder. The methods includes administering to the subject a therapeutically effective amount of a TCR (e.g., an isolated TCR or a TCR expressed on an isolated cell), pharmaceutical composition, or a plurality of the cells of the invention, thereby treating the subject.

In some embodiments, the PRAME-associated disease or disorder is PRAME-associated cancer.

In some embodiments, the PRAME-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, uterine corpus endometrial carcinoma, uterine carcinosarcoma, testicular germ cell tumor, uveal melanoma, kidney renal papillary cell carcinoma, kidney renal clear cell carcinoma, thymoma, colon adenocarcinoma, cervical squamous cell carcinoma, cervical tumor, pancreatic adenocarcinoma, liver cancer, hepatocellular carcinoma, mesothelioma, or a recurrent non-small cell lung cancer.

In some embodiments of the invention, a TCR (e.g., an isolated TCR or a TCR expressed on an isolated cell), pharmaceutical composition, or a plurality of the cells of the invention is administered to the subject in combination with a second therapeutic agent.

The TCR, the pharmaceutical composition, or the plurality of cells may be administered subcutaneously, intravenously, intradermally, intraperitoneally, orally, intramuscularly or intracranially to the subject.

In one aspect, the present invention provides an isolated nucleic acid molecule encoding a T cell receptor (TCR), wherein the TCR binds specifically to an HLA-A2 presented cancer testis antigen preferentially expressed antigen in melanoma (PRAME) peptide comprising the amino acid sequence of SLLQHLIGL (SEQ ID NO:930) (PRAME 425-433), wherein the TCR comprises an alpha chain variable domain comprising a complementary determining region (CDR)3, wherein the CDR3 comprises the amino acid sequence of any one of the alpha chain variable domain CDR3 amino acid sequences set forth in Table 8.

In another aspect, the present invention provides an isolated nucleic acid molecule encoding a T cell receptor (TCR), wherein the TCR binds specifically to an HLA-A2 presented cancer testis antigen preferentially expressed antigen in melanoma (PRAME) peptide comprising the amino acid sequence of SLLQHLIGL (SEQ ID NO:930) (PRAME 425-433), wherein the TCR comprises a beta chain variable domain comprising a complementary determining region (CDR)3, wherein the CDR3 comprises the amino acid sequence of any one of the beta chain variable domain CDR3 amino acid sequences set forth in Table 8.

In some embodiments, the isolated nucleic acid molecule encodes at least one TCR alpha chain variable domain and/or at least one beta chain variable domain.

In some embodiments, the TCR comprises alpha chain variable domain complementary determining regions (CDR) 1, CDR2, and CDR3 contained within any one of the alpha chain variable domain sequences listed in Table 8; and beta chain variable domain CDR1, CDR2 and CDR3 contained within any one of the beta chain variable domain sequences listed in Table 8.

In some embodiments, the TCR (e.g., isolated TCR or TCR expressed on an isolated cell) comprises alpha chain variable domain having an amino acid sequence that has at least 85% amino acid identity to the entire amino acid sequence of any one of the amino acid sequences of the alpha chain variable domain amino acid sequences listed in Table 8.

In some embodiments, the TCR comprises beta chain variable domain having an amino acid sequence that has at least 85% amino acid identity to the entire amino acid sequence of any one of the amino acid sequences of the beta chain variable domain amino acid sequences listed in Table 8.

In some embodiments, the TCR comprises (a) an alpha chain variable domain having an amino acid sequence that has at least 85% amino acid identity to the entire amino acid sequence of any one of the amino acid sequences of the alpha chain variable domain amino acid sequences listed in Table 8; and (b) a beta chain variable domain having an amino acid sequence that has at least 85% amino acid identity to the entire amino acid sequence of any one of the amino acid sequences of the beta chain variable domain amino acid sequences listed in Table 8.

In some embodiments, the isolated antigen-binding protein comprises (a) an alpha chain variable domain CDR1 domain having an amino acid sequence selected from the group consisting of SEQ ID NOs: 289, 295, 301, 307, 313, 319, 325, 331, 337, 343, 349, 355, 361, 367, 373, 379, 385, 391, 397, 403, 409, 415, 421, 427, 433, 439, 445, 451, 457, 463, 469, 475, 481, 487, 493, 499, 505, 511, 517, and 523; (b) an alpha chain variable domain CDR2 domain having an amino acid sequence selected from the group consisting of SEQ ID NOs: 290, 296, 302, 308, 314, 320, 326, 332, 338, 344, 350, 356, 362, 368, 374, 380, 386, 392, 398, 404, 410, 416, 422, 428, 434, 440, 446, 452, 458, 464, 470, 476, 482, 488, 494, 500, 506, 512, 518, and 524; (c) an alpha chain variable domain CDR3 domain having an amino acid sequence selected from the group consisting of SEQ ID NOs: 291, 297, 303, 309, 315, 321, 327, 333, 339, 345, 351, 357, 363, 369, 375, 381, 387, 393, 399, 405, 411, 417, 423, 429, 435, 441, 447, 453, 459, 465, 471, 477, 483, 489, 495, 501, 507, 513, 519, and 525; (d) a beta chain variable domain CDR1 having an amino acid sequence selected from the group consisting of SEQ ID NOs: 292, 298, 304, 310, 316, 322, 328, 334, 340, 346, 352, 358, 364, 370, 376, 382, 388, 394, 400, 406, 412, 418, 424, 430, 436, 442, 448, 454, 460, 466, 472, 478, 484, 490, 496, 502, 508, 514, 520, and 526; (e) a beta chain variable domain CDR2 having an amino acid sequence selected from the group consisting of SEQ ID NOs: 293, 299, 305, 311, 317, 323, 329, 335, 341, 347, 353, 359, 365, 371, 377, 383, 389, 395, 401, 407, 413, 419, 425, 431, 437, 443, 449, 455, 461, 467, 473, 479, 485, 491, 497, 503, 509, 515, 521, and 527; and (f) a beta chain variable domain CDR3 having an amino acid sequence selected from the group consisting of SEQ ID NOs: 294, 300, 306, 312, 318, 324, 330, 336, 342, 348, 354, 360, 366, 372, 378, 384, 390, 396, 402, 408, 414, 420, 426, 432, 438, 444, 450, 456, 462, 468, 474, 480, 486, 492, 498, 504, 510, 516, 522, and 528.

In some embodiments, the TCR comprises an alpha chain variable domain/beta chain variable domain amino acid sequence pair selected from the group consisting of SEQ ID NOs: 825/827, 845/847, 853/855, 857/859, 865/867, 873/875, 885/887, 893/805, 897/899, 901/903, 913/915, and 925/927.

In some embodiments, the TCR comprises an alpha chain variable domain/beta chain variable domain amino acid sequence pair selected from the group consisting of SEQ ID NOs: 769/771, 773/775, 777/779, 781/783, 785/787, 789/791, 793/795, 797/799, 801/803, 805/807, 809/811, 813/815, 817/819, 821/823, 825/827, 829/831, 833/835, 837/839, 841/843, 845/847, 849/851, 853/855, 857/859, 861/863, 865/867, 869/871, 873/875, 877/879, 881/883, 885/

887, 889/891, 893/805, 897/899, 901/903, 905/907, 909/911, 913/915, 917/919, 921/923, and 925/927.

In some embodiments, the isolated antigen-binding protein comprises (a) an alpha chain variable domain CDR1 encoded by a nucleic acid sequence selected from the group consisting of SEQ ID NOs: 529, 535, 541, 547, 553, 559, 565, 571, 577, 583, 589, 595, 601, 607, 613, 619, 625, 631, 637, 643, 649, 655, 661, 667, 673, 679, 685, 691, 697, 703, 709, 715, 721, 727, 733, 739, 745, 751, 757, and 763; (b) an alpha chain variable domain CDR2 encoded by a nucleic acid sequence selected from the group consisting of SEQ ID NOs: 530, 536, 542, 548, 554, 560, 566, 572, 578, 584, 590, 596, 602, 608, 614, 620, 626, 632, 638, 644, 650, 656, 662, 668, 674, 680, 686, 692, 698, 704, 710, 716, 722, 728, 734, 740, 746, 752, 758, and 764; (c) an alpha chain variable domain CDR3 encoded by a nucleic acid sequence selected from the group consisting of SEQ ID NOs: 531, 537, 543, 549, 555, 561, 567, 573, 579, 585, 591, 597, 603, 609, 615, 621, 627, 633, 639, 645, 651, 657, 663, 669, 675, 681, 687, 693, 699, 705, 711, 717, 723, 729, 735, 741, 747, 753, 759, and 765; (d) a beta chain variable domain CDR1 encoded by a nucleic acid sequence selected from the group consisting of SEQ ID NOs: 532, 538, 544, 550, 556, 562, 568, 574, 580, 586, 592, 598, 604, 610, 616, 622, 628, 634, 640, 646, 652, 658, 664, 670, 676, 682, 688, 694, 700, 706, 712, 718, 724, 730, 736, 742, 748, 754, 760, and 766; (e) a beta chain variable domain CDR2 encoded by a nucleic acid sequence selected from the group consisting of SEQ ID NOs: 533, 539, 545, 551, 557, 563, 569, 575, 581, 587, 593, 599, 605, 611, 617, 623, 629, 635, 641, 647, 653, 659, 665, 671, 677, 683, 689, 695, 701, 707, 713, 719, 725, 731, 737, 743, 749, 755, 761, and 767; and (f) a beta chain variable domain CDR3 encoded by a nucleic acid sequence selected from the group consisting of SEQ ID NOs: 534, 540, 546, 552, 558, 564, 570, 576, 582, 588, 594, 600, 606, 612, 618, 624, 630, 636, 642, 648, 654, 660, 666, 672, 678, 684, 690, 696, 702, 708, 714, 720, 726, 732, 738, 744, 750, 756, 762, and 768.

In some embodiments, the TCR comprises an alpha chain variable domain/beta chain variable domain nucleic acid sequence pair selected from the group consisting of SEQ ID NOs: 770/772, 774/776, 778/780, 782/784, 786/788, 790/792, 794/796, 798/800, 802/804, 806/808, 810/812, 814/816, 818/820, 822/824, 826/828, 830/832, 834/836, 838/840, 842/844, 846/848, 850/852, 854/856, 858/860, 862/864, 866/868, 870/872, 874/876, 878/880, 882/884, 886/888, 890/892, 894/896, 898/900, 902/904, 906/908, 910/912, 914/916, 918/920, 922/924, and 926/928.

The present invention also provides vectors comprising an isolated nucleic acid molecule of the invention and isolated cells comprising a vector of the invention.

In one aspect, the present invention provides a method of treating a subject having a PRAME-associated disease or disorder, comprising administering to the subject a plurality of the cells comprising a vector of the invention, thereby treating the subject.

In some embodiments, the PRAME-associated disease or disorder is PRAME-associated cancer.

In some embodiments, the PRAME-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, uterine corpus endometrial carcinoma, uterine carcinosarcoma, testicular germ cell tumor, uveal melanoma, kidney renal papillary cell carcinoma, kidney renal clear cell carcinoma, thymoma, colon adenocarcinoma, cervical squamous cell carcinoma, cervical tumor, pancreatic adenocarcinoma, liver cancer, hepatocellular carcinoma, mesothelioma, or a recurrent non-small cell lung cancer.

In some embodiments, a plurality of cells is administered to the subject in combination with a second therapeutic agent.

The present invention is further illustrated by the following detailed description.

DETAILED DESCRIPTION

The present invention provides T cell receptors (TCRs) that were generated against a PRAME peptide antigen in the context of MHC (HLA-A2). The unique TCR sequences identified have shown specific binding to the small peptide PRAME presented in the groove of an HLA molecule.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

The term "comprising" or "comprises" is used herein in reference to compositions, methods, and respective component(s) thereof, that are essential to the disclosure, yet open to the inclusion of unspecified elements, whether essential or not.

The term "consisting of" refers to compositions, methods, and respective components thereof as described herein, which are exclusive of any element not recited in that description of the embodiment.

The term "T cell receptor" (TCR), as used herein, refers to an immunoglobulin superfamily member having a variable binding domain, a constant domain, a transmembrane region, and a short cytoplasmic tail; see, e.g., Janeway et al.,

*Immunobiology: The Immune System in Health and Disease,* 3rd Ed., Current Biology Publications, p. 4:33, 1997) capable of specifically binding to an antigen peptide bound to a MHC receptor. A TCR can be found on the surface of a cell and generally is comprised of a heterodimer having $\alpha$ and $\beta$ chains (also known as TCR$\alpha$ and TCR$\beta$, respectively), or $\gamma$ and $\delta$ chains (also known as TCR$\gamma$ and TCR$\beta$, respectively). Like immunoglobulins, the extracellular portion of TCR chains (e.g., $\alpha$-chain, $\beta$-chain) contain two immunoglobulin regions, a variable region (e.g., TCR variable $\alpha$ region or V$\alpha$ and TCR variable $\beta$ region or V$\beta$; typically amino acids 1 to 116 based on Kabat numbering at the N-terminus), and one constant region (e.g., TCR constant domain $\alpha$ or C$\alpha$ and typically amino acids 117 to 259 based on Kabat, TCR constant domain $\beta$ or C$\beta$, typically amino acids 117 to 295 based on Kabat) adjacent to the cell membrane. Also, like immunoglobulins, the variable domains contain complementary determining regions (CDRs) separated by framework regions (FRs). In certain embodiments, a TCR is found on the surface of T cells (or T lymphocytes) and associates with the CD3 complex. The source of a TCR of the present disclosure may be from various animal species, such as a human, mouse, rat, rabbit or other mammal. In preferred embodiments, the source of a TCR of the present invention is a mouse genetically engineered to produce TCRs comprising human alpha and beta chains (see, e.g., PCT Publication No. WO 2016/164492, the entire contents of which are incorporated herein by reference).

The term "variable region" (variable region of an alpha chain (V$\alpha$), variable region of a beta chain (V$\beta$)) as used herein denotes each of the alpha and beta chains which is involved directly in binding the TCR to the antigen.

The "constant region" of the alpha chain and of the beta chain are not involved directly in binding of a TCR to an antigen, but exhibit various effector functions.

The term "antigen" as used herein is meant any substance that causes the immune system to produce antibodies or specific cell-mediated immune responses against it. A disease-associated antigen is any substance that is associated with any disease that causes the immune system to produce antibodies or a specific-cell mediated response against it.

The term "PRAME" or "preferentially expressed antigen in melanoma" refers to the well-known cancer-testis antigen (CTA) that is re-expressed in numerous cancer types.

The nucleotide sequence of PRAME is known and may be found in, for example, GenBank Accession Nos. NM_001291715.2 (SEQ ID NO: 931), NM_001291716.2 (SEQ ID NO: 932), NM_001291717.2 (SEQ ID NO: 933), NM_001291719.2 (SEQ ID NO: 934), NM_001318126.1 (SEQ ID NO: 935), NM_001318127.1 (SEQ ID NO: 936), NM_006115.5 (SEQ ID NO: 937), NM_206956.3 (SEQ ID NO: 938), NM_206955.2 (SEQ ID NO: 939), NM_206954.3 (SEQ ID NO: 940), and NM_206953.2 (SEQ ID NO: 941). The amino acid sequence of full-length PRAME is known and may be found in, for example, GenBank as Accession Nos. NP_001278646.1 (SEQ ID NO: 942), NP_006106.1 (SEQ ID NO: 943), NP_996837.1 (SEQ ID NO: 944), NP_996836.1 (SEQ ID NO: 945), NP_996839.1 (SEQ ID NO: 946), NP_996838.1 (SEQ ID NO: 947), NP_001278644.1 (SEQ ID NO: 948), NP_001305055.1 (SEQ ID NO: 949), NP_001305056.1 (SEQ ID NO: 950), NP_001278648.1 (SEQ ID NO: 951), and NP_001278645.1 (SEQ ID NO: 952). The term "PRAME" includes recombinant PRAME or a fragment thereof. The term also encompasses PRAME or a fragment thereof coupled to, for example, histidine tag, mouse or human Fc, or a signal sequence such as ROR1. In certain embodiments, the term comprises PRAME, or a fragment thereof, in the context of HLA-A2, linked to HLA-A2 or as displayed by HLA-A2. As used herein, the numbering of certain PRAME amino acid residues within the full-length PRAME sequence is with respect to SEQ ID NO: 944.

The term "HLA" refers to the human leukocyte antigen (HLA) system or complex, which is a gene complex encoding the major histocompatibility complex (MHC) proteins in humans. These cell-surface proteins are responsible for the regulation of the immune system in humans. HLAs corresponding to MHC class I (A, B, and C) present peptides from inside the cell.

The term "HLA-A" refers to the group of human leukocyte antigens (HLA) that are coded for by the HLA-A locus. HLA-A is one of three major types of human MHC class I cell surface receptors. The receptor is a heterodimer, and is composed of a heavy $\alpha$ chain and smaller $\beta$ chain. The $\alpha$ chain is encoded by a variant HLA-A gene, and the $\beta$ chain ($\beta$2-microglobulin) is an invariant $\beta$2 microglobulin molecule.

The term "HLA-A2" (which may also be referred to as HLA-A2*01 or HLA-A*0201 or HLA-A*02:01) is one particular class I major histocompatibility complex (MHC) allele group at the HLA-A locus; the $\alpha$ chain is encoded by the HLA-A*02 gene and the $\beta$ chain is encoded by the $\beta$2-microglobulin or B2M locus.

The term "specifically binds," or "binds specifically to", or the like, means that TCR forms a complex with an antigen that is relatively stable under physiologic conditions. Specific binding can be characterized by an equilibrium dissociation constant of at least about $1\times10^{-6}$ M or less, for example, $1\times10^{-8}$ M or less (e.g., a smaller KD denotes a tighter binding). Methods for determining whether two molecules specifically bind are well known in the art and include, for example, equilibrium dialysis, surface plasmon resonance, and the like. As described herein, the TCRs of the invention bind specifically to an HLA-A2 presented cancer testis preferentially expressed antigen in melanoma (PRAME) peptide, e.g., a peptide comprising amino acid residues 312-320 or 425-433 of PRAME (e.g., of the full-length PRAME sequence of SEQ ID NO: 944).

The term "off-target peptide" refers to a peptide that differs by 1, 2, 3, 4, 5 or more amino acids from a target peptide (e.g., a PRAME 312-320 peptide or a PRAME 425-433 peptide). In certain embodiments, the term includes a peptide that differs by less than or equal to 3 amino acids than the target peptide. For example, for a 9-mer peptide, if 1, 2, or 3 amino acids are not identical to the target peptide, it is considered an "off-target" peptide. In certain embodiments, amino acid identity is expressed in terms of 'degree of similarity' (DoS). If 6 or more amino acids within a 9-mer peptide are identical, the DoS is 6. In certain embodiments, a peptide with DoS≤6 is considered an "off-target" peptide. The term "off-target" peptide also refers to a peptide that is similar to the target peptide based on sequence homology, is predicted to bind to HLA-A2 and is comprised in a protein that is expressed in essential, normal tissues. Accordingly, in some embodiments a TCR of the present disclosure can bind to an HLA-A2-presented PRAME peptide (e.g., a peptide comprising amino acid residues 312-320 or 425-433 of PRAME) with an affinity corresponding to a $K_D$ value that is at least ten-fold lower than its affinity for binding to an off-target peptide.

The term "isolated" refers to a composition, compound, substance, or molecule altered by the hand of man from the natural state. For example, a composition or substance that occurs in nature is isolated if it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein. More particularly, an isolated TCR can refer to a TCR that has been removed from a cell, for example, a TCR that has been purified. TCRs can also be expressed by an isolated cell, e.g., a cell that has been isolated from an animal or a cell from cell culture. In this context, the isolated cell can express the TCR on its surface (i.e., the cell can "present" the TCR).

The term "recombinant", as used herein, refers to TCRs of the invention created, expressed, isolated or obtained by technologies or methods known in the art as recombinant DNA technology which include, e.g., DNA splicing and transgenic expression. The term refers to TCRs expressed in a non-human mammal (including transgenic non-human mammals, e.g., transgenic mice), or a cell (e.g., CHO cells) expression system or isolated from a recombinant combinatorial human antibody library.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

The term "polypeptide" is meant to refer to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides useful in accordance with the present disclosure in general will be generally between about 0.1 to 100 kDa or greater up to about 1000 kDa, preferably between about 0.1, 0.2, 0.5, 1, 2, 5, 10, 20, 30 and 50 kDa as judged by standard molecule sizing techniques such as centrifugation or SDS-polyacrylamide gel electrophoresis.

The term "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g., promoter) for the expression of the inserted DNA. Common vectors include plasmid vectors and phage vectors.

In some embodiments, TCRs of the invention may be conjugated to a moiety such as a ligand, a detectable moiety, or a therapeutic moiety ("immunoconjugate"), such as a cytotoxin, an anti-cancer drug, or any other therapeutic moiety useful for treating a disease or condition including PRAME-associated disease or disorder, such as a PRAME-associated cancer.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "KD", also known as $K_D$ or $K_d$, is intended to refer to the equilibrium dissociation constant of a particular biomolecule and its binding partner. KD measurements are particularly useful for assessing protein-protein interactions, e.g. as in an antigen-binding protein-antigen interaction. The smaller the value of the KD, the greater (or e.g. stronger) the binding interaction or affinity between the antigen-binding protein and antigen (e.g. target). The larger the value of the KD, the weaker the binding interaction or affinity between the antigen-binding protein and antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence identity can be calculated using an algorithm, for example, the Needleman Wunsch algorithm (Needleman and Wunsch 1970, *J. Mol. Biol.* 48: 443-453) for global alignment, or the Smith Waterman algorithm (Smith and Waterman 1981, *J Mol. Biol.* 147: 195-197) for local alignment. Another preferred algorithm is described by Dufresne et al in *Nature Biotechnology* in 2002 (vol. 20, pp. 1269-71) and is used in the software GenePAST (GQ Life Sciences, Inc. Boston, MA).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 96%, 97%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence of the invention to a database containing a large number of sequences from different organisms is the computer program BLAST, especially BLASTP or TBLASTN, using default parameters. See, e.g., Altschul et al. (1990) *J Mol. Biol.* 215: 403-410 and (1997) *Nucleic Acids Res.* 25:3389-3402, each of which is herein incorporated by reference.

A "patient-derived TCR" is a TCR that is produced by isolating the alpha and beta chains of a PRAME reactive TCR isolated from the T-lymphocytes that mediated in vivo regression of a tumor in a subject having a PRAME-associated cancer.

An "affinity-matured TCR" is a TCR that is produced by mutagenesis and selection in vitro. For example, untargeted or targeted (e.g., oligonucleotide-directed) mutagenesis can be performed to introduce variation in TCR sequences, and the subsequent TCRs can then be screened for affinity against a target, e.g., by use of phage display.

The term "activates a T cell response having a signal to noise ratio stronger or equal to a patient-derived PRAME-specific TCR" or "activates a T cell response having a signal to noise ratio stronger or equal to an affinity-matured PRAME-specific TCR" is meant to refer to an increase, i.e., about 2-fold or more, an amplification, i.e., about 2-fold, an augmentation, i.e., about 2-fold, or a boost of a physiological activity, i.e., about 2-fold, i.e., T cell signaling, as measured by, for example, a luminescent bioassay. Reference to a greater T cell response, or a stronger T cell response or an activation signal, may be used interchangeably. Various measurements and assays of T cell response or T cell activation are well known to the skilled artisan.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) *The Art, Science and Technology of Pharmaceutical Compounding*). The term "effective amount" is intended to encompass contexts such as a pharmaceutically effective amount or therapeutically effective amount. For example, in certain embodiments, the effective amount is capable of achieving a beneficial state, beneficial outcome, functional activity in a screening assay, or improvement of a clinical condition.

As described herein, a TCR of the invention may be "administered" to a subject. "Administering" a TCR of the invention includes, but is not limited to, administration of a cell expressing a TCR of the invention (e.g., an effector cell such as a T cell), administration of a nucleic acid expressing a TCR of the invention (e.g., a vector expressing such a TCR), and administration of a polypeptide comprising a TCR of the invention, wherein the polypeptide has been formatted for such administration (e.g., a bispecific polypeptide comprising a TCR chain and a CD3-binding antibody chain).

As used herein, the term "subject" refers to an animal, preferably a mammal, in need of amelioration, prevention and/or treatment of a PRAME-associated disease or disorder, such as a PRAME-associated cancer (e.g., a PRAME-positive cancer). The term includes human subjects who have or are at risk of having a PRAME-associated disease or disorder, such as a PRAME-associated cancer.

As used herein, "anti-cancer drug" means any agent useful to treat or ameliorate or inhibit cancer including, but not limited to, cytotoxins and agents such as antimetabolites, alkylating agents, anthracyclines, antibiotics, antimitotic agents, procarbazine, hydroxyurea, asparaginase, corticosteroids, cyclophosphamide, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "prevent", "preventing", "prevention", "prophylactic treatment" and the like are meant to refer to reducing the probability of developing a disorder or condition in a subject, who does not have, but is at risk of or susceptible to developing a disorder or condition. Prevention and the like do not mean preventing a subject from ever getting the specific disease or disorder. Prevention may require the administration of multiple doses. Prevention can include the prevention of a recurrence of a disease in a subject for whom all disease symptoms were eliminated, or prevention of recurrence in a relapsing-remitting disease.

II. PRAME T Cell (TCRs) and Compositions Comprising PRAME TCRS

T cells are a subgroup of cells which, together with other immune cell types (polymorphonuclear, eosinophils, basophils, mast cells, B-cells, NK cells), constitute the cellular component of the immune system. Under physiological conditions T cells function in immune surveillance and in the elimination of foreign antigen. However, under pathological conditions there is compelling evidence that T cells play a major role in the causation and propagation of disease. In these disorders, breakdown of T cell immunological tolerance, either central or peripheral is a fundamental process in the causation of autoimmune disease.

T cells bind epitopes on small antigenic determinants on the surface of antigen-presenting cells that are associated with a major histocompatibility complex (MHC; in mice) or human leukocyte antigen (HLA; in humans) complex. T cells bind these epitopes through a T cell receptor (TCR) complex on the surface of the T cell. T cell receptors are heterodimeric structures composed of two types of chains: an $\alpha$ (alpha) and $\beta$ (beta) chain, or a $\gamma$ (gamma) and $\delta$ (delta) chain. The $\alpha$ chain is encoded by the nucleic acid sequence located within the $\alpha$ locus (on human or mouse chromosome 14), which also encompasses the entire $\delta$ locus, and the $\beta$ chain is encoded by the nucleic acid sequence located within the $\beta$ locus (on mouse chromosome 6 or human chromosome 7). The majority of T cells have an $\alpha\beta$ TCR; while a minority of T cells bears a $\gamma\delta$ TCR.

T cell receptor $\alpha$ and $\beta$ polypeptides (and similarly $\gamma$ and $\delta$ polypeptides) are linked to each other via a disulfide bond. Each of the two polypeptides that make up the TCR contains an extracellular domain comprising constant and variable regions, a transmembrane domain, and a cytoplasmic tail (the transmembrane domain and the cytoplasmic tail also being a part of the constant region). The variable region of the TCR determines its antigen specificity, and similar to immunoglobulins, comprises three complementary determining regions (CDRs). The TCR is expressed on most T cells in the body and is known to be involved in the recognition of MHC-restricted antigens. The TCR $\alpha$ chain includes a covalently linked V$\alpha$ and C$\alpha$ region, whereas the $\beta$ chain includes a V$\beta$ region covalently linked to a C$\beta$ region. The V$\alpha$ and V$\beta$ regions form a pocket or cleft that can bind an antigen in the context of a major histocompatibility complex (MHC) (or HLA in humans). TCRs are detection molecules with exquisite specificity, and exhibit, like antibodies, an enormous diversity.

The general structure of TCR molecules and methods of making and using, including binding to a peptide:Major Histocompatibility Complex have been disclosed. See, for example PCT/US98/04274; PCT/US98/20263; WO99/60120.

Non-human animals (e.g., rodents, e.g., mice or rats) can be genetically engineered to express a human or humanized T cell receptor (TCR) comprising a variable domain encoded by at least one human TCR variable region gene segment, as described in, for example, PCT Publication No. WO 2016/164492, the entire contents of which are hereby incorporated herein by reference. For example, the VelociT® mouse technology (Regeneron), a genetically modified mouse that allows for the production of fully human therapeutic TCRs against tumor and/or viral antigens, can be used to produce the TCRs of the invention. Those of skill in the art, through standard mutagenesis techniques, in conjunction with the assays described herein, can obtain altered TCR sequences and test them for particular binding affinity and/or specificity. Useful mutagenesis techniques known in the art include, without limitation, de novo gene synthesis, oligonucleotide-directed mutagenesis, region-specific mutagenesis, linker-scanning mutagenesis, and site-directed mutagenesis by PCR (see, e.g., Sambrook et al. (1989) and Ausubel et al. (1999)).

Briefly, in some embodiments, methods for generating a TCR to a PRAME 312-320 peptide or a PRAME 425-433 peptide may include immunizing a non-human animal (e.g., a rodent, e.g., a mouse or a rat), such as a genetically engineered non-human animal that comprises in its genome an un-rearranged human TCR variable gene locus, with a PRAME 312-320 peptide or a PRAME 425-433 peptide; allowing the animal to mount an immune response to the peptide; isolating from the animal a T cell reactive to the peptide; determining a nucleic acid sequence of a human TCR variable region expressed by the T cell; cloning the human TCR variable region into a nucleotide construct comprising a nucleic acid sequence of a human TCR constant region such that the human TCR variable region is operably linked to the human TCR constant region; and expressing from the construct a human T cell receptor specific for the PRAME 312-320 peptide or a PRAME 425-433 peptide, respectively. In some embodiments, the steps of isolating a T cell, determining a nucleic acid sequence of a human TCR variable region expressed by the T cell, cloning the human TCR variable region into a nucleotide construct comprising a nucleic acid sequence of a human TCR constant region, and expressing a human T cell receptor are performed using standard techniques known to those of skill the art.

In some embodiments, the nucleotide sequence encoding a T cell receptor specific for an antigen of interest is expressed in a cell. In some embodiments, the cell expressing the TCR is selected from a CHO, COS, 293, HeLa, PERC.6™ cell, etc.

In obtaining variant TCR coding sequences, those of ordinary skill in the art will recognize that TCR-derived proteins may be modified by certain amino acid substitutions, additions, deletions, and post-translational modifications, without loss or reduction of biological activity. In particular, it is well known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

In some embodiments, a TCR of the present disclosure can comprise a CDR sequence (e.g., a CDR3 sequence such as a V$\alpha$ CDR3 or a V$\beta$ CDR3) with 1 or more substitutions as compared to a CDR sequence (e.g., a CDR3 sequence such as a V$\alpha$ CDR3 or a V$\beta$ CDR3) of Table 5 or Table 8. For example, a TCR of the present disclosure can comprise a CDR sequence with 1, 2, 3, 4, 5, 6, 7, 8, 9, 10, or more substitutions as compared to a CDR sequence of Table 5 or Table 8. In general, the TCRs of the present invention function by binding to an HLA-A2 presented PRAME 312-320 peptide or a HLA-A2 presented PRAME 425-433 peptide. As used herein, an HLA presented peptide (such as an HLA-A2 presented peptide) can refer to a peptide that is bound to a human leukocyte antigen (HLA) protein, for example, an HLA protein expressed on the surface of a cell. Thus, a TCR that binds to an HLA presented peptide binds to the peptide that is bound by the HLA, and optionally also binds to the HLA itself. Interaction with the HLA can confer specificity for binding to a peptide presented by a particular HLA. In some embodiments, the TCR binds to an isolated HLA presented peptide. In some embodiments, the TCR binds to an HLA presented peptide on the surface of a cell.

In general, the TCRs of the present invention can function by binding to an HLA-A2-presented PRAME peptide (e.g., PRAME 312-320 or PRAME 425-433).

The present invention includes PRAME TCRs that bind a PRAME 312-320 peptide or a PRAME 425-433 peptide in the context of HLA-A2 with high specificity. In some embodiments, the PRAME TCRs do not bind to the PRAME 312-320 peptide or the PRAME 425-433 peptide in the absence of HLA-A2, or such binding is minimal. Further, in some embodiments, the PRAME TCRs do not bind to an off-target peptide in the context of HLA-A2, or such binding is minimal. As used herein, an off-target peptide can refer to a peptide that differs from a target peptide by 1, 2, 3, 4, 5, or more amino acids. In some embodiments, binding specificity can be determined by a) measuring on-target binding (e.g., binding to the HLA-A2 presented PRAME (312-320) peptide or the HLA-A2 presented PRAME (425-433) peptide), b) measuring off-target binding, and c) quantifying the difference between the two, e.g., by calculating a ratio. This ratio can be calculated, for example, by dividing the values obtained in a) and b). Measurement of on-target and off-target binding can be achieved, for example, by measuring % binding to a peptide/HLA tetramer reagent (e.g., a PRAME/HLA tetramer reagent), or by other techniques known in the art. In some embodiments, an on-target binding/off-target binding value (e.g., a value obtained by dividing the values obtained in a) and b) described above) of a TCR of the present disclosure can be greater than 5, greater than 6, greater than 7, greater than 8, greater than 9, greater than 10, greater than 11, greater than 12, greater than 13, greater than 14, greater than 15, greater than 16, greater than 17, greater than 18, greater than 19, greater than 20, greater than 21, greater than 22, greater than 23, greater than 24, greater than 25, greater than 26, greater than 27, greater than 28, greater than 29, greater than 30, greater than 35, greater than 40, greater than 45, greater than 50, greater than 55, greater than 60, greater than 65, greater than 70, greater than 75, greater than 80, greater than 85, greater than 90, greater than 95, greater than 100, greater than 110, greater than 120, greater than 130, greater than 140, greater than 150, greater than 160, greater than 170, greater than 180, greater than 190, greater than 200, greater than 225, greater than 250, greater than 275, greater than 300, greater than 325, greater than 350, greater than 375, greater than 400, greater than 425, greater than 450, greater than 475, greater than 500, greater than 550, greater than 600, greater than 650, greater than 700, greater than 750, greater than 800, greater than 850, greater than 900, greater than 950, greater than 1000, greater than 1100, greater than 1200, greater than 1300, greater than 1400, greater than 1500, greater than 1600, greater than 1700, greater than 1800, greater than 1900, or greater than 2000. In some embodiments, an on-target binding/off-target binding value (e.g., a value obtained by dividing the values obtained in a) and b) described above) can be about 5 to about 20, about 10 to about 30, about 20 to about 80, about 30 to about 70, about 40 to about 60, about 50 to about 250, about 100 to about 200, about 100 to about 1000, about 300 to about 700, about 500 to about 1500, about 800 to about 1200, about 900 to about 1100, about 800 to about 1500, about 1000 to about 1400, or about 1100 to about 1300.

In some embodiments, the invention provides a recombinant antigen-binding protein (e.g., an isolated antigen-binding protein) that binds specifically to a conformational epitope of an HLA-A2 presented human PRAME (312-320) peptide or to a conformational epitope of an HLA-A2 presented human PRAME (425-433) peptide, wherein the antigen-binding protein has a property selected from the group consisting of: (a) binds monomeric HLA-A2: PRAME (312-320) peptide or monomeric PRAME (312-320) peptide with a binding dissociation equilibrium constant ($K_D$) of less than about 20 nM as measured in a surface plasmon resonance assay at 25° C.; (b) binds monomeric HLA-A2: PRAME (425-433) peptide or monomeric PRAME (425-433) peptide with a binding dissociation equilibrium constant ($K_D$) of less than about 25 nM as measured in a surface plasmon resonance assay at 25° C.; (c) binds to HLA-A2: PRAME (312-320) peptide-expressing cells or PRAME (425-433) peptide-expressing cells with an $EC_{50}$ less than about 6 nM and does not bind to cells expressing predicted off-target peptides as determined by luminescence assay; (d) binds to HLA-A2: PRAME (312-320) peptide-expressing cells or PRAME (425-433) peptide-expressing cells with an $EC_{50}$ less than about 1 nM and do not substantially bind to cells expressing predicted off-target peptides as determined by luminescence assay; (e) binds to HLA-A2: PRAME (312-320) peptide-expressing cells or PRAME (425-433) peptide-expressing cells with an $EC_{50}$ less than about 30 nM as determined by flow cytometry assay; (f) binds to HLA-A2: PRAME (312-320) peptide-expressing cells or PRAME (425-433) peptide-expressing cells with an $EC_{50}$ less than about 75 nM as determined by flow cytometry assay; and (g) the conformational epitope comprises one or more amino acids of SEQ ID NO: 944.

In some embodiments, the PRAME TCRs of the present disclosure have specific activity or affinity for PRAME (312-320) or for PRAME (425-433) as measured by an in vitro assay. For example, cells (such as T2 cells) expressing an HLA can be pulsed with a PRAME (312-320) or for PRAME (425-433) polypeptide, or an off-target polypeptide thereby inducing the cells to present the polypeptide bound to the HLA. Alternatively or in addition to using an off-target polypeptide as a control, an off-target HLA (an HLA other than the HLA that is recognized by the TCR of interest) can be used. For example, an off-target HLA can be used to present the PRAME peptide to test for specificity of binding to the HLA-A2-presented PRAME peptide. In addition, a control can be a cell line that expresses neither PRAME nor the target HLA (e.g., HLA-A2). Cells can be co-cultured with a T-cell population expressing the TCR of interest, and activity measured as a function of the amount of a cytokine (such as interferon gamma) produced by the cells. In certain embodiments, the assay can comprise in vitro co-cultures of a TCR-expressing T cell population with $10^{-10}$ M peptide-loaded T2 cells at an effector cell:target cell ratio of 1:1 ($1 \times 10^5$ effector cells/96 well), and interferon gamma measurement 24 hours after co-culture (e.g., by a Meso Scale Discovery (MSD®) Sector Imager). In certain embodiments, the assay can comprise in vitro co-cultures of a TCR-expressing T cell population and effector cell at an effector cell:target cell ratio of 5:1 ($2.5 \times 10^5$ effector cells: $5 \times 10^4$ target cells), and interferon gamma measurement 24 hours after co-culture (e.g., by a Meso Scale Discovery (MSD®) Sector Imager).

Increasing amounts of cytokine detected can serve as an indicator of activity. The activity or specificity of a TCR of interest to its target peptide in comparison to a control (off-target) polypeptide, or the activity or specificity of a TCR of interest to its on-target HLA-bound target peptide in comparison to an off-target HLA-bound target peptide can be 2-fold or greater, 3-fold or greater, 4-fold or greater, 5-fold or greater, 6-fold or greater, 7-fold or greater, 8-fold or greater, 9-fold or greater, 10-fold or greater, 15-fold or greater, 20-fold or greater, 30-fold or greater, 40-fold or greater, 50-fold or greater, 100-fold or greater, 200-fold or greater, 300-fold or greater, 400-fold or greater, 500-fold or greater, 600-fold or greater, 700-fold or greater, 800-fold or greater, 900-fold or greater, 1,000-fold or greater, 1,500-fold or greater. 2,000-fold or greater, 2,500-fold or greater, 3,000-fold or greater, 4,000-fold or greater, 5,000-fold or greater, 10,000-fold or greater, 20,000-fold or greater, 30,000-fold or greater, 40,000-fold or greater, 50,000-fold or greater, 60.000-fold or greater, 70,000-fold or greater, 80,000-fold or greater, 90,000-fold or greater, or 100,000-fold or greater.

In certain embodiments, the PRAME TCRs of the present disclosure are useful in inhibiting the growth of a tumor or delaying the progression of cancer when administered prophylactically to a subject in need thereof and may increase survival of the subject. For example, the administration of a PRAME TCR of the present invention may lead to shrinking of a primary tumor and may prevent metastasis or development of secondary tumors. In certain embodiments, the PRAME TCRs of the present invention are useful in inhibiting the growth of a tumor when administered therapeutically to a subject in need thereof and may increase survival of the subject. For example, the administration of a therapeutically effective amount of a PRAME TCR of the invention to a subject may lead to shrinking and disappearance of an established tumor in the subject.

In some embodiments, the invention provides a TCR (e.g., an isolated TCR or a TCR expressed on an isolated cell) that specifically binds to an HLA-A2 presented PRAME 312-320 peptide, wherein the antigen-binding protein exhibits one or more of the following characteristics: (i) comprises an alpha chain variable domain comprising a complementary determining region (CDR)3, wherein the CDR3 comprises the amino acid sequence of any one of the alpha chain variable domain CDR3 amino acid sequences set forth in Table 3; (ii) comprises a beta chain variable domain comprising a complementary determining region (CDR)3, wherein the CDR3 comprises the amino acid sequence of any one of the beta chain variable domain CDR3 amino acid sequences set forth in Table 3; (iii) comprises a CDR1 of the alpha chain variable domain comprising any one of the CDR1 amino acid sequences set forth in Table 3, or a substantially similar sequence thereof having at least 90%, at least 95%, at least 96%, at least 97%, at least 98% or at least 99% sequence identity, and a CDR2 of the alpha chain variable domain independently comprising any one of the CDR2 amino acid sequences set forth in Table 3, or a substantially similar sequence thereof having at least 90%, at least 95%, at least 96%, at least 97%, at least 98% or at least 99% sequence identity; (iv) comprises a CDR1 of a beta chain variable domain comprising any one of the CDR1 amino acid sequences set forth in Table 3, or a substantially similar sequence thereof having at least 90%, at least 95%, at least 96%, at least 97%, at least 98% or at least 99% sequence identity, and a CDR2 of a beta chain variable domain independently comprising any one of the CDR2 amino acid sequences set forth in Table 3, or a substantially similar sequence thereof having at least 90%, at least 95%, at least 96%, at least 97%, at least 98% or at least 99% sequence identity; (v) comprises an alpha chain variable domain CDR1, CDR2 and CDR3 contained within any one of the alpha chain variable domain sequences listed in Table 5, or a substantially similar sequence thereof having at least 90%, at least 95%, at least 96%, at least 97%, at least 98% or at least 99% sequence identity; and beta chain variable domain CDR1, CDR2 and CDR3 contained within any one of the beta chain variable domain sequences listed in Table 5, or a substantially similar sequence thereof having at least 90%, at least 95%, at least 96%, at least 97%, at least 98% or at least 99% sequence identity; (vi) comprises an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 5; (vii) comprises a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 5; (viii) comprises (a) an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 5; and (b) a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 5; (ix) comprises (a) an alpha chain variable domain CDR1 domain having an amino acid sequence selected from the group consisting of SEQ ID NOs: 1, 7, 13, 19, 25, 31, 37, 43, 49, 55, 61, 67, 73, 79, 85, 91, 97, and 103, or a substantially similar sequence thereof having at least 90%, at least 95%, at least 96%, at least 97%, at least 98% or at least 99% sequence identity; (b) an alpha chain variable domain CDR2 domain having an amino acid sequence selected from the group consisting of SEQ ID NOs: 2, 8, 14, 20, 26, 32, 38, 44, 50, 56, 62, 68, 74, 80, 86, 92, 98, and 104, or a substantially similar sequence thereof having at least 90%, at least 95%, at least 96%, at least 97%, at least 98% or at least 99% sequence identity; (c) an alpha chain variable domain CDR3 domain having an amino acid sequence selected from the group consisting of SEQ ID NOs: 3, 9, 15, 21, 27, 33, 39, 45, 51, 57, 63, 69, 75, 81, 87, 93, 99, and 105, or a substantially similar sequence thereof having at least 90%, at least 95%, at least 96%, at least 97%, at least 98% or at least 99% sequence identity; (d) a beta chain variable domain CDR1 having an amino acid sequence selected from the group consisting of SEQ ID NOs: 4, 10, 16, 22, 28, 34, 40, 46, 52, 58, 64, 70, 76, 82, 88, 94, 100, and 106, or a substantially similar sequence thereof having at least 90%, at least 95%, at least 96%, at least 97%, at least 98% or at least 99% sequence identity; (e) a beta chain variable domain CDR2 having an amino acid sequence selected from the group consisting of SEQ ID NOs: 5, 11, 17, 23, 29, 35, 41, 47, 53, 59, 65, 71, 77, 83, 89, 95, 101, and 107, or a substantially similar sequence thereof having at least 90%, at least 95%, at least 96%, at least 97%, at least 98% or at least 99% sequence identity; and (f) a beta chain variable domain CDR3 having an amino acid sequence selected from the group consisting of SEQ ID NOs: 6, 12, 18, 24, 30, 36, 42, 48, 54, 60, 66, 72, 78, 84, 90, 96, 102, and 108, or a substantially similar sequence thereof having at least 90%, at least 95%, at least 96%, at least 97%, at least 98% or at least 99% sequence identity; (x) comprises an alpha chain variable domain/beta chain variable domain amino acid sequence pair selected from the group consisting of SEQ ID NOs: 217/219, 229/231, 237/239, 241/243, and 285/287, or a substantially similar sequence thereof having at least 90%, at least 95%, at least 96%, at least 97%, at least 98% or at least 99% sequence identity; (xi) comprises an alpha chain variable domain/beta chain variable domain amino acid sequence pair selected from the group consisting of SEQ ID NOs: 217/219, 221/223, 225/227, 229/231, 233/235, 237/239, 241/243, 245/247, 249/251, 253/255, 257/259, 261/263, 265/267, 269/271, 273/275, 277/279, 281/283, and 285/287, or a substantially similar sequence thereof having at least 90%, at least 95%, at least 96%, at least 97%, at least 98% or at least 99% sequence identity; (xii) does not specifically bind to cells expressing predicted off-target peptides but not an HLA-A2 presented PRAME 312-320 peptide, as determined by a luminescence assay; and/or (xiii) activates a T cell response about two times greater than a patient-derived PRAME-specific TCR, e.g., activates a T cell response about two times greater, or about three times greater, or about four times greater than a patient-derived PRAME-specific TCR as determined by a TCR-mediated T cell signaling luminescent bioassay.

In some embodiments, the invention provides a TCR (e.g., an isolated TCR or a TCR expressed on an isolated cell) that specifically binds to an HLA-A2 presented PRAME 425-433 peptide, wherein the antigen-binding protein exhibits one or more of the following characteristics: (i) comprises an alpha chain variable domain comprising a complementary determining region (CDR)3, wherein the CDR3 comprises the amino acid sequence of any one of the alpha chain variable domain CDR3 amino acid sequences set forth in Table 6; (ii) comprises a beta chain variable domain comprising a complementary determining region (CDR)3, wherein the CDR3 comprises the amino acid sequence of any one of the beta chain variable domain CDR3 amino acid sequences set forth in Table 6; (iii) comprises a CDR1 of the alpha chain variable domain comprising any one of the CDR1 amino acid sequences set forth in Table 6, or a substantially similar sequence thereof having at least 90%, at least 95%, at least 96%, at least 97%, at least 98% or at least 99% sequence identity, and a CDR2 of the alpha chain variable domain independently comprising any one of the CDR2 amino acid sequences set forth in Table 6, or a substantially similar sequence thereof having at least 90%, at least 95%, at least 96%, at least 97%, at least 98% or at least 99% sequence identity; (iv) comprises a CDR1 of a beta chain variable domain comprising any one of the CDR1 amino acid sequences set forth in Table 6, or a substantially similar sequence thereof having at least 90%, at least 95%, at least 96%, at least 97%, at least 98% or at least 99% sequence identity, and a CDR2 of a beta chain variable domain independently comprising any one of the CDR2 amino acid sequences set forth in Table 6, or a substantially similar sequence thereof having at least 90%, at least 95%, at least 96%, at least 97%, at least 98% or at least 99% sequence identity; (v) comprises an alpha chain variable domain CDR1, CDR2 and CDR3 contained within any one of the alpha chain variable domain sequences listed in Table 8, or a substantially similar sequence thereof having at least 90%, at least 95%, at least 96%, at least 97%, at least 98% or at least 99% sequence identity; and beta chain variable domain CDR1, CDR2 and CDR3 contained within any one of the beta chain variable domain sequences listed in Table 8, or a substantially similar sequence thereof having at least 90%, at least 95%, at least 96%, at least 97%, at least 98% or at least 99% sequence identity; (vi) comprises an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 8; (vii) comprises a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 8; (viii) comprises (a) an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 8; and (b) a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 8; (ix) comprises (a) an alpha chain variable domain CDR1 domain having an amino acid sequence selected from the group consisting of SEQ ID NOs: 289, 295, 301, 307, 313, 319, 325, 331, 337, 343, 349, 355, 361, 367, 373, 379, 385, 391, 397, 403, 409, 415, 421, 427, 433, 439, 445, 451, 457, 463, 469, 475, 481, 487, 493, 499, 505, 511, 517, and 523, or a substantially similar sequence thereof having at least 90%, at least 95%, at least 96%, at least 97%, at least 98% or at least 99% sequence identity; (b) an alpha chain variable domain CDR2 domain having an amino acid sequence selected from the group consisting of SEQ ID NOs: 290, 296, 302, 308, 314, 320, 326, 332, 338, 344, 350, 356, 362, 368, 374, 380, 386, 392, 398, 404, 410, 416, 422, 428, 434, 440, 446, 452, 458, 464, 470, 476, 482, 488, 494, 500, 506, 512, 518, and 524, or a substantially similar sequence thereof having at least 90%, at least 95%, at least 96%, at least 97%, at least 98% or at least 99% sequence identity; (c) an alpha chain variable domain CDR3 domain having an amino acid sequence selected from the group consisting of SEQ ID NOs: 291, 297, 303, 309, 315, 321, 327, 333, 339, 345, 351, 357, 363, 369, 375, 381, 387, 393, 399, 405, 411, 417, 423, 429, 435, 441, 447, 453, 459, 465, 471, 477, 483, 489, 495, 501, 507, 513, 519, and 525, or a substantially similar sequence thereof having at least 90%, at least 95%, at least 96%, at least 97%, at least 98% or at least 99% sequence identity; (d) a beta chain variable domain CDR1 having an amino acid sequence selected from the group consisting of SEQ ID NOs: 292, 298, 304, 310, 316, 322, 328, 334, 340, 346, 352, 358, 364, 370, 376, 382, 388, 394, 400, 406, 412, 418, 424, 430, 436, 442, 448, 454, 460, 466, 472, 478, 484, 490, 496, 502, 508, 514, 520, and 526, or a substantially similar sequence thereof having at least 90%, at least 95%, at least 96%, at least 97%, at least 98% or at least 99% sequence identity; (e) a beta chain variable domain CDR2 having an amino acid sequence selected from the group consisting of SEQ ID NOs: 293, 299, 305, 311, 317, 323, 329, 335, 341, 347, 353, 359, 365, 371, 377, 383, 389, 395, 401, 407, 413, 419, 425, 431, 437, 443, 449, 455, 461, 467, 473, 479, 485, 491, 497, 503, 509, 515, 521, and 527, or a substantially similar sequence thereof having at least 90%, at least 95%, at least 96%, at least 97%, at least 98% or at least 99% sequence identity; and (f) a beta chain variable domain CDR3 having an amino acid sequence selected from the group consisting of SEQ ID NOs: 294, 300, 306, 312, 318, 324, 330, 336, 342, 348, 354, 360, 366, 372, 378, 384, 390, 396, 402, 408, 414, 420, 426, 432, 438, 444, 450, 456, 462, 468, 474, 480, 486, 492, 498, 504, 510, 516, 522, and 528, or a substantially similar sequence thereof having at least 90%, at least 95%, at least 96%, at least 97%, at least 98% or at least 99% sequence identity; (x) comprises an alpha chain variable domain/beta chain variable domain amino acid sequence pair selected from the group consisting of SEQ ID NOs: 825/827, 845/847, 853/855, 857/859, 865/867, 873/875, 885/887, 893/805, 897/899, 901/903, 913/915, and 925/927, or a substantially similar sequence thereof having at least 90%, at least 95%, at least 96%, at least 97%, at least 98% or at least 99% sequence identity; (xi) comprises an alpha chain variable domain/beta chain variable domain amino acid sequence pair selected from the group consisting of SEQ ID NOs: 769/771, 773/775, 777/779, 781/783, 785/787, 789/791, 793/795, 797/799, 801/803, 805/807, 809/811, 813/815, 817/819, 821/823, 825/827, 829/831, 833/835, 837/839, 841/843, 845/847, 849/851, 853/855, 857/859, 861/863, 865/867, 869/871, 873/875, 877/879, 881/883, 885/887, 889/891, 893/805, 897/899, 901/903, 905/907, 909/911, 913/915, 917/919, 921/923, and 925/927, or a substantially similar sequence thereof having at least 90%, at least 95%, at least 96%, at least 97%, at least 98% or at least 99% sequence identity; (xii) does not specifically bind to cells expressing predicted off-target peptides but not an HLA-A2 presented PRAME 425-433 peptide, as determined by a luminescence assay; and/or (xiii) activates a T cell response about two times greater than a patient-derived PRAME-specific TCR, e.g., activates a T cell response about two times greater, or about three times greater, or about four times greater than a patient-derived PRAME-specific TCR as determined by a TCR-mediated T cell signaling lumines-cent bioassay.

The TCRs of the present invention may possess one or more of the aforementioned biological characteristics, or any combinations thereof. Other biological characteristics of the antigen-binding proteins of the present invention will be evident to a person of ordinary skill in the art from a review of the present disclosure including the working Examples herein.

In certain embodiments, a polynucleotide encoding a PRAME TCR described herein is inserted into a vector. The term "vector" as used herein refers to a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly trans-lation of an operatively linked coding sequence in a par-ticular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1α promoters, ribo-some recognition and binding TATA box, and 3' UTR AAUAAA transcription termination sequence for the effi-cient gene transcription and translation in its respective host cell. Other suitable promoters include the constitutive pro-moter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contem-plated as part of the vectors expressing chimeric antigen receptor. This provides a molecular switch capable of turn-ing on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6×-histidine (SEQ ID NO: 954), c-Myc, and FLAG tags which are incorporated into the expressed TCRs. Thus, the expression vector may be engineered to contain 5' and 3' untranslated regulatory sequences that sometimes can func-tion as enhancer sequences, promoter regions and/or termi-nator sequences that can facilitate or enhance efficient tran-scription of the nucleic acid(s) of interest carried on the expression vector. An expression vector may also be engi-neered for replication and/or expression functionality (e.g., transcription and translation) in a particular cell type, cell location, or tissue type. Expression vectors may include a selectable marker for maintenance of the vector in the host or recipient cell.

Examples of vectors are plasmid, autonomously replicat-ing sequences, and transposable elements. Additional exem-plary vectors include, without limitation, plasmids, phag-emids, cosmids, artificial chromosomes such as yeast artificial chromosome (YAC), bacterial artificial chromo-some (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculo-virus, papillomavirus, and papovavirus (e.g., SV40). Examples of expression vectors are Lenti-X™ Bicistronic Expression System (Neo) vectors (Clontrch), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the TCRs disclosed herein can be ligated into such expression vectors for the expression of the chimeric protein in mam-malian cells.

In certain embodiments, the nucleic acids encoding the TCR of the present invention are provided in a viral vector. A viral vector can be those derived from retrovirus, lenti-virus, or foamy virus. As used herein, the term, "viral vector," refers to a nucleic acid vector construct that includes at least one element of viral origin and has the capacity to be packaged into a viral vector particle. The viral vector can contain the coding sequence for the various proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a TCR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immunodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., *J. Virol.,* 1998; 72: 8463-8471 and Zufferey et al., *J. Virol.* 1998; 72:9873-9880).

Retroviral vectors (i.e., both lentiviral and non-lentiviral) for use in the present invention can be formed using standard cloning techniques by combining the desired DNA sequences in the order and orientation described herein (*Current Protocols in Molecular Biology*, Ausubel, F. M. et al. (eds.) Greene Publishing Associates, (1989), Sections 9.10-9.14 and other standard laboratory manuals; Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol* 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a PRAME TCR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The TCRs of the present invention are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or a may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding a PRAME TCR of the invention carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, the TCRs of the present invention are introduced and expressed in immune effector cells so as to redirect their specificity to a target antigen of interest, e.g., an HLA-A2 displayed PRAME peptide, e.g., amino acid residues 312-320 or 425-433 of PRAME.

The present invention provides methods for making the immune effector cells which express the TCRs as described herein. In some embodiments, the method comprises transfecting or transducing immune effector cells, e.g., immune effector cells isolated from a subject, such as a subject having a PRAME-associated disease or disorder, such that the immune effector cells express one or more TCR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a TCR. In this regard, the immune effector cells may be cultured before or after being genetically modified (i.e., transduced or transfected to express a TCR as described herein).

Prior to in vitro manipulation or genetic modification of the immune effector cells described herein, the source of cells may be obtained from a subject. In particular, the immune effector cells for use with the TCRs as described herein comprise T cells.

T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In some embodiments, cells from the circulating blood of an individual are obtained by apheresis. The apheresis product typically contains lymphocytes, including T cells, monocytes, granulocyte, B cells, other nucleated white blood cells, red blood cells, and platelets. In some embodiments, the cells collected by apheresis may be washed to remove the plasma fraction and to place the cells in an appropriate buffer or media for subsequent processing. In some embodiments of the invention, the cells are washed with PBS. In alternative embodiments, the washed solution lacks calcium and may lack magnesium or may lack many if not all divalent cations. As would be appreciated by those of ordinary skill in the art, a washing step may be accomplished by methods known to those in the art, such as by using a semiautomated flow-through centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention.

PBMC may be used directly for genetic modification with the TCRs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion.

The immune effector cells, such as T cells, can be genetically modified following isolation using known methods, or the immune effector cells can be activated and expanded (or differentiated in the case of progenitors) in vitro prior to being genetically modified. In some embodiments, the immune effector cells, such as T cells, are genetically modified with the chimeric antigen receptors described herein (e.g., transduced with a viral vector comprising a nucleic acid encoding a TCR) and then are activated and expanded in vitro. Methods for activating and expanding T cells are known in the art and are described, for example, in U.S. Pat. Nos. 6,905,874; 6,867,041; 6,797,514; WO2012079000, US 2016/0175358.

The invention provides a population of modified immune effector cells for the treatment of a PRAME-associated disease or disorder, e.g., cancer, the modified immune effector cells comprising a PRAME TCR as disclosed herein.

TCR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

III. Pharmaceutical Compositions

The invention provides therapeutic compositions comprising the PRAME TCRs of the invention or immune effector cells comprising the PRAME TCRs of the invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: *Remington's Pharmaceutical Sciences*, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

Depending on the severity of the condition, the frequency and the duration of the treatment can be adjusted.

In certain embodiments, the initial dose may be followed by administration of a second or a plurality of subsequent doses of PRAME TCRs of the invention or immune effector cells comprising the PRAME TCRs of the invention in an amount that can be approximately the same or less than that of the initial dose, In certain situations, the pharmaceutical composition can be delivered in a controlled release system. In some embodiments, a pump may be used.

Injectable preparations may include dosage forms for intravenous, subcutaneous, intracutaneous, intracranial, intraperitoneal and intramuscular injections, drip infusions, etc. The TCRs, pharmaceutical compositions, and cells described herein can be administered via parenteral administration. The preparations of the present disclosure may be prepared by methods publicly known. For example, the preparations may be prepared, e.g., by dissolving, suspending or emulsifying the antigen-binding protein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

In some embodiments, TCR-expressing immune effector cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective number of cells in the composition is typically greater than $10^2$ cells, and up to $10^6$ up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The TCR expressing immune effector cell populations of the present invention may be administered either alone, or as a pharmaceutical composition in combination with diluents and/or with other components such as IL-2 or other cytokines or cell populations. Briefly, pharmaceutical compositions of the present invention may comprise a TCR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

IV. Therapeutic Uses of PRAME TCRs or Immune Effector Cells Comprising PRAME TCRs The anti-tumor immune response induced in a subject by administering TCR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., *Current Protocols in Immunology*, Edited by: John E. Coligan, Ada M. Kruisbeek, David H. Margulies, Ethan M. Shevach, Warren Strober (2001) John Wiley & Sons, NY, N.Y.

Thus, the PRAME TCRs of the invention are useful, inter alia, for the treatment, prevention and/or amelioration of any disease or disorder associated with or mediated by PRAME. For example, the present invention provides methods for treating a PRAME-associated disease or disorder, such as a PRAME-associated cancer (e.g., a PRAME-positive cancer) (tumor growth inhibition) by administering a PRAME TCR (or pharmaceutical composition comprising a PRAME TCR or a plurality of cells comprising a PRAME TCR) as described herein to a patient in need of such treatment, and PRAME TCRs (or pharmaceutical composition comprising a PRAME TCR) for use in the treatment of a PRAME-associated cancer. The antigen-binding proteins of the present invention are useful for the treatment, prevention, and/or amelioration of disease or disorder or condition such as a PRAME-associated cancer and/or for ameliorating at least one symptom associated with such disease, disorder or condition. In the context of the methods of treatment described herein, the PRAME TCR (or pharmaceutical composition or plurality of cells) may be administered as a monotherapy (i.e., as the only therapeutic agent) or in combination with one or more additional therapeutic agents (examples of which are described elsewhere herein).

Accordingly, the present invention provides for methods of treating an individual diagnosed with or suspected of having, or at risk of developing, a PRAME-associated disease or disorder, e.g., a PRAME-associated cancer, comprising administering the individual a therapeutically effective amount of the TCR-expressing immune effector cells as described herein.

In some embodiments, the invention provides a method of treating a subject diagnosed with a PRAME-positive cancer comprising removing immune effector cells from a subject diagnosed with a PRAME-positive cancer, genetically modifying said immune effector cells with a vector comprising a nucleic acid encoding a TCR of the instant invention, thereby producing a population of modified immune effector cells, and administering the population of modified immune effector cells to the same subject. In some embodiments, the immune effector cells comprise T cells.

The methods for administering the cell compositions described herein includes any method which is effective to result in reintroduction of ex vivo genetically modified immune effector cells that either directly express a TCR of the invention in the subject or on reintroduction of the genetically modified progenitors of immune effector cells that on introduction into a subject differentiate into mature immune effector cells that express the TCR. One method comprises transducing peripheral blood T cells ex vivo with a nucleic acid construct in accordance with the invention and returning the transduced cells into the subject.

In some embodiments of the invention, the compositions described herein are useful for treating subjects suffering from primary or recurrent cancer, including, but not limited to, PRAME-associated cancer, e.g., PRAME-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, or a recurrent non-small cell lung cancer. In some embodiments, the PRAME-associated cancer is an ovarian cancer, a melanoma, a non-small cell lung carcinoma, a hepatocellular carcinoma, a colorectal carcinoma, an esophageal squamous cell carcinoma, an esophageal adenocarcinoma, a stomach cancer, a bladder cancer, a head and neck cancer, a gastric cancer, a synovial sarcoma, uterine corpus endometrial carcinoma, uterine carcinosarcoma, testicular germ cell tumor, uveal melanoma, kidney renal papillary cell carcinoma, kidney renal clear cell carcinoma, thymoma, colon adenocarcinoma, cervical squamous cell carcinoma, cervical tumor, pancreatic adenocarcinoma, liver cancer, hepatocellular carcinoma, mesothelioma, or a myxoid round cell liposarcoma.

The TCRs may be used to treat early stage or late-stage symptoms of the PRAME-associated cancer. In some embodiments, a TCR of the invention may be used to treat advanced or metastatic cancer. The TCRs are useful in reducing or inhibiting or shrinking tumor growth. In certain embodiments, treatment with a TCR of the invention leads to more than 40% regression, more than 50% regression, more than 60% regression, more than 70% regression, more than 80% regression or more than 90% regression of a tumor in a subject. In certain embodiments, the TCRs may be used to prevent relapse of a tumor. In certain embodiments, the TCRs are useful in extending progression-free survival or overall survival in a subject with PRAME-associated cancer. In some embodiments, the TCRs are useful in reducing toxicity due to chemotherapy or radiotherapy while maintaining long-term survival in a patient suffering from PRAME-associated cancer.

One or more TCRs of the present invention may be administered to relieve or prevent or decrease the severity of one or more of the symptoms or conditions of the disease or disorder.

It is also contemplated herein to use one or more TCRs of the present invention prophylactically to patients at risk for developing a disease or disorder such as PRAME-associated disease or disorder, such as a PRAME-associated cancer.

In further embodiments of the invention, the present TCRs are used for the preparation of a pharmaceutical composition for treating patients suffering from PRAME-associated disease or disorder, such as a PRAME-associated cancer. In some embodiments of the invention, the present TCRs are used as adjunct therapy with any other agent or any other therapy known to those skilled in the art useful for treating PRAME-associated cancer.

Combination therapies may include a PRAME TCR of the invention, such as immune effector cell comprising a TCR of the invention, or a pharmaceutical composition of the invention, and any additional therapeutic agent that may be advantageously combined with a TCR of the invention. The TCRs of the present invention may be combined synergistically with one or more anti-cancer drugs or therapy used to treat or inhibit a PRAME-associated disease or disorder, such as PRAME-positive cancer, e.g., a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, uterine corpus endometrial carcinoma, uterine carcinosarcoma, testicular germ cell tumor, uveal melanoma, kidney renal papillary cell carcinoma, kidney renal clear cell carcinoma, thymoma, colon adenocarcinoma, cervical squamous cell carcinoma, cervical tumor, pancreatic adenocarcinoma, liver cancer, hepatocellular carcinoma, mesothelioma, or a recurrent non-small cell lung cancer.

It is contemplated herein to use the TCRs of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more TCRs of the present invention may be used in combination with a PD-1 inhibitor (e.g., an anti-PD-1 antibody such as nivolumab, pembrolizumab, pidilizumab, BGB-A317 or REGN2810), a PD-L1 inhibitor (e.g., an anti-PD-L1 antibody such as avelumab, atezolizumab, durvalumab, MDX-1105, or REGN3504), a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), an NY-ESO-1 inhibitor (e.g., an anti-NY-ESO-1 antibody), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a costimulatory agent, a bispecific antibody (e.g., CD3×CD20 bispecific antibody, a PSMA×CD3 bispecific antibody, or a bispecific antibody that acts as a costimulatory agent, such as a bispecific antibody that binds a tumor antigen and has costimulatory activity), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, surgery, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, the TCRs of the present invention may be used in combination with cancer vaccines including dendritic cell vaccines, oncolytic viruses, tumor cell vaccines, etc. to augment the anti-tumor response.

Examples of cancer vaccines that can be used in combination with TCRs of the present invention include MAGE3 vaccine for melanoma and bladder cancer, MUC1 vaccine for breast cancer, EGFRv3 (e.g., Rindopepimut) for brain cancer (including glioblastoma multiforme), ALVAC-CEA (for CEA+ cancers), and NY-ESO-1 vaccine (e.g., for melanoma).

In certain embodiments, the PRAME TCRs of the invention may be administered in combination with radiation therapy in methods to generate long-term durable anti-tumor responses and/or enhance survival of patients with cancer. In some embodiments, the PRAME TCRs of the invention may be administered prior to, concomitantly or after administering radiation therapy to a cancer patient. For example, radiation therapy may be administered in one or more doses to tumor lesions followed by administration of one or more doses of PRAME TCRs of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of a PRAME TCRs of the invention.

The additional therapeutically active agent(s)/component(s) may be administered prior to, concurrent with, or after the administration of the PRAME TCRs of the present invention. For purposes of the present disclosure, such administration regimens are considered the administration of a PRAME TCR "in combination with" a second therapeutically active component.

The additional therapeutically active component(s) may be administered to a subject prior to administration of a PRAME TCR of the present invention. In other embodiments, the additional therapeutically active component(s) may be administered to a subject after administration of a PRAME TCR of the present invention. In yet other embodiments, the additional therapeutically active component(s) may be administered to a subject concurrent with administration of a PRAME TCR of the present invention. "Concurrent" administration, for purposes of the present invention, includes, e.g., administration of a PRAME TCR and an additional therapeutically active component to a subject in a single dosage form (e.g., co-formulated), or in separate dosage forms administered to the subject within about 30 minutes or less of each other. If administered in separate dosage forms, each dosage form may be administered via the same route; alternatively, each dosage form may be administered via a different route. In any event, administering the components in a single dosage from, in separate dosage forms by the same route, or in separate dosage forms by different routes are all considered "concurrent administration," for purposes of the present disclosure. For purposes of the present disclosure, administration of a PRAME TCR "prior to", "concurrent with," or "after" (as those terms are defined herein above) administration of an additional therapeutically active component is considered administration of a PRAME TCR "in combination with" an additional therapeutically active component).

The present invention is further illustrated by the following Examples, which are not intended to be limiting in any way. The entire contents of all references, patents and published patent applications cited throughout this application are hereby incorporated herein by reference.

EXAMPLES

Example 1. Identification of PRAME Specific T Cell Receptors

Mice humanized for cellular immune system components, VelociT mice (see, e.g., PCT Publication No. WO 2016/164492, the entire contents of which are incorporated herein by reference), were immunized with either a PRAME (312-320) peptide (RLDQLLRHV); SEQ ID NO:929) or a PRAME (425-433) peptide (SLLQHLIGL); SEQ ID NO:930) presented specifically by human HLA-A2, diluted in PBS and mixed with adjuvant, e.g. in equal volume with Complete Freund's Adjuvant (CFA; Chondrex, Inc.). Spleen suspensions from mice immunized with wither peptide were separately obtained and dissociated. Red blood cells were lysed in ACK lysis buffer (Life Technologies), and splenocytes were suspended in RPMI complete media. Isolated splenocytes were sorted and single T cells that bind the PRAME peptide used for immunization (either PRAME (312-320) or PRAME (425-433) in the context of MHC were isolated by fluorescent-activated cell sorting (FACS). Isolated T cells were single well plated and mixed with TCR alpha and beta variable region-specific PCR primers. cDNAs for each single T cell were synthesized via a reverse transcriptase (RT) reaction. Each resulting RT product was then split and transferred into two corresponding wells for subsequent TCR beta and alpha PCRs. One set of the resulting RT products was first amplified by PCR using a 5' degenerate primer specific for TCR beta variable region leader sequence or a 5' degenerate primer specific for TCR alpha chain variable region leader sequence and a 3' primer specific for TCR constant region, to form an amplicon. The amplicons were then amplified again by PCR using a 5' degenerate primer specific for TCR beta variable region framework 1 or a 5' degenerate primer specific for TCR alpha chain variable region framework 1 and a 3' primer specific for TCR constant region, to generate amplicons for cloning. The TCR beta and alpha derived PCR products were cloned into expression vectors containing beta constant region and alpha constant region, respectively. Expression vectors expressing full-length beta and alpha chain pairs were transfected into CHO cells and tested for binding to commercial PRAME/HLA tetramer reagent. CHO cells were incubated with soluble HLA-A2:PRAME (312-320) or HLA:A2:PRAME (425-433) (MBL International, Woburn, MA) tetramer and an antibody specific for mouse TCR constant region (clone H57-597) (Biolegend, San Diego, CA). Samples were then analyzed on an LSRFortessa X-20 (BD Biosciences, San Jose, CA). To calculate percentage of tetramer positive cells, antigen positive (Ag+) gates were set based on a negative control TCR that does not bind to the HLA-A2:PRAME (312-320) or HLA:A2:PRAME (425-433) (MBL International, Woburn, MA) tetramer using FlowJo (LLC, Ashland, OR). All Ag+ TCRs had a FlowJo criteria of ≥1% of cells in Ag+ gate with the mean fluorescence intensity (MFI)≥1000. Ag+ TCRs were determined by Next Generation Sequencing. The total number of TCRs that were identified with PRAME (312-320) and that express identical TCR alpha and beta nucleotide sequences are shown in Table 1 below. Cell frequency, or % tetramer positive cells in the Ag+ gate, is representative of the TCR shown in the first column of Table 1. The total number of TCRs that were identified with PRAME (425-433) and that express identical TCR alpha and beta nucleotide sequences are shown in Table 2 below. Cell frequency, or % tetramer positive cells in the Ag+ gate, is representative of the TCR shown in the first column of Table 2.

A detailed list of the beta chain variable domain CDR1, CDR2, and CDR3 amino acid sequences, and the alpha chain variable domain CDR1, CDR2, and CDR3 amino acid sequences of the TCRs that were identified with PRAME (312-320) as described above are provided in Table 3. A detailed list of the beta chain variable domain CDR1, CDR2, and CDR3 polynucleic acid sequences, and the alpha chain variable domain CDR1, CDR2, and CDR3 polynucleic acid sequences of the TCRs that were identified with PRAME (312-320) as described above are provided in Table 4. Table 5 provides the amino acid and nucleotide sequences of the beta chain variable and alpha chain variable regions of the TCRs that were identified with PRAME (312-320).

A detailed list of the beta chain variable domain CDR1, CDR2, and CDR3 amino acid sequences, and the alpha chain variable domain CDR1, CDR2, and CDR3 amino acid sequences of the TCRs that were identified with PRAME (425-433) as described above are provided in Table 6. A detailed list of the beta chain variable domain CDR1, CDR2, and CDR3 polynucleic acid sequences, and the alpha chain variable domain CDR1, CDR2, and CDR3 polynucleic acid sequences of the TCRs that were identified with PRAME (425-433) as described above are provided in Table 7. Table 8 provides the amino acid and nucleotide sequences of the beta chain variable and alpha chain variable regions of the TCRs that were identified with PRAME (425-433).

Table 9 provides the TCR gene families for the alpha and beta variable and joining regions of the isolated TCRs that were identified with PRAME (312-320) and Table 11 provides the amino acid and polynucleic acid sequence identifiers for alpha and beta variable chains and CDRs of the TCRs that were identified with PRAME (312-320).

Table 10 provides the TCR gene families for the alpha and beta variable and joining regions of the isolated TCRs that were identified with PRAME (425-433) and Table 12 provides the amino acid and polynucleic acid sequence identifiers for alpha and beta variable chains and CDRs of the TCRs that were identified with PRAME (425-433).

TABLE 1

| TCR ID | Total Ag+ TCRs | Cell Frequency ≥1000 MFI, ≥1% |
|---|---|---|
| PN46909 | 21 | 52.60 |
| PN46889 | 21 | 92.50 |
| PN46733 | 2 | 87.90 |
| PN46723 | 52 | 72.50 |
| PN46714 | 1 | 62.10 |
| PN46735 | 1 | 17.90 |
| PN46678 | 1 | 11.00 |
| PN46884 | 3 | 59.00 |
| PN46914 | 1 | 11.50 |
| PN46883 | 13 | 64.70 |
| PN46857 | 1 | 53.90 |
| PN46880 | 5 | 31.90 |
| PN46871 | 2 | 44.70 |
| PN46853 | 2 | 35.40 |
| PN46731 | 1 | 15.70 |
| PN46777 | 99 | 98.90 |
| PN46797 | 1 | 57.30 |
| PN46738 | 1 | 23.00 |

TABLE 2

| TCR ID | Total Ag+ TCRs | Cell Frequency ≥1000 MFI, ≥1% |
|---|---|---|
| PN42365 | 96 | 95.80 |
| PN42879 | 1 | 93.10 |
| PN42774 | 3 | 91.60 |
| PN42498 | 30 | 90.30 |
| PN42558 | 1 | 85.70 |
| PN42386 | 1 | 82.20 |
| PN42378 | 2 | 77.50 |
| PN42776 | 1 | 60.20 |
| PN42455 | 1 | 53.00 |
| PN42840 | 21 | 52.50 |
| PN42795 | 14 | 49.40 |
| PN42870 | 8 | 7.27 |
| PN42689 | 21 | 4.92 |
| PN42888 | 22 | 87.40 |
| PN42450 | 4 | 62.20 |
| PN42750 | 2 | 40.80 |
| PN42562 | 5 | 92.00 |
| PN42483 | 29 | 86.40 |
| PN42712 | 11 | 80.70 |
| PN42561 | 150 | 80.20 |
| PN42442 | 3 | 61.30 |
| PN42476 | 1 | 54.20 |
| PN42496 | 1 | 45.00 |
| PN42655 | 7 | 27.00 |
| PN42677 | 1 | 25.30 |
| PN42706 | 1 | 24.70 |
| PN42654 | 1 | 20.10 |
| PN42441 | 1 | 15.50 |
| PN42683 | 2 | 11.10 |
| PN42845 | 1 | 10.50 |
| PN42826 | 1 | 9.26 |
| PN42707 | 10 | 7.28 |
| PN42833 | 2 | 6.86 |

TABLE 2-continued

| TCR ID | Total Ag+ TCRs | Cell Frequency ≥1000 MFI, ≥1% |
|---|---|---|
| PN42762 | 12 | 4.95 |
| PN42780 | 1 | 4.89 |
| PN42746 | 1 | 4.39 |
| PN42815 | 30 | 4.35 |

TABLE 2-continued

| TCR ID | Total Ag+ TCRs | Cell Frequency ≥1000 MFI, ≥1% |
|---|---|---|
| PN42711 | 1 | 4.26 |
| PN42895 | 3 | 4.09 |
| PN42610 | 1 | 6.08 |

TABLE 3

Amino acid CDR sequences for VelociT TCRs specific for PRAME (312-320)/HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | SEQ ID NO: |
|---|---|---|---|---|---|---|---|---|---|---|---|---|
| PN46678 | TRDTTYY | 1 | RNSFDEQN | 2 | ALSEFDRGST LGRLY | 3 | SGHKS | 4 | YYEKEE | 5 | ASSRDINEKLF | 6 |
| PN46714 | VSGLRG | 7 | LYSAGEE | 8 | AVQADGGSQGNLI | 9 | SGHKS | 10 | YYEKEE | 11 | ASSLDINSPLH | 12 |
| PN46723 | VSGLRG | 13 | LYSAGEE | 14 | AVQEDGGSQGNLI | 15 | SGHKS | 16 | YYEKEE | 17 | ASSRDINEKLF | 18 |
| PN46731 | DSASNY | 19 | IRSNVGE | 20 | AAWNYGQNFV | 21 | PRHDT | 22 | FYEKMQ | 23 | ASSLEGSEAF | 24 |
| PN46733 | NSASDY | 25 | IRSNMDK | 26 | AENNYGQNFV | 27 | MNHNS | 28 | SASEGT | 29 | ASSDWGQGVEAF | 30 |
| PN46735 | TISGTDY | 31 | GLTSN | 32 | ILREYMYSGGG ADGLT | 33 | SGHKS | 34 | YYEKEE | 35 | ASSFQAGVN YGYT | 36 |
| PN46738 | TSENNYY | 37 | QEAYKQQN | 38 | AFGMYSGGGA DGLT | 39 | WSHSY | 40 | SAAADI | 41 | ASSDGTGYY GYT | 42 |
| PN46777 | TSENNYY | 43 | QEAYKQQN | 44 | ALMEYGNKLV | 45 | WSHSY | 46 | SAAADI | 47 | ASSDGTGYYGYT | 48 |
| PN46797 | TSENNYY | 49 | QEAYKQQN | 50 | ALMEYENKLV | 51 | WSHSY | 52 | SAAADI | 53 | ASSDGTGYYGYT | 54 |
| PN46853 | SSNFYA | 55 | MTLNGDE | 56 | ACGGSGNTGKLI | 57 | PRHDT | 58 | FYEKMQ | 59 | ASSSQGQPQH | 60 |
| PN46857 | TRDTTYY | 61 | RNSFDEQN | 62 | ALSEGYGNKLV | 63 | KGHSH | 64 | LQKENI | 65 | ASSHRDDTEAF | 66 |
| PN46871 | DSAIYN | 67 | IQSSQRE | 68 | AVEGTTDSWGKFQ | 69 | PRHDT | 70 | FYEKMQ | 71 | ASSSQGQPQH | 72 |
| PN46880 | YSGSPE | 73 | HISR | 74 | ALSGASGGSYIPT | 75 | KGHSH | 76 | LQKENI | 77 | ASSHRDDTEAF | 78 |
| PN46883 | TRDTTYY | 79 | RNSFDEQN | 80 | ALSVSSYNTDKLI | 81 | KGHSH | 82 | LQKENI | 83 | ASSHRDDTEAF | 84 |
| PN46884 | TRDTTYY | 85 | RNSFDEQN | 86 | ALSEGYNTDKLI | 87 | MDHEN | 88 | SYDVKM | 89 | ASSLGGANTIY | 90 |
| PN46889 | DRGSQS | 91 | IYSNGD | 92 | AVNIPNSGYSTLT | 93 | MNHEY | 94 | SVGEGT | 95 | ASSYWEGTEAF | 96 |
| PN46909 | TSENNYY | 97 | QEAYKQQN | 98 | AFDYGQNFV | 99 | MNHNY | 100 | SVGAGI | 101 | ASSYGGGQTEAF | 102 |
| PN46914 | TRDTTYY | 103 | RNSFDEQN | 104 | ALSEGYNQGGKLI | 105 | MDHEN | 106 | SYDVKM | 107 | ASGADSNQPQH | 108 |

TABLE 4

Nucleic acid CDR sequences for VelociT TCRs specific for PRAME (312-320) / HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | SEQ ID NO: |
|---|---|---|---|---|---|---|---|---|---|---|---|---|
| PN46678 | ACCCGTG ATACTAC TTATTAC | 109 | CGGAACTCT TTTGATGAG CAAAAT | 110 | GCTCTGAGTGAGTTTG ACAGAGGCTCAACCC TGGGGAGGCTATAC | 111 | TCTGGGC ACAAGA GT | 112 | TATTATG AGAAAGA AGAG | 113 | GCCAGCAGCCGGGA CATTAATGAAAAC TGTTT | 114 |
| PN46714 | GTCAGCG GTTTAAG AGGG | 115 | CTGTATTCA GCTGGGGAA GAA | 116 | GCTGTGCAGGCCGAT GGAGGAAGCCAAGGA AATCTCATC | 117 | TCTGGGC ACAAGA GT | 118 | TATTATG AGAAAGA AGAG | 119 | GCCAGCAGCTTGGA CATTAATTCACCCCT CCAC | 120 |
| PN46723 | GTCAGCG GTTTAAG AGGG | 121 | CTGTATTCA GCTGGGGAA GAA | 122 | GCTGTGCAGGAGGAT GGAGGAAGCCAAGGA AATCTCATC | 123 | TCTGGGC ACAAGA GT | 124 | TATTATG AGAAAGA AGAG | 125 | GCCAGCAGCCGGGA CATTAATGAAAAC TGTTT | 126 |

43 44

TABLE 4-continued

Nucleic acid CDR sequences for VelociT TCRs specific for PRAME (312-320) / HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | SEQ ID NO: |
|---|---|---|---|---|---|---|---|---|---|---|---|---|
| PN46731 | GACAGTG CCTCAAA CTAC | 127 | ATTCGTTCA AATGTGGGC GAA | 128 | GCAGCATGGAACTAT GGTCAGAATTTTGTC | 129 | CCTAGAC ACGACA CT | 130 | TTTTATG AAAAGAT GCAG | 131 | GCCAGCAGCTTAGA GGGGTCTGAAGCTT TC | 132 |
| PN46733 | AACAGCG CCTCAGA CTAC | 133 | ATTCGTTCA AATATGGAC AAA | 134 | GCAGAGAATAACTAT GGTCAGAATTTTGTC | 135 | ATGAAC CATAACT CC | 136 | TCAGCTT CTGAGGG TACC | 137 | GCCAGCAGTGACTG GGGACAGGGGGTTG AAGCTTTC | 138 |
| PN46735 | ACAATCA GTGGAAC TGATTAC | 139 | GGTCTTACA AGCAAT | 140 | ATCCTGAGAGAATAC ATGTATTCAGGAGGA GGTGCTGACGGACTC ACC | 141 | TCTGGGC ACAAGA GT | 142 | TATTATG AGAAAGA AGAG | 143 | GCCAGCAGCTTCCA AGCAGGGGTTAACT ATGGCTACACC | 144 |
| PN46738 | ACCAGTG AGAATAA TTATTAT | 145 | CAAGAAGCT TATAAGCAA CAGAAT | 146 | GCTTTCGGTATGTATT CAGGAGGAGGTGCTG ACGGACTCACC | 147 | TGGAGC CACAGCT AT | 148 | TCAGCAG CTGCTGA TATT | 149 | GCCAGCAGTGATGG GACAGGGTACTATG GCTACACC | 150 |
| PN46777 | ACCAGTG AGAATAA TTATTAT | 151 | CAAGAAGCT TATAAGCAA CAGAAT | 152 | GCCCTTATGGAATATG GAAACAAACTGGTC | 153 | TGGAGC CACAGCT AT | 154 | TCAGCAG CTGCTGA TATT | 155 | GCCAGCAGTGATGG GACAGGGTACTATG GCTACACC | 156 |
| PN46797 | ACCAGTG AGAATAA TTATTAT | 157 | CAAGAAGCT TATAAGCAA CAGAAT | 158 | GCCCTTATGGAATATG AAAACAAACTGGTC | 159 | TGGAGC CACAGCT AT | 160 | TCAGCAG CTGCTGA TATT | 161 | GCCAGCAGTGATGG GACAGGGTACTATG GCTACACC | 162 |
| PN46853 | TCCAGCA ATTTTTAT GCC | 163 | ATGACTTTA AATGGGGAT | 164 | GCCTGTGGGGGTTCTG GCAACACAGGCAAAC TAATC | 165 | CCTAGAC ACGACA CT | 166 | TTTTATG AAAAGAT GCAG | 167 | GCCAGCAGCTCCCA GGGTCAGCCCCAGC AT | 168 |
| PN46857 | ACCCGTG ATACTAC TTATTAC | 169 | CGGAACTCT TTTGATGAG CAAAAT | 170 | GCTCTGAGTGAGGGA TATGGAAACAAACTG GTC | 171 | AAAGGA CACAGTC AT | 172 | CTCCAGA AAGAAAA TATC | 173 | GCCAGCTCACACAG GGACGACACTGAAG CTTTC | 174 |
| PN46871 | GATAGCG CTATTTA CAAC | 175 | ATTCAGTCA AGTCAGAGA GAG | 176 | GCTGTGGAGGGGACA ACTGACAGCTGGGGG AAATTCCAG | 177 | CCTAGAC ACGACA CT | 178 | TTTTTATG AAAAGAT GCAG | 179 | GCCAGCAGCTCCCA GGGTCAGCCCCAGC AT | 180 |
| PN46880 | TATTCTG GGAGTCC TGAA | 181 | CACATCTCT AGA | 182 | GCTCTAAGTGGGGCAT CAGGAGGAAGCTACA TACCTACA | 183 | AAAGGA CACAGTC AT | 184 | CTCCAGA AAGAAAA TATC | 185 | GCCAGCTCACACAG GGACGACACTGAAG CTTTC | 186 |
| PN46883 | ACCCGTG ATACTAC TTATTAC | 187 | CGGAACTCT TTTGATGAG CAAAAT | 188 | GCTCTGAGTGTATCAT CTTATAACACCGACAA GCTCATC | 189 | AAAGGA CACAGTC AT | 190 | CTCCAGA AAGAAAA TATC | 191 | GCCAGCTCACACAG GGATGACACTGAAG CTTTC | 192 |
| PN46884 | ACCCGTG ATACTAC TTATTAC | 193 | CGGAACTCT TTTGATGAG CAAAAT | 194 | GCTCTGAGTGAGGGG TATAACACCGACAAG CTCATC | 195 | ATGGAC CATGAA AAT | 196 | TCATATG ATGTTAA AATG | 197 | GCCAGCAGTTTAGG GGGGGCGAACACCA TATAT | 198 |
| PN46889 | GACCGAG GTTCCCA GTCC | 199 | ATATACTCC AATGGTGAC | 200 | GCCGTGAACATTCCGA ATTCAGGATACAGCA CCCTCACC | 201 | ATGAAC CATGAAT AC | 202 | TCAGTTG GTGAGGG TACA | 203 | GCCAGCAGTTACTG GGAGGGCACTGAAG CTTTC | 204 |
| PN46909 | ACCAGTG AGAATAA TTATTAT | 205 | CAAGAAGCT TATAAGCAA CAGAAT | 206 | GCTTTCGACTATGGTC AGAATTTTGTC | 207 | ATGAAC CATAACT AC | 208 | TCAGTTG GTGCTGG TATC | 209 | GCCAGCAGTTACGG GGGGGGGCAGACTG AAGCTTTC | 210 |
| PN46914 | ACCCGTG ATACTAC TTATTAC | 211 | CGGAACTCT TTTGATGAG CAAAAT | 212 | GCTCTGAGTGAGGGTT ATAACCAGGAGGAA AGCTTATC | 213 | ATGGAC CATGAA AAT | 214 | TCATATG ATGTTAA AATG | 215 | GCCAGCGGGGCAGA TAGCAATCAGCCCC AGCAT | 216 |

TABLE 5

Amino acid and nucleic acid sequences for VelociT TCRs
specific for PRAME (312-320)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN46678<br>Vα | AQKVTQAQPEISVVEKEDVTLDCVYETRDTTYYLFWYKQPPSGELVFLIRRNSFD<br>EQNEISGRYSWNFQKSTSSFNFTITASQVVDSAVYFCALSEFDRGSTLGRLYFGR<br>GTQLTVWP (SEQ ID NO: 217)<br>GCTCAGAAGGTAACTCAAGCGCAGCCTGAAATTTCTGTGGTGGAGAAGGAG<br>GATGTGACCTTGGACTGTGTGTATGAAACCCGTGATACTACTTATTACTTATT<br>CTGGTACAAGCAACCACCAAGTGGAGAATTGGTTTTCCTTATTCGTCGGAAC<br>TCTTTTGATGAGCAAAATGAAATAAGTGGTCGGTATTCTTGGAACTTCCAGA<br>AATCCACCAGTTCCTTCAACTTCACCATCACAGCCTCACAAGTCGTGGACTCA<br>GCAGTATACTTCTGTGCTCTGAGTGAGTTTGACAGAGGCTCAACCCTGGGGA<br>GGCTATACTTTGGAAGAGGAACTCAGTTGACTGTCTGGCCT (SEQ ID NO: 218) |
| PN46678<br>Vβ | DAGVTQSPTHLIKTRGQQVTLRCSPISGHKSVSWYQQVLGQGPQFIFQYYEKEER<br>GRGNFPDRFSARQFPNYSSELNVNALLLGDSALYLCASSRDINEKLFFGSGTQLS<br>VL (SEQ ID NO: 219)<br>GACGCTGGAGTCACCCAAAGTCCCACACACCTGATCAAAACGAGAGGACAG<br>CAAGTGACTCTGAGATGCTCTCCTATCTCTGGGCACAAGAGTGTGTCCTGGTA<br>CCAACAGGTCCTGGGTCAGGGGCCCCAGTTTATCTTTCAGTATTATGAGAAA<br>GAAGAGAGAGGAAGAGGAAACTTCCCTGATCGATTCTCAGCTCGCCAGTTCC<br>CTAACTATAGCTCTGAGCTGAATGTGAACGCCTTGTTGCTGGGGGACTCGGC<br>CCTGTATCTCTGTGCCAGCAGCCGGGACATTAATGAAAAACTGTTTTTTGGCA<br>GTGGAACCCAGCTCTCTGTCTTG (SEQ ID NO: 220) |
| PN46714<br>Vα | EDQVTQSPEALRLQEGESSSLNCSYTVSGLRGLFWYRQDPGKGPEFLFTLYSAGE<br>EKEKERLKATLTKKESFLHITAPKPEDSATYLCAVQADGGSQGNLIFGKGTKLSV<br>KP (SEQ ID NO: 221)<br>GAAGACCAGGTGACGCAGAGTCCCGAGGCCCTGAGACTCCAGGAGGGAGAG<br>AGTAGCAGTCTCAACTGCAGTTACACAGTCAGCGGTTTAAGAGGGCTGTTCT<br>GGTATAGGCAAGATCCTGGGAAAGGCCCTGAATTCCTCTTCACCCTGTATTC<br>AGCTGGGGAAGAAAAGGAGAAAGAAAGGCTAAAAGCCACATTAACAAAGA<br>AGGAAAGCTTTCTGCACATCACAGCCCCTAAACCTGAAGACTCAGCCACTTA<br>TCTCTGTGCTGTGCAGGCCGATGGAGGAAGCCAAGGAAATCTCATCTTTGGA<br>AAAGGCACTAAACTCTCTGTTAAACCA (SEQ ID NO: 222) |
| PN46714<br>Vβ | DAGVTQSPTHLIKTRGQQVTLRCSPISGHKSVSWYQQVLGQGPQFIFQYYEKEER<br>GRGNFPDRFSARQFPNYSSELNVNALLLGDSALYLCASSLDINSPLHFGNGTRLT<br>VT (SEQ ID NO: 223)<br>GACGCTGGAGTCACCCAAAGTCCCACACACCTGATCAAAACGAGAGGACAG<br>CAAGTGACTCTGAGATGCTCTCCTATCTCTGGGCACAAGAGTGTGTCCTGGTA<br>CCAACAGGTCCTGGGTCAGGGGCCCCAGTTTATCTTTCAGTATTATGAGAAA<br>GAAGAGAGAGGAAGAGGAAACTTCCCTGATCGATTCTCAGCTCGCCAGTTCC<br>CTAACTATAGCTCTGAGCTGAATGTGAACGCCTTGTTGCTGGGGGACTCGGC<br>CCTGTATCTCTGTGCCAGCAGCTTGGACATTAATTCACCCCTCCACTTTGGGA<br>ACGGGACCAGGCTCACTGTGACA (SEQ ID NO: 224) |
| PN46723<br>Vα | EDQVTQSPEALRLQEGESSSLNCSYTVSGLRGLFWYRQDPGKGPEFLFTLYSAGE<br>EKEKERLKATLTKKESFLHITAPKPEDSATYLCAVQEDGGSQGNLIFGKGTKLSV<br>KP (SEQ ID NO: 225)<br>GAAGACCAGGTGACGCAGAGTCCCGAGGCCCTGAGACTCCAGGAGGGAGAG<br>AGTAGCAGTCTCAACTGCAGTTACACAGTCAGCGGTTTAAGAGGGCTGTTCT<br>GGTATAGGCAAGATCCTGGGAAAGGCCCTGAATTCCTCTTCACCCTGTATTC<br>AGCTGGGGAAGAAAAGGAGAAAGAAAGGCTAAAAGCCACATTAACAAAGA<br>AGGAAAGCTTTCTGCACATCACAGCCCCTAAACCTGAAGACTCAGCCACTTA<br>TCTCTGTGCTGTGCAGGAGGATGGAGGAAGCCAAGGAAATCTCATCTTTGGA<br>AAAGGCACTAAACTCTCTGTTAAACCA (SEQ ID NO: 226) |
| PN46723<br>Vβ | DAGVTQSPTHLIKTRGQQVTLRCSPISGHKSVSWYQQVLGQGPQFIFQYYEKEER<br>GRGNFPDRFSARQFPNYSSELNVNALLLGDSALYLCASSRDINEKLFFGSGTQLS<br>VL (SEQ ID NO: 227)<br>GACGCTGGAGTCACCCAAAGTCCCACACACCTGATCAAAACGAGAGGACAG<br>CAAGTGACTCTGAGATGCTCTCCTATCTCTGGGCACAAGAGTGTGTCCTGGTA<br>CCAACAGGTCCTGGGTCAGGGGCCCCAGTTTATCTTTCAGTATTATGAGAAA<br>GAAGAGAGAGGAAGAGGAAACTTCCCTGATCGATTCTCAGCTCGCCAGTTCC<br>CTAACTATAGCTCTGAGCTGAATGTGAACGCCTTGTTGCTGGGGGACTCGGC<br>CCTGTATCTCTGTGCCAGCAGCCGGGACATTAATGAAAAACTGTTTTTTGGCA<br>GTGGAACCCAGCTCTCTGTCTTG (SEQ ID NO: 228) |
| PN46731<br>Vα | GENVEQHPSTLSVQEGDSAVIKCTYSDSASNYFPWYKQELGKRPQLIIDIRSNVG<br>EKKDQRIAVTLNKTAKHFSLHITETQPEDSAVYFCAAWNYGQNFVFGPGTRLSV<br>LP (SEQ ID NO: 229)<br>GGAGAGAATGTGGAGCAGCATCCTTCAACCCTGAGTGTCCAGGAGGGAGAC |

TABLE 5-continued

Amino acid and nucleic acid sequences for VelociT TCRs
specific for PRAME (312-320)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
|  | AGCGCTGTTATCAAGTGTACTTATTCAGACAGTGCCTCAAACTACTTCCCTTG<br>GTATAAGCAAGAACTTGGAAAAAGACCTCAGCTTATTATAGACATTCGTTCA<br>AATGTGGGCGAAAAGAAAGACCAACGAATTGCTGTTACATTGAACAAGACA<br>GCCAAACATTTCTCCCTGCACATCACAGAGACCCAACCTGAAGACTCGGCTG<br>TCTACTTCTGTGCAGCATGGAACTATGGTCAGAATTTTGTCTTTGGTCCCGGA<br>ACCAGATTGTCCGTGCTGCCC (SEQ ID NO: 230) |
| PN46731<br>Vβ | AAGVIQSPRHLIKEKRETATLKCYPI<u>PRHDTVY</u>WYQQGPGQDPQFLIS<u>FYEKMQS</u><br>DKGSIPDRFSAQQFSDYHSELNMSS<u>LELGDSALYFC</u><u>ASSLEGSEAFF</u>GQGTRLTV<br>V (SEQ ID NO: 231)<br>GCTGCTGGAGTCATCCAGTCCCCAAGACATCTGATCAAAGAAAAGAGGGAA<br>ACAGCCACTCTGAAATGCTATCCTATC<u>CCTAGACACGACACTGTCTACTGGTA</u><br>CCAGCAGGGTCCAGGTCAGGACCCCCC<u>AGTTCCTCATTTCGTTTTATGAAAAG</u><br><u>ATGCAGAGCGATAAAGGAAGCATCCCTGATCGATTCTCAGCTCAACAGTTCA</u><br>GTGACTATCATTCTGAACTGAACATGAGCTCCTTGGGAGCTGGGGGACTCAGC<br>CCTGTACTTCTGTGCCAGCAGCTTAGAGGGGTCTGAAGCTTTCTTTGGACAAG<br>GCACCAGACTCAC<u>AGTTGTA</u> (SEQ ID NO: 232) |
| PN46733<br>Vα | GESVGLHLPTLSVQEGDNSI<u>INCAYSNSASDY</u>FIWYKQESGKGPQF<u>IIDIRSNMDK</u><br>RQGQRVTVLLNKTVKHLSLQIAATQPGDSAVYFC<u>AENNYGQNFV</u>FGPGTRLSVL<br>P (SEQ ID NO: 233)<br>GGAGAGAGTGTGGGGCTGCATCTTCCTACCCTGAGTGTCCAGGAGGGTGACA<br>ACTCTATTATCAACTGTGCTTATTC<u>AAACAGCGCCT</u>CAG<u>ACTACTTCATTTGG</u><br>TACAAGCAAGAATCTGGAAAAGGTCCTCAATTCATTATAGACATTCGTTCAA<br><u>ATATGGACAAAAGGCAAGGCCAAAGAGTCACCGTTTTATTGAATAAGACAGT</u><br><u>GAAACATCTCT</u>CTCTGCAAATTGCAGCTACTCAACCTGGAGACTCAGCTGTCT<br>ACTTTTGTGC<u>AGAGAATAACTATGGTCAGAATTTTGTCTTTGGTCCCGGAACC</u><br>AGATTGTCCGTGCTGCCC (SEQ ID NO: 234) |
| PN46733<br>Vβ | NAGVTQTPKFQVLKTGQSMTLQCAQ<u>DMNHNSMY</u>WYRQDPGMGLRLIY<u>YSASE</u><br><u>GTTDKGEVPNGYNVSRLNKREFSLRLESAAPSQTSVYFC</u><u>ASSDWGQGVEAFF</u>GQ<br>GTRLTVV (SEQ ID NO: 235)<br>AATGCTGGTGTCACTCAGACCCCAAAATTCCAGGTCCTGAAGACAGGACAGA<br>GCATGACACTGCAGTGTGCCCAGGAT<u>ATGAACCATAACTCCATGTACTGGTA</u><br>TCGACAAGACCCAGGCATGGGACTGAGGCTGATTTATTAC<u>TCAGCTTCTGAG</u><br><u>GGTACCACTGACAAAGGAGAAGTCCCCAATGGCTACAATGTCTCCAGATTAA</u><br><u>ACAAACGGGAGTTCTCGCTCAGGCTGGAGTCGGCTGCTCCCTCCCAGACATC</u><br>TGTGTACTTCTGTGCCAGCAGTGACTGGGGACAGGGGGTTGAAGCTTTCTTTG<br>GACAAGGCACCAGACTCACAGTTGTA (SEQ ID NO: 236) |
| PN46735<br>Vα | DAKTTQPNSMESNEEEPVHLPCNHSTISGTDYIHWYRQLPSQGPEYVIHGLTSNV<br>NNRMASLAIAEDRKSSTLILHRATL<u>RDAAVYYC</u><u>ILREYMYSGGGADGLT</u>FGKGT<br>HLIIQP (SEQ ID NO: 237)<br>GATGCTAAGACCACACAGCCAAATTCAATGGAGAGTAACGAAGAAGAGCCT<br>GTTCACTTGCCTTGTAACCACTCCACAATCAGTGGAACTGATTACATACATTG<br>GTATCGACAGCTTCCCTCCCAGGG<u>TCCAGAGTACGTGATTCATGGTCTTACAA</u><br><u>GCAATGTGAACAACAGAATGGCCTCTCTGGCAATCGCTGAAGACAGAAAGTC</u><br><u>CAGTACCTTGATCCTGCACCGTGCTACCTTGAGAGATGCTGCTGTGTACTACT</u><br>GCATCCTGAGAGAATACATGTATTCAGGAGGAGGTGCTGACGGACTCACCTT<br>TGGCAAAGGGACTCATCTAATCATCCAGCCC (SEQ ID NO: 238) |
| PN46735<br>Vβ | DAGVTQSPTHLIKTRGQQVTLRCSP<u>ISGHKSVSWY</u>QQVLGQGPQFIF<u>QYYEKEER</u><br>GRGNFPDRFSARQFPNYSSELNVNA<u>LLLGDSALYLC</u><u>ASSFQAGVNYGYT</u>FGSGT<br>RLTVV (SEQ ID NO: 239)<br>GACGCTGGAGTCACCCAAAGTCCCACACACCTGATCAAAACGAGAGGACAG<br>CAAGTGACTCTGAGATGCTCTCCTATCTCTGGGCACAAGAGTGTGTCCTGGTA<br>CCAACAGGTCCTGGGTCAGGGGCCCCC<u>AGTTTATCTTTCAGTATTATGAGAAA</u><br><u>GAAGAGAGAGGGAAGAGGAAACTTCCCTGATCGATTCTCAGCTCGCCAGTTCC</u><br>CTAACTATAGCTCTGAGCTGAATGTGAACGCCTTGTTGCTGGGGGGACTCGGC<br>CCTGTATCTCTGTGCCAGCAGCTTCCAAGCAGGGGTTAACTATGGCTACACCT<br>TCGGTTCGGGGACCAGGTTAACCGTTGTA (SEQ ID NO: 240) |
| PN46738<br>Vα | AQTVTQSQPEMSVQEAETVTLSCTYDTS<u>ENNYYLF</u>WYKQPPSRQMILV<u>IRQEAY</u><br><u>KQQNATENRFSVNFQKAAKSFSLKISDSQLGDTAMYFC</u><u>AFGMYSGGGADGLTF</u><br>GKGTHLIIQP (SEQ ID NO: 241)<br>GCCCAGACAGTCACTCAGTCTCAACCAGAGATGTCTGTGCAGGAGGCAGAGA<br>CTGTGACCCTGAGTTGCACATATGAC<u>ACCAGTGAGAATAATTATTATTTGTTC</u><br>TGGTACAAGCAGCCTCCCAGCAGGCAGATGATTCTCGTTATTCGC<u>CAAGAAG</u><br><u>CTTATAAGCAACAGAATGCAACGGAGAATCGTTTCTCTGTGAACTTCCAGAA</u><br>AGCAGCCAAATCCTTCAGTCTCAAGATCTCAGACTCACAGCTGGGGGACACT<br>GCGATGTATTTCTGT<u>GCTTTCGGTATGTATTCAGGAGGAGGTGCTGACGGACT</u> |

TABLE 5-continued

Amino acid and nucleic acid sequences for VelociT TCRs
specific for PRAME (312-320)/HLA-A2

|  | Domain Sequences<br>Amino Acid Sequence (SEQ ID NO); CDR1, CDR2, and<br>CDR3 sequences are underlined |
| --- | --- |
| Domain<br>name | Nucleic Acid Sequence (SEQ ID NO); CDR1, CDR2, and<br>CDR3 sequences are underlined |

CACCTTTGGCAAAGGGACTCATCTAATCATCCAGCCC (SEQ ID NO: 242)

PN46738
Vβ
DAGITQSPRYKITETGRQVTLMCHQTWSHSYMFWYRQDLGHGLRLIYYSAAADI
TDKGEVPDGYVVSRSKTENFPLTLESATRSQTSVYFCASSDGTYYGYTFGSGTR
LTVV (SEQ ID NO: 243)
GATGCTGGAATCACCCAGAGCCCAAGATACAAGATCACAGAGACAGGAAGG
CAGGTGACCTTGATGTGTCACCAGACTTGGAGCCACAGCTATATGTTCTGGT
ATCGACAAGACCTGGGACATGGGCTGAGGCTGATCTATTACTCAGCAGCTGC
TGATATTACAGATAAAGGAGAAGTCCCCGATGGCTATGTTGTCTCCAGATCC
AAGACAGAGAATTTCCCCCTCACTCTGGAGTCAGCTACCCGCTCCCAGACAT
CTGTGTATTTCTGCGCCAGCAGTGATGGGACAGGGTACTATGGCTACACCTTC
GGTTCGGGGACCAGGTTAACCGTTGTA (SEQ ID NO: 244)

PN46777
Vα
AQTVTQSQPEMSVQEAETVTLSCTYDTSENNYYLFWYKQPPSRQMILVIRQEAY
KQQNATENRFSVNFQKAAKSFSLKISDSQLGDTAMYFCALMEYGNKLVFGAGTI
LRVKS (SEQ ID NO: 245)
GCCCAGACAGTCACTCAGTCTCAACCAGAGATGTCTGTGCAGGAGGCAGAGA
CTGTGACCCTGAGTTGCACATATGACACCAGTGAGAATAATTATTATTTGTTC
TGGTACAAGCAGCCTCCCAGCAGGCAGATGATTCTCGTTATTCGCCAAGAAG
CTTATAAGCAACAGAATGCAACGGAGAATCGTTTCTCTGTGAACTTCCAGAA
AGCAGCCAAATCCTTCAGTCTCAAGATCTCAGACTCACAGCTGGGGGACACT
GCGATGTATTTCTGTGCCCTTATGGAATATGGAAACAAACTGGTCTTTGGCGC
AGGAACCATTCTGAGAGTCAAGTCC (SEQ ID NO: 246)

PN46777
Vβ
DAGITQSPRYKITETGRQVTLMCHQTWSHSYMFWYRQDLGHGLRLIYYSAAADI
TDKGEVPDGYVVSRSKTENFPLTLESATRSQTSVYFCASSDGTYYGYTFGSGTR
LTVV (SEQ ID NO: 247)
GATGCTGGAATCACCCAGAGCCCAAGATACAAGATCACAGAGACAGGAAGG
CAGGTGACCTTGATGTGTCACCAGACTTGGAGCCACAGCTATATGTTCTGGT
ATCGACAAGACCTGGGACATGGGCTGAGGCTGATCTATTACTCAGCAGCTGC
TGATATTACAGATAAAGGAGAAGTCCCCGATGGCTATGTTGTCTCCAGATCC
AAGACAGAGAATTTCCCCCTCACTCTGGAGTCAGCTACCCGCTCCCAGACAT
CTGTGTATTTCTGCGCCAGCAGTGATGGGACAGGGTACTATGGCTACACCTTC
GGTTCGGGGACCAGGTTAACCGTTGTA (SEQ ID NO: 248)

PN46797
Vα
AQTVTQSQPEMSVQEAETVTLSCTYDTSENNYYLFWYKQPPSRQMILVIRQEAY
KQQNATENRFSVNFQKAAKSFSLKISDSQLGDTAMYFCALMEYENKLVFGAGTI
LRVKS (SEQ ID NO: 249)
GCCCAGACAGTCACTCAGTCTCAACCAGAGATGTCTGTGCAGGAGGCAGAGA
CTGTGACCCTGAGTTGCACATATGACACCAGTGAGAATAATTATTATTTGTTC
TGGTACAAGCAGCCTCCCAGCAGGCAGATGATTCTCGTTATTCGCCAAGAAG
CTTATAAGCAACAGAATGCAACGGAGAATCGTTTCTCTGTGAACTTCCAGAA
AGCAGCCAAATCCTTCAGTCTCAAGATCTCAGACTCACAGCTGGGGGACACT
GCGATGTATTTCTGTGCCCTTATGGAATATGAAAACAAACTGGTCTTTGGCGC
AGGAACCATTCTGAGAGTCAAGTCC (SEQ ID NO: 250)

PN46797
Vβ
DAGITQSPRYKITETGRQVTLMCHQTWSHSYMFWYRQDLGHGLRLIYYSAAADI
TDKGEVPDGYVVSRSKTENFPLTLESATRSQTSVYFCASSDGTYYGYTFGSGTR
LTVV (SEQ ID NO: 251)
GATGCTGGAATCACCCAGAGCCCAAGATACAAGATCACAGAGACAGGAAGG
CAGGTGACCTTGATGTGTCACCAGACTTGGAGCCACAGCTATATGTTCTGGT
ATCGACAAGACCTGGGACATGGGCTGAGGCTGATCTATTACTCAGCAGCTGC
TGATATTACAGATAAAGGAGAAGTCCCCGATGGCTATGTTGTCTCCAGATCC
AAGACAGAGAATTTCCCCCTCACTCTGGAGTCAGCTACCCGCTCCCAGACAT
CTGTGTATTTCTGCGCCAGCAGTGATGGGACAGGGTACTATGGCTACACCTTC
GGTTCGGGGACCAGGTTAACCGTTGTA (SEQ ID NO: 252)

PN46853
Vα
ILNVEQSPQSLHVQEGDSTNFTCSFPSSNFYALHWYRWETAKSPEALFVMTLNG
DEKKKGRISATLNTKEGYSYLYIKGSQPEDSATYLCACGGSGNTGKLIFGQGTTL
QVKP (SEQ ID NO: 253)
ATACTGAACGTGGAACAAAGTCCTCAGTCACTGCATGTTCAGGAGGGGAGACA
GCACCAATTTCACCTGCAGCTTCCCTTCCAGCAATTTTTATGCCTTACACTGG
TACAGATGGGAAACTGCAAAAAGCCCCGAGGCCTTGTTTGTAATGACTTTAA
ATGGGGGATGAAAAGAAGAAAGGACGAATAAGTGCCACTCTTAATACCAAGG
AGGGTTACAGCTATTTGTACATCAAAGGATCCCAGCCTGAAGACTCAGCCAC
ATACCTCTGTGCCTGTGGGGGTTCTGGCAACACAGGCAAACTAATCTTTGGG
CAAGGGACAACTTTACAAGTAAAACCA (SEQ ID NO: 254)

PN46853
Vβ
AAGVIQSPRHLIKEKRETATLKCYPIPRHDTVYWYQQGPGQDPQFLISFYEKMQS
DKGSIPDRFSAQQFSDYHSELNMSSLELGDSALYFCASSSQGQPQHFGDGTRLSIL
(SEQ ID NO: 255)

TABLE 5-continued

Amino acid and nucleic acid sequences for VelociT TCRs
specific for PRAME (312-320)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| | GCTGCTGGAGTCATCCAGTCCCCAAGACATCTGATCAAAGAAAAGAGGGAA<br>ACAGCCACTCTGAAATGCTATCCTATCCCTAGACACGACACTGTCTACTGGTA<br>CCAGCAGGGTCCAGGTCAGGACCCCCAGTTCCTCATTTCGTTTTATGAAAAG<br>ATGCAGAGCGATAAAGGAAGCATCCCTGATCGATTCTCAGCTCAACAGTTCA<br>GTGACTATCATTCTGAACTGAACATGAGCTCCTTGGAGCTGGGGGACTCAGC<br>CCTGTACTTCTGTGCCAGCAGCTCCCAGGGTCAGCCCCAGCATTTTGGTGATG<br>GGACTCGACTCTCCATCCTA (SEQ ID NO: 256) |
| PN46857<br>Vα | AQKVTQATREISVVEKEDVTLDCVYETRDTTYYLFWYKQPPSGELVFLIRRNSFD<br>EQNEISGRYSWNFQKSTSSFNFTITASQVVDSAVYFCALSEGYGNKLVFGAGTIL<br>RVKS (SEQ ID NO: 257)<br>GCTCAGAAGGTAACTCAAGCGACTAGAGAAATTTCTGTGGTGGAGAAGGAG<br>GATGTGACCTTGGACTGTGTGTATGAAACCCGTGATACTACTTATTACTTATT<br>CTGGTACAAGCAACCACCAAGTGGAGAATTGGTTTTCCTTATTCGTCGGAAC<br>TCTTTTGATGAGCAAAATGAAATAAGTGGTCGGTATTCTTGGAACTTCCAGA<br>AATCCACCAGTTCCTTCAACTTCACCATCACAGCCTCACAAGTCGTGGACTCA<br>GCAGTATACTTCTGTGCTCTGAGTGAGGGGATATGGAAACAAACTGGTCTTTG<br>GCGCAGGAACCATTCTGAGAGTCAAGTCC (SEQ ID NO: 258) |
| PN46857<br>Vβ | NAGVMQNPRHLVRRRGQEARLRCSPMKGHSHVYWYRQLPEEGLKFMVYLQKE<br>NIIDESGMPKERFSAEFPKEGPSILRIQQVVRGDSAAYFCASSHRDDTEAFFGQGT<br>RLTVV (SEQ ID NO: 259)<br>AATGCCGGCGTCATGCAGAACCCAAGACACCTGGTCAGGAGGAGGGGACAG<br>GAGGCAAGACTGAGATGCAGCCCAATGAAAGGACACAGTCATGTTTACTGGT<br>ATCGGCAGCTCCCAGAGGAAGGTCTGAAATTCATGGTTTATCTCCAGAAAGA<br>AAATATCATAGATGAGTCAGGAATGCCAAAGGAACGATTTTCTGCTGAATTT<br>CCCAAAGAGGGCCCCAGCATCCTGAGGATCCAGCAGGTAGTGCGAGGAGAT<br>TCGGCAGCTTATTTCTGTGCCAGCTCACACAGGGACGACACTGAAGCTTTCTT<br>TGGACAAGGCACCAGACTCACAGTTGTA (SEQ ID NO: 260) |
| PN46871<br>Vα | KQEVTQIPAALSVPEGENLVLNCSFTDSAIYNLQWFRQDPGKGLTSLLLIQSSQRE<br>QTSGRLNASLDKSSGRSTLYIAASQPGDSATYLCAVEGTTDSWGKFQFGAGTQV<br>WTP (SEQ ID NO: 261)<br>AAACAGGAGGTGACGCAGATTCCTGCAGCTCTGAGTGTCCCAGAAGGAGAA<br>AACTTGGTTCTCAACTGCAGTTTCACTGATAGCGCTATTTACAACCTCCAGTG<br>GTTTAGGCAGGACCCTGGGAAAGGTCTCACATCTCTGTTGCTTATTCAGTCAA<br>GTCAGAGAGAGCAAACAAGTGGAAGACTTAATGCCTCGCTGGATAAATCATC<br>AGGACGTAGTACTTTATACATTGCAGCTTCTCAGCCTGGTGACTCAGCCACCT<br>ACCTCTGTGCTGTGGAGGGGACAACTGACAGCTGGGGGAAATTCCAGTTTGG<br>AGCAGGGACCCAGGTTGTGGTCACCCCA (SEQ ID NO: 262) |
| PN46871<br>Vβ | AAGVIQSPRHLIKEKRETATLKCYPIPRHDTVYWYQQGPGQDPQFLISFYEKMQS<br>DKGSIPDRFSAQQFSDYHSELNMSSLELGDSALYFCASSSQGQPQHFGDGTRLSIL<br>(SEQ ID NO: 263)<br>GCTGCTGGAGTCATCCAGTCCCCAAGACATCTGATCAAAGAAAAGAGGGAA<br>ACAGCCACTCTGAAATGCTATCCTATCCCTAGACACGACACTGTCTACTGGTA<br>CCAGCAGGGTCCAGGTCAGGACCCCCAGTTCCTCATTTCGTTTTATGAAAAG<br>ATGCAGAGCGATAAAGGAAGCATCCCTGATCGATTCTCAGCTCAACAGTTCA<br>GTGACTATCATTCTGAACTGAACATGAGCTCCTTGGAGCTGGGGGACTCAGC<br>CCTGTACTTCTGTGCCAGCAGCTCCCAGGGTCAGCCCCAGCATTTTGGTGATG<br>GGACTCGACTCTCCATCCTA (SEQ ID NO: 264) |
| PN46880<br>Vα | AQRVTQPEKLLSVFKGAPVELKCNYSYSGSPELFWYVQYSRQRLQLLLRHISRES<br>IKGFTADLNKGETSFHLKKPFAQEEDSAMYYCALSGASGGSYIPTFGRGTSLIVH<br>P (SEQ ID NO: 265)<br>GCCCAGAGAGTGACTCAGCCCGAGAAGCTCCTCTCTGTCTTTAAAGGGGCCC<br>CAGTGGAGCTGAAGTGCAACTATTCCTATTCTGGGAGTCCTGAACTCTTCTGG<br>TATGTCCAGTACTCCAGACAACGCCTCCAGTTACTCTTGAGACACATCTCTAG<br>AGAGAGCATCAAAGGCTTCACTGCTGACCTTAACAAAGGCGAGACATCTTTC<br>CACCTGAAGAAACCATTTGCTCAAGAGGAAGACTCAGCCATGTATTACTGTG<br>CTCTAAGTGGGGCATCAGGAGGAAGCTACATACCTACATTTGGAAGAGGAAC<br>CAGCCTTATTGTTCATCCG (SEQ ID NO: 266) |
| PN46880<br>Vβ | NAGVMQNPRHLVRRRGQEARLRCSPMKGHSHVYWYRQLPEEGLKFMVYLQKE<br>NIIDESGMPKERFSAEFPKEGPSILRIQQVVRGDSAAYFCASSHRDDTEAFFGQGT<br>RLTVV (SEQ ID NO: 267)<br>AATGCCGGCGTCATGCAGAACCCAAGACACCTGGTCAGGAGGAGGGGACAG<br>GAGGCAAGACTGAGATGCAGCCCAATGAAAGGACACAGTCATGTTTACTGGT<br>ATCGGCAGCTCCCAGAGGAAGGTCTGAAATTCATGGTTTATCTCCAGAAAGA<br>AAATATCATAGATGAGTCAGGAATGCCAAAGGAACGATTTTCTGCTGAATTT<br>CCCAAAGAGGGCCCCAGCATCCTGAGGATCCAGCAGGTAGTGCGAGGAGAT |

TABLE 5-continued

Amino acid and nucleic acid sequences for VelociT TCRs
specific for PRAME (312-320)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| | TCGGCAGCTTATTTCTGTGCCAGCTCACACAGGGACGACACTGAAGCTTTCTT<br>TGGACAAGGCACCAGACTCACAGTTGTA (SEQ ID NO: 268) |
| PN46883<br>Vα | AQKVTQAQTEISVVEKEDVTLDCVYETRDTTYYLFWYKQPPSGELVFLIRRNSF<br>DEQNEISGRYSWNFQKSTSSFNFTITASQVVDSAVYFCALSVSSYNTDKLIFGTGT<br>RLQVFP (SEQ ID NO: 269)<br>GCTCAGAAGGTAACTCAAGCGCAGACTGAAATTTCTGTGGTGGAGAAGGAG<br>GATGTGACCTTGGACTGTGTGTATGAAACCCGTGATACTACTTATTACTTATT<br>CTGGTACAAGCAACCACCAAGTGGAGAATTGGTTTTCCTTATTCGTCGGAAC<br>TCTTTTGATGAGCAAAATGAAATAAGTGGTCGGTATTCTTGGAACTTCCAGA<br>AATCCACCAGTTCCTTCAACTTCACCATCACAGCCTCACAAGTCGTGGACTCA<br>GCAGTATACTTCTGTGCTCTGAGTGTATCATCTTATAACACCGACAAGCTCAT<br>CTTTGGGACTGGGACCAGATTACAAGTCTTTCCA (SEQ ID NO: 270) |
| PN46883<br>Vβ | NAGVMQNPRHLVRRRGQEARLRCSPMKGHSHVYWYRQLPEEGLKFMVYLQKE<br>NIIDESGMPKERFSAEFPKEGPSILRIQQVVRGDSAAYFCASSHRDDTEAFFGQGT<br>RLTVV (SEQ ID NO: 271)<br>AATGCCGGCGTCATGCAGAACCCAAGACACCTGGTCAGGAGGAGGGGACAG<br>GAGGCAAGACTGAGATGCAGCCCAATGAAAGGACACAGTCATGTTTACTGGT<br>ATCGGCAGCTCCCAGAGGAAGGTCTGAAATTCATGGTTTATCTCCAGAAAGA<br>AAATATCATAGATGAGTCAGGAATGCCAAAGGAACGATTTTCTGCTGAATTT<br>CCCAAAGAGGGCCCCAGCATCCTGAGGATCCAGCAGGTAGTGCGAGGAGAT<br>TCGGCAGCTTATTTCTGTGCCAGCTCACACAGGGATGACACTGAAGCTTTCTT<br>TGGACAAGGCACCAGACTCACAGTTGTA (SEQ ID NO: 272) |
| PN46884<br>Vα | AQKVTQAQPEISVVEKEDVTLDCVYETRDTTYYLFWYKQPPSGELVFLIRRNSFD<br>EQNEISGRYSWNFQKSTSSFNFTITASQVVDSAVYFCALSEGYNTDKLIFGTGTRL<br>QVFP (SEQ ID NO: 273)<br>GCTCAGAAGGTAACTCAAGCGCAGCCTGAAATTTCTGTGGTGGAGAAGGAG<br>GATGTGACCTTGGACTGTGTGTATGAAACCCGTGATACTACTTATTACTTATT<br>CTGGTACAAGCAACCACCAAGTGGAGAATTGGTTTTCCTTATTCGTCGGAAC<br>TCTTTTGATGAGCAAAATGAAATAAGTGGTCGGTATTCTTGGAACTTCCAGA<br>AATCCACCAGTTCCTTCAACTTCACCATCACAGCCTCACAAGTCGTGGACTCA<br>GCAGTATACTTCTGTGCTCTGAGTGAGGGGTATAACACCGACAAGCTCATCT<br>TTGGGACTGGGACCAGATTACAAGTCTTTCCA (SEQ ID NO: 274) |
| PN46884<br>Vβ | DVKVTQSSRYLVKRTGEKVFLECVQDMDHENMFWYRQDPGLGLRLIYFSYDVK<br>MKEKGDIPEGYSVSREKKERFSLILESASTNQTSMYLCASSLGGANTIYFGEGSW<br>LTVV (SEQ ID NO: 275)<br>GATGTGAAAGTAACCCAGAGCTCGAGATATCTAGTCAAAAGGACGGGAGAG<br>AAAGTTTTTCTGGAATGTGTCCAGGATATGGACCATGAAAATATGTTCTGGTA<br>TCGACAAGACCCAGGTCTGGGGCTACGGCTGATCTATTTCTCATATGATGTTA<br>AAATGAAAGAAAAAGGAGATATTCCTGAGGGGTACAGTGTCTCTAGAGAGA<br>AGAAGGAGCGCTTCTCCCTGATTCTGGAGTCCGCCAGCACCAACCAGACATC<br>TATGTACCTCTGTGCCAGCAGTTTAGGGGGGGGCGAACACCATATATTTTGGA<br>GAGGGAAGTTGGCTCACTGTTGTA (SEQ ID NO: 276) |
| PN46889<br>Vα | QKEVEQNSGPLSVPEGAIASLNCTYSDRGSQSFFWYRQYSGKSPELIMSIYSNGD<br>KEDGRFTAQLNKASQYVSLLIRDSQPSDSATYLCAVNIPNSGYSTLTFGKGTMLL<br>VSP (SEQ ID NO: 277)<br>CAGAAGGAGGTGGAGCAGAATTCTGGACCCCTCAGTGTTCCAGAGGGGAGCC<br>ATTGCCTCTCTCAACTGCACTTACAGTGACCGAGGTTCCCAGTCCTTCTTCTG<br>GTACAGACAATATTCTGGGAAAAGCCCTGAGTTGATAATGTCCATATACTCC<br>AATGGTGACAAAGAAGATGAAGGTTTACAGCACAGCTCAATAAAGCCAGC<br>CAGTATGTTTCTCTGCTCATCAGAGACTCCCAGCCCAGTGATTCAGCCACCTA<br>CCTCTGTGCCGTGAACATTCCGAATTCAGGATACAGCACCCTCACCTTTGGGA<br>AGGGGACTATGCTTCTAGTCTCTCCA (SEQ ID NO: 278) |
| PN46889<br>Vβ | NAGVTQTPKFRVLKTGQSMTLLCAQDMNHEYMYWYRQDPGMGLRLIHYSVGE<br>GTTAKGEVPDGYNVSRLKKQNFLLGLESAAPSQTSVYFCASSYWEGTEAFFGQG<br>TRLTVV (SEQ ID NO: 279)<br>AATGCTGGTGTCACTCAGACCCCAAAATTCCGGGTCCTGAAGACAGGACAGA<br>GCATGACACTGCTGTGTGCCCAGGATATGAACCATGAATACATGTACTGGTA<br>TCGACAAGACCCAGGCATGGGGCTGAGGCTGATTCATTACTCAGTTGGTGAG<br>GGTACAACTGCCAAAGGAGAGGTCCCTGATGGCTACAATGTCTCCAGATTAA<br>AAAAACAGAATTTCCTGCTGGGGTTGGAGTCGGCTGCTCCCTCCCAAACATC<br>TGTGTACTTCTGTGCCAGCAGTTACTGGGAGGGCACTGAAGCTTTCTTTGGAC<br>AAGGCACCAGACTCACAGTTGTA (SEQ ID NO: 280) |
| PN46909<br>Vα | AQTVTQSQPEMSVQEAETVTLSCTYDTSENNYYLFWYKQPPSRQMILVIRQEAY<br>KQQNATENRFSVNFQKAAKSFSLKISDSQLGDTAMYFCAFDYGQNFVFGPGTRL |

TABLE 5-continued

Amino acid and nucleic acid sequences for VelociT TCRs
specific for PRAME (312-320)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| | SVLP (SEQ ID NO: 281)<br>GCCCAGACAGTCACTCAGTCTCAACCAGAGATGTCTGTGCAGGAGGCAGAGA<br>CTGTGACCCTGAGTTGCACATATGACACCAGTGAGAATAATTATTATTTGTTC<br>TGGTACAAGCAGCCTCCCAGCAGGCAGATGATTCTCGTTATTCGCCAAGAAG<br>CTTATAAGCAACAGAATGCAACGGAGAATCGTTTCTCTGTGAACTTCCAGAA<br>AGCAGCCAAATCCTTCAGTCTCAAGATCTCAGACTCACAGCTGGGGGACACT<br>GCGATGTATTTCTGTGCTTTCGACTATGGTCAGAATTTTGTCTTTGGTCCCGG<br>AACCAGATTGTCCGTGCTGCCC (SEQ ID NO: 282) |
| PN46909<br>Vβ | NAGVTQTPKFRILKIGQSMTLQCAQDMNHNYMYWYRQDPGMGLKLIYYSVGA<br>GITDKGEVPNGYNVSRSTTEYFPPLRLELAAPSQTSVYFCASSYGGGQTEAFFGQG<br>TRLTVV (SEQ ID NO: 283)<br>AATGCTGGTGTCACTCAGACCCCAAAATTCCGCATCCTGAAGATAGGACAGA<br>GCATGACACTGCAGTGTGCCCAGGATATGAACCATAACTACATGTACTGGTA<br>TCGACAAGACCCAGGCATGGGGCTGAAGCTGATTTATTATTCAGTTGGTGCT<br>GGTATCACTGATAAAGGAGAAGTCCCGAATGGCTACAACGTCTCCAGATCAA<br>CCACAGAGTATTTCCCGCTCAGGCTGGAGTTGGCTGCTCCCTCCCAGACATCT<br>GTGTACTTCTGTGCCAGCAGTTACGGGGGGGGGCAGACTGAAGCTTTCTTTG<br>GACAAGGCACCAGACTCACAGTTGTA (SEQ ID NO: 284) |
| PN46914<br>Vα | AQKVTQAQPEISVVEKEDVTLDCVYETRDTTYYLFWYKQPPSGELVFLIRRNSFD<br>EQNEISGRYSWNFQKSTSSFNFTITASQVVDSAVYFCALSEGYNQGGKLIFGQGT<br>ELSVKP (SEQ ID NO: 285)<br>GCTCAGAAGGTAACTCAAGCGCAGCCTGAAATTTCTGTGGTGGAGAAGGAG<br>GATGTGACCTTGGACTGTGTGTATGAAACCCGTGATACTACTTATTACTTATT<br>CTGGTACAAGCAACCACCAAGTGGAGAATTGGTTTTCCTTATTCGTCGGAAC<br>TCTTTTGATGAGCAAAATGAAATAAGTGGTCGGTATTCTTGGAACTTCCAGA<br>AATCCACCAGTTCCTTCAACTTCACCATCACAGCCTCACAAGTCGTGGACTCA<br>GCAGTATACTTCTGTGCTCTGAGTGAGGGTTATAACCAGGGAGGAAAGCTTA<br>TCTTCGGACAGGGAACGGAGTTATCTGTGAAACCC (SEQ ID NO: 286) |
| PN46914<br>Vβ | DVKVTQSSRYLVKRTGEKVFLECVQDMDHENMFWYRQDPGLGLRLIYFSYDVK<br>MKEKGDIPEGYSVSREKKERFSLILESASTNQTSMYLCASGADSNQPQHFGDGTR<br>LSIL (SEQ ID NO: 287)<br>GATGTGAAAGTAACCCAGAGCTCGAGATATCTAGTCAAAAGGACGGGAGAG<br>AAAGTTTTTCTGGAATGTGTCCAGGATATGGACCATGAAAATATGTTCTGGTA<br>TCGACAAGACCCAGGTCTGGGGCTACGGCTGATCTATTTCTCATATGATGTTA<br>AAATGAAAGAAAAAGGAGATATTCCTGAGGGGTACAGTGTCTCTAGAGAGA<br>AGAAGGAGCGCTTCTCCCTGATTCTGGAGTCCGCCAGCACCAACCAGACATC<br>TATGTACCTCTGTGCCAGCGGGGCAGATAGCAATCAGCCCCAGCATTTTGGT<br>GATGGGACTCGACTCTCCATCCTA (SEQ ID NO: 288) |

TABLE 6

Amino acid CDR sequences for VelociT TCRs specific for PRAME (425-433)/HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | TCR ID |
|---|---|---|---|---|---|---|---|---|---|---|---|---|
| PN42365 | SVFSS | 289 | VVTGGEV | 290 | AANGGSQGNLI | 291 | SGHDT | 292 | YYEEEE | 293 | ASSLQDYGYT | 294 |
| PN42378 | TISGTDY | 295 | GLTSN | 296 | ILRPDSWGKFQ | 297 | SGHDT | 298 | YYEEEE | 299 | ASSLQDYGYT | 300 |
| PN42386 | SVFSS | 301 | VVTGGEV | 302 | ATNGGSQGNLI | 303 | SGHDT | 304 | YYEEEE | 305 | ASSLQDYGYT | 306 |
| PN42441 | TISGTDY | 307 | GLTSN | 308 | IRRPGNQFY | 309 | MNHEY | 310 | SMNVEV | 311 | ASSLWTGSEAF | 312 |
| PN42442 | SVFSS | 313 | VVTGGEV | 314 | AGGTSGTYKYI | 315 | MNHEY | 316 | SMNVEV | 317 | ASSPGTANYGYT | 318 |
| PN42450 | YSGSPE | 319 | HISR | 320 | ALGNTDKLI | 321 | MDHEN | 322 | SYDVKM | 323 | ASSSPRTGWYGYT | 324 |
| PN42455 | TISGTDY | 325 | GLTSN | 326 | ILRPDSWGKFQ | 327 | SGHDT | 328 | YYEEEE | 329 | ASSLVDYGYT | 330 |
| PN42476 | TISGTDY | 331 | GLTSN | 332 | ILRPDSWGKFQ | 333 | MDHEY | 334 | SMNVEV | 335 | ASSLGGVDERLS | 336 |
| PN42483 | SVFSS | 337 | VVTGGEV | 338 | AGDGGSQGNLI | 339 | MNHEY | 340 | SMNVEV | 341 | ASSLGGADEKLF | 342 |

TABLE 6-continued

Amino acid CDR sequences for VelociT TCRs specific for PRAME (425-433)/HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | TCR ID |
|---|---|---|---|---|---|---|---|---|---|---|---|---|
| PN42496 | TISGTDY | 343 | GLTSN | 344 | ILGQGAQKLV | 345 | MNHEY | 346 | SMNVEV | 347 | ASSLWTGGGYT | 348 |
| PN42498 | SVFSS | 349 | VVTGGEV | 350 | AGDGGSQGNLI | 351 | SGHDT | 352 | YYEEEE | 353 | ASSLVDYGYT | 354 |
| PN42558 | DSVNN | 355 | IPSGT | 356 | VLGGGSQGNLI | 357 | SGHDT | 358 | YYEEEE | 359 | ASSFTDYGYT | 360 |
| PN42561 | TISGTDY | 361 | GLTSN | 362 | ILRDGTGNQFY | 363 | MNHEY | 364 | SMNVEV | 365 | ASSLWTGGGYT | 366 |
| PN42562 | SVFSS | 367 | VVTGGEV | 368 | AGGPSGTYKYI | 369 | MNHEY | 370 | SMNVEV | 371 | ASSPGTPNYGYT | 372 |
| PN42610 | DRGSQS | 373 | IYSNGD | 374 | AGNYGQNFV | 375 | PRHDT | 376 | FYEKMQ | 377 | ASSIGLNQPQH | 378 |
| PN42654 | TISGTDY | 379 | GLTSN | 380 | ILRDGIGNQFY | 381 | MNHEY | 382 | SMNVEV | 383 | ASSLWTGGGYT | 384 |
| PN42655 | TISGTDY | 385 | GLTSN | 386 | ILRPDSWGKFQ | 387 | MNHEY | 388 | SMNVEV | 389 | ASSLWTGGGYT | 390 |
| PN42677 | TISGTDY | 391 | GLTSN | 392 | ILRDGTGNQFY | 393 | MNHEY | 394 | SMNVEV | 395 | ASSSTGYYGYT | 396 |
| PN42683 | TISGTDY | 397 | GLTSN | 398 | ILRDREYGNKLV | 399 | MNHEY | 400 | SMNVEV | 401 | ASSLWTGGGYT | 402 |
| PN42689 | SVFSS | 403 | VVTGGEV | 404 | AEDGGSQGNLI | 405 | SGHDT | 406 | YYEEEE | 407 | ASSLSDYGYT | 408 |
| PN42706 | DSVNN | 409 | IPSGT | 410 | AVEASGTYKYI | 411 | MNHEY | 412 | SMNVEV | 413 | ASSWGTGGYGYT | 414 |
| PN42707 | NSASDY | 415 | IRSNMDK | 416 | AENKRDNYGQNFV | 417 | MNHEY | 418 | SMNVEV | 419 | ASSFWVNTEAF | 420 |
| PN42711 | DSVNN | 421 | IPSGT | 422 | AVGSSNGYKLS | 423 | MNHEY | 424 | SMNVEV | 425 | ASSPGTGGFSPLH | 426 |
| PN42712 | DSVNN | 427 | IPSGT | 428 | AVGSSNDYKLS | 429 | MNHEY | 430 | SMNVEV | 431 | ASSPGTGGFSPLH | 432 |
| PN42746 | NSASDY | 433 | IRSNMDK | 434 | AENRQDNYGQNFV | 435 | MNHEY | 436 | SMNVEV | 437 | ASSLWVNTEAF | 438 |
| PN42750 | TISGTDY | 439 | GLTSN | 440 | ILRPDSWGKFQ | 441 | MDHEN | 442 | SYDVKM | 443 | ASSTVRQGNYGYT | 444 |
| PN42762 | TISGTDY | 445 | GLTSN | 446 | ILNTGTASKLT | 447 | MNHEY | 448 | SMNVEV | 449 | ASSLSSNTEAF | 450 |
| PN42774 | DRGSQS | 451 | IYSNGD | 452 | AVNRGTDKLI | 453 | SGHDT | 454 | YYEEEE | 455 | ASSWTDYGYT | 456 |
| PN42776 | TISGTDY | 457 | GLTSN | 458 | ILRPDSWGKFQ | 459 | SGHDT | 460 | YYEEEE | 461 | ASSWTDYGYT | 462 |
| PN42780 | SVFSS | 463 | VVTGGEV | 464 | AGGTSGTYKYI | 465 | MNHEY | 466 | SMNVEV | 467 | ASSPGTPNYGYT | 468 |
| PN42795 | NSASQS | 469 | VYSSGN | 470 | VVNGGSQGNLI | 471 | SGHDT | 472 | YYEEEE | 473 | ASSVGDYGYT | 474 |
| PN42815 | NSASDY | 475 | IRSNMDK | 476 | AENNYGQNFV | 477 | MNHEY | 478 | SMNVEV | 479 | ASSLWDSSPLH | 480 |
| PN42826 | NSMFDY | 481 | ISSIKDK | 482 | AASAGSARQLT | 483 | MNHEY | 484 | SMNVEV | 485 | ASSLYTHTEAF | 486 |
| PN42833 | TISGNEY | 487 | GLKNN | 488 | IVRDTTSGTYKYI | 489 | MNHEY | 490 | SMNVEV | 491 | ASSLSSTGFSPLH | 492 |
| PN42840 | SVFSS | 493 | VVTGGEV | 494 | AEGGGSQGNLI | 495 | SGHDT | 496 | YYEEEE | 497 | ASSWTDYGYT | 498 |
| PN42845 | SVFSS | 499 | VVTGGEV | 500 | AGIRSNDYKLS | 501 | MNHEY | 502 | SMNVEV | 503 | ASSSWTAHTEAF | 504 |
| PN42870 | SVFSS | 505 | VVTGGEV | 506 | AENSGGGADGLT | 507 | SGHDT | 508 | YYEEEE | 509 | ASSFTDYGYT | 510 |
| PN42879 | SVFSS | 511 | VVTGGEV | 512 | AGEDFGNEKLT | 513 | SGHDT | 514 | YYEEEE | 515 | ASSWADYGYT | 516 |
| PN42888 | SSNFYA | 517 | MTLNGDE | 518 | AFLTGNQFY | 519 | MDHEN | 520 | SYDVKM | 521 | ASSTVRQGNYGYT | 522 |
| PN42895 | NSMFDY | 523 | ISSIKDK | 524 | AASAGSARQLT | 525 | MNHEY | 526 | SMNVEV | 527 | ASSLWSNTEAF | 528 |

TABLE 7

Nucleic acid CDR sequences for VelociT TCRs specific for PRAME (425-433)/HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | TCR ID |
|---|---|---|---|---|---|---|---|---|---|---|---|---|
| PN42365 | AGTGTTT TTTCCAG C | 529 | GTAGTTACG GGTGGAGAA GTG | 530 | GCCGCTAATGGAGGA AGCCAAGGAAATCTC ATC | 531 | TCTGGGC ATGACA CT | 532 | TATTATG AGGAGGA AGAG | 533 | GCCAGCAGCTTACA GGACTATGGCTACA CC | 534 |
| PN42378 | ACAATCA GTGGAAC TGATTAC | 535 | GGTCTTACA AGCAAT | 536 | ATCCTGCGGCCTGACA GCTGGGGGAAATTCC AG | 537 | TCTGGGC ATGACA CT | 538 | TATTATG AGGAGGA AGAG | 539 | GCCAGCAGCTTACA GGACTATGGCTACA CC | 540 |
| PN42386 | AGTGTTT TTTCCAG C | 541 | GTAGTTACG GGTGGAGAA GTG | 542 | GCCACTAATGGAGGA AGCCAAGGAAATCTC ATC | 543 | TCTGGGC ATGACA CT | 544 | TATTATG AGGAGGA AGAG | 545 | GCCAGCAGCTTACA GGACTATGGCTACA CC | 546 |
| PN42441 | ACAATCA GTGGAAC TGATTAC | 547 | GGTCTTACA AGCAAT | 548 | ATCAGGCGGCCCGGT AACCAGTTCTAT | 549 | ATGAAC CATGAGT AT | 550 | TCAATGA ATGTTGA GGTG | 551 | GCCAGCAGTTTATG GACAGGGTCTGAAG CTTTC | 552 |
| PN42442 | AGTGTTT TTTCCAG C | 553 | GTAGTTACT GGTGGAGAA GTG | 554 | GCAGGAGGGACCTCA GGAACCTACAAATAC ATC | 555 | ATGAAC CATGAGT AT | 556 | TCAATGA ATGTTGA GGTG | 557 | GCCAGCAGTCCAGG GACAGCTAACTATG GCTACACC | 558 |
| PN42450 | TATTCTG GGAGTCC TGAA | 559 | CACATCTCT AGA | 560 | GCTCTAGGGAACACC GACAAGCTCATC | 561 | ATGGAC CATGAA AAT | 562 | TCATATG ATGTTAA AATG | 563 | GCCAGCAGTTCGCC CAGGACAGGGTGGT ATGGCTACACC | 564 |
| PN42455 | ACAATCA GTGGAAC TGATTAC | 565 | GGTCTTACA AGCAAT | 566 | ATCCTGCGGCCTGACA GCTGGGGGAAATTCC AG | 567 | TCTGGGC ATGACA CT | 568 | TATTATG AGGAGGA AGAG | 569 | GCCAGCAGCTTGGT GGATTATGGCTACA CC | 570 |
| PN42476 | ACAATCA GTGGAAC TGATTAC | 571 | GGTCTTACA AGCAAT | 572 | ATCCTGCGGCCTGACA GCTGGGGGAAATTCC AG | 573 | ATGGAC CATGAGT AT | 574 | TCAATGA ATGTTGA GGTG | 575 | GCCAGCAGTTTAGG GGGCGTGGATGAAA GACTGTCT | 576 |
| PN42483 | AGTGTTT TTTCCAG C | 577 | GTAGTTACG GGTGGAGAA GTG | 578 | GCAGGGGATGGAGGA AGCCAAGGAAATCTC ATC | 579 | ATGAAC CATGAGT AT | 580 | TCAATGA ATGTTGA GGTG | 581 | GCCAGCAGTTTAGG GGGCGCGGATGAAA AACTGTTT | 582 |
| PN42496 | ACAATCA GTGGAAC TGATTAC | 583 | GGTCTTACA AGCAAT | 584 | ATCCTGGGTCAGGGA GCCCAGAAGCTGGTA | 585 | ATGAAC CATGAGT AT | 586 | TCAATGA ATGTTGA GGTG | 587 | GCCAGCAGTTTATG GACAGGGGGCGGCT ACACC | 588 |
| PN42498 | AGTGTTT TTTCCAG C | 589 | GTAGTTACG GGTGGAGAA GTG | 590 | GCAGGGGATGGAGGA AGCCAAGGAAATCTC ATC | 591 | TCTGGGC ATGACA CT | 592 | TATTATG AGGAGGA AGAG | 593 | GCCAGCAGCTTGGT GGATTATGGCTACA CC | 594 |
| PN42558 | GACTCTG TGAACAA T | 595 | ATTCCCTCA GGGACA | 596 | GTCCTAGGGGGAGGA AGCCAAGGAAATCTC ATC | 597 | TCTGGGC ATGACA CT | 598 | TATTATG AGGAGGA AGAG | 599 | GCCAGCAGCTTTAC AGACTATGGCTACA CC | 600 |
| PN42561 | ACAATCA GTGGAAC TGATTAC | 601 | GGTCTTACA AGCAAT | 602 | ATCCTGAGAGACGGG ACCGGTAACCAGTTCT AT | 603 | ATGAAC CATGAGT AT | 604 | TCAATGA ATGTTGA GGTG | 605 | GCCAGCAGTTTATG GACAGGGGGTGGCT ACACC | 606 |
| PN42562 | AGTGTTT TTTCCAG C | 607 | GTAGTTACG GGTGGAGAA GTG | 608 | GCAGGAGGACCCTCA GGAACCTACAAATAC ATC | 609 | ATGAAC CATGAGT AT | 610 | TCAATGA ATGTTGA GGTG | 611 | GCCAGCAGTCCCGG GACACCTAACTATG GCTACACC | 612 |
| PN42610 | GACCGAG GTTCCCA GTCC | 613 | ATATACTCC AATGGTGAC | 614 | GCCGGGAACTATGGT CAGAATTTTGTC | 615 | CCTAGAC ACGACA CT | 616 | TTTTATG AAAAGAT GCAG | 617 | GCCAGCAGCATCGG ACTTAATCAGCCCC AGCAT | 618 |
| PN42654 | ACAATCA GTGGAAC TGATTA | 619 | GGTCTTACA AGCAAT | 620 | ATCCTGAGAGACGGC ATCGGTAACCAGTTCT AT | 621 | ATGAAC CATGAGT AT | 622 | TCAATGA ATGTTGA GGTG | 623 | GCCAGCAGTTTATG GACAGGGGGAGGCT ACACC | 624 |
| PN42655 | ACAATCA GTGGAAC TGATTAC | 625 | GGTCTTACA AGCAAT | 626 | ATCCTGCGGCCTGACA GCTGGGGGAAATTCC AG | 627 | ATGAAC CATGAGT AT | 628 | TCAATGA ATGTTGA GGTG | 629 | GCCAGCAGTTTATG GACAGGGGGAGGCT ACACC | 630 |
| PN42677 | ACAATCA GTGGAAC TGATTAC | 631 | GGTCTTACA AGCAAT | 632 | ATCCTGAGAGACGGC ACCGGTAACCAGTTCT AT | 633 | ATGAAC CATGAGT AT | 634 | TCAATGA ATGTTGA GGTG | 635 | GCCAGCAGTTCGAC AGGGTACTATGGCT ACACC | 636 |

TABLE 7-continued

Nucleic acid CDR sequences for VelociT TCRs specific for PRAME (425-433)/HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | TCR ID |
|---|---|---|---|---|---|---|---|---|---|---|---|---|
| PN42683 | ACAATCA GTGGAAC TGATTAC | 637 | GGTCTTACA AGCAAT | 638 | ATCCTGAGAGACCGG GAATATGGAAACAAA CTGGTC | 639 | ATGAAC CATGAGT AT | 640 | TCAATGA ATGTTGA GGTG | 641 | GCCAGCAGTTTATG GACAGGGGGCGGCT ACACC | 642 |
| PN42689 | AGTGTTT TTTCCAG C | 643 | GTAGTTACG GGTGGAGAA GTG | 644 | GCAGAAGATGGAGGA AGCCAAGGAAATCTC ATC | 645 | TCTGGGC ATGACA CT | 646 | TATTATG AGGAGGA AGAG | 647 | GCCAGCAGCTTATC AGACTATGGCTACA CC | 648 |
| PN42706 | GACTCTG TGAACAA T | 649 | ATTCCCTCA GGGACA | 650 | GCTGTGGAGGCCTCA GGAACCTACAAATAC ATC | 651 | ATGAAC CATGAGT AT | 652 | TCAATGA ATGTTGA GGTG | 653 | GCCAGCAGTTGGGG GACAGGGGGCTATG GCTACACC | 654 |
| PN42707 | AACAGCG CCTCAGA CTAC | 655 | ATTCGTTCA AATATGGAC AAA | 656 | GCAGAGAATAAGCGG GATAACTATGGTCAG AATTTTGTC | 657 | ATGAAC CATGAGT AT | 658 | TCAATGA ATGTTGA GGTG | 659 | GCCAGCAGTTTCTG GGTGAACACTGAAG CTTTC | 660 |
| PN42711 | GACTCTG TGAACAA T | 661 | ATTCCCTCA GGGACA | 662 | GCTGTGGGGGAGTTCTA ACGGCTACAAGCTCA GC | 663 | ATGAAC CATGAGT AT | 664 | TCAATGA ATGTTGA GGTG | 665 | GCCAGCAGTCCCGG GACAGGGGGATTTT CACCCCTCCAC | 666 |
| PN42712 | GACTCTG TGAACAA T | 667 | ATTCCCTCA GGGACA | 668 | GCTGTGGGGGAGTTCTA ACGACTACAAGCTCA GC | 669 | ATGAAC CATGAGT AT | 670 | TCAATGA ATGTTGA GGTG | 671 | GCCAGCAGTCCCGG GACAGGGGGATTTT CACCCCTCCAC | 672 |
| PN42746 | AACAGCG CCTCAGA CTAC | 673 | ATTCGTTCA AATATGGAC AAA | 674 | GCAGAGAATAGGCAG GATAACTATGGTCAG AATTTTGTC | 675 | ATGAAC CATGAGT AT | 676 | TCAATGA ATGTTGA GGTG | 677 | GCCAGCAGTTTATG GGTTAACACTGAAG CTTTC | 678 |
| PN42750 | ACAATCA GTGGAAC TGATTAC | 679 | GGTCTTACA AGCAAT | 680 | ATCCTGCGGCCTGACA GCTGGGGGAAGTTCC AG | 681 | ATGGAC CATGAA AAT | 682 | TCATATG ATGTTAA AATG | 683 | GCCAGCAGTACCGT GAGGCAGGGGAACT ATGGCTACACC | 684 |
| PN42762 | ACAATCA GTGGAAC TGATTAC | 685 | GGTCTTACA AGCAAT | 686 | ATCCTGAATACCGGCA CTGCCAGTAAACTCAC c | 687 | ATGAAC CATGAGT AT | 688 | TCAATGA ATGTTGA GGTG | 689 | GCCAGCAGTTTATC GTCGAACACTGAAG CTTTC | 690 |
| PN42774 | GACCGAG GTTCCCA GTCC | 691 | ATATACTCC AATGGTGAC | 692 | GCCGTGAACAGAGGC ACCGACAAGCTCATC | 693 | TCTGGGC ATGACA CT | 694 | TATTATG AGGAGGA AGAG | 695 | GCCAGCAGCTGGAC AGACTATGGCTACA CC | 696 |
| PN42776 | ACAATCA GTGGAAC TGATTAC | 697 | GGTCTTACA AGCAAT | 698 | ATCCTGCGGCCTGACA GCTGGGGGAAATTCC AG | 699 | TCTGGGC ATGACA CT | 700 | TATTATG AGGAGGA AGAG | 701 | GCCAGCAGCTGGAC AGACTATGGCTACA CC | 702 |
| PN42780 | AGTGTTT TTTCCAG C | 703 | GTAGTTACG GGTGGAGAA GTG | 704 | GCAGGAGGAACCTCA GGAACCTACAAATAC ATC | 705 | ATGAAC CATGAGT AT | 706 | TCAATGA ATGTTGA GGTG | 707 | GCCAGCAGTCCCGG GACACCCAACTATG GCTACACC | 708 |
| PN42795 | AACAGTG CTTCTCA GTCT | 709 | GTATACTCC AGTGGTAAT | 710 | GTGGTGAATGGAGGA AGCCAAGGAAATCTC ATC | 711 | TCTGGGC ATGACA CT | 712 | TATTATG AGGAGGA AGAG | 713 | GCCAGCAGCGTAGG GGACTATGGCTACA CC | 714 |
| PN42815 | AACAGCG CCTCAGA CTAC | 715 | ATTCGTTCA AATATGGAC AAA | 716 | GCAGAGAACAACTAT GGTCAGAATTTTGTC | 717 | ATGAAC CATGAGT AT | 718 | TCAATGA ATGTTGA GGTG | 719 | GCCAGCAGTTTATG GGACAGTTCACCCC TCCAC | 720 |
| PN42826 | AACAGCA TGTTTGA TTAT | 721 | ATAAGTTCC ATTAAGGAT AAA | 722 | GCAGCAAGCGCCGGT TCTGCAAGGCAACTG ACC | 723 | ATGAAC CATGAGT AT | 724 | TCAATGA ATGTTGA GGTG | 725 | GCCAGCAGTTTATA CACCCACACTGAAG CTTTC | 726 |
| PN42833 | ACCATCA GTGGAAA TGAGTAT | 727 | GGTCTAAAA AACAAT | 728 | ATCGTCAGAGACACT ACCTCAGGAACCTAC AAATACATC | 729 | ATGAAC CATGAGT AT | 730 | TCAATGA ATGTTGA GGTG | 731 | GCCAGCAGTTTATC CTCGACAGGTTTTT CACCCCTCCAC | 732 |
| PN42840 | AGTGTTT TTTCCAG C | 733 | GTAGTTACG GGTGGAGAA GTG | 734 | GCAGAGGGGGGGAGGA AGCCAAGGAAATCTC ATC | 735 | TCTGGGC ATGACA CT | 736 | TATTATG AGGAGGA AGAG | 737 | GCCAGCAGCTGGAC AGACTATGGCTACA CC | 738 |
| PN42845 | AGTGTTT TTTCCAG C | 739 | GTAGTTACG GGTGGAGAA GTG | 740 | GCAGGGATACGTTCTA ACGACTACAAGCTCA GC | 741 | ATGAAC CATGAGT AT | 742 | TCAATGA ATGTTGA GGTG | 743 | GCCAGCAGTTCCTG GACAGCCCACACTG AAGCTTTC | 744 |

TABLE 7-continued

Nucleic acid CDR sequences for VelociT TCRs specific for PRAME (425-433)/HLA-A2

| TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | TCR ID |
|---|---|---|---|---|---|---|---|---|---|---|---|---|
| PN42870 | AGTGTTT TTTCCAG C | 745 | GTAGTTACG GGTGGAGAA GTG | 746 | GCAGAAAATTCAGGA GGAGGTGCTGACGGA CTCACC | 747 | TCTGGGC ATGACA CT | 748 | TATTATG AGGAGGA AGAG | 749 | GCCAGCAGCTTCAC AGACTATGGCTACA CC | 750 |
| PN42879 | AGTGTTT TTTCCAG C | 751 | GTAGTTACG GGTGGAGAA GTG | 752 | GCAGGAGAGGACTTT GGAAATGAGAAATTA ACC | 753 | TCTGGGC ATGACA CT | 754 | TATTATG AGGAGGA AGAG | 755 | GCCAGCAGCTGGGC GGATTATGGCTACA CC | 756 |
| PN42888 | TCCAGCA ATTTTTAT GCC | 757 | ATGACTTTA AATGGGGAT GAA | 758 | GCCTTTCTCACCGGTA ACCAGTTCTAT | 759 | ATGGAC CATGAA AAT | 760 | TCATATG ATGTTAA AATG | 761 | GCCAGCAGTACCGT GAGGCAGGGGAACT ATGGCTACACC | 762 |
| PN42895 | AACAGCA TGTTTGA TTAT | 763 | ATAAGTTCC ATTAAGGAT AAA | 764 | GCAGCAAGCGCCGGT TCTGCAAGGCAACTG ACC | 765 | ATGAAC CATGAGT AT | 766 | TCAATGA ATGTTGA GGTG | 767 | GCCAGCAGTTTATG GTCGAACACTGAAG CTTTC | 768 |

TABLE 8

Amino acid and nucleic acid sequences for VelociT TCRs
specific for PRAME (425-433)/HLA-A2

Domain name

Domain Sequences
Amino Acid Sequence (SEQ ID NO); CDR1, CDR2, and CDR3 sequences are underlined
Nucleic Acid Sequence
(SEQ ID NO); CDR1, CDR2, and CDR3 sequences are underlined

PN42365
Vα

TQLLEQSPQFLSIQEGENLTVYCNSSSVFSSLQWYRQEPGEGPVLLVTVVTGGEV
KKLKRLTFQFGDARKDSSLHITAAQPGDTGLYLCAANGGSQGNLIFGKGTKLSV
KP (SEQ ID NO: 769)
ACCCAGCTGCTGGAGCAGAGCCCTCAGTTTCTAAGCATCCAAGAGGGAGAAA
ATCTCACTGTGTACTGCAACTCCTCAAGTGTTTTTTCCAGCTTACAATGGTAC
AGACAGGAGCCTGGGGAAGGTCCTGTCCTCCTGGTGACAGTAGTTACGGGTG
GAGAAGTGAAGAAGCTGAAGAGACTAACCTTTCAGTTTGGTGATGCAAGAA
AGGACAGTTCTCTCCACATCACTGCGGCCCAGCCTGGTGATACAGGCCTCTA
CCTCTGTGCCGCTAATGGAGGAAGCCAAGGAAATCTCATCTTTGGAAAAGGC
ACTAAACTCTCTGTTAAACCA (SEQ ID NO: 770)

PN42365
Vβ

DAGVTQSPTHLIKTRGQQVTLRCSPKSGHDTVSWYQQALGQGPQFIFQYYEEEE
RQRGNFPDRFSGHQFPNYSSELNVNALLLGDSALYLCASSLQDYGYTFGSGTRL
TVV (SEQ ID NO: 771)
GACGCTGGAGTCACCCAAAGTCCCACACACCTGATCAAAACGAGAGGACAG
CAAGTGACTCTGAGATGCTCTCCTAAGTCTGGGCATGACACTGTGTCCTGGTA
CCAACAGGCCCTGGGTCAGGGGCCCCAGTTTATCTTTCAGTATTATGAGGAG
GAAGAGAGACAGAGAGGCAACTTCCCTGATCGATTCTCAGGTCACCAGTTCC
CTAACTATAGCTCTGAGCTGAATGTGAACGCCTTGTTGCTGGGGGACTCGGC
CCTCTATCTCTGTGCCAGCAGCTTACAGGACTATGGCTACACCTTCGGTTCGG
GGACCAGGTTAACCGTTGTA (SEQ ID NO: 772)

PN42378
Vα

DAKTTQPNSMESNEEEPVHLPCNHSTISGTDYIHWYRQLPSQGPEYVIHGLTSNV
NNRMASLAIAEDRKSSTLILHRSTLRDAAVYYCILRPDSWGKFQFGAGTQVVVT
P (SEQ ID NO: 773)
GATGCTAAGACCACACAGCCAAATTCAATGGAGAGTAACGAAGAAGAGCCT
GTTCACTTGCCTTGTAACCACTCCACAATCAGTGGAACTGATTACATACATTG
GTATCGACAGCTTCCCTCCCAGGGTCCAGAGTACGTGATTCATGGTCTTACAA
GCAATGTGAACAACAGAATGGCCTCTCTGGCAATCGCTGAAGACAGAAAGTC
CAGTACCTTGATCCTGCACCGTTCTACCTTGAGAGATGCTGCTGTGTACTACT
GCATCCTGCGGCCTGACAGCTGGGGGAAATTCCAGTTTGGAGCAGGGACCCA
GGTTGTGGTCACCCCA (SEQ ID NO: 774)

PN42378
Vβ

DAGVTQSPTHLIKTRGQQVTLRCSPKSGHDTVSWYQQALGQGPQFIFQYYEEEE
RQRGNFPDRFSGHQFPNYSSELNVNALLLGDSALYLCASSLQDYGYTFGSGTRL
TVV (SEQ ID NO: 775)
GACGCTGGAGTCACCCAAAGTCCCACACACCTGATCAAAACGAGAGGACAG
CAAGTGACTCTGAGATGCTCTCCTAAGTCTGGGCATGACACTGTGTCCTGGTA
CCAACAGGCCCTGGGTCAGGGGCCCCAGTTTATCTTTCAGTATTATGAGGAG
GAAGAGAGACAGAGAGGCAACTTCCCTGATCGATTCTCAGGTCACCAGTTCC
CTAACTATAGCTCTGAGCTGAATGTGAACGCCTTGTTGCTGGGGGACTCGGC
CCTCTATCTCTGTGCCAGCAGCTTACAGGACTATGGCTACACCTTCGGTTCGG
GGACCAGGTTAACCGTTGTA (SEQ ID NO: 776)

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42386<br>Vα | TQLLEQSPQFLSIQEGENLTVYCNS<u>SSVFSS</u>LQWYRQEPGEGPVLLVTVVTGGEV<br>KKLKRLTFQFGDARKDSSLHITAAQ<u>PGDTG</u>LYLC<u>ATNGGSQGNL</u>IFGKGTKLSV<br>KP (SEQ ID NO: 777)<br>ACCCAGCTGCTGGAGCAGAGCCCTCAGTTTCTAAGCATCCAAGAGGGAGAAA<br>ATCTCACTGTGTACTGCAACTCCTCA<u>AGTGTTTTTT</u>CCAGCTTACAATGGTAC<br>AGACAGGAGCCTGGGGAAGGTCCTGTCCTCCTGGTGA<u>CAGTAGTTACGGGTG</u><br><u>GAGAAGTGAAGAAGCTGAAGAGACTAACCTTTCAGTTT</u>GGTGATGCAAGAA<br>AGGACAGTTCTCTCCACATCACTGCGGCCCAGCCTGGTGATACAGGCCTCTA<br>CCTCTGTG<u>CCACTAATGGAGGAAGCCAAGGAAATCTCATC</u>TTTGGAAAAGGC<br>ACTAAACTCTCTGTTAAACCA (SEQ ID NO: 778) |
| PN42386<br>Vβ | DAGVTQSPTHLIKTRGQQVTLRCSPK<u>SGHDT</u>VSWYQQALGQGPQFIFQ<u>YYEEEE</u><br>RQRGNFPDRFSGHQFPNYSSELNVNALLLGDSALYLC<u>ASSLQDYG</u>TFGSGTRL<br>TVV (SEQ ID NO: 779)<br>GACGCTGGAGTCACCCAAAGTCCCACACACCTGATCAAAACGAGAGGACAG<br>CAAGTGACTCTGAGATGCTCTCCTAAGTCTGGGCATGACACTGTGTCCTGGTA<br>CCAACAGGCCCTGGGTCAGGGGCCCCAGTTTATCTTTC<u>AGTATTATGAGGAG</u><br><u>GAAGAGAGACAGAGAGGC</u>AACTTCCCTGATCGATTCTCAGGTCACCAGTTCC<br>CTAACTATAGCTCTGAGCTGAATGTGAACGCCTTGTTGCTGGGGGACTCGGC<br>CCTCTATCTCTGT<u>GCCAGCAGCTTACAGGACTATGG</u>CTACACCTTCGGTTCGG<br>GGACCAGGTTAACCGTTGTA (SEQ ID NO: 780) |
| PN42441<br>Vα | DAKTTQPNSMESNEEEPVHLPCNHSTI<u>SGTDY</u>IHWYRQLPSQGPEYVIH<u>GLTSNV</u><br>NNRMASLAIAEDRKSSTLILHRATLRDAAVYYC<u>IRRPGNQFY</u>FGTGTSLTVIP<br>(SEQ ID NO: 781)<br>GATGCTAAGACCACACAGCCAAATTCAATGGAGAGTAACGAAGAAGAGCCT<br>GTTCACTTGCCTTGTAACCACTCC<u>ACAATCAGTGG</u>AACTGATTA<u>CATACATTG</u><br>GTATCGACAGCTTCCCTCCCAGGGTCCAGAGTACGTGATTCAT<u>GGTCTTACAA</u><br><u>GCAAT</u>GTGAACAACAGAATGGCCTCTCTGGCAATCGCTGAAGACAGAAAGTC<br>CAGTACCTTGATCCTGCACCGTGCTACCTTGAGAGATGCTGCTGTGTACTACT<br>GC<u>ATCAGGCGGCCCGG</u>TAACCAGTTCTATTTTGGGACAGGGACAAGTTTGAC<br>GGTCATTCCA (SEQ ID NO: 782) |
| PN42441<br>Vβ | EAQVTQNPRYLITVTGKKLTVTCSQN<u>MNHEY</u>MSWYRQDPGLGLRQIYY<u>SMNVE</u><br>VTDKGDVPEGYKVSRKEKRNFPLILESPSPNQTSLYFC<u>ASSLWTGSEAFF</u>GQGTR<br>LTVV (SEQ ID NO: 783)<br>GAAGCCCAAGTGACCCAGAACCCAAGATACCTCATCACAGTGACTGGAAAG<br>AAGTTAACAGTGACTTGTTCTCAGAATAT<u>GAACCATGAGTA</u>TATGTCCTGGTA<br>TCGACAAGACCCAGGGCTGGGCTTAAGGCAGATCTACTATT<u>CAATGAATGTT</u><br><u>GAGGT</u>GACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGT<u>GCCAGCAGTTTATGGACAGGGTCTGAAGCTTTCTTTGGA</u><br>CAAGGCACCAGACTCACAGTTGTA (SEQ ID NO: 784) |
| PN42442<br>Vα | TQLLEQSPQFLSIQEGENLTVYCNS<u>SSVFSS</u>LQWYRQEPGEGPVLLVTVVTGGEV<br>KKLKRLTFQFGDARKDSSLHITAAQ<u>PGDTG</u>LYLC<u>AGGTSGTYKYI</u>FGTGTRLKV<br>LA (SEQ ID NO: 785)<br>ACCCAGCTGCTGGAGCAGAGCCCTCAGTTTCTAAGCATCCAAGAGGGAGAAA<br>ATCTCACTGTGTACTGCAACTCCTCA<u>AGTGTTTTTT</u>CCAGCTTACAATGGTAC<br>AGACAGGAGCCTGGGGAAGGTCCTGTCCTCCTGGTGACAGTAGTTACTGGTG<br><u>GAGAAGTGAAGAAGCTGAAGAGACTAACCTTTCAGTTT</u>GGTGATGCAAGAA<br>AGGACAGTTCTCTCCACATCACTGCGGCCCAGCCTGGTGATACAGGCCTCTA<br>CCTCTGTG<u>CAGGAGGGGACCTCAGGAACCTACAAATACATC</u>TTTGGAACAGGC<br>ACCAGGCTGAAGGTTTTAGCA (SEQ ID NO: 786) |
| PN42442<br>Vβ | EAQVTQNPRYLITVTGKKLTVTCSQN<u>MNHEY</u>MSWYRQDPGLGLRQIYY<u>SMNVE</u><br>VTDKGDVPEGYKVSRKEKRNFPLILESPSPNQTSLYFC<u>ASSPGTANYG</u>YTFGSGT<br>RLTVV (SEQ ID NO: 787)<br>GAAGCCCAAGTGACCCAGAACCCAAGATACCTCATCACAGTGACTGGAAAG<br>AAGTTAACAGTGACTTGTTCTCAGAATAT<u>GAACCATGAGTA</u>TATGTCCTGGTA<br>TCGACAAGACCCAGGGCTGGGCTTAAG<u>GCAGATCTACTATT</u>CAATGAATGTT<br><u>GAGGT</u>GACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGT<u>GCCAGCAGTCCAGGGACAGCTAACTATGGCTACACCTTC</u><br>GGTTCGGGGACCAGGTTAACCGTTGTA (SEQ ID NO: 788) |

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42450<br>Vα | AQRVTQPEKLLSVFKGAPVELKCNYS<u>YSGSPELF</u>WYVQYSRQRLQLLLR<u>HISRES</u><br>IKGFTADLNKGETSFHLKKPFAQEED<u>SAMYYCALGNTDKLI</u>FGTGTRLQVFP<br>(SEQ ID NO: 789)<br>GCCCAGAGAGTGACTCAGCCCGAGAAGCTCCTCTCTGTCTTTAAAGGGGCCC<br>CAGTGGAGCTGAAGTGCAACTATTCC<u>TATTCTGGGAGTCCTGAACTCTTCTGG</u><br>TATGTCCAGTACTCCAGACAACGCCTCCAGTTACTCTTGAGA<u>CACATCTCTAG</u><br><u>AGAGAG</u>CATCAAAGGCTTCACTGCTGACCTTAACAAAGGCGAGACATCTTTC<br>CACCTGAAGAAACCATTTGCTCAAGAGGAAGACT<u>CAGCCATGTATTACTGTG</u><br><u>CTCTAGGGAACACCGACAAGCTCATC</u>TTTGGGACTGGGACCAGATTACAAGT<br>CTTTCCA (SEQ ID NO: 790) |
| PN42450<br>Vβ | DVKVTQSSRYLVKRTGEKVFLECVQD<u>MDHENM</u>FWYRQDPGLGLRLIYF<u>SYDVK</u><br><u>M</u>KEKGDIPEGYSVSREKKERFSLILESASTNQTSMYLC<u>ASSSPRTGWYGYT</u>FGSG<br>TRLTVV (SEQ ID NO: 791)<br>GATGTGAAAGTAACCCAGAGCTCGAGATATCTAGTCAAAAGGACGGGAGAG<br>AAAGTTTTTCTGGAATGTGTCCAGGATATGGACCATGAAAATATGTTCTGGTA<br>TCGACAAGACCCAGGTCTGGGGCTACGGCTGATCTATTTC<u>TCATATGATGTTA</u><br><u>AAATGAAAGAAAAAGGAG</u>ATATTCCTGAGGGGTACAGTGTCTCTAGAGAGA<br>AGAAGGAGCGCTTCTCCCTGATTCTGGAGTCCGCCAGCACCAACCAGACATC<br>TATGTACCTCTGT<u>GCCAGCAGTTCGCCCAGGACAGGGTGGTATGGCTACACC</u><br>TTCGGTTCGGGGACCAGGTTAACCGTTGTA (SEQ ID NO: 792) |
| PN42455<br>Vα | DAKTTQPNSMESNEEEPVHLPCNHSTI<u>SGTDY</u>IHWYRQLPSQGPEYVIHG<u>LTSNV</u><br><u>N</u>NRMASLAIAEDRKSSTLILHRSTLRDAAVYYC<u>ILRPDSWGKFQF</u>GAGTQVVVT<br>P (SEQ ID NO: 793)<br>GATGCTAAGACCACACAGCCAAATTCAATGGAGAGTAACGAAGAAGAGCCT<br>GTTCACTTGCCTTGTAACCACTCC<u>ACAATCAGTGGAACTGATTACATACATTG</u><br>GTATCGACAGCTTCCCTCCCAGGGTCCAGAGTACGTGATTCAT<u>GGTCTTACAA</u><br><u>GCAAT</u>GTGAACAACAGAATGGCCTCTCTGGCAATCGCTGAAGACAGAAAGTC<br>CAGTACCTTGATCCTGCACCGTTCTACCTTGAGAGATGCTGCTGTGTACTACT<br>GC<u>ATCCTGCGGCCTGACAGCTGGGGGAAATTC</u>CAGTTTGGAGCAGGGACCCA<br>GGTTGTGGTCACCCCA (SEQ ID NO: 794) |
| PN42455<br>Vβ | DAGVTQSPTHLIKTRGQQVTLRCSPK<u>SGHDT</u>VSWYQQALGQGPQFIFQ<u>YYEEEE</u><br><u>R</u>QRGNFPDRFSGHQFPNYSSELNVNALLLGDSALYLC<u>ASSLVDYGYT</u>FGSGTRL<br>TVV (SEQ ID NO: 795)<br>GACGCTGGAGTCACCCAAAGCCCCACACACCTGATCAAAACGAGAGGACAG<br>CAAGTGACTCTGAGATGCTCTCCTAAGT<u>CTGGGCATGACACT</u>GTGTCCTGGTA<br>CCAACAGGCCCTGGGTCAGGGGCCCCAGTTTATCTTTCAG<u>TATTATGAGGAG</u><br><u>GAAGAGAG</u>ACAGAGAGGCAACTTCCCTGATCGATTCTCAGGTCACCAGTTCC<br>CTAACTATAGCTCTGAGCTGAATGTGAACGCCTTGTTGCTGGGGGACTCGGC<br>CCTCTATCTCTGTGCCAGCAGCTTGGTGGATTATGGCTACACCTTCGGTTCGG<br>GGACCAGGTTAACCGTTGTA (SEQ ID NO: 796) |
| PN42476<br>Vα | DAKTTQPNSMESNEEEPVHLPCNHSTI<u>SGTDY</u>IHWYRQLPSQGPEYVIHG<u>LTSNV</u><br><u>N</u>NRMASLAIAEDRKSSTLILHRSTLRD<u>AAVYYCILRPDSWGKFQF</u>GAGTQVVVT<br>P (SEQ ID NO: 797)<br>GATGCTAAGACCACACAGCCAAATTCAATGGAGAGTAACGAAGAAGAGCCT<br>GTTCACTTGCCTTGTAACCACTCC<u>ACAATCAGTGGAACTGATTACATACATTG</u><br>GTATCGACAGCTTCCCTCCCAGGGTCCAGAGTACGTGATTCAT<u>GGTCTTACAA</u><br><u>GCAAT</u>GTGAACAACAGAATGGCCTCTCTGGCAATCGCTGAAGACAGAAAGTC<br>CAGTACCTTGATCCTGCACCGTTCTACCTTGAGAGATGCTGCTGTGTACTACT<br>GC<u>ATCCTGCGGCCTGACAGCTGGGGGAAATTC</u>CAGTTTGGAGCAGGGACCCA<br>GGTTGTGGTCACCCCA (SEQ ID NO: 798) |
| PN42476<br>Vβ | EAQVTQSPRYLITVTGKKLTVTCSQN<u>MDHEYM</u>SWYRQDPGLGLRQIYY<u>SMNVE</u><br>VTDKGDVPEGYKVPRKEKRSFPLILESPCCSQTPLYLC<u>ASSLGGVDERLS</u>FGSGT<br>QLSVL (SEQ ID NO: 799)<br>GAAGCCCAAGTGACCCAGAGCCCAAGATACCTCATCACAGTGACTGGAAAG<br>AAGTTAACAGTGACTTGTTCTCAGAATATGGACCATGAGTATATGTCCTGGTA<br>TCGACAGGACCCGGGGCTGGGCCTAAG<u>GCAGATCTACTATTCAATGAATGTT</u><br><u>GAGGT</u>GACAGATAAGGGAGATGTTCCTGAAGGGTACAAAGTCCCTCGAAAA<br>GAGAAGAGGAGTTTCCCCCTGATCCTGGAGTCGCCCTGCTGCAGCCAGACCC<br>CTCTGTACCTCTGT<u>GCCAGCAGTTTAGGGGGCGTGGATGAAAGACTGTCTTTT</u><br>GGCAGTGGAACCCAGCTCTCCGTCTTG (SEQ ID NO: 800) |

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42483 Vα | TQLLEQSPQFLSIQEGENLTVYCNSSSVFSSLQWYRQEPGEGPVLLVTVVTGGEV KKLKRLTFQFGDARKDSSLHITAAQPGDTGLYLCAGDGGSQGNLIFGKGTKLSV KP (SEQ ID NO: 801) ACCCAGCTGCTGGAGCAGAGCCCTCAGTTTCTAAGCATCCAAGAGGGAGAAA ATCTCACTGTGTACTGCAACTCCTCAAGTGTTTTTTCCAGCTTACAATGGTAC AGACAGGAGCCTGGGGAAGGTCCTGTCCTCCTGGTGACAGTAGTTACGGGTG GAGAAGTGAAGAAGCTGAAGAGACTAACCTTTCAGTTTGGTGATGCAAGAA AGGACAGTTCTCTCCACATCACTGCGGCCCAGCCTGGTGATACAGGCCTCTA CCTCTGTGCAGGGGATGGAGGAAGCCAAGGAAATCTCATCTTTGGAAAAGGC ACTAAACTCTCTGTTAAACCA (SEQ ID NO: 802) |
| PN42483 Vβ | EAQVTQSPRYLITVTGKKLTVTCSQNMNHEYMSWYRQDPGLGLRQIYYSMNVE VTDKGDVPEGYKVSRKEKRNFPLILESPSPNQTSLYFCASSLGGADEKLFFGSGT QLSVL (SEQ ID NO: 803) GAAGCCCAAGTGACCCAGAGCCCAAGATACCTCATCACAGTGACTGGAAAG AAGTTAACAGTGACTTGTTCTCAGAATATGAACCATGAGTATATGTCCTGGTA TCGACAAGACCCAGGGCTGGGCTTAAGGCAGATCTACTATTCAATGAATGTT GAGGTGACTGATAAGGGAGATGTTCCTGAAGGGTACAAAGTCTCTCGAAAA GAGAAGAGGAATTTCCCCCTGATCCTGGAGTCGCCCAGCCCCAACCAGACCT CTCTGTACTTCTGTGCCAGCAGTTTAGGGGGCGCGGATGAAAAACTGTTTTTT GGCAGTGGAACCCAGCTCTCTGTCTTG (SEQ ID NO: 804) |
| PN42496 Vα | DAKTTQPNSMESNEEEPVHLPCNHSTISGTDYIHWYRQLPSQGPEYVIHGLTSNV NNRMASLAIAEDRKSSTLILHRATLRDAAVYYCILGQGAQKLVFGQGTRLTINP (SEQ ID NO: 805) GATGCTAAGACCACACAGCCAAATTCAATGGAGAGTAACGAAGAAGAGCCT GTTCACTTGCCTTGTAACCACTCCACAATCAGTGGAACTGATTACATACATTG GTATCGACAGCTTCCCTCCCAGGGTCCAGAGTACGTGATTCATGGTCTTACAA GCAATGTGAACAACAGAATGGCCTCTCTGGCAATCGCTGAAGACAGAAAGTC CAGTACCTTGATCCTGCACCGTGCTACCTTGAGAGATGCTGCTGTGTACTACT GCATCCTGGGTCAGGGAGCCCAGAAGCTGGTATTTGGCCAAGGAACCAGGCT GACTATCAACCCA (SEQ ID NO: 806) |
| PN42496 Vβ | EAQVTQNPRYLITVTGKKLTVTCSQNMNHEYMSWYRQDPGLGLRQIYYSMNVE VTDKGDVPEGYKVSRKEKRNFPLILESPSPNQTSLYFCASSLWTGGGYTFGSGTR LTVV (SEQ ID NO: 807) GAAGCCCAAGTGACCCAGAACCCAAGATACCTCATCACAGTGACTGGAAAG AAGTTAACAGTGACTTGTTCTCAGAATATGAACCATGAGTATATGTCCTGGTA TCGACAAGACCCAGGGCTGGGCTTAAGGCAGATCTACTATTCAATGAATGTT GAGGTGACTGATAAGGGAGATGTTCCTGAAGGGTACAAAGTCTCTCGAAAA GAGAAGAGGAATTTCCCCCTGATCCTGGAGTCGCCCAGCCCCAACCAGACCT CTCTGTACTTCTGTGCCAGCAGTTTATGGACAGGGGGCGGCTACACCTTCGGT TCGGGGACCAGGTTAACCGTTGTA (SEQ ID NO: 808) |
| PN42498 Vα | TQLLEQSPQFLSIQEGENLTVYCNSSSVFSSLQWYRQEPGEGPVLLVTVVTGGEV KKLKRLTFQFGDARKDSSLHITAAQPGDTGLYLCAGDGGSQGNLIFGKGTKLSV KP (SEQ ID NO: 809) ACCCAGCTGCTGGAGCAGAGCCCTCAGTTTCTAAGCATCCAAGAGGGAGAAA ATCTCACTGTGTACTGCAACTCCTCAAGTGTTTTTTCCAGCTTACAATGGTAC AGACAGGAGCCTGGGGAAGGTCCTGTCCTCCTGGTGACAGTAGTTACGGGTG GAGAAGTGAAGAAGCTGAAGAGACTAACCTTTCAGTTTGGTGATGCAAGAA AGGACAGTTCTCTCCACATCACTGCGGCCCAGCCTGGTGATACAGGCCTCTA CCTCTGTGCAGGGGATGGAGGAAGCCAAGGAAATCTCATCTTTGGAAAAGGC ACTAAACTCTCTGTTAAACCA (SEQ ID NO: 810) |
| PN42498 Vβ | DAGVTQSPTHLIKTRGQQVTLRCSPKSGHDTVSWYQQALGQGPQFIFQYYEEEE RQRGNFPDRFSGHQFPNYSSELNVNALLLGDSALYLCASSLVDYGYTFGSGTRL TVV (SEQ ID NO: 811) GACGCTGGAGTCACCCAAAGTCCCACACACCTGATCAAAACGAGAGGACAG CAAGTGACTCTGAGATGCTCTCCTAAGTCTGGGCATGACACTGTGTCCTGGTA CCAACAGGCCCTGGGTCAGGGGCCCCAGTTTATCTTTCAGTATTATGAGGAG AAGAGAGACAGAGAGGCAACTTCCCTGATCGATTCTCAGGTCACCAGTTCC CTAACTATAGCTCTGAGCTGAATGTGAACGCCTTGTTGCTGGGGGACTCGGC CCTCTATCTCTGTGCCAGCAGCTTGGTGGATTATGGCTACACCTTCGGTTCGG GGACCAGGTTAACCGTTGTA (SEQ ID NO: 812) |

TABLE 8-continued

Amino acid and nucleic acid sequences for VelociT TCRs
specific for PRAME (425-433)/HLA-A2

Domain Sequences
Amino Acid Sequence (SEQ ID NO); CDR1, CDR2, and CDR3 sequences are
underlined
Nucleic Acid Sequence
Domain   (SEQ ID NO); CDR1, CDR2, and CDR3 sequences are
name     underlined PN42558   GIQVEQSPPDLILQEGANSTLRCNFSDSVNNLQWFHQNPWGQLINLFYIPSGTKQ
Vα       NGRLSATTVATERYSLLYISSSQTTDSGVYFCVLGGGSQGNLIFGKGTKLSVKP
        (SEQ ID NO: 813)
        GGAATACAAGTGGAGCAGAGTCCTCCAGACCTGATTCTCCAGGAGGGAGCC
        AATTCCACGCTGCGGTGCAATTTTTCTGACTCTGTGAACAATTTGCAGTGGTT
        TCATCAAAACCCTTGGGGACAGCTCATCAACCTGTTTTACATTCCCTCAGGGA
        CAAAACAGAATGGAAGATTAAGCGCCACGACTGTCGCTACGGAACGCTACA
        GCTTATTGTACATTTCCTCTTCCCAGACCACAGACTCAGGCGTTTATTTCTGT
        GTCCTAGGGGGAGGAAGCCAAGGAAATCTCATCTTTGGAAAAGGCACTAAA
        CTCTCTGTTAAACCA (SEQ ID NO: 814)

PN42558   DAGVTQSPTHLIKTRGQQVTLRCSPKSGHDTVSWYQQALGQGPQFIFQYYEEEE
Vβ       RQRGNFPDRFSGHQFPNYSSELNVNALLLGDSALYLCASSFTDYGYTFGSGTRLT
        W (SEQ ID NO: 815)
        GACGCTGGAGTCACCCAAAGTCCCACACACCTGATCAAAACGAGAGGACAG
        CAAGTGACTCTGAGATGCTCTCCTAAGTCTGGGCATGACACTGTGTCCTGGTA
        CCAACAGGCCCTGGGTCAGGGGCCCCAGTTTATCTTTCAGTATTATGAGGAG
        GAAGAGAGAGACAGAGAGGCAACTTCCCTGATCGATTCTCAGGTCACCAGTTCC
        CTAACTATAGCTCTGAGCTGAATGTGAACGCCTTGTTGCTGGGGGACTCGGC
        CCTCTATCTCTGTGCCAGCAGCTTTACAGACTATGGCTACACCTTCGGTTCGG
        GGACCAGGTTAACCGTTGTA (SEQ ID NO: 816)

PN42561   DAKTTQPNSMESNEEEPVHLPCNHSTISGTDYIHWYRQLPSQGPEYVIHGLTSNV
Vα       NNRMASLAIAEDRKSSTLILHRATLRDAAVYYCILRDGTGNQFYFGTGTSLTVIP
        (SEQ ID NO: 817)
        GATGCTAAGACCACACAGCCAAATTCAATGGAGAGTAACGAAGAAGAGCCT
        GTTCACTTGCCTTGTAACCACTCCACAATCAGTGGAACTGATTACATACATTG
        GTATCGACAGCTTCCCTCCCAGGGTCCAGAGTACGTGATTCATGGTCTTACAA
        GCAATGTGAACAACAGAATGGCCTCTCTGGCAATCGCTGAAGACAGAAAGTC
        CAGTACCTTGATCCTGCACCGTGCTACCTTGAGAGATGCTGCTGTGTACTACT
        GCATCCTGAGAGACGGGACCGGTAACCAGTTCTATTTTGGGACAGGGACAAG
        TTTGACGGTCATTCCA (SEQ ID NO: 818)

PN42561   EAQVTQNPRYLITVTGKKLTVTCSQNMNHEYMSWYRQDPGLGLRQIYYSMNVE
Vβ       VTDKGDVPEGYKVSRKEKRNFPLILESPSPNQTSLYFCASSLWTGGGYTFGSGTR
        LTVV(SEQ ID NO: 819)
        GAAGCCCAAGTGACCCAGAACCCAAGATACCTCATCACAGTGACTGGAAAG
        AAGTTAACAGTGACTTGTTCTCAGAATATGAACCATGAGTATATGTCCTGGTA
        TCGACAAGACCCAGGGCTGGGCTTAAGGCAGATCTACTATTCAATGAATGTT
        GAGGTGACTGATAAGGGAGATGTTCCTGAAGGGTACAAAGTCTCTCGAAAA
        GAGAAGAGGAATTTCCCCCTGATCCTGGAGTCGCCCAGCCCCAACCAGACCT
        CTCTGTACTTCTGTGCCAGCAGTTTATGGACAGGGGGTGGCTACACCTTCGGT
        TCGGGGACCAGGTTAACCGTTGTA (SEQ ID NO: 820)

PN42562   TQLLEQSPQFLSIQEGENLTVYCNSSSVFSSLQWYRQEPGEGPVLLVTVVTGGEV
Vα       KKLKRLTFQFGDARKDSSLHITAAQPGDTGLYLCAGGPSGTYKYIFGTGTRLKV
        LA (SEQ ID NO: 821)
        ACCCAGCTGCTGGAGCAGAGCCCTCAGTTTCTAAGCATCCAAGAGGGAGAAA
        ATCTCACTGTGTACTGCAACTCCTCAAGTGTTTTTTCCAGCTTACAATGGTAC
        AGACAGGAGCCTGGGGAAGGTCCTGTCCTCCTGGTGACAGTAGTTACGGGTG
        GAGAAGTGAAGAAGCTGAAGAGACTAACCTTTCAGTTTGGTGATGCAAGAA
        AGGACAGTTCTCTCCACATCACTGCGGCCCAGCCTGGTGATACAGGCCTCTA
        CCTCTGTGCAGGAGGACCCTCAGGAACCTACAAATACATCTTTGGAACAGGC
        ACCAGGCTGAAGGTTTTAGCA (SEQ ID NO: 822)

PN42562   EAQVTQNPRYLITVTGKKLTVTCSQNMNHEYMSWYRQDPGLGLRQIYYSMNVE
Vβ       VTDKGDVPEGYKVSRKEKRNFPLILESPSPNQTSLYFCASSPGTPNYGYTFGSGT
        RLTVV (SEQ ID NO: 823)
        GAAGCCCAAGTGACCCAGAACCCAAGATACCTCATCACAGTGACTGGAAAG
        AAGTTAACAGTGACTTGTTCTCAGAATATGAACCATGAGTATATGTCCTGGTA
        TCGACAAGACCCAGGGCTGGGCTTAAGGCAGATCTACTATTCAATGAATGTT
        GAGGTGACTGATAAGGGAGATGTTCCTGAAGGGTACAAAGTCTCTCGAAAA
        GAGAAGAGGAATTTCCCCCTGATCCTGGAGTCGCCCAGCCCCAACCAGACCT
        CTCTGTACTTCTGTGCCAGCAGTCCCGGGACACCTAACTATGGCTACACCTTC
        GGTTCGGGGACCAGGTTAACCGTTGTA (SEQ ID NO: 824)

TABLE 8-continued

Amino acid and nucleic acid sequences for VelociT TCRs
specific for PRAME (425-433)/HLA-A2

Domain Sequences
Amino Acid Sequence (SEQ ID NO); CDR1, CDR2, and CDR3 sequences are
underlined
Nucleic Acid Sequence
Domain (SEQ ID NO); CDR1, CDR2, and CDR3 sequences are
name underlined PN42610   QKEVEQNSGPLSVPEGAIASLNCTYSDRGSQSFFWYRQYSGKSPELIMSIYSNGD
Vα        KEDGRFTAQLNKASQYVSLLIRDSQPSDSATYLCAGNYGQNFVFGPGTRLSVLP
          (SEQ ID NO: 825)
          CAGAAGGAGGTGGAGCAGAATTCTGGACCCCTCAGTGTTCCAGAGGGAGCC
          ATTGCCTCTCTCAACTGCACTTACAGTGACCGAGGTTCCCAGTCCTTCTTCTG
          GTACAGACAATATTCTGGGAAAAGCCCTGAGTTGATAATGTCCATATACTCC
          AATGGTGACAAAGAAGATGGAAGGTTTACAGCACAGCTCAATAAAGCCAGC
          CAGTATGTTTCTCTGCTCATCAGAGACTCCCAGCCCAGTGATTCAGCCACCTA
          CCTCTGTGCCGGGAACTATGGTCAGAATTTTGTCTTTGGTCCCGGAACCAGAT
          TGTCCGTGCTGCCC (SEQ ID NO: 826)

PN42610   AAGVIQSPRHLIKEKRETATLKCYPIPRHDTVYWYQQGPGQDPQFLISFYEKMQS
Vβ        DKGSIPDRFSAQQFSDYHSELNMSSLELGDSALYFCASSIGLNQPQHFGDGTRLSI
          L (SEQ ID NO: 827)
          GCTGCTGGAGTCATCCAGTCCCCAAGACATCTGATCAAAGAAAAGAGGGAA
          ACAGCCACTCTGAAATGCTATCCTATCCCTAGACACGACACTGTCTACTGGTA
          CCAGCAGGGTCCAGGTCAGGACCCCCAGTTCCTCATTTCGTTTTATGAAAAG
          ATGCAGAGCGATAAAGGAAGCATCCCTGATCGATTCTCAGCTCAACAGTTCA
          GTGACTATCATTCTGAACTGAACATGAGCTCCTTGGAGCTGGGGGACTCAGC
          CCTGTACTTCTGTGCCAGCAGCATCGGACTTAATCAGCCCCAGCATTTTGGTG
          ATGGGACTCGACTCTCCATCCTA (SEQ ID NO: 828)

PN42654   DAKTTQPNSMESNEEEPVHLPCNHSTISGTDYIHWYRQLPSQGPEYVIHGLTSNV
Vα        NNRMASLAIAEDRKSSTLILHRATLRDAAVYYCILRDGIGNQFYFGTGTSLTVIP
          (SEQ ID NO: 829)
          GATGCTAAGACCACACAGCCAAATTCAATGGAGAGTAACGAAGAAGAGCCT
          GTTCACTTGCCTTGTAACCACTCCACAATCAGTGGAACTGATTACATACATTG
          GTATCGACAGCTTCCCTCCCAGGGTCCAGAGTACGTGATTCATGGTCTTACAA
          GCAATGTGAACAACAGAATGGCCTCTCTGGCAATCGCTGAAGACAGAAAGTC
          CAGTACCTTGATCCTGCACCGTGCTACCTTGAGAGATGCTGCTGTGTACTACT
          GCATCCTGAGAGACGGCATCGGTAACCAGTTCTATTTTGGGACAGGGACAAG
          TTTGACGGTCATTCCA (SEQ ID NO: 830)

PN42654   EAQVTQNPRYLITVTGKKLTVTCSQNMNHEYMSWYRQDPGLGLRQIYYSMNVE
Vβ        VTDKGDVPEGYKVSRKEKRNFPLILESPSPNQTSLYFCASSLWTGGGYTFGSGTR
          LTVV(SEQ ID NO: 831)
          GAAGCCCAAGTGACCCAGAACCCAAGATACCTCATCACAGTGACTGGAAAG
          AAGTTAACAGTGACTTGTTCTCAGAATATGAACCATGAGTATATGTCCTGGTA
          TCGACAAGACCCAGGGCTGGGCTTAAGGCAGATCTACTATTCAATGAATGTT
          GAGGTGACTGATAAGGGAGATGTTCCTGAAGGGTACAAAGTCTCTCGAAAA
          GAGAAGAGGAATTTCCCCCTGATCCTGGAGTCGCCCAGCCCCAACCAGACCT
          CTCTGTACTTCTGTGCCAGCAGTTTATGGACAGGGGGAGGCTACACCTTCGGT
          TCGGGGACCAGGTTAACCGTTGTA (SEQ ID NO: 832)

PN42655   DAKTTQPNSMESNEEEPVHLPCNHSTISGTDYIHWYRQLPSQGPEYVIHGLTSNV
Vα        NNRMASLAIAEDRKSSTLILHRSTLRDAAVYYCILRPDSWGKFQFGAGTQVVVT
          P (SEQ ID NO: 833)
          GATGCTAAGACCACACAGCCAAATTCAATGGAGAGTAACGAAGAAGAGCCT
          GTTCACTTGCCTTGTAACCACTCCACAATCAGTGGAACTGATTACATACATTG
          GTATCGACAGCTTCCCTCCCAGGGTCCAGAGTACGTGATTCATGGTCTTACAA
          GCAATGTGAACAACAGAATGGCCTCTCTGGCAATCGCTGAAGACAGAAAGTC
          CAGTACCTTGATCCTGCACCGTTCTACCTTGAGAGATGCTGCTGTGTACTACT
          GCATCCTGCGGCCTGACAGCTGGGGGAAATTCCAGTTTGGAGCAGGGACCCA
          GGTTGTGGTCACCCCA (SEQ ID NO: 834)

PN42655   EAQVTQNPRYLITVTGKKLTVTCSQNMNHEYMSWYRQDPGLGLRQIYYSMNVE
Vβ        VTDKGDVPEGYKVSRKEKRNFPLILESPSPNQTSLYFCASSLWTGGGYTFGSGTR
          LTVV (SEQ ID NO: 835)
          GAAGCCCAAGTGACCCAGAACCCAAGATACCTCATCACAGTGACTGGAAAG
          AAGTTAACAGTGACTTGTTCTCAGAATATGAACCATGAGTATATGTCCTGGTA
          TCGACAAGACCCAGGGCTGGGCTTAAGGCAGATCTACTATTCAATGAATGTT
          GAGGTGACTGATAAGGGAGATGTTCCTGAAGGGTACAAAGTCTCTCGAAAA
          GAGAAGAGGAATTTCCCCCTGATCCTGGAGTCGCCCAGCCCCAACCAGACCT
          CTCTGTACTTCTGTGCCAGCAGTTTATGGACAGGGGGAGGCTACACCTTCGGT
          TCGGGGACCAGGTTAACCGTTGTA (SEQ ID NO: 836)

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42677<br>Vα | DAKTTQPNSMESNEEEPVHLPCNHSTISGTDYIHWYRQLPSQGPEYVIHGLTSNV<br>NNRMASLAIAEDRKSSTLILHRATLRDAAVYYCILRDGTGNQFYFGTGTSLTVIP<br>(SEQ ID NO: 837)<br>GATGCTAAGACCACACAGCCAAATTCAATGGAGAGTAACGAAGAAGAGCCT<br>GTTCACTTGCCTTGTAACCACTCCACAATCAGTGGAACTGATTACATACATTG<br>GTATCGACAGCTTCCCTCCCAGGGTCCAGAGTACGTGATTCATGGTCTTACAA<br>GCAATGTGAACAACAGAATGGCCTCTCTGGCAATCGCTGAAGACAGAAAGTC<br>CAGTACCTTGATCCTGCACCGTGCTACCTTGAGAGATGCTGCTGTGTACTACT<br>GCATCCTGAGAGACGGCACCGGTAACCAGTTCTATTTTGGGACAGGGACAAG<br>TTTGACGGTCATTCCA (SEQ ID NO: 838) |
| PN42677<br>Vβ | EAQVTQNPRYLITVTGKKLTVTCSQNMNHEYMSWYRQDPGLGLRQIYYSMNVE<br>VTDKGDVPEGYKVSRKEKRNFPLILESPSPNQTSLYFCASSSTGYYGYTFGSGTR<br>LTVV (SEQ ID NO: 839)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACTATTCAATGAATGTT<br>GAGGTGACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGTGCCAGCAGTTCGACAGGGTACTATGGCTACACCTTCGGT<br>TCGGGGACCAGGTTAACCGTTGTA (SEQ ID NO: 840) |
| PN42683<br>Vα | DAKTTQPNSMESNEEEPVHLPCNHSTISGTDYIHWYRQLPSQGPEYVIHGLTSNV<br>NNRMASLAIAEDRKSSTLILHRATLRDAAVYYCILRDREYGNKLVFGAGTILRVK<br>S (SEQ ID NO: 841)<br>GATGCTAAGACCACACAGCCAAATTCAATGGAGAGTAACGAAGAAGAGCCT<br>GTTCACTTGCCTTGTAACCACTCCACAATCAGTGGAACTGATTACATACATTG<br>GTATCGACAGCTTCCCTCCCAGGGTCCAGAGTACGTGATTCATGGTCTTACAA<br>GCAATGTGAACAACAGAATGGCCTCTCTGGCAATCGCTGAAGACAGAAAGTC<br>CAGTACCTTGATCCTGCACCGTGCTACCTTGAGAGATGCTGCTGTGTACTACT<br>GCATCCTGAGAGACCGGGAATATGGAAACAAACTGGTCTTTGGCGCAGGAA<br>CCATTCTGAGAGTCAAGTCC (SEQ ID NO: 842) |
| PN42683<br>Vβ | EAQVTQNPRYLITVTGKKLTVTCSQNMNHEYMSWYRQDPGLGLRQIYYSMNVE<br>VTDKGDVPEGYKVSRKEKRNFPLILESPSPNQTSLYFCASSLWTGGGYTFGSGTR<br>LTVV (SEQ ID NO: 843)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACTATTCAATGAATGTT<br>GAGGTGACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGTGCCAGCAGTTTATGGACAGGGGGCGGCTACACCTTCGGT<br>TCGGGGACCAGGTTAACCGTTGTA (SEQ ID NO: 844) |
| PN42689<br>Vα | TQLLEQSPQFLSIQEGENLTVYCNSSSVFSSLQWYRQEPGEGPVLLVTVVTGGEV<br>KKLKRLTFQFGDARKDSSLHITAAQPGDTGLYLCAEDGGSQGNLIFGKGTKLSV<br>KP (SEQ ID NO: 845)<br>ACCCAGCTGCTGGAGCAGAGCCCTCAGTTTCTAAGCATCCAAGAGGGAGAAA<br>ATCTCACTGTGTACTGCAACTCCTCAAGTGTTTTTTCCAGCTTACAATGGTAC<br>AGACAGGAGCCTGGGGAAGGTCCTGTCCTCCTGGTGACAGTAGTTACGGGTG<br>GAGAAGTGAAGAAGCTGAAGAGACTAACCTTTCAGTTTGGTGATGCAAGAA<br>AGGACAGTTCTCTCCACATCACTGCGGCCCAGCCTGGTGATACAGGCCTCTA<br>CCTCTGTGCAGAAGATGGAGGAAGCCAAGGAAATCTCATCTTTGGAAAAGGC<br>ACTAAACTCTCTGTTAAACCA (SEQ ID NO: 846) |
| PN42689<br>Vβ | DAGVTQSPTHLIKTRGQQVTLRCSPKSGHDTVSWYQQALGQGPQFIFQYYEEEE<br>RQRGNFPDRFSGHQFPNYSSELNVNALLLGDSALYLCASSLSDYGYTFGSGTRLT<br>VV (SEQ ID NO: 847)<br>GACGCTGGAGTCACCCAAAGTCCCACACACCTGATCAAAACGAGAGGACAG<br>CAAGTGACTCTGAGATGCTCTCCTAAGTCTGGGCATGACACTGTGTCCTGGTA<br>CCAACAGGCCCTGGGTCAGGGGCCCCAGTTTATCTTTCAGTATTATGAGGAG<br>GAAGAGAGACAGAGAGGCAACTTCCCTGATCGATTCTCAGGTCACCAGTTCC<br>CTAACTATAGCTCTGAGCTGAATGTGAACGCCTTGTTGCTGGGGGACTCGGC<br>CCTCTATCTCTGTGCCAGCAGCTTATCAGACTATGGCTACACCTTCGGTTCGG<br>GGACCAGGTTAACCGTTGTA (SEQ ID NO: 848) |

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42706<br>Vα | GIQVEQSPPDLILQEGANSTLRCNFS<u>DSVNN</u>LQWFHQNPWGQLINLFY<u>IPSGTKQ</u><br>NGRLSATTVATERYSLLYISSSQTTDSGVYFC<u>AVEASGTYKY</u>IFGTGTRLKVLA<br>(SEQ ID NO: 849)<br>GGAATACAAGTGGAGCAGAGTCCTCCAGACCTGATTCTCCAGGAGGGAGCC<br>AATTCCACGCTGCGGTGCAATTTTTCT<u>GACTCTGTGAACAATTT</u>GCAGTGGTT<br>TCATCAAAACCCTTGGGGACAGCTCATCAACCTGTTTTAC<u>ATTCCCTCAGGGA</u><br>CAAAACAGAATGGAAGATTAAGCGCCACGACTGTCGCTACGGAACGCTACA<br>GCTTATTGTACATTTCCTCTTCCCAGACCACAGACTCAGGCGTTTATTTCTGT<br><u>GCTGTGGAGGCCTCAGGAACCTACAAATACAT</u>CTTTGGAACAGGCACCAGGC<br>TGAAGGTTTTAGCA (SEQ ID NO: 850) |
| PN42706<br>Vβ | EAQVTQNPRYLITVTGKKLTVTCSQN<u>MNHEYM</u>SWYRQDPGLGLRQIYY<u>SMNVE</u><br>VTDKGDVPEGYKVSRKEKRNFPLILESPSPNQTSLYFC<u>ASSWGTGGYGYT</u>FGSGT<br><u>R</u>LTVV (SEQ ID NO: 851)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACT<u>ATTCAATGAATGTT</u><br><u>GAGGT</u>GACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGT<u>GCCAGCAGTTGGGGGACAGGGGGGCTATGGCTACACCTT</u><br>CGGTTCGGGGACCAGGTTAACCGTTGTA (SEQ ID NO: 852) |
| PN42707<br>Vα | GESVGLHLPTLSVQEGDNSIINCAYS<u>NSASDY</u>FIWYKQESGKGPQFII<u>DIRSNMDK</u><br>RQGQRVTVLLNKTVKHLSLQIAATQPGDSAVYFC<u>AENKRDNYGQNF</u>VFGPGTR<br>LSVLP (SEQ ID NO: 853)<br>GGAGAGAGTGTGGGGCTGCATCTTCCTACCCTGAGTGTCCAGGAGGGTGACA<br>ACTCTATTATCAACTGTGCTTATTCA<u>AACAGCGCCT</u>CAGAC<u>TACTTCATTTGG</u><br>TACAAGCAAGAATCTGGAAAAGGTCC<u>TCAATTCATTATAGAC</u>ATTCGTTCAA<br>ATATGGACAAAAGGCAAGGCCAAAGAGTCACCGTTTTATTGAATAAGACAGT<br>GAAACATCTCTCTCTGCAAATTGCAGCTACTCAACCTGGAGACTCAGCTGTCT<br>ACTTTTGTGCAGAGAATAAGCGGGATAACTATGGTCAGAATTTTGTCTTTGGT<br>CCCGGAACCAGATTGTCCGTGCTGCCC (SEQ ID NO: 854) |
| PN42707<br>Vβ | EAQVTQNPRYLITVTGKKLTVTCSQN<u>MNHEYM</u>SWYRQDPGLGLRQIYY<u>SMNVE</u><br>VTDKGDVPEGYKVSRKEKRNFPLILESPSPNQTSLYFC<u>ASSFWVNTEAFF</u>GQGTR<br>LTVV (SEQ ID NO: 855)<br>GAAGCCCAAGTGACCCAGAACCCAAGATACCTCATCACAGTGACTGGAAAG<br>AAGTTAACAGTGACTTGTTCTCAGAAT<u>ATGAACCATGAGTAT</u>ATGTCCTGGTA<br>TCGACAAGACCCAGGGCTGGGCTTAAGGCAGATCTACT<u>ATTCAATGAATGTT</u><br><u>GAGGT</u>GACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGT<u>GCCAGCAGTTTCTGGGTGAACACTGAAGCTTTCTTTGGA</u><br>CAAGGCACCAGACTCACAGTTGTA (SEQ ID NO: 856) |
| PN42711<br>Vα | GIQVEQSPPDLILQEGVNSTLRCNFS<u>DSVNN</u>LQWFHQNPWGQLINLFY<u>IPSGTKQ</u><br>NGRLSATTVATERYSLLYISSSRTTDSGVYFC<u>AVGSSNGYKLSF</u>GAGTTVTVRA<br>(SEQ ID NO: 857)<br>GGAATACAAGTGGAGCAGAGTCCTCCAGACCTGATTCTCCAGGAGGGAGTCA<br>ATTCCACGCTGCGGTGCAATTTTTCT<u>GACTCTGTGAACAATTT</u>GCAGTGGTTT<br>CATCAAAACCCTTGGGGACAGCTCATCAACCTGTTTTAC<u>ATTCCCTCAGGGAC</u><br>AAAACAGAATGGAAGATTAAGCGCCACGACTGTGGCTACGGAACGCTACAG<br>CTTATTGTACATTTCCTCTTCCCGGACCACAGACTCAGGCGTTTATTTCTGT<u>GC</u><br><u>TGTGGGGAGTTCTAACGGCTACAAGCTCAGC</u>TTTGGAGCTGGAACCACAGTA<br>ACTGTAAGAGCA (SEQ ID NO: 858) |
| PN42711<br>Vβ | EAQVTQNPRYLITVTGKKLTVTCSQN<u>MNHEYM</u>SWYRQDPGLGLRQIYY<u>SMNVE</u><br>VTDKGDVPEGYKVSRKEKRNFPLILESPSPNQTSLYFC<u>ASSPGTGGFSPLHF</u>GNGT<br><u>R</u>LTVT (SEQ ID NO: 859)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACT<u>ATTCAATGAATGTT</u><br><u>GAGGT</u>GACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGT<u>GCCAGCAGTCCCGGGACAGGGGGATTTTCACCCCTCCAC</u><br>TTTGGGAACGGGACCAGGCTCACTGTGACA (SEQ ID NO: 860) |

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42712<br>Vα | GIQVEQSPPDLILQEGANSTLRCNFSDSVNNLQWFHQNPWGQLINLFYIPSGTKQ<br>NGRLSATTVATERYSLLYISSSQTTDSGVYFCAVGSSNDYKLSFGAGTTVTVRA<br>(SEQ ID NO: 861)<br>GGAATACAAGTGGAGCAGAGTCCTCCAGACCTGATTCTCCAGGAGGGAGCC<br>AATTCCACGCTGCGGTGCAATTTTTCTGACTCTGTGAACAATTTGCAGTGGTT<br>TCATCAAAACCCTTGGGGACAGCTCATCAACCTGTTTTACATTCCCTCAGGGA<br>CAAAACAGAATGGAAGATTAAGCGCCACGACTGTCGCTACGGAACGCTACA<br>GCTTATTGTACATTTCCTCTTCCCAGACCACAGACTCAGGCGTTTATTTCTGT<br>GCTGTGGGGAGTTCTAACGACTACAAGCTCAGCTTTGGAGCCGGAACCACAG<br>TAACTGTAAGAGCA (SEQ ID NO: 862) |
| PN42712<br>Vβ | EAQVTQNPRYLITVTGKKLTVTCSQNMNHEYMSWYRQDPGLGLRQIYYSMNVE<br>VTDKGDVPEGYKVSRKEKRNFPLILESPSPNQTSLYFCASSPGTGGFSPLHFGNGT<br>RLTVT (SEQ ID NO: 863)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACTATTCAATGAATGTT<br>GAGGTGACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGTGCCAGCAGTCCCGGGACAGGGGGGATTTTCACCCCTCCAC<br>TTTGGGAACGGGACCAGGCTCACTGTGACA (SEQ ID NO: 864) |
| PN42746<br>Vα | GESVGLHLPTLSVQEGDNSIINCAYSNSASDYFIWYKQESGKGPQFIIDIRSNMDK<br>RQGQRVTVLLNKTVKHLSLQIAATQPGDSAVYFCAENRQDNYGQNFVFGPGTR<br>LSVLP (SEQ ID NO: 865)<br>GGAGAGAGTGTGGGGCTGCATCTTCCTACCCTGAGTGTCCAGGAGGGTGACA<br>ACTCTATTATCAACTGTGCTTATTCAAACAGCGCCTCAGACTACTTCATTTGG<br>TACAAGCAAGAATCTGGAAAAGGTCCTCAATTCATTATAGACATTCGTTCAA<br>ATATGGACAAAAGGCAAGGCCAAAGAGTCACCGTTTTATTGAATAAGACAGT<br>GAAACATCTCTCTCTGCAAATTGCAGCTACTCAACCTGGAGACTCAGCTGTCT<br>ACTTTTGTGCAGAGAATAGGCAGGATAACTATGGTCAGAATTTTGTCTTTGGT<br>CCCGGAACCAGATTGTCCGTGCTGCCC (SEQ ID NO: 866) |
| PN42746<br>Vβ | EAQVTQNPRYLITVTGKKLTVTCSQNMNHEYMSWYRQDPGLGLRQIYYSMNVE<br>VTDKGDVPEGYKVSRKEKRNFPLILESPSPNQTSLYFCASSLWVNTEAFFGQGTR<br>LTVV (SEQ ID NO: 867)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACTATTCAATGAATGTT<br>GAGGTGACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGTGCCAGCAGTTTATGGGTTAACACTGAAGCTTTCTTTGGA<br>CAAGGCACCAGACTCACAGTTGTA (SEQ ID NO: 868) |
| PN42750<br>Vα | DAKTTQPNSMESNEEEPVHLPCNHSTISGTDYIHWYRQLPSQGPEYVIHGLTSN<br>NNRMASLAIAEDRKSSTLILHRSTLRDAAVYYCILRPDSWGKFQFGAGTQVVVT<br>P (SEQ ID NO: 869)<br>GATGCTAAGACCACACAGCCAAATTCAATGGAGAGTAACGAAGAAGAGCCT<br>GTTCACTTGCCTTGTAACCACTCCACAATCAGTGGAACTGATTACATACATTG<br>GTATCGACAGCTTCCCTCCCAGGGTCCAGAGTACGTGATTCATGGTCTTACAA<br>GCAATGTGAACAACAGAATGGCCTCTCTGGCAATCGCTGAAGACAGAAAGTC<br>CAGTACCTTGATCCTGCACCGTTCTACCTTGAGAGATGCTGCTGTGTACTACT<br>GCATCCTGCGGCCTGACAGCTGGGGGAAGTTCCAGTTTGGAGCAGGGACCCA<br>GGTTGTGGTCACCCCA (SEQ ID NO: 870) |
| PN42750<br>Vβ | DVKVTQSSRYLVKRTGEKVFLECVQDMDHENMFWYRQDPGLGLRLIYFSYDVK<br>MKEKGDIPEGYSVSREKKERFSLILESASTNQTSMYLCASSTVRQGNYGYTFGSG<br>TRLTVV (SEQ ID NO: 871)<br>GATGTGAAAGTAACCCAGAGCTCGAGATATCTAGTCAAAAGGACGGGAGAG<br>AAAGTTTTTCTGGAATGTGTCCAGGATATGGACCATGAAAATATGTTCTGGTA<br>TCGACAAGACCCAGGTCTGGGGCTACGGCTGATCTATTTCTCATATGATGTTA<br>AAATGAAAGAAAAAGGAGATATTCCTGGAGGGGTACAGTGTCTCTAGAGAGA<br>AGAAGGAGCGCTTCTCCCTGATTCTGGAGTCCGCCAGCACCAACCAGACATC<br>TATGTACCTCTGTGCCAGCAGTACCGTGAGGCAGGGGGAACTATGGCTACACC<br>TTCGGTTCGGGGACCAGGTTAACCGTTGTA (SEQ ID NO: 872) |

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42762<br>Vα | DAKTTQPNSMESNEEEPVHLPCNHSTISGTDYIHWYRQLPSQGPEYVIHGLTSN<br>NNRMASLAIAEDRKSSTLILHRATLRDAAVYYCILNTGTASKLTFGTGTRLQVTL<br>(SEQ ID NO: 873)<br>GATGCTAAGACCACACAGCCAAATTCAATGGAGAGTAACGAAGAAGAGCCT<br>GTTCACTTGCCTTGTAACCACTCCACAATCAGTGGAACTGATTACATACATTG<br>GTATCGACAGCTTCCCTCCCAGGGTCCAGAGTACGTGATTCATGGTCTTACAA<br>GCAATGTGAACAACAGAATGGCCTCTCTGGCAATCGCTGAAGACAGAAAGTC<br>CAGTACCTTGATCCTGCACCGTGCTACCTTGAGAGATGCTGCTGTGTACTACT<br>GCATCCTGAATACCGGCACTGCCAGTAAACTCACCTTTGGGACTGGAACAAG<br>ACTTCAGGTCACGCTC (SEQ ID NO: 874) |
| PN42762<br>Vβ | EAQVTQNPRYLITVTGKKLTVTCSQNMNHEYMSWYRQDPGLGLRQIYYSMNVE<br>VTDKGDVPEGYKVSRKEKRNFPLILESPSPNQTSLYFCASSLSSNTEAFFGQGTRL<br>TVV (SEQ ID NO: 875)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACTATTCAATGAATGTT<br>GAGGTGACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGTGCCAGCAGTTTATCGTCGAACACTGAAGCTTTCTTTGGA<br>CAAGGCACCAGACTCACAGTTGTA (SEQ ID NO: 876) |
| PN42774<br>Vα | QKEVEQNSGPLSVPEGAIASLNCTYSDRGSQSFFWYRQYSGKSPELIMSIYSNGD<br>KEDGRFTAQLNKASQYVSLLIRDSQPSDSATYLCAVNRGTDKLIFGTGTRLQVFP<br>(SEQ ID NO: 877)<br>CAGAAGGAGGTGGAGCAGAATTCTGGACCCCTCAGTGTTCCAGAGGGAGCC<br>ATTGCCTCTCTCAACTGCACTTACAGTGACCGAGGTTCCCAGTCCTTCTTCTG<br>GTACAGACAATATTCTGGGAAAAGCCCTGAGTTGATAATGTCCATATACTCC<br>AATGGTGACAAAGAAGATGGAAGGTTTACAGCACAGCTCAATAAAGCCAGC<br>CAGTATGTTTCTCTGCTCATCAGAGACTCCCAGCCCAGTGATTCAGCCACCTA<br>CCTCTGTGCCGTGAACAGAGGCACCGACAAGCTCATCTTTGGGACTGGGACC<br>AGATTACAAGTCTTTCCA (SEQ ID NO: 878) |
| PN42774<br>Vβ | DAGVTQSPTHLIKTRGQQVTLRCSPKSGHDTVSWYQQALGQGPQFIFQYYEEEE<br>RQRGNFPDRFSGHQFPNYSSELNVNALLLGDSALYLCASSWTDYGYTFGSGTRL<br>TVV (SEQ ID NO: 879)<br>GACGCTGGAGTCACCCAAAGTCCCACACACCTGATCAAAACGAGAGGACAG<br>CAAGTGACTCTGAGATGCTCTCCTAAGTCTGGGCATGACACTGTGTCCTGGTA<br>CCAACAGGCCCTGGGTCAGGGGCCCCAGTTTATCTTTCAGTATTATGAGGAG<br>GAAGAGAGACAGAGAGGCAACTTCCCTGATCGATTCTCAGGTCACCAGTTCC<br>CTAACTATAGCTCTGAGCTGAATGTGAACGCCTTGTTGCTGGGGGACTCGGC<br>CCTCTATCTCTGTGCCAGCAGCTGGACGACTATGGCTACACCTTCGGTTCGG<br>GGACCAGGTTAACCGTTGTA (SEQ ID NO: 880) |
| PN42776<br>Vα | DAKTTQPNSMESNEEEPVHLPCNHSTISGTDYIHWYRQLPSQGPEYVIHGLTSNV<br>NNRMASLAIAEDRKSSTLILHRSTLRDAAVYYCILRPDSWGKFQFGAGTQVVVT<br>P (SEQ ID NO: 881)<br>GATGCTAAGACCACACAGCCAAATTCAATGGAGAGTAACGAAGAAGAGCCT<br>GTTCACTTGCCTTGTAACCACTCCACAATCAGTGGAACTGATTACATACATTG<br>GTATCGACAGCTTCCCTCCCAGGGTCCAGAGTACGTGATTCATGGTCTTACAA<br>GCAATGTGAACAACAGAATGGCCTCTCTGGCAATCGCTGAAGACAGAAAGTC<br>CAGTACCTTGATCCTGCACCGTTCTACCTTGAGAGATGCTGCTGTGTACTACT<br>GCATCCTGCGGCCTGACAGCTGGGGGAAATTCCAGTTTGGAGCAGGGACCCA<br>GGTTGTGGTCACCCCA (SEQ ID NO: 882) |
| PN42776<br>Vβ | DAGVTQSPTHLIKTRGQQVTLRCSPKSGHDTVSWYQQALGQGPQFIFQYYEEEE<br>RQRGNFPDRFSGHQFPNYSSELNVNALLLGDSALYLCASSWTDYGYTFGSGTRL<br>TVV (SEQ ID NO: 883)<br>GACGCTGGAGTCACCCAAAGTCCCACACACCTGATCAAAACGAGAGGACAG<br>CAAGTGACTCTGAGATGCTCTCCTAAGTCTGGGCATGACACTGTGTCCTGGTA<br>CCAACAGGCCCTGGGTCAGGGGCCCCAGTTTATCTTTCAGTATTATGAGGAG<br>GAAGAGAGACAGAGAGGCAACTTCCCTGATCGATTCTCAGGTCACCAGTTCC<br>CTAACTATAGCTCTGAGCTGAATGTGAACGCCTTGTTGCTGGGGGACTCGGC<br>CCTCTATCTCTGTGCCAGCAGCTGGACAGACTATGGCTACACCTTCGGTTCGG<br>GGACCAGGTTAACCGTTGTA (SEQ ID NO: 884) |

TABLE 8-continued

Amino acid and nucleic acid sequences for VelociT TCRs
specific for PRAME (425-433)/HLA-A2

Domain Sequences
Amino Acid Sequence (SEQ ID NO); CDR1, CDR2, and CDR3 sequences are
underlined
Nucleic Acid Sequence
Domain   (SEQ ID NO); CDR1, CDR2, and CDR3 sequences are
name     underlined PN42780  TQLLEQSPQFLSIQEGENLTVYCNSSSVFSSLQWYRQEPGEGPVLLVTVVTGGEV
Vα       KKLKRLTFQFGDARKDSSLHITAAQPGDTGLYLCAGGTSGTYKYIFGTGTRLKV
         LA (SEQ ID NO: 885)
         ACCCAGCTGCTGGAGCAGAGCCCTCAGTTTCTAAGCATCCAAGAGGGAGAAA
         ATCTCACTGTGTACTGCAACTCCTCAAGTGTTTTTTCCAGCTTACAATGGTAC
         AGACAGGAGCCTGGGGAAGGTCCTGTCCTCCTGGTGACAGTAGTTACGGGTG
         GAGAAGTGAAGAAGCTGAAGAGACTAACCTTTCAGTTTGGTGATGCAAGAA
         AGGACAGTTCTCTCCACATCACTGCGGCCCAGCCTGGTGATACAGGCCTCTA
         CCTCTGTGCAGGAGGAACCTCAGGAACCTACAAATACATCTTTGGAACAGGC
         ACCAGGCTGAAGGTTTTAGCA (SEQ ID NO: 886)

PN42780  EAQVTQNPRYLITVTGKKLTVTCSQNMNHEYMSWYRQDPGLGLRQIYYSMNVE
Vβ       VTDKGDVPEGYKVSRKEKRNFPLILESPSPNQTSLYFCASSPGTPNYGYTFGSGT
         RLTVV (SEQ ID NO: 887)
         GAAGCCCAAGTGACCCAGAACCCAAGATACCTCATCACAGTGACTGGAAAG
         AAGTTAACAGTGACTTGTTCTCAGAATATGAACCATGAGTATATGTCCTGGTA
         TCGACAAGACCCAGGGCTGGGCTTAAGGCAGATCTACTATTCAATGAATGTT
         GAGGTGACTGATAAGGGAGATGTTCCTGAAGGGTACAAAGTCTCTCGAAAA
         GAGAAGAGGAATTTCCCCCTGATCCTGGAGTCGCCCAGCCCCAACCAGACCT
         CTCTGTACTTCTGTGCCAGCAGTCCCGGGACACCCAACTATGGCTACACCTTC
         GGTTCGGGGACCAGGTTAACCGTTGTA (SEQ ID NO: 888)

PN42795  RKEVEQDPGPFNVPEGATVAFNCTYSNSASQSFFWYRQDCRKEPKLLMSVYSSG
Vα       NEDGRFTAQLNRASQYISLLIRDSKLSDSATYLCVVNGGSQGNLIFGKGTKLSVK
         P (SEQ ID NO: 889)
         CGGAAGGAGGTGGAGCAGGATCCTGGACCCTTCAATGTTCCAGAGGGAGCC
         ACTGTCGCTTTCAACTGTACTTACAGCAACAGTGCTTCTCAGTCTTTCTTCTG
         GTACAGACAGGATTGCAGGAAAGAACCTAAGTTGCTGATGTCCGTATACTCC
         AGTGGTAATGAAGATGGAAGGTTTACAGCACAGCTCAATAGAGCCAGCCAG
         TATATTTCCCTGCTCATCAGAGACTCCAAGCTCAGTGATTCAGCCACCTACCT
         CTGTGTGGTGAATGGAGGAAGCCAAGGAAATCTCATCTTTGGAAAAGGCACT
         AAACTCTCTGTTAAACCA (SEQ ID NO: 890)

PN42795  DAGVTQSPTHLIKTRGQQVTLRCSPKSGHDTVSWYQQALGQGPQFIFQYYEEEE
Vβ       RQRGNFPDRFSGHQFPNYSSELNVNALLLGDSALYLCASSVGDYGYTFGSGTRL
         TVV (SEQ ID NO: 891)
         GACGCTGGAGTCACCCAAAGTCCCACACACCTGATCAAAACGAGAGGACAG
         CAAGTGACTCTGAGATGCTCTCCTAAGTCTGGGCATGACACTGTGTCCTGGTA
         CCAACAGGCCCTGGGTCAGGGGCCCCAGTTTATCTTTCAGTATTATGAGGAG
         GAAGAGAGACAGAGAGGCAACTTCCCTGATCGATTCTCAGGTCACCAGTTCC
         CTAACTATAGCTCTGAGCTGAATGTGAACGCCTTGTTGCTGGGGGACTCGGC
         CCTCTATCTCTGTGCCAGCAGCGTAGGGGACTATGGCTACACCTTCGGTTCGG
         GGACCAGGTTAACCGTTGTA (SEQ ID NO: 892)

PN42815  GESVGLHLPTLSVQEGDNSIINCAYSNSASDYFIWYKQESGKGPQFIIDIRSNMDK
Vα       RQGQRVTVLLNKTVKHLSLQIAATQPGDSAVYFCAENNYGQNFVFGPGTRLSVL
         P (SEQ ID NO: 893)
         GGAGAGAGTGTGGGGCTGCATCTTCCTACCCTGAGTGTCCAGGAGGGTGACA
         ACTCTATTATCAACTGTGCTTATTCAAACAGCGCCTCAGACTACTTCATTTGG
         TACAAGCAAGAATCTGGAAAAGGTCCTCAATTCATTATAGACATTCGTTCAA
         ATATGGACAAAAGGCAAGGCCAAAGAGTCACCGTTTTATTGAATAAGACAGT
         GAAACATCTCTCTCTGCAAATTGCAGCTACTCAACCTGGAGACTCAGCTGTCT
         ACTTTTGTGCAGAGAACAACTATGGTCAGAATTTTGTCTTTGGTCCCGGAACC
         AGATTGTCCGTGCTGCCC (SEQ ID NO: 894)

PN42815  EAQVTQNPRYLITVTGKKLTVTCSQNMNHEYMSWYRQDPGLGLRQIYYSMNVE
Vβ       VTDKGDVPEGYKVSRKEKRNFPLILESPSPNQTSLYFCASSLWDSSPLHFGNGTR
         LTVT (SEQ ID NO: 895)
         GAAGCCCAAGTGACCCAGAACCCAAGATACCTCATCACAGTGACTGGAAAG
         AAGTTAACAGTGACTTGTTCTCAGAATATGAACCATGAGTATATGTCCTGGTA
         TCGACAAGACCCAGGGCTGGGCTTAAGGCAGATCTACTATTCAATGAATGTT
         GAGGTGACTGATAAGGGAGATGTTCCTGAAGGGTACAAAGTCTCTCGAAAA
         GAGAAGAGGAATTTCCCCCTGATCCTGGAGTCGCCCAGCCCCAACCAGACCT
         CTCTGTACTTCTGTGCCAGCAGTTTATGGGACAGTTCACCCCTCCACTTTGGG
         AACGGGACCAGGCTCACTGTGACA (SEQ ID NO: 896)

TABLE 8-continued

Amino acid and nucleic acid sequences for VelociT TCRs
specific for PRAME (425-433)/HLA-A2

Domain Sequences
Amino Acid Sequence (SEQ ID NO); CDR1, CDR2, and CDR3 sequences are
underlined
Nucleic Acid Sequence
Domain     (SEQ ID NO); CDR1, CDR2, and CDR3 sequences are
name       underlined PN42826    DQQVKQNSPSLSVQEGRISILNCDYTNSMFDYFLWYKKYPAEGPTFLISISSIKDK
Vα         NEDGRFTVFLNKSAKHLSLHIVPSQPGDSAVYFCAASAGSARQLTFGSGTQLTVL
           P (SEQ ID NO: 897)
           GACCAGCAAGTTAAGCAAAATTCACCATCCCTGAGCGTCCAGGAAGGAAGA
           ATTTCTATTCTGAACTGTGACTATACTAACAGCATGTTTGATTATTTCCTATGG
           TACAAAAAATACCCTGCTGAAGGTCCTACATTCCTGATATCTATAAGTTCCAT
           TAAGGATAAAAATGAAGATGGAAGATTCACTGTTTTCTTAAACAAAAGTGCC
           AAGCACCTCTCTCTGCACATTGTGCCCTCCCAGCCTGGAGACTCTGCAGTGTA
           CTTCTGTGCAGCAAGCGCCGGTTCTGCAAGGCAACTGACCTTTGGATCTGGG
           ACACAATTGACTGTTTTACCT (SEQ ID NO: 898)

PN42826    EAQVTQNPRYLITVTGKKLTVTCSQNMNHEYMSWYRQDPGLGLRQIYYSMNVE
Vβ         VTDKGDVPEGYKVSRKEKRNFPLILESPSPNQTSLYFCASSLYTHTEAFFGQGTR
           LTVV (SEQ ID NO: 899)
           GAAGCCCAAGTGACCCAGAACCCAAGATACCTCATCACAGTGACTGGAAAG
           AAGTTAACAGTGACTTGTTCTCAGAATATGAACCATGAGTATATGTCCTGGTA
           TCGACAAGACCCAGGGCTGGGCTTAAGGCAGATCTACTATTCAATGAATGTT
           GAGGTGACTGATAAGGGAGATGTTCCTGAAGGGTACAAAGTCTCTCGAAAA
           GAGAAGAGGAATTTCCCCCTGATCCTGGAGTCGCCCAGCCCCAACCAGACCT
           CTCTGTACTTCTGTGCCAGCAGTTTATACACCCACACTGAAGCTTTCTTTGGA
           CAAGGCACCAGACTCACAGTTGTA (SEQ ID NO: 900)

PN42833    DAKTTQPPSMDCAEGRAANLPCNHSTISGNEYVYWYRQIHSQGPQYIIHGLKNN
Vα         ETNEMASLIITEDRKSSTLILPHATLRDTAVYYCIVRDTTSGTYKYIFGTGTRLKV
           LA (SEQ ID NO: 901)
           GATGCTAAGACCACCCAGCCCCCCTCCATGGATTGCGCTGAAGGAAGAGCTG
           CAAACCTGCCTTGTAATCACTCTACCATCAGTGGAAATGAGTATGTGTATTGG
           TATCGACAGATTCACTCCCAGGGGCCACAGTATATCATTCATGGTCTAAAAA
           ACAATGAAACCAATGAAATGGCCTCTCTGATCATCACAGAAGACAGAAAGTC
           CAGCACCTTGATCCTGCCCCACGCTACGCTGAGAGACACTGCTGTGTACTATT
           GCATCGTCAGAGACACTACCTCAGGAACCTACAAATACATCTTTGGAACAGG
           CACCAGGCTGAAGGTTTTAGCA (SEQ ID NO: 902)

PN42833    EAQVTQNPRYLITVTGKKLTVTCSQNMNHEYMSWYRQDPGLGLRQIYYSMNVE
Vβ         VTDKGDVPEGYKVSRKEKRNFPLILESPSPNQTSLYFCASSLSSTGFSPLHFGNGT
           RLTVT (SEQ ID NO: 903)
           GAAGCCCAAGTGACCCAGAACCCAAGATACCTCATCACAGTGACTGGAAAG
           AAGTTAACAGTGACTTGTTCTCAGAATATGAACCATGAGTATATGTCCTGGTA
           TCGACAAGACCCAGGGCTGGGCTTAAGGCAGATCTACTATTCAATGAATGTT
           GAGGTGACTGATAAGGGAGATGTTCCTGAAGGGTACAAAGTCTCTCGAAAA
           GAGAAGAGGAATTTCCCCCTGATCCTGGAGTCGCCCAGCCCCAACCAGACCT
           CTCTGTACTTCTGTGCCAGCAGTTTATCCTCGACAGGTTTTTCACCCCTCCACT
           TTGGGAACGGGACCAGGCTCACTGTGACA (SEQ ID NO: 904)

PN42840    TQLLEQSPQFLSIQEGENLTVYCNSSSVFSSLQWYRQEPGEGPVLLVTVVTGGEV
Vα         KKLKRLTFQFGDARKDSSLHITAAQPGDTGLYLCAEGGGSQGNLIFGKGTKLSV
           KP (SEQ ID NO: 905)
           ACCCAGCTGCTGGAGCAGAGCCCTCAGTTTCTAAGCATCCAAGAGGGAGAAA
           ATCTCACTGTGTACTGCAACTCCTCAAGTGTTTTTTTCCAGCTTACAATGGTAC
           AGACAGGAGCCTGGGGAAGGTCCTGTCCTCCTGGTGACAGTAGTTACGGGTG
           GAGAAGTGAAGAAGCTGAAGAGACTAACCTTTCAGTTTGGTGATGCAAGAA
           AGGACAGTTCTCTCCACATCACTGCGGCCCAGCCTGGTGATACAGGCCTCTA
           CCTCTGTGCAGAGGGGGGAGGAAGCCAAGGAAATCTCATCTTTGGAAAAGG
           CACTAAACTCTCTGTTAAACCA (SEQ ID NO: 906)

PN42840    DAGVTQSPTHLIKTRGQQVTLRCSPKSGHDTVSWYQQALGQGPQFIFQYYEEEE
Vβ         RQRGNFPDRFSGHQFPNYSSELNVNALLLGDSALYLCASSWTDYGYTFGSGTRL
           TVV (SEQ ID NO: 907)
           GACGCTGGAGTCACCCAAAGTCCCACACACCTGATCAAAACGAGAGGACAG
           CAAGTGACTCTGAGATGCTCTCCTAAGTCTGGGCATGACACTGTGTCCTGGTA
           CCAACAGGCCCTGGGTCAGGGGCCCCAGTTTATCTTTCAGTATTATGAGGAG
           GAAGAGAGACAGAGAGGCAACTTCCCTGATCGATTCTCAGGTCACCAGTTCC
           CTAACTATAGCTCTGAGCTGAATGTGAACGCCTTGTTGCTGGGGGACTCGGC
           CCTCTATCTCTGTGCCAGCAGCTGGACAGACTATGGCTACACCTTCGGTTCGG
           GGACCAGGTTAACCGTTGTA (SEQ ID NO: 908)

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br><u>Nucleic Acid</u> Sequence<br>(SEQ ID NO); CDR1, CDR2, and CDR3 sequences are <u>underlined</u> |
|---|---|
| PN42845<br>Vα | TQLLEQSPQFLSIQEGENLTVYCNS<u>SSVFSSL</u>QWYRQEPGEGPVLLVT<u>VVTGGEV</u><br>KKLKRLTFQFGDARKDSSLHITAAQPGDTGLYLC<u>AGIRSNDYKLS</u>FGAGTTVTV<br>RA (SEQ ID NO: 909)<br>ACCCAGCTGCTGGAGCAGAGCCCTCAGTTTCTAAGCATCCAAGAGGGAGAAA<br>ATCTCACTGTGTACTGCAACTCCTCA<u>AGTGTTTTTTCC</u>AGCTTACAATGGTAC<br>AGACAGGAGCCTGGGGAAGGTCCTGTCCTCCTGGTGACA<u>GTAGTTACGGGTG</u><br><u>GAGAAGT</u>GAAGAAGCTGAAGAGACTAACCTTTCAGTTTGGTGATGCAAGAA<br>AGGACAGTTCTCTCCACATCACTGCGGCCCAGCCTGGTGATACAGGCCTCTA<br>CCTCTGTGCA<u>GGGATACGTTCTAACGACTACAAGCTC</u>AGCTTTGGAGCCGGA<br>ACCACAGTAACTGTAAGAGCA (SEQ ID NO: 910) |
| PN42845<br>Vβ | EAQVTQNPRYLITVTGKKLTVTCSQN<u>MNHEYMS</u>WYRQDPGLGLRQIYYS<u>MNVE</u><br>VTDKGDVPEGYKVSRKEKRNFPLILESPSPNQTSLYFC<u>ASSSWTAHTEAFF</u>GQGT<br><u>R</u>LTVV (SEQ ID NO: 911)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACTAT<u>TCAATGAATGTT</u><br><u>GAGGT</u>GACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGT<u>GCCAGCAGTTCCTGGACAGCCCACACTGAAGCTTTC</u>TTT<br>GGACAAGGCACCAGACTCACAGTTGTA (SEQ ID NO: 912) |
| PN42870<br>Vα | TQLLEQSPQFLSIQEGENLTVYCNS<u>SSVFSSL</u>QWYRQEPGEGPVLLVT<u>VVTGGEV</u><br>KKLKRLTFQFGDARKDSSLHITAAQPGDTGLYLC<u>AENSGGGADGLT</u>FGKGTHLII<br>QP (SEQ ID NO: 913)<br>ACCCAGCTGCTGGAGCAGAGCCCTCAGTTTCTAAGCATCCAAGAGGGAGAAA<br>ATCTCACTGTGTACTGCAACTCCTCA<u>AGTGTTTTTTCC</u>AGCTTACAATGGTAC<br>AGACAGGAGCCTGGGGAAGGTCCTGTCCTCCTGGTGACA<u>GTAGTTACGGGTG</u><br><u>GAGAAGT</u>GAAGAAGCTGAAGAGACTAACCTTTCAGTTTGGTGATGCAAGAA<br>AGGACAGTTCTCTCCACATCACTGCGGCCCAGCCTGGTGATACAGGCCTCTA<br>CCTCTGTGCA<u>GAAAATTCAGGAGGAGGTGCTGACGGACTCACC</u>TTTGGCAAA<br>GGGACTCATCTAATCATCCAGCCC (SEQ ID NO: 914) |
| PN42870<br>Vβ | DAGVTQSPTHLIKTRGQQVTLRCSPK<u>SGHDT</u>VSWYQQALGQGPQFIFQ<u>YYEEEE</u><br>RQRGNFPDRFSGHQFPNYSSELNVNALLLGDSALYLC<u>ASSFTDYGYT</u>FGSGTRLT<br>W (SEQ ID NO: 915)<br>GACGCTGGAGTCACCCAAAGTCCCACACACCTGATCAAAACGAGAGGACAG<br>CAAGTGACTCTGAGATGCTCTCCTAAGT<u>CTGGGCATGACACT</u>GTGTCCTGGTA<br>CCAACAGGCCCTGGGTCAGGGGCCCCAGTTTATCTTTC<u>AGTATTATGAGGAG</u><br><u>GAAGAGAGA</u>CAGAGAGGCAACTTCCCTGATCGATTCTCAGGTCACCAGTTCC<br>CTAACTATAGCTCTGAGCTGAATGTGAACGCCTTGTTGCTGGGGGACTCGGC<br>CCTCTATCTCTGT<u>GCCAGCAGCTTCACAGACTATGGCTACACC</u>TTCGGTTCGG<br>GGACCAGGTTAACCGTTGTA (SEQ ID NO: 916) |
| PN42879<br>Vα | TQLLEQSPQFLSIQEGENLTVYCNS<u>SSVFSSL</u>QWYRQEPGEGPVLLVT<u>VVTGGEV</u><br>KKLKRLTFQFGDARKDSSLHITAAQPGDTGLYLC<u>AGEDFGNEKLT</u>FGTGTRLTII<br>P (SEQ ID NO: 917)<br>ACCCAGCTGCTGGAGCAGAGTCCTCAGTTTCTAAGCATCCAAGAGGGAGAAA<br>ATCTCACTGTGTACTGCAACTCCTCA<u>AGTGTTTTTTCC</u>AGCTTACAATGGTAC<br>AGACAGGAGCCTGGGGAAGGTCCTGTCCTCCTGGTGACA<u>GTAGTTACGGGTG</u><br><u>GAGAAGT</u>GAAGAAGCTGAAGAGACTAACCTTTCAGTTTGGTGATGCAAGAA<br>AGGACAGTTCTCTCCACATCACTGCGGCCCAGCCTGGTGATACAGGCCTCTA<br>CCTCTGTGCA<u>GGAGAGGACTTTGGAAATGAGAAATTAACC</u>TTTGGGACTGGA<br>ACAAGACTCACCATCATACCC (SEQ ID NO: 918) |
| PN42879<br>Vβ | DAGVTQSPTHLIKTRGQQVTLRCSPK<u>SGHDT</u>VSWYQQALGQGPQFIFQ<u>YYEEEE</u><br>RQRGNFPDRFSGHQFPNYSSELNVNALLLGDSALYLC<u>ASSWADYGYT</u>FGSGTRL<br>TVV(SEQ ID NO: 919)<br>GACGCTGGAGTCACCCAAAGTCCCACACACCTGATCAAAACGAGAGGACAG<br>CAAGTGACTCTGAGATGCTCTCCTAAGT<u>CTGGGCATGACACT</u>GTGTCCTGGTA<br>CCAACAGGCCCTGGGTCAGGGGCCCCAGTTTATCTTTC<u>AGTATTATGAGGAG</u><br><u>GAAGAGAGA</u>CAGAGAGGCAACTTCCCTGATCGATTCTCAGGTCACCAGTTCC<br>CTAACTATAGCTCTGAGCTGAATGTGAACGCCTTGTTGCTGGGGGACTCGGC<br>CCTCTATCTCTGT<u>GCCAGCAGCTGGGCGGATTATGGCTACACC</u>TTCGGTTCGG<br>GGACCAGGTTAACCGTTGTA (SEQ ID NO: 920) |

TABLE 8-continued

Amino acid and nucleic acid sequences for VelociT TCRs
specific for PRAME (425-433)/HLA-A2

| Domain name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN42888 Vα | ILNVEQSPQSLHVQEGDSTNFTCSFPSSNFYALHWYRWETAKSPEALFVMTLNG<br>DEKKKGRISATLNTKEGYSYLYIKGSQPEDSATYLCAFLTGNQFYFGTGTSLTVIP<br>(SEQ ID NO: 921)<br>ATACTGAACGTGGAACAAAGTCCTCAGTCACTGCATGTTCAGGAGGGAGACA<br>GCACCAATTTCACCTGCAGCTTCCCTTCCAGCAATTTTTATGCCTTACACTGG<br>TACAGATGGGAAACTGCAAAAGCCCCGAGGCCTTGTTTGTAATGACTTTAA<br>ATGGGGATGAAAAGAAGAAAGGACGAATAAGTGCCACTCTTAATACCAAGG<br>AGGGTTACAGCTATTTGTACATCAAAGGATCCCAGCCTGAAGACTCAGCCAC<br>ATACCTCTGTGCCTTTCTCACCGGTAACCAGTTCTATTTTGGGACAGGGACAA<br>GTTTGACGGTCATTCCA (SEQ ID NO: 922) |
| PN42888 Vβ | DVKVTQSSRYLVKRTGEKVFLECVQDMDHENMFWYRQDPGLGLRLIYFSYDVK<br>MKEKGDIPEGYSVSREKKERFSLILESASTNQTSMYLCASSTVRQGNYGYTFGSG<br>TRLTVV (SEQ ID NO: 923)<br>GATGTGAAAGTAACCCAGAGCTCGAGATATCTAGTCAAAAGGACGGGAGAG<br>AAAGTTTTTCTGGAATGTGTCCAGGATATGGACCATGAAAATATGTTCTGGTA<br>TCGACAAGACCCAGGTCTGGGGCTACGGCTGATCTATTTCTCATATGATGTTA<br>AAATGAAAGAAAAAGGAGATATTCCTGAGGGGTACAGTGTCTCTAGAGAGA<br>AGAAGGAGCGCTTCTCCCTGATTCTGGAGTCCGCCAGCACCAACCAGACATC<br>TATGTACCTCTGTGCCAGCAGTACCGTGAGGCAGGGGAACTATGGCTACACC<br>TTCGGTTCGGGGACCAGGTTAACCGTTGTA (SEQ ID NO: 924) |
| PN42895 Vα | DQQVKQSSPSLSVQEGRISILNCDYTNSMFDYFLWYKKYPAEGPTFLISISSIKDK<br>NEDGRFTVFLNKSAKHLSLHIVPSQPGDSAVYFCAASAGSARQLTFGSGTQLTVL<br>P (SEQ ID NO: 925)<br>GACCAGCAAGTTAAGCAAAGTTCACCATCCCTGAGCGTCCAGGAAGGAAGA<br>ATTTCTATTCTGAACTGTGACTATACTAACAGCATGTTTGATTATTTCCTATGG<br>TACAAAAAATACCCTGCTGAAGGTCCTACATTCCTGATATCTATAAGTTCCAT<br>TAAGGATAAAAATGAAGATGGAAGATTCACTGTTTTCTTAAACAAAAGTGCC<br>AAGCACCTCTCTCTGCACATTGTGCCCTCCCAGCCTGGAGACTCTGCAGTGTA<br>CTTCTGTGCAGCAAGCGCCGGTTCTGCAAGGCAACTGACCTTTGGATCTGGG<br>ACACAATTGACTGTTTTACCT (SEQ ID NO: 926) |
| PN42895 Vβ | EAQVTQNPRYLITVTGKKLTVTCSQNMNHEYMSWYRQDPGLGLRQIYYSMNVE<br>VTDKGDVPEGYKVSRKEKRNFPLILESPSPNQTSLYFCASSLWSNTEAFFGQGTR<br>LTVV (SEQ ID NO: 927)<br>GAAGCCCAAGTGACCCAGAACCCAAGATACCTCATCACAGTGACTGGAAAG<br>AAGTTAACAGTGACTTGTTCTCAGAATATGAACCATGAGTATATGTCCTGGTA<br>TCGACAAGACCCAGGGCTGGGCTTAAGGCAGATCTACTATTCAATGAATGTT<br>GAGGTGACTGATAAGGGAGATGTTCCTGAAGGGTACAAAGTCTCTCGAAAA<br>GAGAAGAGGAATTTCCCCCTGATCCTGGAGTCGCCCAGCCCCAACCAGACCT<br>CTCTGTACTTCTGTGCCAGCAGTTTATGGTCGAACACTGAAGCTTTCTTTGGA<br>CAAGGCACCAGACTCACAGTTGTA (SEQ ID NO: 928) |

TABLE 9

Variable (V) and joining (J) region gene families for the α and β chains of VelociT TCRs specific for PRAME (312-320)/HLA-A2

| TCR ID | Vβ | Jβ | Vα | Jα |
|---|---|---|---|---|
| PN46909 | 6-6 | 1-1 | 38-1 | 26 |
| PN46889 | 6-2 | 1-1 | 12-2 | 11 |
| PN46733 | 6-1 | 1-1 | 13-2 | 26 |
| PN46723 | 5-5 | 1-4 | 20-1 | 42 |
| PN46714 | 5-5 | 1-6 | 20-1 | 42 |
| PN46735 | 5-5 | 1-2 | 26-2 | 45 |
| PN46678 | 5-5 | 1-4 | 19-1 | 18 |
| PN46884 | 28-1 | 1-3 | 19-1 | 34 |
| PN46914 | 28-1 | 1-5 | 19-1 | 23 |
| PN46883 | 18-1 | 1-1 | 19-1 | 34 |
| PN46857 | 18-1 | 1-1 | 19-1 | 47 |
| PN46880 | 18-1 | 1-1 | 16-1 | 6 |
| PN46871 | 13-1 | 1-5 | 21-1 | 24 |
| PN46853 | 13-1 | 1-5 | 24-1 | 37 |
| PN46731 | 13-1 | 1-1 | 13-1 | 26 |

TABLE 9-continued

Variable (V) and joining (J) region gene families for the α and β chains of VelociT TCRs specific for PRAME (312-320)/HLA-A2

| TCR ID | Vβ | Jβ | Vα | Jα |
|---|---|---|---|---|
| PN46777 | 10-2 | 1-2 | 38-1 | 47 |
| PN46797 | 10-2 | 1-2 | 38-1 | 47 |
| PN46738 | 10-2 | 1-2 | 38-1 | 45 |

TABLE 10

Variable (V) and joining (J) region gene families for the α and β chains of VelociT TCRs specific for PRAME (425-433)/HLA-A2

| TCR ID | Vb | Jb | Va | Ja |
|---|---|---|---|---|
| PN42365 | 5-6 | 1-2 | 27-1 | 42-1 |
| PN42879 | 5-6 | 1-2 | 27-1 | 48-1 |
| PN42774 | 5-6 | 1-2 | 12-2 | 34-1 |

TABLE 10-continued

Variable (V) and joining (J) region gene families for the α and β chains of VelociT TCRs specific for PRAME (425-433)/HLA-A2

| TCR ID | Vb | Jb | Va | Ja |
|---|---|---|---|---|
| PN42498 | 5-6 | 1-2 | 27-1 | 42-1 |
| PN42558 | 5-6 | 1-2 | 22-1 | 42-1 |
| PN42386 | 5-6 | 1-2 | 27-1 | 42-1 |
| PN42378 | 5-6 | 1-2 | 26-2 | 24-1 |
| PN42776 | 5-6 | 1-2 | 26-2 | 24-1 |
| PN42455 | 5-6 | 1-2 | 26-2 | 24-1 |
| PN42840 | 5-6 | 1-2 | 27-1 | 42-1 |
| PN42795 | 5-6 | 1-2 | 12-1 | 42-1 |
| PN42870 | 5-6 | 1-2 | 27-1 | 45-1 |
| PN42689 | 5-6 | 1-2 | 27-1 | 42-1 |
| PN42888 | 28-1 | 1-2 | 24-1 | 49-1 |
| PN42450 | 28-1 | 1-2 | 16-1 | 34-1 |
| PN42750 | 28-1 | 1-2 | 26-2 | 24-1 |
| PN42562 | 27-1 | 1-2 | 27-1 | 40-1 |
| PN42483 | 27-1 | 1-4 | 27-1 | 42-1 |
| PN42712 | 27-1 | 1-6 | 22-1 | 20-1 |
| PN42561 | 27-1 | 1-2 | 26-2 | 49-1 |
| PN42442 | 27-1 | 1-2 | 27-1 | 40-1 |
| PN42476 | 27-1 | 1-4 | 26-2 | 24-1 |

TABLE 10-continued

Variable (V) and joining (J) region gene families for the α and β chains of VelociT TCRs specific for PRAME (425-433)/HLA-A2

| TCR ID | Vb | Jb | Va | Ja |
|---|---|---|---|---|
| PN42496 | 27-1 | 1-2 | 26-2 | 54-1 |
| PN42655 | 27-1 | 1-2 | 26-2 | 24-1 |
| PN42677 | 27-1 | 1-2 | 26-2 | 49-1 |
| PN42706 | 27-1 | 1-2 | 22-1 | 40-1 |
| PN42654 | 27-1 | 1-2 | 26-2 | 49-1 |
| PN42441 | 27-1 | 1-1 | 26-2 | 49-1 |
| PN42683 | 27-1 | 1-2 | 26-2 | 47-1 |
| PN42845 | 27-1 | 1-1 | 27-1 | 20-1 |
| PN42826 | 27-1 | 1-1 | 29/DV5 | 22-1 |
| PN42707 | 27-1 | 1-1 | 13-2 | 26-1 |
| PN42833 | 27-1 | 1-6 | 26-1 | 40-1 |
| PN42762 | 27-1 | 1-1 | 26-2 | 44-1 |
| PN42780 | 27-1 | 1-2 | 27-1 | 40-1 |
| PN42746 | 27-1 | 1-1 | 13-2 | 26-1 |
| PN42815 | 27-1 | 1-6 | 13-2 | 26-1 |
| PN42711 | 27-1 | 1-6 | 22-1 | 20-1 |
| PN42895 | 27-1 | 1-1 | 29/DV5 | 22-1 |
| PN42610 | 13-1 | 1-5 | 12-2 | 26-1 |

TABLE 11

Amino acid and polynucleic acid sequence identifiers for TCR alpha and beta variable chains and CDRs that were identified with PRAME (312-320).

| | Amino Acid Sequences | | | | | | | |
|---|---|---|---|---|---|---|---|---|
| | | α CDRs | | | | β CDRs | | |
| TCR ID | Vα | CDR1 | CDR2 | CDR3 | Vβ | CDR1 | CDR2 | CDR3 |
| | | | | | SEQ ID NO: | | | |
| PN46678 | 217 | 1 | 2 | 3 | 219 | 4 | 5 | 6 |
| PN46714 | 221 | 7 | 8 | 9 | 223 | 10 | 11 | 12 |
| PN46723 | 225 | 13 | 14 | 15 | 227 | 16 | 17 | 18 |
| PN46731 | 229 | 19 | 20 | 21 | 231 | 22 | 23 | 24 |
| PN46733 | 233 | 25 | 26 | 27 | 235 | 28 | 29 | 30 |
| PN46735 | 237 | 31 | 32 | 33 | 239 | 34 | 35 | 36 |
| PN46738 | 241 | 37 | 38 | 39 | 243 | 40 | 41 | 42 |
| PN46777 | 245 | 43 | 44 | 45 | 247 | 46 | 47 | 48 |
| PN46797 | 249 | 49 | 50 | 51 | 251 | 52 | 53 | 54 |
| PN46853 | 253 | 55 | 56 | 57 | 255 | 58 | 59 | 60 |
| PN46857 | 257 | 61 | 62 | 63 | 259 | 64 | 65 | 66 |
| PN46871 | 261 | 67 | 68 | 69 | 263 | 70 | 71 | 72 |
| PN46880 | 265 | 73 | 74 | 75 | 267 | 76 | 77 | 78 |
| PN46883 | 269 | 79 | 80 | 81 | 271 | 82 | 83 | 84 |
| PN46884 | 273 | 85 | 86 | 87 | 275 | 88 | 89 | 90 |
| PN46889 | 277 | 91 | 92 | 93 | 279 | 94 | 95 | 96 |
| PN46909 | 281 | 97 | 98 | 99 | 283 | 100 | 101 | 102 |
| PN46914 | 285 | 103 | 104 | 105 | 287 | 106 | 107 | 108 |

| | Polynucleic Acid Sequences | | | | | | | |
|---|---|---|---|---|---|---|---|---|
| | | α CDRs | | | | β CDRs | | |
| TCR ID | Vα | CDR1 | CDR2 | CDR3 | Vβ | CDR1 | CDR2 | CDR3 |
| | | | | | SEQ ID NO: | | | |
| PN46678 | 218 | 109 | 110 | 111 | 220 | 112 | 113 | 114 |
| PN46714 | 222 | 115 | 116 | 117 | 224 | 118 | 119 | 120 |
| PN46723 | 226 | 121 | 122 | 123 | 228 | 124 | 125 | 126 |
| PN46731 | 230 | 127 | 128 | 129 | 232 | 130 | 131 | 132 |
| PN46733 | 234 | 133 | 134 | 135 | 236 | 136 | 137 | 138 |
| PN46735 | 238 | 139 | 140 | 141 | 240 | 142 | 143 | 144 |
| PN46738 | 242 | 145 | 146 | 147 | 244 | 148 | 149 | 150 |
| PN46777 | 246 | 151 | 152 | 153 | 248 | 154 | 155 | 156 |
| PN46797 | 250 | 157 | 158 | 159 | 252 | 160 | 161 | 162 |
| PN46853 | 254 | 163 | 164 | 165 | 256 | 166 | 167 | 168 |
| PN46857 | 258 | 169 | 170 | 171 | 260 | 172 | 173 | 174 |
| PN46871 | 262 | 175 | 176 | 177 | 264 | 178 | 179 | 180 |
| PN46880 | 266 | 181 | 182 | 183 | 268 | 184 | 185 | 186 |
| PN46883 | 270 | 187 | 188 | 189 | 272 | 190 | 191 | 192 |
| PN46884 | 274 | 193 | 194 | 195 | 276 | 196 | 197 | 198 |

TABLE 11-continued

Amino acid and polynucleic acid sequence identifiers for TCR alpha and beta
variable chains and CDRs that were identified with PRAME (312-320).

| PN46889 | 278 | 199 | 200 | 201 | 280 | 202 | 203 | 204 |
| PN46909 | 282 | 205 | 206 | 207 | 284 | 208 | 209 | 210 |
| PN46914 | 286 | 211 | 212 | 213 | 288 | 214 | 215 | 216 |

TABLE 12

Amino acid and polynucleic acid sequence identifiers for TCR alpha and beta
variable chains and CDRs that were identified with PRAME (425-433).

| | | Amino Acid Sequences | | | | | | |
| | | α CDRs | | | | β CDRs | | |
| TCR ID | Vα | CDR1 | CDR2 | CDR3 | Vβ | CDR1 | CDR2 | CDR3 |
| | | | | SEQ ID NO: | | | | |
|---|---|---|---|---|---|---|---|---|
| PN42365 | 769 | 289 | 290 | 291 | 771 | 292 | 293 | 294 |
| PN42378 | 773 | 295 | 296 | 297 | 775 | 298 | 299 | 300 |
| PN42386 | 777 | 301 | 302 | 303 | 779 | 304 | 305 | 306 |
| PN42441 | 781 | 307 | 308 | 309 | 783 | 310 | 311 | 312 |
| PN42442 | 785 | 313 | 314 | 315 | 787 | 316 | 317 | 318 |
| PN42450 | 789 | 319 | 320 | 321 | 791 | 322 | 323 | 324 |
| PN42455 | 793 | 325 | 326 | 327 | 795 | 328 | 329 | 330 |
| PN42476 | 797 | 331 | 332 | 333 | 799 | 334 | 335 | 336 |
| PN42483 | 801 | 337 | 338 | 339 | 803 | 340 | 341 | 342 |
| PN42496 | 805 | 343 | 344 | 345 | 807 | 346 | 347 | 348 |
| PN42498 | 809 | 349 | 350 | 351 | 811 | 352 | 353 | 354 |
| PN42558 | 813 | 355 | 356 | 357 | 815 | 358 | 359 | 360 |
| PN42561 | 817 | 361 | 362 | 363 | 819 | 364 | 365 | 366 |
| PN42562 | 821 | 367 | 368 | 369 | 823 | 370 | 371 | 372 |
| PN42610 | 825 | 373 | 374 | 375 | 827 | 376 | 377 | 378 |
| PN42654 | 829 | 379 | 380 | 381 | 831 | 382 | 383 | 384 |
| PN42655 | 833 | 385 | 386 | 387 | 835 | 388 | 389 | 390 |
| PN42677 | 837 | 391 | 392 | 393 | 839 | 394 | 395 | 396 |
| PN42683 | 841 | 397 | 398 | 399 | 843 | 400 | 401 | 402 |
| PN42689 | 845 | 403 | 404 | 405 | 847 | 406 | 407 | 408 |
| PN42706 | 849 | 409 | 410 | 411 | 851 | 412 | 413 | 414 |
| PN42707 | 853 | 415 | 416 | 417 | 855 | 418 | 419 | 420 |
| PN42711 | 857 | 421 | 422 | 423 | 859 | 424 | 425 | 426 |
| PN42712 | 861 | 427 | 428 | 429 | 863 | 430 | 431 | 432 |
| PN42746 | 865 | 433 | 434 | 435 | 867 | 436 | 437 | 438 |
| PN42750 | 869 | 439 | 440 | 441 | 871 | 442 | 443 | 444 |
| PN42762 | 873 | 445 | 446 | 447 | 875 | 448 | 449 | 450 |
| PN42774 | 877 | 451 | 452 | 453 | 879 | 454 | 455 | 456 |
| PN42776 | 881 | 457 | 458 | 459 | 883 | 460 | 461 | 462 |
| PN42780 | 885 | 463 | 464 | 465 | 887 | 466 | 467 | 468 |
| PN42795 | 889 | 469 | 470 | 471 | 891 | 472 | 473 | 474 |
| PN42815 | 893 | 475 | 476 | 477 | 895 | 478 | 479 | 480 |
| PN42826 | 897 | 481 | 482 | 483 | 899 | 484 | 485 | 486 |
| PN42833 | 901 | 487 | 488 | 489 | 903 | 490 | 491 | 492 |
| PN42840 | 905 | 493 | 494 | 495 | 907 | 496 | 497 | 498 |
| PN42845 | 909 | 499 | 500 | 501 | 911 | 502 | 503 | 504 |
| PN42870 | 913 | 505 | 506 | 507 | 915 | 508 | 509 | 510 |
| PN42879 | 917 | 511 | 512 | 513 | 919 | 514 | 515 | 516 |
| PN42888 | 921 | 517 | 518 | 519 | 923 | 520 | 521 | 522 |
| PN42895 | 925 | 523 | 524 | 525 | 927 | 526 | 527 | 528 |

| | | Polynucleic Acid Sequences | | | | | | |
| | | α CDRs | | | | β CDRs | | |
| TCR ID | Vα | CDR1 | CDR2 | CDR3 | Vβ | CDR1 | CDR2 | CDR3 |
| | | | | SEQ ID NO: | | | | |
|---|---|---|---|---|---|---|---|---|
| PN42365 | 770 | 529 | 530 | 531 | 772 | 532 | 533 | 534 |
| PN42378 | 774 | 535 | 536 | 537 | 776 | 538 | 539 | 540 |
| PN42386 | 778 | 541 | 542 | 543 | 780 | 544 | 545 | 546 |
| PN42441 | 782 | 547 | 548 | 549 | 784 | 550 | 551 | 552 |
| PN42442 | 786 | 553 | 554 | 555 | 788 | 556 | 557 | 558 |
| PN42450 | 790 | 559 | 560 | 561 | 792 | 562 | 563 | 564 |
| PN42455 | 794 | 565 | 566 | 567 | 796 | 568 | 569 | 570 |
| PN42476 | 798 | 571 | 572 | 573 | 800 | 574 | 575 | 576 |
| PN42483 | 802 | 577 | 578 | 579 | 804 | 580 | 581 | 582 |
| PN42496 | 806 | 583 | 584 | 585 | 808 | 586 | 587 | 588 |

TABLE 12-continued

Amino acid and polynucleic acid sequence identifiers for TCR alpha and beta
variable chains and CDRs that were identified with PRAME (425-433).

| | | | | | | | | |
|---|---|---|---|---|---|---|---|---|
| PN42498 | 810 | 589 | 590 | 591 | 812 | 592 | 593 | 594 |
| PN42558 | 814 | 595 | 596 | 597 | 816 | 598 | 599 | 600 |
| PN42561 | 818 | 601 | 602 | 603 | 820 | 604 | 605 | 606 |
| PN42562 | 822 | 607 | 608 | 609 | 824 | 610 | 611 | 612 |
| PN42610 | 826 | 613 | 614 | 615 | 828 | 616 | 617 | 618 |
| PN42654 | 830 | 619 | 620 | 621 | 832 | 622 | 623 | 624 |
| PN42655 | 834 | 625 | 626 | 627 | 836 | 628 | 629 | 630 |
| PN42677 | 838 | 631 | 632 | 633 | 840 | 634 | 635 | 636 |
| PN42683 | 842 | 637 | 638 | 639 | 844 | 640 | 641 | 642 |
| PN42689 | 846 | 643 | 644 | 645 | 848 | 646 | 647 | 648 |
| PN42706 | 850 | 649 | 650 | 651 | 852 | 652 | 653 | 654 |
| PN42707 | 854 | 655 | 656 | 657 | 856 | 658 | 659 | 660 |
| PN42711 | 858 | 661 | 662 | 663 | 860 | 664 | 665 | 666 |
| PN42712 | 862 | 667 | 668 | 669 | 864 | 670 | 671 | 672 |
| PN42746 | 866 | 673 | 674 | 675 | 868 | 676 | 677 | 678 |
| PN42750 | 870 | 679 | 680 | 681 | 872 | 682 | 683 | 684 |
| PN42762 | 874 | 685 | 686 | 687 | 876 | 688 | 689 | 690 |
| PN42774 | 878 | 691 | 692 | 693 | 880 | 694 | 695 | 696 |
| PN42776 | 882 | 697 | 698 | 699 | 884 | 700 | 701 | 702 |
| PN42780 | 886 | 703 | 704 | 705 | 888 | 706 | 707 | 708 |
| PN42795 | 890 | 709 | 710 | 711 | 892 | 712 | 713 | 714 |
| PN42815 | 894 | 715 | 716 | 717 | 896 | 718 | 719 | 720 |
| PN42826 | 898 | 721 | 722 | 723 | 900 | 724 | 725 | 726 |
| PN42833 | 902 | 727 | 728 | 729 | 904 | 730 | 731 | 732 |
| PN42840 | 906 | 733 | 734 | 735 | 908 | 736 | 737 | 738 |
| PN42845 | 910 | 739 | 740 | 741 | 912 | 742 | 743 | 744 |
| PN42870 | 914 | 745 | 746 | 747 | 916 | 748 | 749 | 750 |
| PN42879 | 918 | 751 | 752 | 753 | 920 | 754 | 755 | 756 |
| PN42888 | 922 | 757 | 758 | 759 | 924 | 760 | 761 | 762 |
| PN42895 | 926 | 763 | 764 | 765 | 928 | 766 | 767 | 768 |

Example 2. Dose-Dependent T Cell Receptor Activation

A Jurkat cell line lacking endogenous TCRα and TCRβ expression was generated by gene disruption. These cells were then engineered with a genomic landing pad site that allowed single copy Cre recombinase-mediated insertion of transgenic TCR constructs. An Activator Protein 1 (AP1) response element-driven luciferase reporter was subsequently incorporated into this parental bioassay cell line. Specific TCR bioassay lines were generated by Cre-mediated insertion of constructs expressing the VelociT®-derived TCRα and TCRβ sequences.

Jurkat bioassay lines expressing TCR constructs were sorted to homogeneity using Flourescence-Activated Cell Sorting (FACS), then tested in peptide-MHC stimulation assays. HEK293T cells (HLA-A2*01) were plated in assay wells with varying dilutions of antigenic PRAME peptide (PRAME 425-433; SEQ ID NO: 930) or an irrelevant HLA-A2 restricted peptide (SLLMWITQC; SEQ ID NO: 953). These dilutions were made as indicated in Table 13.

TABLE 13

Peptide dilutions for testing dose response of anti-PRAME TCRs

| Dilution | Concentration (µM) | Irrelevant peptide (µg/ml) | PRAME (425-433) peptide (µg/ml) |
|---|---|---|---|
| 1 | 100 | 109 | 98.9 |
| 2 | 20 | 21.8 | 19.8 |
| 3 | 4 | 4.4 | 4.0 |
| 4 | 0.8 | 0.87 | 0.79 |
| 5 | 0.16 | 0.17 | 0.16 |
| 6 | 0.032 | 0.035 | 0.032 |
| 7 | 0.0064 | 0.0070 | 0.0063 |
| 8 | 0.00128 | 0.0014 | 0.0013 |

TABLE 13-continued

Peptide dilutions for testing dose response of anti-PRAME TCRs

| Dilution | Concentration (µM) | Irrelevant peptide (µg/ml) | PRAME (425-433) peptide (µg/ml) |
|---|---|---|---|
| 9 | 0.000256 | 0.00028 | 0.00025 |
| 10 | 0.0000512 | 5.6E−5 | 5.1E−5 |
| 11 | 0.00001024 | 1.1E−5 | 1.0E−5 |
| 12 | 0 (no peptide) | 0 | 0 |

After a 2 hour incubation, engineered Jurkat cells were added to wells at a 3:1 Jurkat:293T cell ratio and incubated a further 5 hours. Luciferase reporter activity was determined by measuring endpoint luminescence output in assay wells. PRAME-specific TCRs mediated dose-dependent AP1 reporter activation in response to HLA-A2*01 HEK293T cells pulsed with cognate peptide, but not those cells pulsed with the irrelevant peptide. EC50 data is shown in Table 14, below.

TABLE 14

Antigen-specific response of HLA-A2/PRAME (425-433)-specific TCRs
in a Jurkat cell bioassay, normalized to negative control

| TCR ID | EC50 (µM) |
|---|---|
| PN42365 | 0.01594 |
| PN42386 | 0.02711 |
| PN42441 | 0.8205 |
| PN42442 | 0.2324 |
| PN42450 | 0.03355 |
| PN42483 | * |
| PN42496 | 0.02937 |
| PN42498 | 0.002418 |
| PN42558 | 0.2614 |
| PN42561 | 0.0137 |

TABLE 14-continued

Antigen-specific response of HLA-A2/PRAME (425-433)-specific TCRs
in a Jurkat cell bioassay, normalized to negative control

| TCR ID | EC50 (μM) |
| --- | --- |
| PN42562 | 0.02807 |
| PN42610 | * |
| PN42654 | * |
| PN42655 | |
| PN42677 | * |
| PN42683 | * |
| PN42689 | 0.0095 |
| PN42706 | 0.7274 |
| PN42707 | 0.01182 |
| PN42711 | 0.05688 |
| PN42712 | 0.01329 |
| PN42746 | 0.04598 |
| PN42762 | 114.8 |
| PN42774 | 0.8757 |
| PN42780 | 1.255 |
| PN42795 | 0.2454 |
| PN42815 | 0.1261 |
| PN42826 | 4.915 |
| PN42833 | 0.04786 |
| PN42840 | 0.03092 |

TABLE 14-continued

Antigen-specific response of HLA-A2/PRAME (425-433)-specific TCRs
in a Jurkat cell bioassay, normalized to negative control

| TCR ID | EC50 (μM) |
| --- | --- |
| PN42845 | 0.911 |
| PN42870 | 0.1302 |
| PN42879 | * |
| PN42888 | 0.0119 |
| PN42895 | 0.94 |

* Not above negative control/did not respond in assay

EQUIVALENTS

Those skilled in the art will recognize or be able to ascertain, using no more than routine experimentation, many equivalents to the specific embodiments of the invention described herein. such equivalents are intended to be encompassed by the following claims. The contents of all references, patents and published patent applications cited throughout this application are incorporated herein by reference.

We claim:

1. A T cell receptor (TCR) that binds specifically to an HLA-A2 presented preferentially expressed antigen in melanoma (PRAME) peptide, wherein the TCR comprises a TCR alpha chain and a TCR beta chain, and wherein the TCR alpha chain comprises an alpha chain variable domain comprising a complementarity determining region (CDR) 1, a CDR2, and a CDR3 comprising the amino acid sequences of SEQ ID NOs: 493, 494, and 495, respectively, and the TCR beta chain comprises a beta chain variable domain comprising a CDR1, a CDR2, and a CDR3 comprising the amino acid sequences of SEQ ID NOs: 496, 497, and 498, respectively.

2. The TCR of claim 1.

3. A polynucleotide molecule comprising a) a polynucleotide sequence that encodes the alpha chain variable domain of the TCR as set forth in claim 1; and/or b) a polynucleotide sequence that encodes the beta chain variable domain of the TCR as set forth in claim 1.

4. A vector comprising the polynucleotide molecule of claim 3.

5. An cell expressing the vector of claim 4.

6. A pharmaceutical composition comprising the isolated cell of claim 5 and a pharmaceutically acceptable carrier or diluent.

7. The polynucleotide molecule of claim 3, wherein the polynucleotide sequence that encodes the alpha chain variable domain comprises the nucleotide sequence of SEQ ID NO: 906.

8. The polynucleotide molecule of claim 3, wherein the polynucleotide sequence that encodes the beta chain variable domain comprises the nucleotide sequence of SEQ ID NO: 908.

9. A cell expressing the polynucleotide molecule of claim 3.

10. A method of treating a subject having a PRAME-associated disease or disorder, comprising administering to the subject a therapeutically effective amount of the TCR as set forth in claim 1, thereby treating the subject.

11. The method of claim 10, wherein the PRAME-associated disease or disorder is PRAME-associated cancer.

12. The method of claim 11, wherein the PRAME-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, uterine corpus endometrial carcinoma, uterine carcinosarcoma, testicular germ cell tumor, uveal melanoma, kidney renal papillary cell carcinoma, kidney renal clear cell carcinoma, thymoma, colon adenocarcinoma, cervical squamous cell carcinoma, cervical tumor, pancreatic adenocarcinoma, liver cancer, hepatocellular carcinoma, mesothelioma, or a recurrent non-small cell lung cancer.

13. The method of claim 10, wherein the TCR is administered to the subject in combination with a second therapeutic agent.

14. The method of claim 10, wherein the TCR administered subcutaneously, intravenously, intradermally, intraperitoneally, orally, intramuscularly or intracranially to the subject.

15. The TCR of claim 1, further comprising a detectable moiety.

16. A pharmaceutical composition comprising the TCR of claim 1 and a pharmaceutically acceptable carrier or diluent.

17. A cell presenting the TCR of claim 1.

18. A pharmaceutical composition comprising the cell of claim 17.

19. A cell comprising a first polynucleotide molecule, wherein the first polynucleotide molecule comprises a polynucleotide sequence that encodes the alpha chain variable domain of the TCR as set forth in claim 1; and a second polynucleotide molecule, wherein the second polynucleotide molecule comprises a polynucleotide sequence that encodes the beta chain variable domain of the TCR as set forth in claim 1.

20. The cell of claim 19, wherein the polynucleotide sequence that encodes the alpha chain variable domain of the TCR comprises the nucleotide sequence of SEQ ID NO: 906, and wherein the polynucleotide sequence that encodes the beta chain variable domain of the TCR comprises the nucleotide sequence of SEQ ID NO: 908.

21. The cell of claim 19, wherein the first polynucleotide molecule is contained within a vector.

22. The cell of claim 19, wherein the second polynucleotide molecule is contained within a vector.

23. The cell of claim 19, wherein the first polynucleotide molecule and the second polynucleotide molecule are contained within a vector.

24. A pharmaceutical composition comprising the cell of claim 19.

25. A pharmaceutical composition comprising the cell of any one of claims 19-23.

26. A method of treating a subject having an PRAME-associated disease or disorder, comprising administering to the subject a plurality of the cells of any one of claims 5, 17, and 19-23, thereby treating the subject.

27. The method of claim 26, wherein the PRAME-associated disease or disorder is PRAME-associated cancer.

28. The method of claim 27, wherein the PRAME-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, uterine corpus endometrial carcinoma, uterine carcinosarcoma, testicular germ cell tumor, uveal melanoma, kidney renal papillary cell carcinoma, kidney renal clear cell carcinoma, thymoma, colon adenocarcinoma, cervical squamous cell carcinoma, cervical tumor, pancreatic adenocarcinoma, liver cancer, hepatocellular carcinoma, mesothelioma, or a recurrent non-small cell lung cancer.

29. The method of claim 26, wherein the plurality of cells is administered to the subject in combination with a second therapeutic agent.

30. The method of claim 26, wherein the plurality of cells is administered subcutaneously, intravenously, intradermally, intraperitoneally, orally, intramuscularly or intracranially to the subject.

* * * * *